(12) United States Patent
Huang

(10) Patent No.: US 6,955,905 B2
(45) Date of Patent: Oct. 18, 2005

(54) PR/SET-DOMAIN CONTAINING NUCLEIC ACIDS, POLYPEPTIDES, ANTIBODIES AND METHODS OF USE

(75) Inventor: Shi Huang, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 10/200,012

(22) Filed: Jul. 18, 2002

(65) Prior Publication Data

US 2004/0014192 A1 Jan. 22, 2004

Related U.S. Application Data

(60) Provisional application No. 60/421,147, filed on Jul. 18, 2001.

(51) Int. Cl.$^7$ .................. C12N 9/10; C12N 15/00; C12N 5/00; C12Q 1/48; C07H 21/04
(52) U.S. Cl. ............... 435/193; 435/15; 435/320.1; 435/69.1; 435/325; 435/252.3; 536/23.2; 530/350
(58) Field of Search ............... 435/193, 15, 320.1, 435/69.1, 252.3, 325; 536/23.2; 530/350

(56) References Cited

PUBLICATIONS

Bork, Genome Research, 10:398–400, 2000.*
Seffernick et al., J. Bacteriol. 183(8):2405–2410, 2001.*
Van de Loo et al., Proc. Natl. Acad. Sci. 92:6743–6747, 1995.*
Broun et al., Science 282:1315–1317, 1998.*
Witkowski et al., Biochemistry 38:11643–11650, 1999.*
Arakawa et al., "Identification and characterization of the ARP1 gene, a target for the human acute leukemia ALL1 gene," Proc. Natl. Acad. Sci. USA 95:4573–8 (1998).
Baffa et al., "Involvement of the ALL–1 gene in a solid tumor," Proc. Natl. Acad. Sci. USA 92:4922–6 (1995).
Bannister et al., "Selective recognition of methylated lysine 9 on histone H3 by the HP1 chromo domain," Nature 410:120–124 (2001).
Buyse et al., "The retinoblastoma protein binds to RIZ, a zinc finger protein that shares an epitope with the adenovirus E1A protein," Proc. Natl. Acad. Sci. USA 92:4467–4471 (1995).
Buyse et al., "Physical mapping of the retinoblastoma–interacting zinc finger gene RIZ to D1S228 on chromosome 1p36," Genomics 34:119–121 (1996).
Caldas and Aparicio, "Cell memory and cancer—the story of the trithorax and Polycomb group genes," Cancer & Metastasis Reviews 18:313–29 (1999).
Chadwick et al., "Candidate tumor suppressor RIZ is frequently involved in colorectal carcinogenesis;" Proc. Natl. Acad. Sci. USA 97:2662–2667 (2000).
Chesi et al., "The t(4;14) translocation in myeloma dysregulates both FGFR3 and a novel gene, MMSET, resulting in IgH/MMSET hybrid transcripts," Blood 92:3025–34 (1998).

Chittka and Chao, "Identification of a zinc finger protein whose subcellular distribution is regulated by serum and nerve growth factor," Proc. Natl. Acad. Sci. USA 96:10705–10710 (1999).
Connolly et al., "Identification of a region of frequent loss of heterozygosity at 11q24 in colorectal cancer," Cancer Research 59:2806–9 (1999).
Corda et al. "Interaction between Set1p and checkpoint protein Mec3p in DNA repair and telomere functions," Nature Genetics 21:204–8 (1999).
Cardoso et al., "Specific interaction between the XNP/ATR–X gene product and the SET domain of the human EZH2 protein," Human Molecular Genetics 7(4):679–684 (1998).
Cui et al., "Association of SET domain and myotubularin–related proteins modulates growth control," Nature Genetics 18:331–337 (1998).
Devlin et al., "High frequency of chromosome 9 deletion in ovarian cancer: evidence for three tumour–suppressor loci," British Journal of Cancer 73:420–3 (1996).
Djabali et al., "A trithorax–like gene is interrupted by chromosome 11q23 translocations in acute leukaemias," [published erratum appears in Nat. Genet. (1993) 4:431], Nature Genetics 2:113–8 (1992).
Du et al., "Hypermethylation in human cancers of the RIZ1 tumor suppressor gene, a member of a histone/protein methyltransferase superfamily," Cancer Research 61:8094–8099 (2001).
Fears et al., "Intergenic splicing of MDS1 and EVI1 occurs in normal tissues as well as in myeloid leukemia and produces a new member of the PR domain family," Proc. Natl. Acad. Sci. USA 93:1642–1647 (1996).
Fidanza et al., "Double knockout of the ALL–1 gene blocks hematopoietic differentiation in vitro," Cancer Research 56:1179–83 (1996).

(Continued)

Primary Examiner—Rebecca E. Prouty
Assistant Examiner—Delia M. Ramirez
(74) Attorney, Agent, or Firm—McDermott Will & Emery LLP

(57) ABSTRACT

The present invention provides an isolated nucleic acid molecule encoding a PFM/SET polypeptide. Also provided is an isolated nucleic acid molecule encoding a functional fragment of a PFM/SET polypeptide that contains a PR, SET, PRAZ or PKZL domain of a PFM/SET polypeptide of the invention. Further provided by the invention are PFM/SET polypeptides, and functional fragments thereof that contain a PR, SET, PRAZ or PKZL domain of a PFM/SET polypeptide. The invention also provides PFM/SET antibodies, PFM/SET modulatory compounds, and related methods. The molecules of the invention can be used in methods of screening for a compound that modulates PFM/SET polypeptide histone methyltransferase activity and to modulate cell proliferation to prevent or treat proliferative disorders, including cancer. Additionally, the molecules and methods of the invention can be used to diagnose and prognose proliferative disorders.

9 Claims, 13 Drawing Sheets

OTHER PUBLICATIONS

GenBank Accession No.: 10257424 (Jan. 7, 2002).
GenBank Accession No.: 13274746 (Mar. 17, 2001).
GenBank Accession No.: 13375635 (Mar. 18, 2001).
GenBank Accession No.: 13628859 (Apr. 16, 2001).
GenBank Accession No.: 18550030 (May 13, 2002).
GenBank Accession No.: 912371.1 (Jul. 26, 1995).
GenBank Accession No.: AA014148 (Jan. 21, 1997).
GenBank Accession No.: AA085455.1 (Aug. 1, 1997).
GenBank Accession No.: AA095564.1 (Oct. 25, 1996).
GenBank Accession No.: AA140269.1 (Feb. 11, 1997).
GenBank Accession No.: AA270924.1 (Mar. 26, 1997).
GenBank Accession No.: AA279563.1 (Aug. 15, 1997).
GenBank Accession No.: AA324539.1 (Apr. 20, 1997).
GenBank Accession No.: AA331245.1 (Apr. 21, 1997).
GenBank Accession No.: AA403165.1 (May 16, 1994).
GenBank Accession No.: AA468023.1 (Aug. 13, 1997).
GenBank Accession No.: AA468074.1 (Aug. 13, 1997).
GenBank Accession No.: AA490433.1 (Aug. 15, 1997).
GenBank Accession No.: AA499407.1 (Jul. 1, 1997).
GenBank Accession No.: AA509936.1 (Jul. 8, 1997).
GenBank Accession No.: AA511711 (Jul. 8, 1997).
GenBank Accession No.: AA624796.1 (Oct. 14, 1997).
GenBank Accession No.: AA635466.1 (Oct. 31, 1997).
GenBank Accession No.: AA639997.1 (Oct. 23, 1997).
GenBank Accession No.: AA667932.1 (Nov. 19, 1997).
GenBank Accession No.: AA716121.1 (Dec. 29, 1997).
GenBank Accession No.: AA759024.1 (Dec. 29, 1998).
GenBank Accession No.: AA807222.1 (Apr. 7, 1998).
GenBank Accession No.: AA884744 (Jan. 4, 1999).
GenBank Accession No.: AA917968 (Jun. 23, 1998).
GenBank Accession No.: AA936703.1 (Jun. 10, 1998).
GenBank Accession No.: AB033057 (Nov. 11, 1999).
GenBank Accession No.: AB051462.1 (Feb. 7, 2001).
GenBank Accession No.: AC005283 (Oct. 7, 2000).
GenBank Accession No.: AC010432.6 (Oct. 24, 2000).
GenBank Accession No.: AC012054 (Oct. 19,1999).
GenBank Accession No.: AC013602.4 (Apr. 25, 2001).
GenBank Accession No.: AC015497 (Apr. 11, 2000).
GenBank Accession No.: AC018740 (Jul. 7, 2000).
GenBank Accession No.: AC025451.5 (Jun. 7, 2001).
GenBank Accession No.: AC092836.4 (May 29, 2002).
GenBank Accession No.: AC118140.3 (Jun. 1, 2002).
GenBank Accession No.: AF086123.1 (Aug. 29, 1998).
GenBank Accession No.: AF274347.1 (Jun. 21, 2000).
GenBank Accession No.: AF274348.1 (Jun. 21, 2000).
GenBank Accession No.: AF275816 (Jun. 23, 2000).
GenBank Accession No.: AF275817 (Jul. 23, 2000).
GenBank Accession No.: AF275818 (Jul. 23, 2000).
GenBank Accession No.: AF276513 (Jun. 26, 2000).
GenBank Accession No.: AF287261 (Jul. 30, 2001).
GenBank Accession No.: AF294278 (Nov. 21, 2000).
GenBank Accession No.: AF319458 (Dec. 12, 2000).
GenBank Accession No.: AF346626 (Apr. 3, 2001).
GenBank Accession No.: AI002388.1 (Jul. 23, 1998).
GenBank Accession No.: AI049009 (Jul. 8, 1998).
GenBank Accession No.: AI092401.1 (Oct. 23, 1998).
GenBank Accession No.: AI242496.1 (Nov. 4, 1998).
GenBank Accession No.: AI278689 (Jan. 28, 1999).
GenBank Accession No.: AI348386.1 (Feb. 13, 1999).
GenBank Accession No.: AI352242.2 (Feb. 13, 1999).
GenBank Accession No.: AI357201.1 (Jan. 6, 1999).
GenBank Accession No.: AI383837.1 (Mar. 28, 1999).
GenBank Accession No.: AI610587.1 (May 13, 1999).
GenBank Accession No.: AI699177.1 (Dec. 16, 1999).
GenBank Accession No.: AI705990.1 (Jun. 3, 1999).
GenBank Accession No.: AI816535.1 (Jul. 9, 1999).
GenBank Accession No.: AI879547.1 (Aug. 23, 1999).
GenBank Accession No.: AI887341.1 (Sep. 1, 1999).
GenBank Accession No.: AI907429.1 (Mar. 30, 2000).
GenBank Accession No.: AI909958.1 (Mar. 30, 2000).
GenBank Accession No.: AI917820.1 (Dec. 17, 1999).
GenBank Accession No.: AK000234 (Feb. 22, 2000).
GenBank Accession No.: AK017846.1 (Jul. 5, 2001).
GenBank Accession No.: AK022595.1 (Sep. 29, 2000).
GenBank Accession No.: AL035087.20 (Jul. 27, 2000).
GenBank Accession No.: AL056584 (Jun. 3, 1999).
GenBank Accession No.: AL120271.1 (Feb. 25, 2000).
GenBank Accession No.: AL137711 (Feb. 18, 2000).
GenBank Accession No.: AL137784.14 (Oct. 26, 2000).
GenBank Accession No.: AL535257 (Feb. 13, 2001).
GenBank Accession No.: AL548156.1 (Feb. 16, 2001).
GenBank Accession No.: AL555671 (Feb. 16, 2001).
GenBank Accession No.: AL578116 (Feb. 16, 2001).
GenBank Accession No.: AP000686 (May 30, 2000).
GenBank Accession No.: AP001618.1 (Jun. 3, 2000).
GenBank Accession No.: AP001619.1 (Jun. 3, 2000).
GenBank Accession No.: AP001745.1 (May 30, 2000).
GenBank Accession No.: AU018120 (Oct. 19, 1998).
GenBank Accession No.: AU124563 (Oct. 23, 2000).
GenBank Accession No.: AU128198.1 (Oct. 24,2000).
GenBank Accession No.: AU130916 (Oct. 24, 200).
GenBank Accession No.: AU147298.1 (Oct. 25, 2000).
GenBank Accession No.: AU148392 (Oct. 25, 2000).
GenBank Accession No.: AU152780.1 (Oct. 25, 2000).
GenBank Accession No.: AV705547.1 (Oct. 9, 2000).
GenBank Accession No.: AV752467 (Oct. 19, 2000).
GenBank Accession No.: AW027068.1 (Mar. 9, 2000).
GenBank Accession No.: AW129728.1 (Oct. 25, 1999).
GenBank Accession No.: AW131841.1 (Oct. 27, 1999).
GenBank Accession No.: AW157409.1 (Nov. 4, 1999).
GenBank Accession No.: AW163472.1 (Nov. 9, 1999).
GenBank Accession No.: AW176331.1 (Nov. 16, 1999).
GenBank Accession No.: AW245524.1 (Jan. 7, 2000).
GenBank Accession No.: AW245967.1 (Jan. 7, 2000).
GenBank Accession No.: AW246726.1 (Jan. 7, 2000).
GenBank Accession No.: AW273736.1 (Jan. 3, 2000).
GenBank Accession No.: AW274834.1 (Jan. 3, 2000).
GenBank Accession No.: AW430084.1 (Apr. 25, 2001).
GenBank Accession No.: AW501914.1 (Mar. 1, 2000).
GenBank Accession No.: AW503893.1 (Mar. 2, 2000).
GenBank Accession No.: AW529888.1 (Mar. 6, 2000).
GenBank Accession No.: AW532948.1 (Mar. 6, 2000).
GenBank Accession No.: AW968153.1 (Jun. 1, 2000).
GenBank Accession No.: AW968839.1 (Jun. 1, 2000).
GenBank Accession No.: AW978331.1 (Jun. 2, 2000).
GenBank Accession No.: AW986692.1 (Jun. 2, 2000).
GenBank Accession No.: AW992560.1 (Jun. 5, 2000).
GenBank Accession No.: BB612390.1 (Oct. 26, 2001).
GenBank Accession No.: BE014950.1 (Jul. 9, 2000).
GenBank Accession No.: BE018920.1 (Jun. 6, 2000).
GenBank Accession No.: BE048089.1 (Oct. 20, 2000).
GenBank Accession No.: BE074968.1 (Jun. 9, 2000).
GenBank Accession No.: BE074969.1 (Jun. 9, 2000).
GenBank Accession No.: BE074974.1 (Jun. 9, 2000).
GenBank Accession No.: BE096110.1 (Jun. 12, 2000).
GenBank Accession No.: BE096155.1 (Jun. 12, 2000).
GenBank Accession No.: BE096442.1 (Jun. 12, 2000).

GenBank Accession No.: BE096447.1 (Jun. 12, 2000).
GenBank Accession No.: BE113370.1 (Jun. 13, 2000).
GenBank Accession No.: BE232487.1 (Jul. 10, 2000).
GenBank Accession No.: BE244872.1 (Oct. 3, 2001).
GenBank Accession No.: BE246083.1 (Oct. 3, 2001).
GenBank Accession No.: BE247252.1 (Oct. 3, 2001).
GenBank Accession No.: BE266801.1 (Jul. 13, 2000).
GenBank Accession No.: BE294489.1 (Jul. 20, 2000).
GenBank Accession No.: BE304522.1 (Jul. 13, 2000).
GenBank Accession No.: BE305526.1 (Oct. 26, 2000).
GenBank Accession No.: BE536337.1 (Aug. 9, 2000).
GenBank Accession No.: BE617458.1 (Oct. 20, 2000).
GenBank Accession No.: BE648497.1 (Sep. 6, 2000).
GenBank Accession No.: BE732157.1 (Sep. 15, 2000).
GenBank Accession No.: BE744525.1 (Sep. 15, 2000).
GenBank Accession No.: BE791132.1 (Sep. 20, 2000).
GenBank Accession No.: BE793683.1 (Sep. 20, 2000).
GenBank Accession No.: BE797607.1 (Sep. 20, 2000).
GenBank Accession No.: BE798564.1 (Sep. 20, 2000).
GenBank Accession No.: BE867579.1 (Oct. 20, 2000).
GenBank Accession No.: BE870276.1 (Oct. 20, 2000).
GenBank Accession No.: BE883835.1 (Oct. 20, 2000).
GenBank Accession No.: BE884008.1 (Oct. 20, 2000).
GenBank Accession No.: BE896201.1 (Oct. 20, 2000).
GenBank Accession No.: BE897305.1 (Oct. 20, 2000).
GenBank Accession No.: BE956829.1 (Oct. 4, 2000).
GenBank Accession No.: BE962422.1 (Dec. 14, 2000).
GenBank Accession No.: BE980340.1 (Oct. 5, 2000).
GenBank Accession No.: BE994100.1 (Oct. 5, 2000).
GenBank Accession No.: BF061011.1 (Oct. 16, 2000).
GenBank Accession No.: BF133687.1 (Oct. 24, 2000).
GenBank Accession No.: BF161282.1 (Oct. 30, 2000).
GenBank Accession No.: BF182733.1 (Oct. 31, 2000).
GenBank Accession No.: BF245288.1 (Nov. 14, 2000).
GenBank Accession No.: BF309152.1 (Nov. 21, 2000).
GenBank Accession No.: BF333514.1 (Nov. 22, 2000).
GenBank Accession No.: BF346948.1 (Nov. 22, 2000).
GenBank Accession No.: BF525120.1 (Dec. 11, 2000).
GenBank Accession No.: BF529537.1 (Dec. 11, 2000).
GenBank Accession No.: BF673051.1 (Dec. 21, 2000).
GenBank Accession No.: BF685622.1 (Dec. 22, 2000).
GenBank Accession No.: BF693866.1 (Dec. 22, 2000).
GenBank Accession No.: BF770200 (Jan. 12, 2001).
GenBank Accession No.: BF814715.1 (Jan. 12, 2001).
GenBank Accession No.: BF904312.1 (Jan. 18, 2001).
GenBank Accession No.: BF982577.1 (Jan. 23, 2001).
GenBank Accession No.: BG086572.1 (Jan. 26, 2001).
GenBank Accession No.: BG177268.1 (Feb. 6, 2001).
GenBank Accession No.: BG196219.1 (Apr. 21, 2001).
GenBank Accession No.: BG311741.1 (Jul. 5, 2001).
GenBank Accession No.: BG389847.1 (Mar. 12, 2001).
GenBank Accession No.: BG470196.1 (Mar. 21, 2001).
GenBank Accession No.: BG481345.1 (Mar. 21, 2001).
GenBank Accession No.: BG498843.1 (Mar. 27, 2001).
GenBank Accession No.: BG678255.1 (May 1, 2001).
GenBank Accession No.: BG745296.1 (May 15, 2001).
GenBank Accession No.: BG746115.1 (May 15, 2001).
GenBank Accession No.: BG753045.1 (May 15, 2001).
GenBank Accession No.: BG753749.1 (May 15, 2001).
GenBank Accession No.: BG822286.1 (May 22, 2001).
GenBank Accession No.: BG914332.1 (Jun. 5, 2001).
GenBank Accession No.: BG922564.1 (Jun. 5, 2001).
GenBank Accession No.: BI021983.1 (Jun. 14, 2001).
GenBank Accession No.: BI116711.1 (Jun. 26, 2001).
GenBank Accession No.: BI117664.1 (Jun. 26, 2001).
GenBank Accession No.: BM722342.1 (Mar. 1, 2002).
GenBank Accession No.: D59353.1 (Aug. 8, 1995).
GenBank Accession No.: G05930.1 (Oct. 29, 1995).
GenBank Accession No.: G13751 (Mar. 30, 2000).
GenBank Accession No.: G36915 (Dec. 31, 1997).
GenBank Accession No.: G37367 (Mar. 31, 1998).
GenBank Accession No.: G20316.1 (Jul. 24, 1996).
GenBank Accession No.: G51347.1 (Mar. 30, 2000).
GenBank Accession No.: G52735 (Mar. 30, 2000).
GenBank Accession No.: H63042.1 (Aug. 13, 1996).
GenBank Accession No.: H85444.1 (Nov. 14, 1995).
GenBank Accession No.: H85725.1 (Nov. 21, 1995).
GenBank Accession No.: NM_021619 (Jul. 31, 2001).
GenBank Accession No.: NM_021620 (Nov. 29, 2000).
GenBank Accession No.: N32595.1 (Jan. 10, 1996).
GenBank Accession No.: M79273 (May 26, 1992).
GenBank Accession No.: R14616.1 (Apr. 13, 1995).
GenBank Accession No.: R15498.1 (May 16, 1995).
GenBank Accession No.: R15777.1 (Apr. 13, 1995).
GenBank Accession No.: R16283.1 (Apr. 13, 1995).
GenBank Accession No.: R35195.1 (May 2, 1995).
GenBank Accession No.: R37802.1 (May 4, 1995).
GenBank Accession No.: R42665.1 (May 22, 1995).
GenBank Accession No.: R45605.1 (May 22, 1995).
GenBank Accession No.: R50855.1 (May 18, 1995).
GenBank Accession No.: T16683.1 (Jul. 25, 1996).
GenBank Accession No.: U76371.1 (Feb. 4, 1997).
GenBank Accession No.: U76373.2 (Sep. 13, 1999).
GenBank Accession No.: U76374.2 (Sep. 13, 1999).
GenBank Accession No.: W11621 (Oct. 2, 1997).
GenBank Accession No.: W33556 (May 13, 1996).
GenBank Accession No.: W72745.1 (Oct. 17, 1996).
GenBank Accession No.: W04738.1.
GenBank Accession No.: XM_006873 (Aug. 27, 2001).
GenBank Accession No.: XM_016215 (Oct. 16, 2001).
GenBank Accession No.: Z21651.1 (Apr. 20, 1993).
GenBank Accession No.: Z65361.1 (Oct. 23, 1995).
GenBank Accession No.: Z96314 (Jun. 6, 1997).
Gu et al., "The t(4;11) chromosome translocation of human acute leukemias fuses the ALL–1 gene, related to *Drosophila trithorax*, to the AF–4 gene," *Cell* 71:701–8 (1992).
He et al., "RIZ1, but not the alternative RIZ2 product of the same gene, is underexpressed in breast cancer, and forced RIZ1 expression causes G2–M cell cycle arrest and/or apoptosis," *Cancer Res.* 58:4238–4244 (1998).
Hornigold et al., "Mutation of the 9q34 gene TSC1 in sporadic bladder cancer," *Oncogene* 18:2657–61 (1999).
Huang, S., "Blimp–1 is the murine homolog of the human transcriptional repressor PRDI–BF1 [letter]," *Cell* 78:9 (1994).
Huang, S., "The retinoblastoma protein–interacting zinc finger gene RIZ in 1p36–linked cancers," *Front Biosci.* 4:D528–532 (1999).
Huang, S., "Histone methyltransferases, diet nutrients and tumor suppressors" *Nature Reviews* 2:469–476 (2002).
Huang et al., "The PR Domain of the Rb–binding Zinc Finger Protein RIZ1 Is a Protein Binding Interface and Is Related to the SET Domain Functioning in Chromatin–mediated Gene Expression," *J. Biol. Chem.* 273:15933–15939 (1998).
Jiang and Huang, "Adenovirus Expressing RIZ1 in tumor suppressor gene therapy of microsatellite unstable colorectal cancers," *Cancer Research* 61:1796–1798 (2001).

Jiang and Huang, "The yin–yang of PR–domain family genes in tumorigenesis," *Histol. Histopathol.* 15:109–117 (2000).

Jiang et al., "Decreased RIZ1 expression but not RIZ2 in hepatoma and suppression of hepatoma tumorigenicity by RIZ1," *Int. J. Cancer* 83:541–547 (1999).

Jones and Gelbart, "The Drosophila Polycomb–group gene Enhancer of zeste contains a region with sequence similarity to trithorax," *Mol. Cell Biol.* 13:6357–6366 (1993).

Koreth et al. "11q23.1 and 11q25–qter YACs suppress tumour growth in vivo," *Oncogene* 18:1157–64 (1999).

Koreth et al., "Allelic deletions at chromosome 11q22–q23.1 and 11q25–qterm are frequent in sporadic breast but not colorectal cancers," *Oncogene* 14:431–7 (1997).

Lachner et al. "Methylation of histone H3 lysine 9 creates a binding site for HP1 proteins," *Nature* 410:116–120 (2001).

Launonen et al., "Chromosome 11q22.3–q25 LOH in ovarian cancer: association with a more aggressive disease course and involved subregions," *Gynecologic Oncology* 71:299–304 (1998).

Lin et al. "Repression of c–myc transcription by Blimp–1, an inducer of terminal B cell differentiation," *Science* 276:596–598 (1997).

Mock et al. "The B–lymphocyte maturation promoting transcription factor BLIMP1/PRDI–BF1 maps to D6S447 on human chromosome 6q21–q22.1 and the syntenic region of mouse chromosome 10," *Genomics* 37:24–28 (1996).

Muraosa et al. "cDNA cloning of a novel protein containing two zinc–finger domains that may function as a transcription factor for the human heme–oxygenase–1 gene," *Eur. J..Biochem.* 235:471–479 (1996).

Nakata et al. "Identification of a new commonly deleted region within a 2–oM interval of chromosome 11p11 in breast cancers," *Eur. J. Cancer* 34:417–21 (1998).

Piao et al., "Frequent frameshift mutations of RIZ in human gastrointestinal and endometrial carcinomas with microsatellite instability," *Cancer Res.* 60:4701–4704 (2000).

Rea et al. "Regulation of chromatin structure by site–specific histone H3 methyltransferases," *Nature* 406:593–599 (2000).

Rozenblatt–Rosen et al., "The C–terminal SET domains of ALL–1 and TRITHORAX interact with the IN11 and SNR1 proteins, components of the SWI/SNF complex", *Proc. Natl. Acad. Sci. USA* 95:4152–4157 (1998).

Schichman et al. "ALL–1 partial duplication in acute leukemia," *Proc. Natl. Acad. Sci. USA* 91:6236–9 (1994).

Simoneau et al., "Four tumor suppressor loci on chromosome 9q in bladder cancer: evidence for two novel candidate regions at 9q22.3 and 9q31," *Oncogene* 18:157–63 (1999).

Steele–Perkins et al. "Tumor formation and activation of RIZ1, and Rb–binding member of a nuclear protein–methyltransferase superfamily," *Genes & Development* 15:2250–2262 (2001).

Tkachuk et al., "Involvement of a homolog of *Drosophila trithorax* by 11q23 chromosomal translocations in acute leukemias," *Cell* 71:691–700 (1992).

Tschiersch et al., "The protein encoded by the Drosophila position–effect variegation suppressor gene Su(vsf)3–9 combines domains of antagonistic regulators of homeotic gene complexes," *EMBO J.* 13:3822–3831 (1994).

Uzawa et al., "Evidence for two distinct tumor–suppressor gene loci on the long arm of chromosome 11 in human oral cancer," *International Journal of Cancer* 67:510–4 (1996).

Van Alewijk et al., "Identification of a homozygous deletion at 8p12–21 in a human prostate cancer xenograft," *Genes, Chromosomes & Cancer* 24:119–26 (1999).

Verma et al., "Chromosomal basis of adenocarcinoma of the prostate," *Cancer Investigation* 17:441–7 (1999).

Vocke et al., "Analysis of 99 microdissected prostate carcinomas reveals a high frequency of allelic loss on chromosome 8p12–21," *Cancer Research* 56:2411–6 (1996).

Yang and Huang, "PFM1 (PRDM4), a New Member of the PR–Domain Family, Maps to a Tumor Suppressor Locus on Human Chromosome 12q23–q24.1," *Genomics* 61:319–325 (1999).

Yu et al., "MLL, a mammalian trithorax–group gene, functions as a transcriptional maintenance factor in morphogenesis," *Proc. Natl. Acad. Sci. USA* 95:10632–6 (1998).

* cited by examiner

FIGURE 1

PFM6 AMINO ACID SEQUENCE

```
  1 MCQNFFIDSC AAHGPPTFVK DSAVDKGHPN RSALSLPPGL RIGPSGIPQA
 51 GLGVWNEASD LPLGLHFGPY EGRITEDEEA ANNGYSWLVR RACHFTKGRN
101 CYEYVDGKDK SWANWMRYVN CARDDEEQNL VAFQYHRQIF YRTCRVIRPG
151 CELLVWYGDE YGQELGIKWG SKWKKEEPKP EIHPCPSCCL AFSSQKFLSQ
201 HVERNHSSQN FPGPSARKLL QPENPCPGDQ NQEQQYPDPH SRNDKTKGQE
251 IKERSKLLNK RTWQREISRA FSSPPKGQMG SCRVGKRIME EESRTGQKVN
301 PGNTGKLFVG VGISRIAKVK YGECGQGFSV KSDVITHQRT HTGEKLYVCR
351 ECGRGFSWKS HLLIHQRIHT GEKPYVCREC GRGFSWQSVL LTHQRTHTGE
401 KPYVCRECGR GFSRQSVLLT HQRRHTGEKP YVCRECGRGF SRQSVLLTHQ
451 RRHTGEKPYV CRECGRGFSW QSVLLTHQRT HTGEKPYVCR ECGRGFSWQS
501 VLLTHQRTHT GEKPYVCREC GRGFSNKSHL LRHQRTHTGE KPYVCRECGR
551 GFRDKSHLLR HQRTHTGEKP YVCRECGRGF RDKSNLLSHQ RTHTGEKPYV
601 CRECGRGFSN KSHLLRHQRT HTGEKPYVCR ECGRGFRNKS HLLRHQRTHT
651 GEKPYVCREC GRGFSDRSSL CYHQRTHTGE KPYVCREDE
```

FIGURE 2

PFM7 AMINO ACID SEQUENCE

```
   1  MSAYSVPSTF  AQASLPVHNQ  VLPSIESVDG  SDPLATLQTP  LGRLEAKEEE
  51  DEDEDEDTEE  DEEEDGEDTD  LDDWEPDPPR  PFDPHDLWCE  ECNNAHASVC
 101  PKHGPLHPIP  NRPVLTRARA  SLPLVLYIDR  FLGGVFSKRR  IPKRTQFGPV
 151  EGPLVRGSEL  KDCYIHLKVS  LDKGDRKERD  LHEDLWFELS  DETLCNWMMF
 201  VRPAQNHLEQ  NLVAYQYGHH  VYYTTIKNVE  PKQELKVWYA  ASYAEFVNQK
 251  IHDISEEERK  VLREQEKNWP  CYECNRRFIS  SEQLQQHLNS  HDEKLDVFSR
 301  TRGRGRGRGK  RRFGPGRRPG  RPPKFIRLEI  TSENGEKSDD  GTQDLLHFPT
 351  KEQFDEAEPA  TLNGLDQPEQ  TTIPIPQLPQ  ETQSSLEHEP  ETHTLHLQPQ
 401  HEESVVPTQS  TLTADDMRRA  KRIRLELQNA  ALQHLFIRKS  FRPFKCLQCG
 451  KAFREKDKLD  QHLRFHGREG  NCPLTCDLCN  KGFISSTSLE  SHMKLHSDQK
 501  TYSCIFCPES  FDRLDLLKDH  VAIHINDGYF  TCPTCKKRFP  DFIQVKKHVR
 551  SFHSEKIYQC  TECDKAFCRP  DKLRLHMLRH  SDRKDFLCST  CGKQFKRKDK
 601  LREHMQRMHN  PEREAKKADR  ISRSKTFKPR  ITSTDYDSFT  FKCRLCMMGF
 651  RRRGMLVNHL  SKRHPDMKIE  EVPELTLPII  KPNRDYFCQY  CDKVYKSASK
 701  RKAHILKNHP  GAELPPSIRK  LRPAGPGEPD  PMLSTHTQLT  GTIATPPVCC
 751  PHCSKQYSSK  TKMVQHIRKK  HPEFAQLSNT  IHTPLTTAVI  SATPAVLTTD
 801  SATGETVVTT  DLLTQAMTEL  SQTLTTDYRT  PQGDYQRIQY  IPVSQSASGL
 851  QQPQHIQLQV  VQVASATSPH  QSQQSTVDVG  QLHDPQPYPQ  HAIQVQHIQV
 901  SGQPLSPSAQ  QAQQGLSPSH  IQGSSSTQGQ  ALQQQQQQQQ  NSSVQHTYLP
 951  SAWNSFRGYS  SEIQMMTLPP  GQFVITDSGV  ATPVTTGQVK  AVTSGHYVLS
1001  ESQSELEEKQ  TSALSGGVQV  EPPAHSDSLD  PQTNSQQQTT  QYIITTTTNG
1051  NGSSEVHITK  P
```

FIGURE 3

PFM9 AMINO ACID SEQUENCE

```
  1  MMGSVLPAEA  LVLKTGLKAP  GLALAEVITS  DILHSFLYGR  WRNVLGEQLF
 51  EDKSHHASPK  TAFTAEVLAQ  SFSGEVQKLS  SLVLPAEVII  AQSSIPGEGL
101  GIFSKTWIKA  GTEMGPFTGR  VIAPEHVDIC  KNNNLMWEVF  NEDGTVRYFI
151  DASQEDHRSW  MTYIKCARNE  QEQNLEVVQI  GTSIFYKAIE  MIPPDQELLV
201  WYGNSHNTFL  GIPGVPGLEE  DQKKNKHEDF  HPADSAAGPA  GRMRCVICHR
251  GFNSRSNLRS  HMRIHTLDKP  FVCRFCNRRF  SQSSTLRNHV  RLHTGERPYK
301  CQVCQSAYSQ  LAGLRAHQKS  ARHRPPSTAL  QAHSPALPAP  HAHAPALAAA
351  AAAAAAAAH   HLPAMVL
```

FIGURE 4

PFM10 AMINO ACID SEQUENCE

```
  1  MHGAARAPAT  SVSADCCIPA  GLRLGPVPGT  FKLGKYLSDR  REPGPKKKVL
 51  TIQTSAHQVR  MVRGELVDES  GGSPLEWIGL  IRAARNSQEQ  TLEAIADLPG
101  GQIFYRALRD  VQPGEELTVW  YSNSLAQWFD  IPTTATPTHD  EKGEERYICW
151  YCWRTFRYPN  SLKAHLRFHC  VFSGGGGGAF  LHHEHAARQG  AVPAADGLGL
201  SPKPPAPDFA  APSQAGTLRP  HPLGPPPVQA  CGAREGIKRE  ASSAPSATSP
251  TPGKWGQPKK  GKEQLDRALD  MSGAARGQGH  FLGIVGGSSA  GVGSLAFYPG
301  VRSAFKPAGL  ARAAAAAHGD  PYREESSSKQ  GAGLALGRLL  GGGRACGRPG
351  SGENSAAGGA  GHHHHHHAHH  HHHPKCLLAG  DPPPPPPPGL  PCSGALRGFP
401  LLSVPPEEAS  AFKHVERAPP  AAAALPGARY  AQLPPAPGLP  LERCALPPLD
451  PGGLKAYPGG  ECSHLPAVMP  AFTVYNGELL  YGSPATTAYY  PLKLHFGGLL
501  KYPESISYFS  GPAAAALSPA  ELGSLASIDR  EIAMHNQQLS  EMAAGKGRGR
551  LDSGTLPPAV  AAAGGTGGGG  SGGSGAGKPK  TGHLCLYCGK  LYSRKYGLKI
601  HMRTHTGYKP  LKCKVCLRPF  GDPSNLNKHI  RLHAEGNTPY  RCEFCGKVLV
651  RRRDLERHVK  SRHPGQSLLA  KAGDGPGAEP  GYPPEPGDPK  SDDSDVDVCF
701  TDDQSDPEVG  GGGERDL
```

FIGURE 5

PFM11 AMINO ACID SEQUENCE

```
  1  MALPRPSEAV  PQDKVCYPPE  SSPQNLAAYY  TPFPSYGHYR  NSLATVEEDF
 51  QPFRQLEAAA  SAAPAMPPFP  FRMAPPLLSP  GLGLQREPLY  DLPWYSKLPP
101  WYPIPHVPRE  VPPFLSSSHE  YAGASSEDLG  HQIIGGDNES  GPCCGPDTLI
151  PPPPADASLL  PEGLRTSQLL  PCSPSKQSED  GPKPSNQEGK  SPARFQFTEE
201  DLHFVLYGVT  PSLEHPASLH  HAISGLLVPP  DSSGSDSLPQ  TLDKDSLQLP
251  EGLCLMQTVF  GEVPHFGVFC  SSFIAKGVRF  GPFQGKVVNA  SEVKTYGDNS
301  VMWEIFEDGH  LSHFIDGKGG  TGNWMSYVNC  ARFPKEQNLV  AVQCQGHIFY
351  ESCKEIHQNQ  ELLVWYGDCY  EKFLDIPVSL  QVTEPGKQPS  GPSEESAEGY
401  RCERCGKVFT  YKYYRDKHLK  YTPCVDKGDR  KFPCSLCKRS  FEKRDRLRIH
451  ILHVHEKHRP  HKCSTCGKCF  SQSSSLNKHM  RVHSGDRPYQ  CVYCTKRFTA
501  SSILRTHIRQ  HSGEKPFKCK  YCGKSFASHA  AHDSHVRRSH  KEDDGCSCSI
551  CGKIFSDQET  FYSHMKFHED  Y
```

FIGURE 6

PFM12 AMINO ACID SEQUENCE

```
  1  MPRRRPPASG  AAQFPERIAT  RSPDPIPLCT  FQRQPRAAPV  QPPCRLFFVT
 51  FAGCGHRWRS  ESKPGWISRS  RSGIALRAAR  PPGSSPPRPA  APRPPPPGGV
101  VAEAPGDVVI  PRPRVQPMRV  ARGGPWTPNP  AFREAESWSQ  IGNQRVSEQL
151  LETSLGNEVS  DTEPLSPASA  GLRRNPALPP  GPFAQNFSWG  NQENLPPALG
201  KIANGGGTGA  GKAECGYETE  SHLLEPHEIP  LNVNTHKFSD  CEFPYEFCTV
251  CFSPFKLLGM  SGVEGVWNQH  SRSASMHTFL  NHSATGIREA  GCRKDMPVSE
301  MAEDGSEEIM  FIWCEDCSQY  HDSECPELGP  VVMVKDSFVL  SRARSWPASG
351  HVHTQAGQGM  RGYEDRDRAD  PQQLPEAVPA  GLVRRLSGQQ  LPCRSTLTWG
401  RLCHLVAQGR  SSLPPNLEIR  RLEDGAEGVF  AITQLVKRTQ  FGPFESRRVA
451  KWEKESAFPL  KVFQKDGHPV  CFDTSNEDDC  NWMMLVRPAA  EAEHQNLTAY
501  QHGSDVYFTT  SRDIPPGTEL  RVWYAAFYAK  KMDKPMLKQA  GSGVHAAGTP
551  ENSAPVESEP  SQWACKVCSA  TFLELQLLNE  HLLGHLEQAK  SLPPGSQSEA
601  AAPEKEQDTP  RGEPPAVPES  ENVATKEQKK  KPRRGRKPKV  SKAEQPLVIV
651  EDKEPTEQVA  EIITEVPPDE  PVSATPDERI  MELVLGKLAT  TTTDTSSVPK
701  FTHHQNNTIT  LKRSLILSSR  HGIRRKLIKQ  LGEHKRVYQC  NICSKIFQNS
751  SNLSRHVRSH  GDKLFKCEEC  AKLFSRKESL  KQHVSYKHSR  NEVDGEYRYR
801  CGTCEKTFRI  ESALEFHNCR  TDDKTFQCEM  CFRFFSTNSN  LSKHKKKHGD
851  KKFACEVCSK  MFYRKDVMLD  HQRRHLEGVR  RVKREDLEAG  GENLVRYKKE
901  PSGCPVCGKV  FSCRSNMNKH  LLTHGDKKYT  CEICGRKFFR  VDVLRDHIHV
951  H
```

FIGURE 7

PFM13 AMINO ACID SEQUENCE

```
   1  MRSKARARKL AKSDGDVVNN MYEPNRDLLA SHSAEDEAED SAMSPIPVGS
  51  PPPFPTSEDF TPKEGSPYEA PVYIPEDIPI PADFELRESS IPGAGLGVWA
 101  KRKMEAGERL GPCVVVPRAA AKETDFGWEQ ILTDVEVSPQ EGCITKISED
 151  LGSEKFCVDA NQAGAGSWLK YIRVACSCDD QNLTMCQISE QVIYYKVIKD
 201  IEPGEELLVH VKEGVYPLGT VPPGLDEEPT FRCDECDELF QSKLDLRRHK
 251  KYTCGSVGAA LYEGLAEELK PEGLGGGSGQ AHECKDCERM FPNKYSLEQH
 301  MVIHTEEREY KCDQCPKAFN WKSNFIRHQM SHDSGKRFEC ENCVKVFTDP
 351  SNLQRHIRSQ HVGARAHACP DCGKTFATSS GLKQHKHIHS TVKPFICEVC
 401  HKSYTQFSNL CRHKRMHADC RTQIKCKDCG QMFSTTSSLN KHRRFCEGKN
 451  HYTPGGIFAP GLPLTPSPMM DKAKPSPSLN HASLGFNEYF PYRPHPGSLP
 501  FSTAPPTFPA LTPGFPGIFP PSLYPRPPLL PPTSLLKSPL NHTQDAKLPS
 551  PLGNPALPLV SAVSNSSQGT TAAAGPEEKF ESRLEDSCVE KLKTRSSDMS
 601  DGSDFEDVNT TTGTDLDTTT GTGSDLDSDV DSDPDKDKGK GNVAEVPVFY'
 651  SQHSFFPPPD EQLLTATGAA GDSIKAIASI AEKYFGPGFM GMQEKKLGSL
 701  PYHSAFPFQF LPNFPHSLYP FTDRALAHNL LVKAEPKSPR DALKVGGPSA
 751  ECPFDLTTKP KDVKPILPMP KGPSAPASGE EQPLDLSIGS RARASQNGGG
 801  REPRKNHVYG ERKLGAGEGL PQVCPARMPQ QPPLHYAKPS PFFMDPIYRV
 851  EKRKVTDPVG ALKEKYLRPS PLLFHPQMSA IETMTEKLES FAAMKADSGS
 901  SLQPLPHHPF NFRSPPPTLS DPILRKGKER YTCRYCGKIF PRSANLTRHL
 951  RTHTGEQPYR RCKYCDRSFS ISSNLQRHVR NIHNKEKPFK CHLCNRCFGQ
1001  QTNLDRHLKK HEHENAPVSQ HPGVLTNHLG TSASSPTSES DNHALLDEKE
1051  DSYFSEIRNF IANSEMNQAS TRTEKRADMQ IVDGSAQCPG LASEKQEDVE
1101  EEDDDDLEED DEDSLAGKSQ DDTVSPAPEP QAAYEDEEDE EPAASLAVGF
1151  DHTRRCAEDH EGGLLALEPM PTFGKGLDLR RAAEEAFEVK DVLNSTLDSE
1201  ALKHTLCRQA KNQAYAMMLS LSEDTPLHTP SQGSLDAWLK VTGATSESGA
1251  FHPINHL
```

FIGURE 8

PFM14 AMINO ACID SEQUENCE

```
  1  MEEAEELLLE  GKKALQLARE  PRLGLDLGWN  PSGEGCTQGL  KDVPPEPTRD
 51  ILALKSLPRG  LALGPSLAKE  QRLGVWCVGD  PLQPGLLWGP  LEEESASKEK
101  GEGVKPRQEE  NLSLGPWGDV  CACEQSSGWT  SLVQRGRLES  EGNVAPVRIS
151  ERLHLQVYQL  VLPGSELLLW  PQPSSEGPSL  TQPGLDKEAA  VAVVTEVESA
201  VQQEVASPGE  DAAEPCIDPG  SQSPSGIQAE  NMVSPGLKFP  TQDRISKDSQ
251  PLGPLLQDGD  VDEECPAQAQ  MPPELQSNSA  TQQDPDGSGA  SFSSSARGTQ
301  PHGYLAKKLH  SPSDQCPPRA  KTPEPGAQQS  GFPTLSRSPP  GPAGSSPKQG
351  RRYRCGECGK  AFLQLCHLKK  HAFVHTGHKP  FLCTECGKSY  SSEESFKAHM
401  LGHRGVRPFP  CPQCDKAYGT  QRDLKEHQVV  HSGARPFACD  QCGKAFARRP
451  SLRLHRKTHQ  VPAAPAPCPC  PVCGRPLANQ  GSLRNHMRLH  TGEKPFLCPH
501  CGRAFRQRGN  LRGHLRLHTG  ERPYRCPHCA  DAFPQLPELR  RHLISHTGEA
551  HLCPVCGKAL  RDPHTLRAHE  RLHSGERPFP  CPQCGRAYTL  ATKLRRHLKS
601  HLEDKPYRCP  TCGMGYTLPQ  SLRRHQLSHR  PEAPCSPPSV  PSAASEPTVV
651  LLQAEPQLLD  THREEEVSPA  RDVVEVTISE  SQEKCFVVPE  EPDAAPSLVL
701  IHKDMGLGAW  AEVVEVEMGT
```

FIGURE 9

BOP AMINO ACID SEQUENCE

```
  1  MENVEVFTAE  GKGRGLKATK  EFWAADIIFA  ERAYSAVVFD  SLVNFVCHTC
 51  FKRQEKLHRC  GQCKFAHYCD  RTCQKDAWLN  HKNECSAIKR  YGKVLAARIM
101  WRVEREGTGL  TEGCLVSVDD  LQNHVEHFGE  EEQKDLRVDV  DTFLQYWPPQ
151  SQQFSMQYIS  HIFGVVINCN  GFTLSDQRGL  QAVGVGIFPN  LGLVNHDCWP
201  NCTVIFNNGK  RIELRALGKI  SEGEELTVSY  IDFLNVSEER  KRQLKKQYYF
251  DCTCEHCQKK  LKDDLFLGVK  DNPKQPSQEV  VKEMIQFSKD  TLEKIDKARS
301  EGLYHEVVVK  LCRECLEKQE  PVFADTNIYM  LRMLSIVSEV  LSYLQAFEEA
351  SFYARRMVDG  YMKLYHPNNA  QLGMAVMRAG  LTNWHAGNIE  VGHGMICKAY
401  AILLVTHGPS  HPITKDLEAM  RVQTEMELRM  FRQNEFMYYK  MREAALNNQP
451  MQVMAEPSNE  PSPALFHKKQ
```

SET27H SET DOMAIN AMINO ACID SEQUENCE

KFAVVVQPSP IDGMGVFAAE PIPAYKKIGE LRGESISVRE
ARRRAKRQQR IMIVEVSDKR AIDASQSPDA MRYNNHSCSP
NTVLRIRQGR VEFYALRPIA AGEELTA

B

SET DOMAIN ENCODING NUCLEOTIDE SEQUENCE

AAGTTCGCCG TCGTCGTGCA GCCAAGTCCC ATCGACGGGA TGGGCGTGTT
CGCAGCGGAG CCGATCCCCG CGTACAAGAA GATCGGAGAG TTGCGTGGCG
AGTCGATCAG CGTGCGGGAG GCGCGTCGGC GAGCCAAGCG GCAGCAGCGC

ATCATGATCG TCGAGGTGTC CGACAAGCGG GCGATCGATG CGTCGCAATC
CCCAGACGCC ATGCGCTACA ACAACCACTC ATGCTCGCCC AACACCGTGC
TGCGCATCCG CCAGGGGCGG GTCGAGTTCT ACGCCTTGCG CCCGATCGCT
GCCGGAGAAG AACTGACGGC C

FIGURE 11

|  |  | BOX A |
|---|---|---|
| SUV39H1 | 253 | GRGWGVRTLEKIRKNSFVMEYVGEIITSEE-(24)- |
| EZH2 | 621 | VAGWGIFIKDPVQKNEFISEYCGEIISQDE-(21)- |
| HRX/ALL1/MLL1 | 3838 | IHGRGLFCKRNIDAGEMVIEYAGNVIRSIQ-(22)- |

| PRDI-BF1 | 60 | EEVIGVMSKEYIPKGTRFGPLIGEIYTNDT-(19)- |
|---|---|---|
| RIZ1 | 39 | KTRIGVWATKPILKGKKFGPFVGDKKKRSQ-(16)- |

| RUBISCO ISMT |  |  |
|---|---|---|
| P.SATIVUM | 61 | LQEEGVITAKTPVKASVVTEGLGLVALKDI-(136)- |
| A. THALIANA | 56 | LRDQGVVSGKSVAEPAVVPEGLGLVARRDI-(128)- |

|  | BOX B |
|---|---|
| SUV39H1 | VYTVDAAYY--GNISHFVNHSCDPNLQVYNVFID-(7)- |
| EZH2 | DFVVDATRK--GNKIRFANHSVNPNCYAKVMMVNG-- |
| HRX/ALL1/MLL1 | EV-VDATMH--GNRARFINHSCEPNCYSRVINIDG-- |

| PRDI-BF1 | HHFIDGFNEEKSNWMRYVNPAHSPREQNLAACQN--- |
|---|---|
| RIZ1 | WMCIDATDPEKGNWLRYVNWACSGEEQNLFPLEI--- |

| RUBISCO ISMT |  |
|---|---|
| P.SATIVUM | LRNENLVVVPMADL--INHSAGVTTEDHAY-(10)- |
| A. THALIANA | LELNRESLTSMFEFEQINHNPAIKTEDYAY-(9)-- |

|  | BOX C |
|---|---|
| SUV39H1 | RIAFF-ATRTIRAGEELTFDYNMQVDPVD |
| EZH2 | DHRIGIF-AKRAIQTGEELFFDYRYSQADAL |
| HRX/ALL1/MLL1 | QKHIVIF-AMRKIYRGEELTYDYKFPIEDAS |

| PRDI-BF1 | GMNIY-FYTIKPIPANQELLVWYCRDFAERL |
|---|---|
| RIZ1 | NRAIY-YKTLKPIAPGEELLVWYNGEDNPEI |

| RUBISCO ISMT |  |
|---|---|
| P.SATIVUM | WDYLFSLKSPLSVKAGEQVYIQYDLNKSNAE |
| A. THALIANA | RDLLFSLKSPVYVKAGEQVYIQYDLNKSNAE |

FIGURE 12

SEQUENCE LISTING

<160> NUMBER OF SEQ ID NOS: 46

<210> SEQ ID NO 1
<211> LENGTH: 2903
<212> TYPE: DNA
<213> ORGANISM: Human
<220> FEATURE:
<221> NAME/KEY: CDS
<222> LOCATION: (10)...(2076)

<400> SEQUENCE: 1

```
gattgtgag atg tgt cag aac ttc ttc att gac agc tgt gct gcc cat ggg      51
          Met Cys Gln Asn Phe Phe Ile Asp Ser Cys Ala Ala His Gly
          1               5                   10
```

-continued

| | |
|---|---|
| ccc cct aca ttt gta aag gac agt gca gtg gac aag ggg cac ccc aac<br>Pro Pro Thr Phe Val Lys Asp Ser Ala Val Asp Lys Gly His Pro Asn<br>15               20                 25               30 | 99 |
| cgt tca gcc ctc agt ctg ccc cca ggg ctg aga att ggg cca tca ggc<br>Arg Ser Ala Leu Ser Leu Pro Pro Gly Leu Arg Ile Gly Pro Ser Gly<br>                35               40               45 | 147 |
| atc cct cag gct ggg ctt gga gta tgg aat gag gca tct gat ctg ccg<br>Ile Pro Gln Ala Gly Leu Gly Val Trp Asn Glu Ala Ser Asp Leu Pro<br>        50               55               60 | 195 |
| ctg ggt ctg cac ttt ggc cct tat gag ggc cga att aca gaa gac gaa<br>Leu Gly Leu His Phe Gly Pro Tyr Glu Gly Arg Ile Thr Glu Asp Glu<br>          65               70               75 | 243 |
| gag gca gcc aac aat gga tac tcc tgg ctg gta aga aga gcc tgc cat<br>Glu Ala Ala Asn Asn Gly Tyr Ser Trp Leu Val Arg Arg Ala Cys His<br>80               85                 90 | 291 |
| ttc acc aag ggg aga aac tgc tat gag tat gtg gat gga aaa gat aaa<br>Phe Thr Lys Gly Arg Asn Cys Tyr Glu Tyr Val Asp Gly Lys Asp Lys<br>95               100             105             110 | 339 |
| tcc tgg gcc aac tgg atg agg tat gtg aac tgt gcc cgg gat gat gaa<br>Ser Trp Ala Asn Trp Met Arg Tyr Val Asn Cys Ala Arg Asp Asp Glu<br>               115             120             125 | 387 |
| gag cag aac ctg gtg gcc ttc cag tac cac agg cag atc ttc tat aga<br>Glu Gln Asn Leu Val Ala Phe Gln Tyr His Arg Gln Ile Phe Tyr Arg<br>          130               135             140 | 435 |
| acc tgc cga gtc att agg cca ggc tgt gaa ctg ctg gtc tgg tat ggg<br>Thr Cys Arg Val Ile Arg Pro Gly Cys Glu Leu Leu Val Trp Tyr Gly<br>               145             150             155 | 483 |
| gat gaa tac ggc cag gaa ctg ggc atc aag tgg ggc agc aag tgg aag<br>Asp Glu Tyr Gly Gln Glu Leu Gly Ile Lys Trp Gly Ser Lys Trp Lys<br>160               165             170 | 531 |
| aaa gag gaa cca aag cca gag atc cat cca tgt ccc tca tgc tgt ctg<br>Lys Glu Glu Pro Lys Pro Glu Ile His Pro Cys Pro Ser Cys Cys Leu<br>175               180             185             190 | 579 |
| gcc ttt tca agt cag aaa ttt ctc agt caa cat gta gaa cgc aat cac<br>Ala Phe Ser Ser Gln Lys Phe Leu Ser Gln His Val Glu Arg Asn His<br>               195             200             205 | 627 |
| tcc tct cag aac ttc cca gga cca tct gca aga aaa ctc ctc caa cca<br>Ser Ser Gln Asn Phe Pro Gly Pro Ser Ala Arg Lys Leu Leu Gln Pro<br>          210               215             220 | 675 |
| gag aat ccc tgc cca ggg gat cag aat cag gag cag caa tat cca gat<br>Glu Asn Pro Cys Pro Gly Asp Gln Asn Gln Glu Gln Gln Tyr Pro Asp<br>               225             230             235 | 723 |
| cca cac agc cgt aat gac aaa acc aaa ggt caa gag atc aaa gaa agg<br>Pro His Ser Arg Asn Asp Lys Thr Lys Gly Gln Glu Ile Lys Glu Arg<br>240               245             250 | 771 |
| tcc aaa ctc ttg aat aaa agg aca tgg cag agg gag att tca agg gcc<br>Ser Lys Leu Leu Asn Lys Arg Thr Trp Gln Arg Glu Ile Ser Arg Ala<br>255               260             265             270 | 819 |
| ttt tct agc cca ccc aaa gga caa atg ggg agc tgt aga gtg gga aaa<br>Phe Ser Ser Pro Pro Lys Gly Gln Met Gly Ser Cys Arg Val Gly Lys<br>               275             280             285 | 867 |
| aga ata atg gaa gaa gag tcc aga aca ggc cag aaa gtg aat cca ggg<br>Arg Ile Met Glu Glu Glu Ser Arg Thr Gly Gln Lys Val Asn Pro Gly<br>          290               295             300 | 915 |
| aac aca ggc aaa tta ttt gtg ggg gta gga atc tca aga att gca aaa<br>Asn Thr Gly Lys Leu Phe Val Gly Val Gly Ile Ser Arg Ile Ala Lys<br>305               310             315 | 963 |
| gtc aag tat gga gag tgt gga caa ggt ttc agt gtt aaa tca gat gtt<br>Val Lys Tyr Gly Glu Cys Gly Gln Gly Phe Ser Val Lys Ser Asp Val | 1011 |

```
                320                 325                 330
att aca cac caa agg aca cat aca ggg gag aag ctc tac gtc tgc agg         1059
Ile Thr His Gln Arg Thr His Thr Gly Glu Lys Leu Tyr Val Cys Arg
335                 340                 345                 350 gag tgt ggg cgg ggc ttt agc tgg aag tca cac ctc ctc att cac cag         1107
Glu Cys Gly Arg Gly Phe Ser Trp Lys Ser His Leu Leu Ile His Gln
                355                 360                 365 agg ata cac aca ggg gag aag ccc tat gtc tgc agg gag tgt ggg cgg         1155
Arg Ile His Thr Gly Glu Lys Pro Tyr Val Cys Arg Glu Cys Gly Arg
            370                 375                 380 ggc ttt agc tgg cag tca gtc ctc ctc act cac cag agg aca cac aca         1203
Gly Phe Ser Trp Gln Ser Val Leu Leu Thr His Gln Arg Thr His Thr
        385                 390                 395 ggg gag aag ccc tat gtc tgc agg gag tgt ggg cgg ggc ttt agc cgg         1251
Gly Glu Lys Pro Tyr Val Cys Arg Glu Cys Gly Arg Gly Phe Ser Arg
    400                 405                 410 cag tca gtc ctc ctc act cac cag agg aga cac aca ggg gag aag ccc         1299
Gln Ser Val Leu Leu Thr His Gln Arg Arg His Thr Gly Glu Lys Pro
415                 420                 425                 430 tat gtc tgc agg gag tgt ggg cgg ggc ttt agc cgg cag tca gtc ctc         1347
Tyr Val Cys Arg Glu Cys Gly Arg Gly Phe Ser Arg Gln Ser Val Leu
                435                 440                 445 ctc act cac cag agg aga cac aca ggg gag aag ccc tat gtc tgc agg         1395
Leu Thr His Gln Arg Arg His Thr Gly Glu Lys Pro Tyr Val Cys Arg
            450                 455                 460 gag tgt ggg cgg ggc ttt agc tgg cag tca gtc ctc ctc act cac cag         1443
Glu Cys Gly Arg Gly Phe Ser Trp Gln Ser Val Leu Leu Thr His Gln
        465                 470                 475 agg aca cac aca ggg gag aag ccc tat gtc tgc agg gag tgt ggg cgg         1491
Arg Thr His Thr Gly Glu Lys Pro Tyr Val Cys Arg Glu Cys Gly Arg
    480                 485                 490 ggc ttt agc tgg cag tca gtc ctc ctc act cac cag agg aca cac aca         1539
Gly Phe Ser Trp Gln Ser Val Leu Leu Thr His Gln Arg Thr His Thr
495                 500                 505                 510 ggg gag aag ccc tat gtc tgc agg gag tgt ggg cgg ggc ttt agc aat         1587
Gly Glu Lys Pro Tyr Val Cys Arg Glu Cys Gly Arg Gly Phe Ser Asn
                515                 520                 525 aag tca cac ctc ctc aga cac cag agg aca cac aca ggg gag aag ccc         1635
Lys Ser His Leu Leu Arg His Gln Arg Thr His Thr Gly Glu Lys Pro
            530                 535                 540 tat gtc tgc agg gag tgt ggg cgg ggc ttt cgc gat aag tca cac ctc         1683
Tyr Val Cys Arg Glu Cys Gly Arg Gly Phe Arg Asp Lys Ser His Leu
        545                 550                 555 ctc aga cac cag agg aca cac aca ggg gag aag ccc tat gtc tgc agg         1731
Leu Arg His Gln Arg Thr His Thr Gly Glu Lys Pro Tyr Val Cys Arg
    560                 565                 570 gag tgt ggg cgg ggc ttt aga gat aag tca aac ctc ctc agt cac cag         1779
Glu Cys Gly Arg Gly Phe Arg Asp Lys Ser Asn Leu Leu Ser His Gln
575                 580                 585                 590 agg aca cac aca ggg gag aag ccc tat gtc tgc agg gag tgt ggg cgg         1827
Arg Thr His Thr Gly Glu Lys Pro Tyr Val Cys Arg Glu Cys Gly Arg
                595                 600                 605 ggc ttt agc aat aag tca cac ctc ctc aga cac cag agg aca cac aca         1875
Gly Phe Ser Asn Lys Ser His Leu Leu Arg His Gln Arg Thr His Thr
            610                 615                 620 ggg gag aag ccc tat gtc tgc agg gag tgt ggg cgg ggc ttt cgc aat         1923
Gly Glu Lys Pro Tyr Val Cys Arg Glu Cys Gly Arg Gly Phe Arg Asn
        625                 630                 635 aag tca cac ctc ctc aga cac cag agg aca cac aca ggg gag aag ccc         1971
```

-continued

| | | | | | | | | | | | | |
|---|---|---|---|---|---|---|---|---|---|---|---|---|
| Lys | Ser | His | Leu | Leu | Arg | His | Gln | Arg | Thr | His | Thr | Gly | Glu | Lys | Pro |
| | 640 | | | | 645 | | | | 650 | | | | | | |

```
tac gtc tgc agg gag tgt ggg cgg ggc ttt agc gat agg tca agc ctc      2019
Tyr Val Cys Arg Glu Cys Gly Arg Gly Phe Ser Asp Arg Ser Ser Leu
655                 660                 665                 670 tgc tat cac cag agg aca cac aca ggg gag aag ccc tac gtc tgc agg      2067
Cys Tyr His Gln Arg Thr His Thr Gly Glu Lys Pro Tyr Val Cys Arg
                675                 680                 685 gag gat gag taagtcatta gtaataaaac ctcatctcaa tagccacaaa              2116
Glu Asp Glu aagacaaatg tggtcaccac acacttgcac accccagctg tgaggtggct tcagcggaag    2176
tctgctgacc ccttatattc cccgagagta taaagagatc ggaaataact gattaaacaa    2236
atccgccact ttcatgacta gagatgagga agaacaaggg atagttctgt aagtgttcgg    2296
gggacatcag catgtgtggt tctttcccgc actgatcccc tccatttttt gtttgttttt    2356
ttgcctcctg ttctaataaa ttttgtctcc atacaaatct gaaccccaag tgtgtacctc    2416
attcttccct tatcactgaa ggcaagaaga gtccagaagg ccacagaga actcatgtgt     2476
tcagctcaag actccacagg aattcaaccc ccagaaagac ataaacttgg agtccgtctg    2536
gtttaattat tggagaatcg attcccaagt ccaggaagag aaatgtaaga ttctagaaag    2596
tcgcagcagg aaagggagtt ccctggtctc ctgggaagtg tggcttcttc tcctaatgga    2656
cacctctcct ctgctgccat actctccctt ggctccccag tctcctctcc tgatctcctc    2716
caatctctgt agcccaagat gtgaaagcca gacaagaaca cgcgtgtgtg tatatatgtg    2776
ttcgggtgtg ggggtatgtg ccctccgtgt aggtaactgt gtgagtgtgg ggggtttcaa    2836
gggtgtgtta ggaacaacgc tcaaaatcct aaggaaactg aacactcgaa cgaaggattc    2896
ttagcaa                                                              2903
```

<210> SEQ ID NO 2
<211> LENGTH: 689
<212> TYPE: PRT
<213> ORGANISM: Human

<400> SEQUENCE: 2

```
Met Cys Gln Asn Phe Phe Ile Asp Ser Cys Ala Ala His Gly Pro Pro
1               5                   10                  15

Thr Phe Val Lys Asp Ser Ala Val Asp Lys Gly His Pro Asn Arg Ser
                20                  25                  30

Ala Leu Ser Leu Pro Pro Gly Leu Arg Ile Gly Pro Ser Gly Ile Pro
            35                  40                  45

Gln Ala Gly Leu Gly Val Trp Asn Glu Ala Ser Asp Leu Pro Leu Gly
        50                  55                  60

Leu His Phe Gly Pro Tyr Glu Gly Arg Ile Thr Glu Asp Glu Glu Ala
65                  70                  75                  80

Ala Asn Asn Gly Tyr Ser Trp Leu Val Arg Arg Ala Cys His Phe Thr
                85                  90                  95

Lys Gly Arg Asn Cys Tyr Glu Tyr Val Asp Gly Lys Asp Lys Ser Trp
                100                 105                 110

Ala Asn Trp Met Arg Tyr Val Asn Cys Ala Arg Asp Asp Glu Glu Gln
            115                 120                 125

Asn Leu Val Ala Phe Gln Tyr His Arg Gln Ile Phe Tyr Arg Thr Cys
        130                 135                 140

Arg Val Ile Arg Pro Gly Cys Glu Leu Leu Val Trp Tyr Gly Asp Glu
145                 150                 155                 160
```

```
Tyr Gly Gln Glu Leu Gly Ile Lys Trp Gly Ser Lys Trp Lys Glu
            165                 170                 175
Glu Pro Lys Pro Glu Ile His Pro Cys Pro Ser Cys Cys Leu Ala Phe
            180                 185                 190
Ser Ser Gln Lys Phe Leu Ser Gln His Val Glu Arg Asn His Ser Ser
            195                 200                 205
Gln Asn Phe Pro Gly Pro Ser Ala Arg Lys Leu Leu Gln Pro Glu Asn
    210                 215                 220
Pro Cys Pro Gly Asp Gln Asn Gln Glu Gln Tyr Pro Asp Pro His
225                 230                 235                 240
Ser Arg Asn Asp Lys Thr Lys Gly Gln Glu Ile Lys Glu Arg Ser Lys
                245                 250                 255
Leu Leu Asn Lys Arg Thr Trp Gln Arg Glu Ile Ser Arg Ala Phe Ser
                260                 265                 270
Ser Pro Pro Lys Gly Gln Met Gly Ser Cys Arg Val Gly Lys Arg Ile
            275                 280                 285
Met Glu Glu Glu Ser Arg Thr Gly Gln Lys Val Asn Pro Gly Asn Thr
    290                 295                 300
Gly Lys Leu Phe Val Gly Val Gly Ile Ser Arg Ile Ala Lys Val Lys
305                 310                 315                 320
Tyr Gly Glu Cys Gly Gln Gly Phe Ser Val Lys Ser Asp Val Ile Thr
                325                 330                 335
His Gln Arg Thr His Thr Gly Glu Lys Leu Tyr Val Cys Arg Glu Cys
                340                 345                 350
Gly Arg Gly Phe Ser Trp Lys Ser His Leu Leu Ile His Gln Arg Ile
                355                 360                 365
His Thr Gly Glu Lys Pro Tyr Val Cys Arg Glu Cys Gly Arg Gly Phe
    370                 375                 380
Ser Trp Gln Ser Val Leu Leu Thr His Gln Arg Thr His Thr Gly Glu
385                 390                 395                 400
Lys Pro Tyr Val Cys Arg Glu Cys Gly Arg Gly Phe Ser Arg Gln Ser
                405                 410                 415
Val Leu Leu Thr His Gln Arg Arg His Thr Gly Glu Lys Pro Tyr Val
                420                 425                 430
Cys Arg Glu Cys Gly Arg Gly Phe Ser Arg Gln Ser Val Leu Leu Thr
                435                 440                 445
His Gln Arg Arg His Thr Gly Glu Lys Pro Tyr Val Cys Arg Glu Cys
    450                 455                 460
Gly Arg Gly Phe Ser Trp Gln Ser Val Leu Leu Thr His Gln Arg Thr
465                 470                 475                 480
His Thr Gly Glu Lys Pro Tyr Val Cys Arg Glu Cys Gly Arg Gly Phe
                485                 490                 495
Ser Trp Gln Ser Val Leu Leu Thr His Gln Arg Thr His Thr Gly Glu
                500                 505                 510
Lys Pro Tyr Val Cys Arg Glu Cys Gly Arg Gly Phe Ser Asn Lys Ser
                515                 520                 525
His Leu Leu Arg His Gln Arg Thr His Thr Gly Glu Lys Pro Tyr Val
    530                 535                 540
Cys Arg Glu Cys Gly Arg Gly Phe Arg Asp Lys Ser His Leu Leu Arg
545                 550                 555                 560
His Gln Arg Thr His Thr Gly Glu Lys Pro Tyr Val Cys Arg Glu Cys
                565                 570                 575
```

```
Gly Arg Gly Phe Arg Asp Lys Ser Asn Leu Leu Ser His Gln Arg Thr
            580                 585                 590
His Thr Gly Glu Lys Pro Tyr Val Cys Arg Glu Cys Gly Arg Gly Phe
        595                 600                 605
Ser Asn Lys Ser His Leu Leu Arg His Gln Arg Thr His Thr Gly Glu
    610                 615                 620
Lys Pro Tyr Val Cys Arg Glu Cys Gly Arg Gly Phe Arg Asn Lys Ser
625                 630                 635                 640
His Leu Leu Arg His Gln Arg Thr His Thr Gly Glu Lys Pro Tyr Val
                645                 650                 655
Cys Arg Glu Cys Gly Arg Gly Phe Ser Asp Arg Ser Ser Leu Cys Tyr
                660                 665                 670
His Gln Arg Thr His Thr Gly Glu Lys Pro Tyr Val Cys Arg Glu Asp
            675                 680                 685
Glu
```

<210> SEQ ID NO 3
<211> LENGTH: 6010
<212> TYPE: DNA
<213> ORGANISM: Human
<220> FEATURE:
<221> NAME/KEY: CDS
<222> LOCATION: (217)...(3399)

<400> SEQUENCE: 3

| | | |
|---|---|---|
| agccctccca ggtgtgggac agaaggggca gagggagggc agaggcttaa aggctgtgag | 60 |
| cagtcagatc aaaaatgaag ccagctcttc ctcacagccg gtagatggaa gtcattttc | 120 |
| cagggcctgg aaggagttgg taggaagact agatttcagc cagcccttgc gccctgtttg | 180 |

```
tgccagcagg caccagcgaa ccaaaagcag gtgtcc atg tct gct tac tct gtg      234
                                    Met Ser Ala Tyr Ser Val
                                     1               5 cct tca act ttt gcc cag gcc tca ttg cca gtt cat aac cag gtg ctg      282
Pro Ser Thr Phe Ala Gln Ala Ser Leu Pro Val His Asn Gln Val Leu
         10                  15                  20 cct tcc atc gag agt gta gat ggg tcc gac cct ttg gca act ctg cag      330
Pro Ser Ile Glu Ser Val Asp Gly Ser Asp Pro Leu Ala Thr Leu Gln
     25                  30                  35 acc cct cta ggc aga ctg gag gcc aaa gag gaa gag gat gag gat gag      378
Thr Pro Leu Gly Arg Leu Glu Ala Lys Glu Glu Glu Asp Glu Asp Glu
 40                  45                  50 gac gag gac act gag gaa gat gag gaa gaa gac ggt gag gac acg gat      426
Asp Glu Asp Thr Glu Glu Asp Glu Glu Glu Asp Gly Glu Asp Thr Asp
55                  60                  65                  70 ctg gat gac tgg gag cca gac ccg ccc cgg ccc ttc gac cca cac gac      474
Leu Asp Asp Trp Glu Pro Asp Pro Pro Arg Pro Phe Asp Pro His Asp
                 75                  80                  85 ttg tgg tgt gag gag tgc aat aac gcg cat gct tca gtg tgt ccg aag      522
Leu Trp Cys Glu Glu Cys Asn Asn Ala His Ala Ser Val Cys Pro Lys
             90                  95                 100 cac ggc ccc ttg cac ccg atc ccc aac cgg ccg gtg ctc acc cgg gcc      570
His Gly Pro Leu His Pro Ile Pro Asn Arg Pro Val Leu Thr Arg Ala
        105                 110                 115 agg gcg agc ctc ccc ctg gtg ctc tac ata gac agg ttt ctg ggc ggg      618
Arg Ala Ser Leu Pro Leu Val Leu Tyr Ile Asp Arg Phe Leu Gly Gly
    120                 125                 130 gtg ttc tcc aag cgg cgc atc ccc aag cgc acc cag ttt ggc ccc gtg      666
Val Phe Ser Lys Arg Arg Ile Pro Lys Arg Thr Gln Phe Gly Pro Val
135                 140                 145                 150
```

```
gag ggg cct ctc gtc agg ggc tcg gag ctg aaa gac tgt tac att cac      714
Glu Gly Pro Leu Val Arg Gly Ser Glu Leu Lys Asp Cys Tyr Ile His
            155                 160                 165 ctc aag gtt tct ctt gat aaa ggg gac agg aaa gaa agg gat tta cat      762
Leu Lys Val Ser Leu Asp Lys Gly Asp Arg Lys Glu Arg Asp Leu His
        170                 175                 180 gaa gac cta tgg ttt gag ttg tct gat gag acg ctt tgt aac tgg atg      810
Glu Asp Leu Trp Phe Glu Leu Ser Asp Glu Thr Leu Cys Asn Trp Met
            185                 190                 195 atg ttt gta cgg cca gcc cag aat cac ctg gag cag aac ctg gtg gct      858
Met Phe Val Arg Pro Ala Gln Asn His Leu Glu Gln Asn Leu Val Ala
200                 205                 210 tac cag tat ggc cac cat gtg tat tat aca acc ata aaa aat gtg gag      906
Tyr Gln Tyr Gly His His Val Tyr Tyr Thr Thr Ile Lys Asn Val Glu
215                 220                 225                 230 ccc aag cag gaa ctg aag gtg tgg tat gcc gca tcc tat gct gag ttc      954
Pro Lys Gln Glu Leu Lys Val Trp Tyr Ala Ala Ser Tyr Ala Glu Phe
            235                 240                 245 gtg aac cag aaa att cat gac att tct gag gaa gaa agg aaa gtt ctt     1002
Val Asn Gln Lys Ile His Asp Ile Ser Glu Glu Glu Arg Lys Val Leu
            250                 255                 260 cga gag caa gag aag aat tgg ccc tgc tat gaa tgt aac cgc cga ttt     1050
Arg Glu Gln Glu Lys Asn Trp Pro Cys Tyr Glu Cys Asn Arg Arg Phe
            265                 270                 275 ata agc tcg gag cag ttg caa cag cat ctc aat tct cat gat gag aaa     1098
Ile Ser Ser Glu Gln Leu Gln Gln His Leu Asn Ser His Asp Glu Lys
            280                 285                 290 cta gat gtg ttt agc aga aca aga ggc aga gga agg gga cga ggc aag     1146
Leu Asp Val Phe Ser Arg Thr Arg Gly Arg Gly Arg Gly Arg Gly Lys
295                 300                 305                 310 agg cga ttc ggt cca ggt cga cgg ccg ggg cgt cct cca aaa ttt atc     1194
Arg Arg Phe Gly Pro Gly Arg Arg Pro Gly Arg Pro Pro Lys Phe Ile
            315                 320                 325 cgc ctg gaa atc acc agc gaa aat ggg gaa aag agt gac gat ggg aca     1242
Arg Leu Glu Ile Thr Ser Glu Asn Gly Glu Lys Ser Asp Asp Gly Thr
            330                 335                 340 cag gac ttg cta cat ttt ccc aca aag gag caa ttt gat gag gct gaa     1290
Gln Asp Leu Leu His Phe Pro Thr Lys Glu Gln Phe Asp Glu Ala Glu
            345                 350                 355 cca gcc act ctg aat ggg ctg gat caa cca gaa cag acc act atc cca     1338
Pro Ala Thr Leu Asn Gly Leu Asp Gln Pro Glu Gln Thr Thr Ile Pro
        360                 365                 370 atc cct cag ctg cca cag gaa acc cag tct tcc ctg gaa cat gaa cca     1386
Ile Pro Gln Leu Pro Gln Glu Thr Gln Ser Ser Leu Glu His Glu Pro
375                 380                 385                 390 gaa act cac acc ctg cac ctg cag ccg cag cat gaa gag agc gtg gtg     1434
Glu Thr His Thr Leu His Leu Gln Pro Gln His Glu Glu Ser Val Val
            395                 400                 405 ccc acc cag agc acg ctg aca gcc gac gac atg cgc aga gcc aag cgc     1482
Pro Thr Gln Ser Thr Leu Thr Ala Asp Asp Met Arg Arg Ala Lys Arg
            410                 415                 420 atc cga ttg gag ctg cag aat gca gct ctt cag cat ctg ttt att cgg     1530
Ile Arg Leu Glu Leu Gln Asn Ala Ala Leu Gln His Leu Phe Ile Arg
            425                 430                 435 aag tcc ttc cgg cct ttt aaa tgc ttg cag tgt ggg aag gcc ttc cgg     1578
Lys Ser Phe Arg Pro Phe Lys Cys Leu Gln Cys Gly Lys Ala Phe Arg
        440                 445                 450 gaa aag gac aaa ctg gac cag cac tta cgc ttc cat ggg cgg gag ggg     1626
Glu Lys Asp Lys Leu Asp Gln His Leu Arg Phe His Gly Arg Glu Gly
455                 460                 465                 470
```

```
aac tgc cca ctg acc tgt gat ctc tgt aac aag ggc ttc atc agc agc    1674
Asn Cys Pro Leu Thr Cys Asp Leu Cys Asn Lys Gly Phe Ile Ser Ser
            475                 480                 485 aca tcc ttg gag agc cac atg aag ctc cac tca gac cag aag act tac    1722
Thr Ser Leu Glu Ser His Met Lys Leu His Ser Asp Gln Lys Thr Tyr
        490                 495                 500 tct tgc att ttt tgc cca gaa tcc ttt gac cgc ctt gat ttg ttg aaa    1770
Ser Cys Ile Phe Cys Pro Glu Ser Phe Asp Arg Leu Asp Leu Leu Lys
    505                 510                 515 gat cat gtg gcc att cat atc aat gat ggc tac ttc acc tgc cca act    1818
Asp His Val Ala Ile His Ile Asn Asp Gly Tyr Phe Thr Cys Pro Thr
520                 525                 530 tgt aag aaa cgg ttc cca gat ttt atc cag gtg aaa aaa cac gtg cgc    1866
Cys Lys Lys Arg Phe Pro Asp Phe Ile Gln Val Lys Lys His Val Arg
535                 540                 545                 550 agc ttc cac tca gaa aag atc tac cag tgc aca gag tgt gac aag gcc    1914
Ser Phe His Ser Glu Lys Ile Tyr Gln Cys Thr Glu Cys Asp Lys Ala
            555                 560                 565 ttc tgt cgc ccc gat aaa ctg cga ctc cac atg ctc cgg cat tcg gac    1962
Phe Cys Arg Pro Asp Lys Leu Arg Leu His Met Leu Arg His Ser Asp
        570                 575                 580 cgc aaa gac ttc ctg tgt tcc acc tgt ggg aag caa ttt aag cga aaa    2010
Arg Lys Asp Phe Leu Cys Ser Thr Cys Gly Lys Gln Phe Lys Arg Lys
    585                 590                 595 gac aaa cta cgg gaa cac atg cag agg atg cat aat cct gag agg gag    2058
Asp Lys Leu Arg Glu His Met Gln Arg Met His Asn Pro Glu Arg Glu
600                 605                 610 gcc aag aaa gcc gac cgc atc agc cgc tcc aag acg ttc aag ccc cgc    2106
Ala Lys Lys Ala Asp Arg Ile Ser Arg Ser Lys Thr Phe Lys Pro Arg
615                 620                 625                 630 atc acg tcc aca gac tac gac agc ttc acg ttc aag tgc cgc ctg tgc    2154
Ile Thr Ser Thr Asp Tyr Asp Ser Phe Thr Phe Lys Cys Arg Leu Cys
            635                 640                 645 atg atg ggc ttc cgg cgg cgc ggc atg ctg gta aat cac tta tcg aag    2202
Met Met Gly Phe Arg Arg Arg Gly Met Leu Val Asn His Leu Ser Lys
        650                 655                 660 aga cac cca gac atg aag ata gaa gag gtg cca gag tta act cta ccc    2250
Arg His Pro Asp Met Lys Ile Glu Glu Val Pro Glu Leu Thr Leu Pro
    665                 670                 675 atc ata aaa ccc aat cgt gat tac ttt tgt cag tat tgc gat aag gtt    2298
Ile Ile Lys Pro Asn Arg Asp Tyr Phe Cys Gln Tyr Cys Asp Lys Val
680                 685                 690 tat aaa agt gcc agc aag cgc aaa gcc cac att ctg aag aac cac cca    2346
Tyr Lys Ser Ala Ser Lys Arg Lys Ala His Ile Leu Lys Asn His Pro
695                 700                 705                 710 gga gca gag ctc cca ccg agc att cgg aag ctc cga ccc gct ggt cct    2394
Gly Ala Glu Leu Pro Pro Ser Ile Arg Lys Leu Arg Pro Ala Gly Pro
            715                 720                 725 gga gag cca gac ccc atg ctg agc aca cac acc cag ctg acg ggc acc    2442
Gly Glu Pro Asp Pro Met Leu Ser Thr His Thr Gln Leu Thr Gly Thr
        730                 735                 740 atc gcc acc cct ccc gtc tgc tgt ccc cac tgc tcc aag cag tac agc    2490
Ile Ala Thr Pro Pro Val Cys Cys Pro His Cys Ser Lys Gln Tyr Ser
    745                 750                 755 agc aag acc aag atg gtc cag cac att cga aag aag cat cca gag ttc    2538
Ser Lys Thr Lys Met Val Gln His Ile Arg Lys Lys His Pro Glu Phe
760                 765                 770 gcc cag ctc tcc aac acc ata cac aca cca ctg acg aca gct gtg atc    2586
Ala Gln Leu Ser Asn Thr Ile His Thr Pro Leu Thr Thr Ala Val Ile
775                 780                 785                 790
```

| | | |
|---|---|---|
| agt gcc acc cca gcg gtt ttg act aca gac agc gcc act gga gag act<br>Ser Ala Thr Pro Ala Val Leu Thr Thr Asp Ser Ala Thr Gly Glu Thr<br>              795                     800                   805 | 2634 |
| gtg gtg acg acg gac ctg ctc acc caa gca atg aca gaa ctg tcc cag<br>Val Val Thr Thr Asp Leu Leu Thr Gln Ala Met Thr Glu Leu Ser Gln<br>           810                     815                    820 | 2682 |
| acc tta acg aca gac tac cga acg cca caa ggg gat tac cag aga att<br>Thr Leu Thr Thr Asp Tyr Arg Thr Pro Gln Gly Asp Tyr Gln Arg Ile<br>              825                     830                   835 | 2730 |
| cag tac atc cct gtg tcg cag tcg gcg tct ggc ctc cag cag cct cag<br>Gln Tyr Ile Pro Val Ser Gln Ser Ala Ser Gly Leu Gln Gln Pro Gln<br>840                     845                    850 | 2778 |
| cac ata cag ctg caa gtg gtt caa gtg gcc tcg gcc act tcc cct cac<br>His Ile Gln Leu Gln Val Val Gln Val Ala Ser Ala Thr Ser Pro His<br>855                     860                    865               870 | 2826 |
| cag tca cag cag tcc act gtg gat gtt ggc cag ctc cat gat cct cag<br>Gln Ser Gln Gln Ser Thr Val Asp Val Gly Gln Leu His Asp Pro Gln<br>              875                     880                   885 | 2874 |
| ccc tac ccc cag cac gcc atc cag gtg cag cac atc cag gta tct ggg<br>Pro Tyr Pro Gln His Ala Ile Gln Val Gln His Ile Gln Val Ser Gly<br>           890                     895                    900 | 2922 |
| cag ccg ttg agt ccc tca gcc cag cag gct cag cag ggg ctc agc ccc<br>Gln Pro Leu Ser Pro Ser Ala Gln Gln Ala Gln Gln Gly Leu Ser Pro<br>           905                     910                    915 | 2970 |
| tcc cac atc cag ggc agt tct tcc aca cag ggg cag gct ctg cag cag<br>Ser His Ile Gln Gly Ser Ser Ser Thr Gln Gly Gln Ala Leu Gln Gln<br>920                     925                    930 | 3018 |
| cag cag cag cag cag cag aat tcc tct gtg cag cac acg tac ctg ccc<br>Gln Gln Gln Gln Gln Gln Asn Ser Ser Val Gln His Thr Tyr Leu Pro<br>935                     940                    945               950 | 3066 |
| agt gct tgg aat tcc ttc cgt ggc tat tca tct gag att caa atg atg<br>Ser Ala Trp Asn Ser Phe Arg Gly Tyr Ser Ser Glu Ile Gln Met Met<br>              955                     960                   965 | 3114 |
| acg ctt cct ccg ggt cag ttt gtg att aca gac agt ggt gtg gca act<br>Thr Leu Pro Pro Gly Gln Phe Val Ile Thr Asp Ser Gly Val Ala Thr<br>           970                     975                    980 | 3162 |
| cca gtt act act ggc cag gtg aag gcg gtt act tcg ggt cat tat gtg<br>Pro Val Thr Thr Gly Gln Val Lys Ala Val Thr Ser Gly His Tyr Val<br>985                     990                    995 | 3210 |
| tta tca gaa agt caa tca gaa ttg gaa gaa aag caa act tct gcc ctc<br>Leu Ser Glu Ser Gln Ser Glu Leu Glu Glu Lys Gln Thr Ser Ala Leu<br>      1000                   1005                  1010 | 3258 |
| tct ggt gga gtc cag gtc gag cca cct gca cac agt gac tcc ctg gac<br>Ser Gly Gly Val Gln Val Glu Pro Pro Ala His Ser Asp Ser Leu Asp<br>1015                  1020                  1025                 1030 | 3306 |
| ccc cag acc aac agc caa cag cag acc aca cag tac atc atc acc acc<br>Pro Gln Thr Asn Ser Gln Gln Gln Thr Thr Gln Tyr Ile Ile Thr Thr<br>                1035                  1040                  1045 | 3354 |
| acc acc aac ggg aac gga agc agc gaa gtg cat atc acc aaa cca<br>Thr Thr Asn Gly Asn Gly Ser Ser Glu Val His Ile Thr Lys Pro<br>            1050                  1055                  1060 | 3399 |
| tgacttccac cctggagctt gaatccagca cccacctcat gtctgttctc ataagtctga | 3459 |
| aagctctgac acgtagagct cttttgtaag atttattatt cactcaagag ttcgaaacc | 3519 |
| acagttttgt ctctcatcca tacactgggg tttattttgc caaggtcatc tttatcaaat | 3579 |
| tgactcttca aaccctcggt ttttgccaca gaacagagat ctttcagggg aaagtagatt | 3639 |
| tcgaggtgga gagaatttgc cttgctcttg agctggtctt ttaacatact gacgagcctt | 3699 |

```
acttttcctt tgtggaaata ttaagtggca tattgtgttc ataccaaagg tggagacagg      3759
atgtgccaag ttcatggtta ctggacttct tattccaagc catggcacca aaggagaagg      3819
ggcattttgt gggtgtgcat taggtctgaa ctgctttatc ttgttttagt tttcagtaat      3879
ttaacaaagg gagcctgctg aataacaaaa ttaaaatgat gaaacaaaag tttgacagtg      3939
atattctgaa gcaaaaactg tcatctaaat ttttcttgct gatttttttt aacttcccta      3999
ttttagaaaa ctattgttgg gctgttggta gtgctttcca cagatgctgg tcctcagtgg      4059
attaggtcag aagctcatgt tctgatagtt cttcattatt tcacaaaggt ggacaacctg      4119
aaagagaaaa ggctgcttga tgtcagcaga atctaaaccc ctacattaaa gctttgcctc      4179
ccattctgtg gttgtggtgg tggtaagaag gagatattgg taccaagaaa aatttccaaa      4239
actattgaga gagagagaga gaaagtattg aaattttgtt ctgccttgca ggatccattt      4299
atcattcatt ggtaaaggat atattccttg ttcttaccaa gtgtacattt aactcttgct      4359
gacatgttca gtgtattta ttacttttaa tgctgtctta aaatgaacat tctttaaagt      4419
tggacaggaa ggtggcattt cttatttatt aacattttta actttaaaca tattgtgact      4479
catctagacc ttttaataag acgatcaact tcacacttag ggaaaaaatt aaaatgtgat      4539
ggccacttct aataattcag gtagttataa gggatctgga agaaatccag tctttatgaa      4599
tatactatta gttgggcatt aaaaaatcag tatatatttt aacttttgt gacatgctaa      4659 cacattttca gaataattat tgcatagtag aatttattac tccagaacag aaagacctta      4719
cttcatttca aatgaagtta attaatttac atttctgggt aaaaactggt tctataaatt      4779
aagtagagta gcttctttat gataaagaca attttctgaa aagtgaacaa ttctgttaaa      4839
agaactttat tgatgtgtag atttcgcact ttatttctga gactgcgttc atgtagttgt      4899
tccccaatgt ttgagtacta agagaacttg agaaaattac ttcataaaca tatggaaact      4959
gaaaatggac tctctttgtg acaaagatat tcaacagaaa atattgaccc tgcattgcaa      5019
aacacaggtt cgggttccct aagtcccaca gtgtaatgat tacaaatatc ctagtgtccg      5079
gtctagaaag actttctagg agaagactag tggaattttc taaaggttca gttttagctt      5139
ttataactta aatttggccc tgttacgttc tttttaattt gaaccataag gtatctcccc      5199
tcccttcagg aataacttat tggaaaactg aaaagaatca ctgaatggaa tgttcatttt      5259
atggcagttg ttttaagttt taaaatacac agaggaaaat attgtggaag gacctctttg      5319
ttgctttccc ttctaagttg tcttcttctt cttcttcttc ttcttcttct ttggtcctta      5379
agtgaaataa agactctaaa actaatttgt atattatcag ccagagatgc ggatggcagt      5439
cgagccaaat cgcatggctt tcagatcagg tattctgcac attcattcca aggtcataga      5499
tttttaaaag gacctggatt tgaagagatg gcaaatgatg agccatcaga aaacttaatt      5559
tggaaaacat gtatgtagcc agtgtggata ttgtggcctc tctcaagaca cattgacact      5619
gtagacttca ttcagtccag tgtgagtatt ttggagtagg ttggatgtag attttgtttt      5679
tatcattgat ttgtaccgac agaaatagac atttcatcat gtaaaattcc tgttattctg      5739
gaaaaaccta ttgttttgat cttcttgttt tctgacttgg aagtatcctt tcaaaaaaac      5799
tcttaagata tctaggtcta aaaagcactt catgagatgc taaagctgac ccactggttg      5859
aaaatgttga ccctatcctg ttatttaaat gtgaacattt attgtacatt cagtgagtta      5919
tagtgttaat agtcttgtgc tatgcagcag gtgtaaaaat taataaatat attttttaat      5979
aaacatgttt gtatgtgtga gtagtcattt c                                    6010
```

-continued

<210> SEQ ID NO 4
<211> LENGTH: 1061
<212> TYPE: PRT
<213> ORGANISM: Human

<400> SEQUENCE: 4

```
Met Ser Ala Tyr Ser Val Pro Ser Thr Phe Ala Gln Ala Ser Leu Pro
1               5                   10                  15

Val His Asn Gln Val Leu Pro Ser Ile Glu Ser Val Asp Gly Ser Asp
            20                  25                  30

Pro Leu Ala Thr Leu Gln Thr Pro Leu Gly Arg Leu Glu Ala Lys Glu
        35                  40                  45

Glu Glu Asp Glu Asp Glu Asp Thr Glu Glu Asp Glu Glu Glu
    50                  55                  60

Asp Gly Glu Asp Thr Asp Leu Asp Asp Trp Glu Pro Asp Pro Arg
65                  70                  75                  80

Pro Phe Asp Pro His Asp Leu Trp Cys Glu Cys Asn Asn Ala His
                85                  90                  95

Ala Ser Val Cys Pro Lys His Gly Pro Leu His Pro Ile Pro Asn Arg
            100                 105                 110

Pro Val Leu Thr Arg Ala Arg Ala Ser Leu Pro Leu Val Leu Tyr Ile
        115                 120                 125

Asp Arg Phe Leu Gly Gly Val Phe Ser Lys Arg Ile Pro Lys Arg
    130                 135                 140

Thr Gln Phe Gly Pro Val Glu Gly Pro Leu Val Arg Gly Ser Glu Leu
145                 150                 155                 160

Lys Asp Cys Tyr Ile His Leu Lys Val Ser Leu Asp Lys Gly Asp Arg
                165                 170                 175

Lys Glu Arg Asp Leu His Glu Asp Leu Trp Phe Glu Leu Ser Asp Glu
            180                 185                 190

Thr Leu Cys Asn Trp Met Met Phe Val Arg Pro Ala Gln Asn His Leu
        195                 200                 205

Glu Gln Asn Leu Val Ala Tyr Gln Tyr Gly His His Val Tyr Tyr Thr
    210                 215                 220

Thr Ile Lys Asn Val Glu Pro Lys Gln Glu Leu Lys Val Trp Tyr Ala
225                 230                 235                 240

Ala Ser Tyr Ala Glu Phe Val Asn Gln Lys Ile His Asp Ile Ser Glu
                245                 250                 255

Glu Glu Arg Lys Val Leu Arg Glu Gln Glu Lys Asn Trp Pro Cys Tyr
            260                 265                 270

Glu Cys Asn Arg Arg Phe Ile Ser Ser Glu Gln Leu Gln Gln His Leu
        275                 280                 285

Asn Ser His Asp Glu Lys Leu Asp Val Phe Ser Arg Thr Arg Gly Arg
    290                 295                 300

Gly Arg Gly Arg Gly Lys Arg Phe Gly Pro Gly Arg Arg Pro Gly
305                 310                 315                 320

Arg Pro Pro Lys Phe Ile Arg Leu Glu Ile Thr Ser Glu Asn Gly Glu
                325                 330                 335

Lys Ser Asp Asp Gly Thr Gln Asp Leu Leu His Phe Pro Thr Lys Glu
            340                 345                 350

Gln Phe Asp Glu Ala Glu Pro Ala Thr Leu Asn Gly Leu Asp Gln Pro
        355                 360                 365

Glu Gln Thr Thr Ile Pro Ile Pro Gln Leu Pro Gln Glu Thr Gln Ser
    370                 375                 380
```

```
Ser Leu Glu His Glu Pro Glu Thr His Thr Leu His Leu Gln Pro Gln
385                 390                 395                 400

His Glu Glu Ser Val Val Pro Thr Gln Ser Thr Leu Thr Ala Asp Asp
            405                 410                 415

Met Arg Arg Ala Lys Arg Ile Arg Leu Glu Leu Gln Asn Ala Ala Leu
        420                 425                 430

Gln His Leu Phe Ile Arg Lys Ser Phe Arg Pro Phe Lys Cys Leu Gln
        435                 440                 445

Cys Gly Lys Ala Phe Arg Glu Lys Asp Lys Leu Asp Gln His Leu Arg
    450                 455                 460

Phe His Gly Arg Glu Gly Asn Cys Pro Leu Thr Cys Asp Leu Cys Asn
465                 470                 475                 480

Lys Gly Phe Ile Ser Ser Thr Ser Leu Glu Ser His Met Lys Leu His
                485                 490                 495

Ser Asp Gln Lys Thr Tyr Ser Cys Ile Phe Cys Pro Glu Ser Phe Asp
                500                 505                 510

Arg Leu Asp Leu Leu Lys Asp His Val Ala Ile His Ile Asn Asp Gly
            515                 520                 525

Tyr Phe Thr Cys Pro Thr Cys Lys Lys Arg Phe Pro Asp Phe Ile Gln
530                 535                 540

Val Lys Lys His Val Arg Ser Phe His Ser Glu Lys Ile Tyr Gln Cys
545                 550                 555                 560

Thr Glu Cys Asp Lys Ala Phe Cys Arg Pro Asp Lys Leu Arg Leu His
                565                 570                 575

Met Leu Arg His Ser Asp Arg Lys Asp Phe Leu Cys Ser Thr Cys Gly
                580                 585                 590

Lys Gln Phe Lys Arg Lys Asp Lys Leu Arg Glu His Met Gln Arg Met
        595                 600                 605

His Asn Pro Glu Arg Glu Ala Lys Lys Ala Asp Arg Ile Ser Arg Ser
610                 615                 620

Lys Thr Phe Lys Pro Arg Ile Thr Ser Thr Asp Tyr Asp Ser Phe Thr
625                 630                 635                 640

Phe Lys Cys Arg Leu Cys Met Met Gly Phe Arg Arg Gly Met Leu
                645                 650                 655

Val Asn His Leu Ser Lys Arg His Pro Asp Met Lys Ile Glu Glu Val
                660                 665                 670

Pro Glu Leu Thr Leu Pro Ile Ile Lys Pro Asn Arg Asp Tyr Phe Cys
        675                 680                 685

Gln Tyr Cys Asp Lys Val Tyr Lys Ser Ala Ser Lys Arg Lys Ala His
        690                 695                 700

Ile Leu Lys Asn His Pro Gly Ala Glu Leu Pro Pro Ser Ile Arg Lys
705                 710                 715                 720

Leu Arg Pro Ala Gly Pro Gly Glu Pro Asp Pro Met Leu Ser Thr His
                725                 730                 735

Thr Gln Leu Thr Gly Thr Ile Ala Thr Pro Val Cys Cys Pro His
            740                 745                 750

Cys Ser Lys Gln Tyr Ser Ser Lys Thr Lys Met Val Gln His Ile Arg
        755                 760                 765

Lys Lys His Pro Glu Phe Ala Gln Leu Ser Asn Thr Ile His Thr Pro
        770                 775                 780

Leu Thr Thr Ala Val Ile Ser Ala Thr Pro Ala Val Leu Thr Asp
785                 790                 795                 800

Ser Ala Thr Gly Glu Thr Val Val Thr Thr Asp Leu Leu Thr Gln Ala
```

```
                805                 810                 815
Met Thr Glu Leu Ser Gln Thr Leu Thr Thr Asp Tyr Arg Thr Pro Gln
            820                 825                 830

Gly Asp Tyr Gln Arg Ile Gln Tyr Ile Pro Val Ser Gln Ser Ala Ser
        835                 840                 845

Gly Leu Gln Gln Pro Gln His Ile Gln Leu Gln Val Val Gln Val Ala
    850                 855                 860

Ser Ala Thr Ser Pro His Gln Ser Gln Gln Ser Thr Val Asp Val Gly
865                 870                 875                 880

Gln Leu His Asp Pro Gln Pro Tyr Pro Gln His Ala Ile Gln Val Gln
                885                 890                 895

His Ile Gln Val Ser Gly Gln Pro Leu Ser Pro Ser Ala Gln Gln Ala
            900                 905                 910

Gln Gln Gly Leu Ser Pro Ser His Ile Gln Gly Ser Ser Thr Gln
        915                 920                 925

Gly Gln Ala Leu Gln Gln Gln Gln Gln Gln Asn Ser Ser Val
    930                 935                 940

Gln His Thr Tyr Leu Pro Ser Ala Trp Asn Ser Phe Arg Gly Tyr Ser
945                 950                 955                 960

Ser Glu Ile Gln Met Met Thr Leu Pro Pro Gly Gln Phe Val Ile Thr
                965                 970                 975

Asp Ser Gly Val Ala Thr Pro Val Thr Thr Gly Gln Val Lys Ala Val
            980                 985                 990

Thr Ser Gly His Tyr Val Leu Ser Glu Ser Gln Ser Glu Leu Glu Glu
        995                 1000                1005

Lys Gln Thr Ser Ala Leu Ser Gly Gly Val Gln Val Glu Pro Pro Ala
    1010                1015                1020

His Ser Asp Ser Leu Asp Pro Gln Thr Asn Ser Gln Gln Thr Thr
1025                1030                1035                1040

Gln Tyr Ile Ile Thr Thr Thr Asn Gly Asn Gly Ser Ser Glu Val
                1045                1050                1055

His Ile Thr Lys Pro
            1060

<210> SEQ ID NO 5
<211> LENGTH: 2208
<212> TYPE: DNA
<213> ORGANISM: Human
<220> FEATURE:
<221> NAME/KEY: CDS
<222> LOCATION: (250)...(1761)

<400> SEQUENCE: 5
gtcttgagga ccatctctcc cggcagcata ccgtgtggct tcacactgct ctgcctctct      60
gaacctcggt ttcttcatct ataaatggg aataagagta agccacctca atggactgtg     120
ggaggcttaa gtaaattgaa gtgccatgca agtagctagc atgcagttgc agctcaatga     180
atattatgat ggccgcagat acgatggcta cagctgggc acccatttcg ggtcacaagg     240 tagggttca atg ttg aag atg gca gag cca att gca tcc ctg atg atc gtg    291
          Met Leu Lys Met Ala Glu Pro Ile Ala Ser Leu Met Ile Val
            1               5                   10 gag tgc cgg gcc tgc ctg aga tgc tca cct ctc ttc ctt tac cag aga       339
Glu Cys Arg Ala Cys Leu Arg Cys Ser Pro Leu Phe Leu Tyr Gln Arg
15                  20                  25                  30 gag aaa gac aga atg acc gag aac atg aag gag tgc ttg gcc cag acc       387
Glu Lys Asp Arg Met Thr Glu Asn Met Lys Glu Cys Leu Ala Gln Thr
```

|  |  |
|---|---|
| aat gca gcc gtg ggg gat atg gtg acg gtg gtg aat ccg agc cag gag<br>Asn Ala Ala Val Gly Asp Met Val Thr Val Val Asn Pro Ser Gln Glu<br>                50                          55                      60 | 435 |
| tat ggc cag ccc tgc tct agg aga ccg gac tcc tcg gcc atg gaa gtt<br>Tyr Gly Gln Pro Cys Ser Arg Arg Pro Asp Ser Ser Ala Met Glu Val<br>                65                          70                      75 | 483 |
| gag ccc aag aaa ctg aaa ggg aag cgc gac ctc atc gtg ccc aaa agc<br>Glu Pro Lys Lys Leu Lys Gly Lys Arg Asp Leu Ile Val Pro Lys Ser<br>80                          85                          90 | 531 |
| ttc cag caa gtg gac ttc tgg ttt tgt gag tcc tgc cag gag tac ttc<br>Phe Gln Gln Val Asp Phe Trp Phe Cys Glu Ser Cys Gln Glu Tyr Phe<br>95                      100                    105                110 | 579 |
| gtg gat gaa tgc cca aac cat ggc ccc ccg gtg ttt gtg tct gac aca<br>Val Asp Glu Cys Pro Asn His Gly Pro Pro Val Phe Val Ser Asp Thr | 627 |
| ccg gtg ccc gtg ggc atc cca gac cgg gcg gcg ctc acc atc cca cag<br>Pro Val Pro Val Gly Ile Pro Asp Arg Ala Ala Leu Thr Ile Pro Gln<br>              130                      135                    140 | 675 |
| ggc atg gag gtg gtc aag gac act agt gga gag agt gac gtg cga tgt<br>Gly Met Glu Val Val Lys Asp Thr Ser Gly Glu Ser Asp Val Arg Cys<br>            145                      150                    155 | 723 |
| gta aac gag gtc atc ccc aag ggc cac atc ttc ggc ccc tat gag ggg<br>Val Asn Glu Val Ile Pro Lys Gly His Ile Phe Gly Pro Tyr Glu Gly<br>160                          165                    170 | 771 |
| cag atc tcc acc cag gac aaa tca gct ggc ttc ttc tcc tgg ctg att<br>Gln Ile Ser Thr Gln Asp Lys Ser Ala Gly Phe Phe Ser Trp Leu Ile<br>175                      180                    185                190 | 819 |
| gtg gac aag aac aac cgc tat aag tcc ata gat ggc tca gac gag acc<br>Val Asp Lys Asn Asn Arg Tyr Lys Ser Ile Asp Gly Ser Asp Glu Thr<br>                      195                      200                205 | 867 |
| gaa gcc aac tgg atg agg tac gtg gtc atc tcc cgg gag gag agg gag<br>Glu Ala Asn Trp Met Arg Tyr Val Val Ile Ser Arg Glu Glu Arg Glu<br>              210                      215                    220 | 915 |
| cag aac ctg ctg gcg ttc cag cac agt gag cgc atc tac ttc cgg gcg<br>Gln Asn Leu Leu Ala Phe Gln His Ser Glu Arg Ile Tyr Phe Arg Ala<br>            225                      230                    235 | 963 |
| tgc agg gac atc cgg cct ggg gag tgg ctg cgg gtc tgg tac agc gag<br>Cys Arg Asp Ile Arg Pro Gly Glu Trp Leu Arg Val Trp Tyr Ser Glu<br>            240                      245                    250 | 1011 |
| gac tac atg aag cgc ctg cac agc atg tcc cag gaa acc att cac cgc<br>Asp Tyr Met Lys Arg Leu His Ser Met Ser Gln Glu Thr Ile His Arg<br>255                          260                    265                270 | 1059 |
| aac ctg gcc aga gga gag aag agg ttg cag agg gag aag tct gag cag<br>Asn Leu Ala Arg Gly Glu Lys Arg Leu Gln Arg Glu Lys Ser Glu Gln<br>                275                      280                    285 | 1107 |
| gtt ctg gat aac cca gaa gac ctg agg ggt ccc att cat ctc tct gtg<br>Val Leu Asp Asn Pro Glu Asp Leu Arg Gly Pro Ile His Leu Ser Val<br>              290                      295                    300 | 1155 |
| ctg aga cag ggc aaa agt ccc tac aag cgt ggc ttc gat gag ggg gat<br>Leu Arg Gln Gly Lys Ser Pro Tyr Lys Arg Gly Phe Asp Glu Gly Asp<br>            305                      310                    315 | 1203 |
| gta cac ccc caa gct aag aag aag aaa att gac ctg att ttc aag gat<br>Val His Pro Gln Ala Lys Lys Lys Lys Ile Asp Leu Ile Phe Lys Asp<br>320                          325                    330 | 1251 |
| gtt ctg gag gcc tca ctg gaa tct gcg aag gtg gaa gcc cac cag ttg<br>Val Leu Glu Ala Ser Leu Glu Ser Ala Lys Val Glu Ala His Gln Leu<br>335                      340                    345                350 | 1299 |
| gcc ctg agc acc tca ctg gtc atc agg aaa gtc ccc aaa tac cag gat<br>Ala Leu Ser Thr Ser Leu Val Ile Arg Lys Val Pro Lys Tyr Gln Asp | 1347 |

-continued

| | | | | | | | | | | | | | | | | |
|---|---|---|---|---|---|---|---|---|---|---|---|---|---|---|---|---|
| | | 355 | | | | 360 | | | | | 365 | | | | | |
| gac | gcc | tac | agt | cag | tgt | gca | aca | aca | atg | acc | cat | ggt | gtg | cag | aat | 1395 |
| Asp | Ala | Tyr | Ser | Gln | Cys | Ala | Thr | Thr | Met | Thr | His | Gly | Val | Gln | Asn | |
| | | 370 | | | | 375 | | | | | 380 | | | | | |
| ata | ggc | cag | acc | cag | ggg | gag | ggg | gac | tgg | aag | gtc | ccc | cag | ggg | gtc | 1443 |
| Ile | Gly | Gln | Thr | Gln | Gly | Glu | Gly | Asp | Trp | Lys | Val | Pro | Gln | Gly | Val | |
| | | | 385 | | | | | 390 | | | | | 395 | | | |
| tcc | aag | gag | cca | ggc | caa | ttg | gag | gat | gaa | gaa | gag | gag | cct | tca | tca | 1491 |
| Ser | Lys | Glu | Pro | Gly | Gln | Leu | Glu | Asp | Glu | Glu | Glu | Glu | Pro | Ser | Ser | |
| | 400 | | | | | 405 | | | | | 410 | | | | | |
| ttc | aag | gcc | gac | agt | cct | gcc | gag | gcc | tcc | ctt | gca | tct | gac | cct | cat | 1539 |
| Phe | Lys | Ala | Asp | Ser | Pro | Ala | Glu | Ala | Ser | Leu | Ala | Ser | Asp | Pro | His | |
| 415 | | | | | 420 | | | | | 425 | | | | | 430 | |
| gaa | ctt | ccc | acc | acc | tct | ttt | tgc | cct | aac | tgt | att | cgc | cta | aag | aag | 1587 |
| Glu | Leu | Pro | Thr | Thr | Ser | Phe | Cys | Pro | Asn | Cys | Ile | Arg | Leu | Lys | Lys | |
| | | | | 435 | | | | | 440 | | | | | 445 | | |
| aag | gtt | cgg | gag | ctc | cag | gca | gaa | tta | gac | atg | ctt | aag | tct | ggg | aaa | 1635 |
| Lys | Val | Arg | Glu | Leu | Gln | Ala | Glu | Leu | Asp | Met | Leu | Lys | Ser | Gly | Lys | |
| | | | | 450 | | | | | 455 | | | | | 460 | | |
| ctt | cct | gag | ccc | ccc | gta | ttg | cca | cca | cag | gta | ctg | gag | ctc | cca | gag | 1683 |
| Leu | Pro | Glu | Pro | Pro | Val | Leu | Pro | Pro | Gln | Val | Leu | Glu | Leu | Pro | Glu | |
| | | 465 | | | | | 470 | | | | | 475 | | | | |
| ttc | tcg | gac | cct | gca | ggt | aag | ttg | gtt | tgg | atg | aga | tta | ttg | tcg | gag | 1731 |
| Phe | Ser | Asp | Pro | Ala | Gly | Lys | Leu | Val | Trp | Met | Arg | Leu | Leu | Ser | Glu | |
| | 480 | | | | | 485 | | | | | 490 | | | | | |
| ggc | aga | gta | cgc | agt | ggg | ctg | tgt | gga | ggg | tagcctaaag ctctctgtgg | | | | | | 1781 |
| Gly | Arg | Val | Arg | Ser | Gly | Leu | Cys | Gly | Gly | | | | | | | |
| 495 | | | | | 500 | | | | | | | | | | | | aaaccacctt ccgggagacc tgaggagtgt aacgtggagg cggctacctc cgtgggtggg      1841 agcccaggtc ctcagtgtct ctggcagacc catcggcagc tctgccaggt gctccatgtg      1901 ttgcccttgt atcctccttg tcaataaagg aagttccgct gcagaagggg tgtgtgctgt      1961 gttcttgacc cgttgccttt ctctggtact ggtgtcttac cccaaagccc aatttctaaa      2021 cccagtcttt ctctgtcccc agtctcaagc agggtgtccc actggagaga tctcttggct      2081 tccctaactt agtccaggaa cacagccttg ttcttctctt cctgaatctc tgtcctgcca      2141 cacatggtcc cagttcccta gcctggagtt ctagaaggat ggagagtgag gggatccagg      2201 ccattca      2208

<210> SEQ ID NO 6
<211> LENGTH: 504
<212> TYPE: PRT
<213> ORGANISM: Human

<400> SEQUENCE: 6

Met Leu Lys Met Ala Glu Pro Ile Ala Ser Leu Met Ile Val Glu Cys
1               5                   10                  15

Arg Ala Cys Leu Arg Cys Ser Pro Leu Phe Leu Tyr Gln Arg Glu Lys
                20                  25                  30

Asp Arg Met Thr Glu Asn Met Lys Glu Cys Leu Ala Gln Thr Asn Ala
            35                  40                  45

Ala Val Gly Asp Met Val Thr Val Asn Pro Ser Gln Glu Tyr Gly
        50                  55                  60

Gln Pro Cys Ser Arg Arg Pro Asp Ser Ser Ala Met Glu Val Glu Pro
65                  70                  75                  80

Lys Lys Leu Lys Gly Lys Arg Asp Leu Ile Val Pro Lys Ser Phe Gln
                85                  90                  95

-continued

```
Gln Val Asp Phe Trp Phe Cys Glu Ser Cys Gln Glu Tyr Phe Val Asp
             100                 105                 110

Glu Cys Pro Asn His Gly Pro Val Phe Val Ser Asp Thr Pro Val
         115                 120                 125

Pro Val Gly Ile Pro Asp Arg Ala Ala Leu Thr Ile Pro Gln Gly Met
         130                 135                 140

Glu Val Val Lys Asp Thr Ser Gly Glu Ser Asp Val Arg Cys Val Asn
145                 150                 155                 160

Glu Val Ile Pro Lys Gly His Ile Phe Gly Pro Tyr Glu Gly Gln Ile
                 165                 170                 175

Ser Thr Gln Asp Lys Ser Ala Gly Phe Phe Ser Trp Leu Ile Val Asp
             180                 185                 190

Lys Asn Asn Arg Tyr Lys Ser Ile Asp Gly Ser Asp Glu Thr Glu Ala
         195                 200                 205

Asn Trp Met Arg Tyr Val Val Ile Ser Arg Glu Glu Arg Glu Gln Asn
     210                 215                 220

Leu Leu Ala Phe Gln His Ser Glu Arg Ile Tyr Phe Arg Ala Cys Arg
225                 230                 235                 240

Asp Ile Arg Pro Gly Glu Trp Leu Arg Val Trp Tyr Ser Glu Asp Tyr
                 245                 250                 255

Met Lys Arg Leu His Ser Met Ser Gln Glu Thr Ile His Arg Asn Leu
             260                 265                 270

Ala Arg Gly Glu Lys Arg Leu Gln Arg Glu Lys Ser Glu Gln Val Leu
         275                 280                 285

Asp Asn Pro Glu Asp Leu Arg Gly Pro Ile His Leu Ser Val Leu Arg
     290                 295                 300

Gln Gly Lys Ser Pro Tyr Lys Arg Gly Phe Asp Glu Gly Asp Val His
305                 310                 315                 320

Pro Gln Ala Lys Lys Lys Ile Asp Leu Ile Phe Lys Asp Val Leu
                 325                 330                 335

Glu Ala Ser Leu Glu Ser Ala Lys Val Glu Ala His Gln Leu Ala Leu
             340                 345                 350

Ser Thr Ser Leu Val Ile Arg Lys Val Pro Lys Tyr Gln Asp Asp Ala
         355                 360                 365

Tyr Ser Gln Cys Ala Thr Thr Met Thr His Gly Val Gln Asn Ile Gly
     370                 375                 380

Gln Thr Gln Gly Glu Gly Asp Trp Lys Val Pro Gln Gly Val Ser Lys
385                 390                 395                 400

Glu Pro Gly Gln Leu Glu Asp Glu Glu Glu Pro Ser Ser Phe Lys
                 405                 410                 415

Ala Asp Ser Pro Ala Glu Ala Ser Leu Ala Ser Asp Pro His Glu Leu
             420                 425                 430

Pro Thr Thr Ser Phe Cys Pro Asn Cys Ile Arg Leu Lys Lys Lys Val
         435                 440                 445

Arg Glu Leu Gln Ala Glu Leu Asp Met Leu Lys Ser Gly Lys Leu Pro
     450                 455                 460

Glu Pro Pro Val Leu Pro Gln Val Leu Glu Leu Pro Glu Phe Ser
465                 470                 475                 480

Asp Pro Ala Gly Lys Leu Val Trp Met Arg Leu Leu Ser Glu Gly Arg
                 485                 490                 495

Val Arg Ser Gly Leu Cys Gly Gly
             500
```

<210> SEQ ID NO 7
<211> LENGTH: 1437
<212> TYPE: DNA
<213> ORGANISM: Human
<220> FEATURE:
<221> NAME/KEY: CDS
<222> LOCATION: (61)...(1161)

<400> SEQUENCE: 7

```
cccgcccacc tccccgtcg gcccggccgt ccccggcgc cggggagctc cgggccgccc         60 atg atg ggc tcc gtg ctc ccg gct gag gcc ctg gtg ctc aag acc ggg        108
Met Met Gly Ser Val Leu Pro Ala Glu Ala Leu Val Leu Lys Thr Gly
1               5                   10                  15 ctg aag gcg ccg gga ctg gcg ctg gcc gag gtt atc acc tcc gac atc        156
Leu Lys Ala Pro Gly Leu Ala Leu Ala Glu Val Ile Thr Ser Asp Ile
            20                  25                  30 ctg cac agc ttc ctg tac ggc cgc tgg cgc aac gtg ctc ggg gag cag        204
Leu His Ser Phe Leu Tyr Gly Arg Trp Arg Asn Val Leu Gly Glu Gln
        35                  40                  45 ctc ttc gag gac aag agc cac cac gcc agc ccc aag aca gcc ttc acc        252
Leu Phe Glu Asp Lys Ser His His Ala Ser Pro Lys Thr Ala Phe Thr
    50                  55                  60 gcc gag gtg ctg gcg cag tcc ttc tcc ggc gaa gtg cag aag ctg tcc        300
Ala Glu Val Leu Ala Gln Ser Phe Ser Gly Glu Val Gln Lys Leu Ser
65                  70                  75                  80 agc ctg gtg ctg cct gcg gag gtg atc atc gct cag agc tcc atc cct        348
Ser Leu Val Leu Pro Ala Glu Val Ile Ile Ala Gln Ser Ser Ile Pro
                85                  90                  95 ggc gag ggc ctc ggc atc ttc tcc aag acg tgg atc aag gcg gga acc        396
Gly Glu Gly Leu Gly Ile Phe Ser Lys Thr Trp Ile Lys Ala Gly Thr
            100                 105                 110 gag atg ggc ccc ttc acc ggc cgc gtg atc gcc ccg gag cac gtg gac        444
Glu Met Gly Pro Phe Thr Gly Arg Val Ile Ala Pro Glu His Val Asp
        115                 120                 125 atc tgc aag aac aac aac ctc atg tgg gag gtg ttc aat gag gat ggc        492
Ile Cys Lys Asn Asn Asn Leu Met Trp Glu Val Phe Asn Glu Asp Gly
    130                 135                 140 acg gtg cgc tac ttc atc gat gcc agc cag gag gac cac cgg agc tgg        540
Thr Val Arg Tyr Phe Ile Asp Ala Ser Gln Glu Asp His Arg Ser Trp
145                 150                 155                 160 atg acc tac atc aag tgt gca cgt aac gaa cag gag cag aac ctg gag        588
Met Thr Tyr Ile Lys Cys Ala Arg Asn Glu Gln Glu Gln Asn Leu Glu
                165                 170                 175 gtg gtc cag atc ggc acc agc atc ttc tac aag gcc att gag atg atc        636
Val Val Gln Ile Gly Thr Ser Ile Phe Tyr Lys Ala Ile Glu Met Ile
            180                 185                 190 cca cct gac cag gaa ctg ctg gtg tgg tac gga aac tca cac aac acc        684
Pro Pro Asp Gln Glu Leu Leu Val Trp Tyr Gly Asn Ser His Asn Thr
        195                 200                 205 ttc ctg ggg atc cca ggt gtg ccc ggg cta gag gag gac cag aaa aag        732
Phe Leu Gly Ile Pro Gly Val Pro Gly Leu Glu Glu Asp Gln Lys Lys
    210                 215                 220 aac aag cat gag gac ttc cac ccg gcg gac tcg gcg gct ggc ccc gcg        780
Asn Lys His Glu Asp Phe His Pro Ala Asp Ser Ala Ala Gly Pro Ala
225                 230                 235                 240 ggc cgc atg cga tgc gtc atc tgc cac cgc ggc ttc aac tcg cgc agc        828
Gly Arg Met Arg Cys Val Ile Cys His Arg Gly Phe Asn Ser Arg Ser
                245                 250                 255 aac ctg cgc tcg cac atg cgc atc cac acg ctg gac aag ccc ttc gtg        876
Asn Leu Arg Ser His Met Arg Ile His Thr Leu Asp Lys Pro Phe Val
```

```
                260                 265                 270
tgc cgc ttc tgc aac cgc cgc ttc agc cag tcg tcc acg ctg cgc aac      924
Cys Arg Phe Cys Asn Arg Arg Phe Ser Gln Ser Ser Thr Leu Arg Asn
        275                 280                 285 cac gtg cgc ctg cac acg ggc gag cgc ccc tac aag tgc cag gtg tgc      972
His Val Arg Leu His Thr Gly Glu Arg Pro Tyr Lys Cys Gln Val Cys
290                 295                 300 cag agc gcc tac tcg cag ctg gcc ggc ctg cgc gcc cac cag aag agc     1020
Gln Ser Ala Tyr Ser Gln Leu Ala Gly Leu Arg Ala His Gln Lys Ser
305                 310                 315                 320 gcg cgg cac cgg ccg ccc agc acc gcg ctg cag gca cac tcg ccc gcg     1068
Ala Arg His Arg Pro Pro Ser Thr Ala Leu Gln Ala His Ser Pro Ala
            325                 330                 335 ctg ccc gcc ccg cac gcg cac gcg ccc gcg ctc gcc gcc gcc gcc gcc     1116
Leu Pro Ala Pro His Ala His Ala Pro Ala Leu Ala Ala Ala Ala Ala
            340                 345                 350 gcc gcc gcc gcc gcc gcc gcg cac cac ctg ccg gcc atg gtg ctg         1161
Ala Ala Ala Ala Ala Ala Ala His His Leu Pro Ala Met Val Leu
355                 360                 365 tgagcgcgcc cgcgccccg ccgggccccg cgcgctcctg ggtccccggc acccggccc     1221 cgcagcgcga ctcgccctcc agccccaacc cccggcccgg cgccgccgcg gagccccgcg   1281
cgctggggtt gcgccccgga ggcggatctc aggcaccccc gccttggccc gtgtcgcaga   1341
tgaggacact gagggcggcg tccctcaccc aggccacgca gctggtgcgg ctgttcggcc   1401
gcctcctctg ggagggggtc cccctgcctg gcctcg                            1437

<210> SEQ ID NO 8
<211> LENGTH: 367
<212> TYPE: PRT
<213> ORGANISM: Human

<400> SEQUENCE: 8

Met Met Gly Ser Val Leu Pro Ala Glu Ala Leu Val Leu Lys Thr Gly
1               5                   10                  15

Leu Lys Ala Pro Gly Leu Ala Leu Ala Glu Val Ile Thr Ser Asp Ile
            20                  25                  30

Leu His Ser Phe Leu Tyr Gly Arg Trp Arg Asn Val Leu Gly Glu Gln
        35                  40                  45

Leu Phe Glu Asp Lys Ser His His Ala Ser Pro Lys Thr Ala Phe Thr
    50                  55                  60

Ala Glu Val Leu Ala Gln Ser Phe Ser Gly Glu Val Gln Lys Leu Ser
65                  70                  75                  80

Ser Leu Val Leu Pro Ala Glu Val Ile Ile Ala Gln Ser Ser Ile Pro
                85                  90                  95

Gly Glu Gly Leu Gly Ile Phe Ser Lys Thr Trp Ile Lys Ala Gly Thr
            100                 105                 110

Glu Met Gly Pro Phe Thr Gly Arg Val Ile Ala Pro Glu His Val Asp
        115                 120                 125

Ile Cys Lys Asn Asn Asn Leu Met Trp Glu Val Phe Asn Glu Asp Gly
    130                 135                 140

Thr Val Arg Tyr Phe Ile Asp Ala Ser Gln Glu Asp His Arg Ser Trp
145                 150                 155                 160

Met Thr Tyr Ile Lys Cys Ala Arg Asn Glu Gln Glu Gln Asn Leu Glu
                165                 170                 175

Val Val Gln Ile Gly Thr Ser Ile Phe Tyr Lys Ala Ile Glu Met Ile
            180                 185                 190
```

-continued

```
Pro Pro Asp Gln Glu Leu Leu Val Trp Tyr Gly Asn Ser His Asn Thr
        195                 200                 205

Phe Leu Gly Ile Pro Gly Val Pro Gly Leu Glu Glu Asp Gln Lys Lys
        210                 215                 220

Asn Lys His Glu Asp Phe His Pro Ala Asp Ser Ala Ala Gly Pro Ala
225                 230                 235                 240

Gly Arg Met Arg Cys Val Ile Cys His Arg Gly Phe Asn Ser Arg Ser
                245                 250                 255

Asn Leu Arg Ser His Met Arg Ile His Thr Leu Asp Lys Pro Phe Val
            260                 265                 270

Cys Arg Phe Cys Asn Arg Arg Phe Ser Gln Ser Ser Thr Leu Arg Asn
        275                 280                 285

His Val Arg Leu His Thr Gly Glu Arg Pro Tyr Lys Cys Gln Val Cys
        290                 295                 300

Gln Ser Ala Tyr Ser Gln Leu Ala Gly Leu Arg Ala His Gln Lys Ser
305                 310                 315                 320

Ala Arg His Arg Pro Pro Ser Thr Ala Leu Gln Ala His Ser Pro Ala
                325                 330                 335

Leu Pro Ala Pro His Ala His Ala Pro Ala Leu Ala Ala Ala Ala Ala
            340                 345                 350

Ala Ala Ala Ala Ala Ala His His Leu Pro Ala Met Val Leu
        355                 360                 365

<210> SEQ ID NO 9
<211> LENGTH: 3234
<212> TYPE: DNA
<213> ORGANISM: Human
<220> FEATURE:
<221> NAME/KEY: CDS
<222> LOCATION: (262)...(2412)

<400> SEQUENCE: 9
ccatgtgacc ctctcgggtg ggactctgca gctgcttcgc agcgcaactc tctcaccaaa      60
ctccgcgccc ttgcgctagc ggtgccaaaa ggctcccgcc ccgattgaaa aggcgcagtg     120
catgcccgcc cgcgtcactc gcgggcgga ggacgcacgt cggggcgcgg ctctctggct      180
agcgcgcagc tccagctctg tcactcgcgc ccttccaagg acctggagca cccgagcgcc     240
tgcctggtgg cggcggcaac a atg cac gga gcc gcc aga gcg cca gcc acc        291
                        Met His Gly Ala Ala Arg Ala Pro Ala Thr
                         1               5                  10 agc gtg agt gcc gac tgc tgc atc ccg gcc ggc ttg cgc ctc gga ccg       339
Ser Val Ser Ala Asp Cys Cys Ile Pro Ala Gly Leu Arg Leu Gly Pro
                15                  20                  25 gtg cct ggt acc ttc aag ctg ggc aag tac ctg tca gac cgc agg gag       387
Val Pro Gly Thr Phe Lys Leu Gly Lys Tyr Leu Ser Asp Arg Arg Glu
            30                  35                  40 ccc ggg cct aag aaa aag gta ttg acc att cag acc tct gcc cac cag       435
Pro Gly Pro Lys Lys Lys Val Leu Thr Ile Gln Thr Ser Ala His Gln
        45                  50                  55 gtg cgc atg gtg aga ggg gag ctg gtg gac gag tcg ggg ggc tcc cct       483
Val Arg Met Val Arg Gly Glu Leu Val Asp Glu Ser Gly Gly Ser Pro
60                  65                  70 ctg gag tgg ata ggg tta atc cgg gca gcc aga aac tcc cag gaa cag       531
Leu Glu Trp Ile Gly Leu Ile Arg Ala Ala Arg Asn Ser Gln Glu Gln
75                  80                  85                  90 act ctg gaa gct att gca gac tta ccc gga gga cag atc ttc tac cga       579
Thr Leu Glu Ala Ile Ala Asp Leu Pro Gly Gly Gln Ile Phe Tyr Arg
```

-continued

```
                95                    100                       105
gca ttg cga gac gtc cag cca ggg gag gag ctg aca gtg tgg tat tct      627
Ala Leu Arg Asp Val Gln Pro Gly Glu Glu Leu Thr Val Trp Tyr Ser
            110                 115                     120 aac tcc ttg gct cag tgg ttc gac atc ccc acc aca gcg act ccg act      675
Asn Ser Leu Ala Gln Trp Phe Asp Ile Pro Thr Thr Ala Thr Pro Thr
            125                 130                 135 cac gac gag aaa ggg gag gag cgc tac atc tgc tgg tac tgc tgg agg      723
His Asp Glu Lys Gly Glu Glu Arg Tyr Ile Cys Trp Tyr Cys Trp Arg
        140                 145                 150 acg ttt aga tac ccc aac agc ctt aag gca cac ctg cgt ttc cac tgc      771
Thr Phe Arg Tyr Pro Asn Ser Leu Lys Ala His Leu Arg Phe His Cys
155                 160                 165                 170 gtg ttc agc ggc ggt gga ggc ggc gcc ttc ctg cac cac gaa cac gcg      819
Val Phe Ser Gly Gly Gly Gly Gly Ala Phe Leu His His Glu His Ala
                175                 180                 185 gct cgc caa ggc gcc gtc cca gcg gct gat ggc ctc ggt ctc tcc cca      867
Ala Arg Gln Gly Ala Val Pro Ala Ala Asp Gly Leu Gly Leu Ser Pro
            190                 195                 200 aaa ccc ccg gcg ccc gat ttc gcc gcg cct tcc cag gca gga act ttg      915
Lys Pro Pro Ala Pro Asp Phe Ala Ala Pro Ser Gln Ala Gly Thr Leu
            205                 210                 215 cga ccc cac ccc ctg ggc ccg cca cca gtt cag gcc tgc ggt gcg cgg      963
Arg Pro His Pro Leu Gly Pro Pro Pro Val Gln Ala Cys Gly Ala Arg
        220                 225                 230 gag ggc atc aag cgc gag gcc tct tcc gcg ccc tcg gcc acc tcg ccg     1011
Glu Gly Ile Lys Arg Glu Ala Ser Ser Ala Pro Ser Ala Thr Ser Pro
235                 240                 245                 250 acc cca ggc aag tgg ggg cag ccc aag aag ggc aag gag cag ctg gac     1059
Thr Pro Gly Lys Trp Gly Gln Pro Lys Lys Gly Lys Glu Gln Leu Asp
                255                 260                 265 cgt gcc ctg gac atg agc gga gcc gcc cga gga caa ggg cac ttc ctc     1107
Arg Ala Leu Asp Met Ser Gly Ala Ala Arg Gly Gln Gly His Phe Leu
            270                 275                 280 ggc atc gtg ggc ggc tcc tcg gcg ggg gtc ggc agc ctg gct ttc tac     1155
Gly Ile Val Gly Gly Ser Ser Ala Gly Val Gly Ser Leu Ala Phe Tyr
            285                 290                 295 ccc ggc gtg cgc tca gct ttc aag ccc gcc ggc cta gcg agg gcg gcg     1203
Pro Gly Val Arg Ser Ala Phe Lys Pro Ala Gly Leu Ala Arg Ala Ala
300                 305                 310 gcg gcc gct cac ggc gac ccc tac cgg gag gag agc agc agc aag caa     1251
Ala Ala Ala His Gly Asp Pro Tyr Arg Glu Glu Ser Ser Ser Lys Gln
315                 320                 325                 330 gga gcc ggc ctc gct ttg ggc agg ctg ctg ggc ggg ggc cgg gcg tgc     1299
Gly Ala Gly Leu Ala Leu Gly Arg Leu Leu Gly Gly Gly Arg Ala Cys
                335                 340                 345 ggg cgc ccc ggg agc ggg gag aac tcg gcg gcg ggc ggc gcg ggt cac     1347
Gly Arg Pro Gly Ser Gly Glu Asn Ser Ala Ala Gly Gly Ala Gly His
            350                 355                 360 cac cat cac cac cac gcg cac cac cac cat ccc aag tgc ctg ctc         1395
His His His His His Ala His His His His Pro Lys Cys Leu Leu
            365                 370                 375 gct ggg gac ccg ccg ccg ccg ccg cct ggc ctg ccc tgc tct ggg         1443
Ala Gly Asp Pro Pro Pro Pro Pro Pro Gly Leu Pro Cys Ser Gly
380                 385                 390 gcc ctg cgc ggc ttc cct ctg ctc tcc gtc ccc ccg gaa gag gcg tcc     1491
Ala Leu Arg Gly Phe Pro Leu Leu Ser Val Pro Pro Glu Glu Ala Ser
395                 400                 405                 410 gcc ttc aag cac gtg gag cgc gcc ccg ccc gca gcc gcc gcg ctg cca     1539
```

-continued

```
Ala Phe Lys His Val Glu Arg Ala Pro Ala Ala Ala Leu Pro
            415                 420                 425 gga gcg cgt tat gcg cag ctg ccc cct gcg ccg ggg ttg ccc ctc gag   1587
Gly Ala Arg Tyr Ala Gln Leu Pro Pro Ala Pro Gly Leu Pro Leu Glu
            430                 435                 440 cgc tgc gcg ctg ccg ccc ctc gac ccg ggc ggt ctc aaa gcc tat ccg   1635
Arg Cys Ala Leu Pro Pro Leu Asp Pro Gly Gly Leu Lys Ala Tyr Pro
            445                 450                 455 ggt ggt gag tgc agc cac ctg ccc gcc gtc atg ccg gcc ttt aca gtc   1683
Gly Gly Glu Cys Ser His Leu Pro Ala Val Met Pro Ala Phe Thr Val
        460                 465                 470 tac aac ggg gag ctg ctc tac ggc tca ccg gcc acc acc gct tat tac   1731
Tyr Asn Gly Glu Leu Leu Tyr Gly Ser Pro Ala Thr Thr Ala Tyr Tyr
475                 480                 485                 490 ccg ctc aaa ttg cac ttc ggc ggg ctg ctg aag tat ccg gag tcc atc   1779
Pro Leu Lys Leu His Phe Gly Gly Leu Leu Lys Tyr Pro Glu Ser Ile
                495                 500                 505 tcc tac ttc agc ggg cct gca gcg gcc gcc cta agc ccc gcc gag ctg   1827
Ser Tyr Phe Ser Gly Pro Ala Ala Ala Ala Leu Ser Pro Ala Glu Leu
                510                 515                 520 ggg tcg ctg gcc agc atc gac cga gag atc gcc atg cac aat cag cag   1875
Gly Ser Leu Ala Ser Ile Asp Arg Glu Ile Ala Met His Asn Gln Gln
            525                 530                 535 ctg tcc gag atg gct gcc ggg aag ggt cgc gga cgc ctg gac tcg ggg   1923
Leu Ser Glu Met Ala Ala Gly Lys Gly Arg Gly Arg Leu Asp Ser Gly
            540                 545                 550 acg ttg cca ccg gcc gtc gcg gcg gcg gga ggc acc ggg ggc ggc ggc   1971
Thr Leu Pro Pro Ala Val Ala Ala Ala Gly Gly Thr Gly Gly Gly Gly
555                 560                 565                 570 agc gga ggc agc ggc gca ggt aag ccc aag acc ggc cac ctg tgc ctc   2019
Ser Gly Gly Ser Gly Ala Gly Lys Pro Lys Thr Gly His Leu Cys Leu
                575                 580                 585 tac tgt ggc aag ctg tac tcg cgc aag tat ggg ctc aag atc cac atg   2067
Tyr Cys Gly Lys Leu Tyr Ser Arg Lys Tyr Gly Leu Lys Ile His Met
                590                 595                 600 cgg acg cac acg ggc tac aag cca ctc aag tgc aaa gtc tgt ctg cgg   2115
Arg Thr His Thr Gly Tyr Lys Pro Leu Lys Cys Lys Val Cys Leu Arg
            605                 610                 615 ccc ttc ggc gac ccc agc aat ctc aac aag cac atc cgg ctg cac gcc   2163
Pro Phe Gly Asp Pro Ser Asn Leu Asn Lys His Ile Arg Leu His Ala
            620                 625                 630 gag ggc aat acg ccc tac cgc tgc gag ttc tgc ggc aag gta ctt gtg   2211
Glu Gly Asn Thr Pro Tyr Arg Cys Glu Phe Cys Gly Lys Val Leu Val
635                 640                 645                 650 cgc cgc cgg gac ctg gag cga cat gtc aag tcc cgc cac cct ggc cag   2259
Arg Arg Arg Asp Leu Glu Arg His Val Lys Ser Arg His Pro Gly Gln
                655                 660                 665 agt ctg ctc gcc aaa gcg ggc gac ggc ccg ggt gcc gag ccc ggc tat   2307
Ser Leu Leu Ala Lys Ala Gly Asp Gly Pro Gly Ala Glu Pro Gly Tyr
                670                 675                 680 ccc ccg gag cct ggg gat ccc aag agc gac gac agt gac gtg gac gtc   2355
Pro Pro Glu Pro Gly Asp Pro Lys Ser Asp Asp Ser Asp Val Asp Val
            685                 690                 695 tgc ttc aca gac gac cag agc gac ccc gag gtt ggg ggc ggg ggg gag   2403
Cys Phe Thr Asp Asp Gln Ser Asp Pro Glu Val Gly Gly Gly Gly Glu
            700                 705                 710 cgc gac ttg taacgagtct tcccgggaag gggcggggtg aggacagaga            2452
Arg Asp Leu
715
```

-continued

```
ggagtcgagg gtttattctc gcagtagagg aactcctggt ggtgggaaga gggacccaat    2512
ggacaaaacc gttttgtttt ttgagagggc gccagatttg aaacagtgag aggtcccaca    2572
tctggtgctg aaactcagag caacagttca gaggtggcgt aaatctggcc acctggagag    2632
ctcgagtgcc accagtacct ccgcaccccg ggcctctgga cttcttggat gagctcaccc    2692
tgaaccgccc aggcggtctg ctcttggtgt tcagaatcac atcaatgcga acgtcacagc    2752
gccttcgagg gcgcagattt taactgccac gtattttta gttgtacttt tctgtggagg    2812
aaattgtgcc ttttgaaacg acgttttgtg tgtgtatttc acgttagcat ttcattgcat    2872
aggcaaaaca ctagtcacaa ttgggtagat gtgacatcca tatacttgtt tacatttat    2932 ctgttctcat gtcaaagact actccttgcc ccattgaata tatagtggta gcaggtgtac    2992
aaattggtca agttgcaatt atttatgaga gaataatgat aaatgtaaaa tatctaaagc    3052
atgaatctaa gagcacgcaa tatataattt taaagaaaat attctatttg gtagaataca    3112
aatgtggtgt gtgttgtttt ataatgactg ctgtacagtg ggtatagtat tttggttttg    3172
gttccagatt gtgcaatctt taagaaaaat aaagatacaa cgagagtttt tgttcactta    3232
gt                                                                    3234
```

<210> SEQ ID NO 10
<211> LENGTH: 717
<212> TYPE: PRT
<213> ORGANISM: Human

<400> SEQUENCE: 10

```
Met His Gly Ala Ala Arg Ala Pro Ala Thr Ser Val Ser Ala Asp Cys
1               5                   10                  15

Cys Ile Pro Ala Gly Leu Arg Leu Gly Pro Val Pro Gly Thr Phe Lys
            20                  25                  30

Leu Gly Lys Tyr Leu Ser Asp Arg Arg Glu Pro Gly Pro Lys Lys Lys
        35                  40                  45

Val Leu Thr Ile Gln Thr Ser Ala His Gln Val Arg Met Val Arg Gly
    50                  55                  60

Glu Leu Val Asp Glu Ser Gly Gly Ser Pro Leu Glu Trp Ile Gly Leu
65                  70                  75                  80

Ile Arg Ala Ala Arg Asn Ser Gln Glu Gln Thr Leu Glu Ala Ile Ala
                85                  90                  95

Asp Leu Pro Gly Gly Gln Ile Phe Tyr Arg Ala Leu Arg Asp Val Gln
            100                 105                 110

Pro Gly Glu Glu Leu Thr Val Trp Tyr Ser Asn Ser Leu Ala Gln Trp
        115                 120                 125

Phe Asp Ile Pro Thr Thr Ala Thr Pro Thr His Asp Glu Lys Gly Glu
    130                 135                 140

Glu Arg Tyr Ile Cys Trp Tyr Cys Trp Arg Thr Phe Arg Tyr Pro Asn
145                 150                 155                 160

Ser Leu Lys Ala His Leu Arg Phe His Cys Val Phe Ser Gly Gly Gly
                165                 170                 175

Gly Gly Ala Phe Leu His His Glu His Ala Ala Arg Gln Gly Ala Val
            180                 185                 190

Pro Ala Ala Asp Gly Leu Gly Leu Ser Pro Lys Pro Ala Pro Ala Asp
        195                 200                 205

Phe Ala Ala Pro Ser Gln Ala Gly Thr Leu Arg Pro His Pro Leu Gly
    210                 215                 220

Pro Pro Pro Val Gln Ala Cys Gly Ala Arg Glu Gly Ile Lys Arg Glu
```

|   |   |   |   |   |   |   |   |   |   |   |   |   |   |   |
|---|---|---|---|---|---|---|---|---|---|---|---|---|---|---|
| 225 | | | | 230 | | | | 235 | | | | 240 | | |

Ala Ser Ser Ala Pro Ser Ala Thr Ser Pro Thr Pro Gly Lys Trp Gly
                  245                  250                  255

Gln Pro Lys Lys Gly Lys Glu Gln Leu Asp Arg Ala Leu Asp Met Ser
             260                  265                  270

Gly Ala Ala Arg Gly Gln Gly His Phe Leu Gly Ile Val Gly Gly Ser
            275                  280                  285

Ser Ala Gly Val Gly Ser Leu Ala Phe Tyr Pro Gly Val Arg Ser Ala
    290                  295                  300

Phe Lys Pro Ala Gly Leu Ala Arg Ala Ala Ala Ala His Gly Asp
305                  310                  315              320

Pro Tyr Arg Glu Glu Ser Ser Ser Lys Gln Gly Ala Gly Leu Ala Leu
            325                  330                  335

Gly Arg Leu Leu Gly Gly Gly Arg Ala Cys Gly Arg Pro Gly Ser Gly
            340                  345                  350

Glu Asn Ser Ala Ala Gly Gly Ala Gly His His His His His His Ala
        355                  360                  365

His His His His Pro Lys Cys Leu Leu Ala Gly Asp Pro Pro
    370                  375                  380

Pro Pro Pro Gly Leu Pro Cys Ser Gly Ala Leu Arg Gly Phe Pro
385                  390                  395              400

Leu Leu Ser Val Pro Pro Glu Glu Ala Ser Ala Phe Lys His Val Glu
            405                  410                  415

Arg Ala Pro Pro Ala Ala Ala Ala Leu Pro Gly Ala Arg Tyr Ala Gln
            420                  425                  430

Leu Pro Pro Ala Pro Gly Leu Pro Leu Glu Arg Cys Ala Leu Pro Pro
            435                  440                  445

Leu Asp Pro Gly Gly Leu Lys Ala Tyr Pro Gly Gly Glu Cys Ser His
    450                  455                  460

Leu Pro Ala Val Met Pro Ala Phe Thr Val Tyr Asn Gly Glu Leu Leu
465                  470                  475              480

Tyr Gly Ser Pro Ala Thr Thr Ala Tyr Tyr Pro Leu Lys Leu His Phe
            485                  490                  495

Gly Gly Leu Leu Lys Tyr Pro Glu Ser Ile Ser Tyr Phe Ser Gly Pro
            500                  505                  510

Ala Ala Ala Ala Leu Ser Pro Ala Glu Leu Gly Ser Leu Ala Ser Ile
        515                  520                  525

Asp Arg Glu Ile Ala Met His Asn Gln Gln Leu Ser Glu Met Ala Ala
    530                  535                  540

Gly Lys Gly Arg Gly Arg Leu Asp Ser Gly Thr Leu Pro Pro Ala Val
545                  550                  555              560

Ala Ala Ala Gly Gly Thr Gly Gly Gly Ser Gly Gly Ser Gly Ala
            565                  570                  575

Gly Lys Pro Lys Thr Gly His Leu Cys Leu Tyr Cys Gly Lys Leu Tyr
            580                  585                  590

Ser Arg Lys Tyr Gly Leu Lys Ile His Met Arg Thr His Thr Gly Tyr
        595                  600                  605

Lys Pro Leu Lys Cys Lys Val Cys Leu Arg Pro Phe Gly Asp Pro Ser
    610                  615                  620

Asn Leu Asn Lys His Ile Arg Leu His Ala Glu Gly Asn Thr Pro Tyr
625                  630                  635              640

Arg Cys Glu Phe Cys Gly Lys Val Leu Val Arg Arg Arg Asp Leu Glu
            645                  650                  655

```
Arg His Val Lys Ser Arg His Pro Gly Gln Ser Leu Leu Ala Lys Ala
            660                 665                 670

Gly Asp Gly Pro Gly Ala Glu Pro Gly Tyr Pro Pro Glu Pro Gly Asp
        675                 680                 685

Pro Lys Ser Asp Asp Ser Asp Val Asp Val Cys Phe Thr Asp Asp Gln
        690                 695                 700

Ser Asp Pro Glu Val Gly Gly Gly Glu Arg Asp Leu
705                 710                 715

<210> SEQ ID NO 11
<211> LENGTH: 2210
<212> TYPE: DNA
<213> ORGANISM: Human
<220> FEATURE:
<221> NAME/KEY: CDS
<222> LOCATION: (203)...(1915)

<400> SEQUENCE: 11
aattccctac cctcgacctg tcgatgcccc gcggccccgc ccgcctctt aagcctggct      60 cagccctcag ggcccgcccg aagtctaccg agcccgagtg gcctaccgag cccgagtggc     120
cccgcagcgt ccaggaggcg cccgctccgc ggtggcgctc ttggaggtgg tgtcggagag     180
ccgccgagcg tgcggtcccg gg atg gct cta ccc cgg cca agt gag gcc gtg     232
                         Met Ala Leu Pro Arg Pro Ser Glu Ala Val
                          1               5                  10 cct cag gac aag gtg tgc tac ccg ccg gag agc agc ccg cag aac ctg      280
Pro Gln Asp Lys Val Cys Tyr Pro Pro Glu Ser Ser Pro Gln Asn Leu
            15                  20                  25 gcc gcg tac tac acg cct ttc ccg tcc tat gga cac tac aga aac agc      328
Ala Ala Tyr Tyr Thr Pro Phe Pro Ser Tyr Gly His Tyr Arg Asn Ser
        30                  35                  40 ctg gcc acc gtg gag gaa gac ttc caa cct ttc cgg cag ctg gag gcc      376
Leu Ala Thr Val Glu Glu Asp Phe Gln Pro Phe Arg Gln Leu Glu Ala
    45                  50                  55 gca gcg tct gct gcc ccc gcc atg ccc ccc ttc ccc ttc cgg atg gcg      424
Ala Ala Ser Ala Ala Pro Ala Met Pro Pro Phe Pro Phe Arg Met Ala
60                  65                  70 cct ccc ttg ctg agc ccg ggt ctg ggc cta cag agg gag cct ctc tac      472
Pro Pro Leu Leu Ser Pro Gly Leu Gly Leu Gln Arg Glu Pro Leu Tyr
75                  80                  85                  90 gat ctg ccc tgg tac agc aag ctg cca ccg tgg tac cca att ccc cac      520
Asp Leu Pro Trp Tyr Ser Lys Leu Pro Pro Trp Tyr Pro Ile Pro His
                95                  100                 105 gtc ccc agg gaa gtg ccg ccc ttc ctg agc agc agc cac gag tac gcg      568
Val Pro Arg Glu Val Pro Pro Phe Leu Ser Ser Ser His Glu Tyr Ala
            110                 115                 120 ggt gcc agc agt gaa gat ctg ggc cac caa atc att ggt ggc gac aac      616
Gly Ala Ser Ser Glu Asp Leu Gly His Gln Ile Ile Gly Gly Asp Asn
        125                 130                 135 gag agt ggc ccg tgt tgt gga cct gac act tta att cca ccg ccc cct      664
Glu Ser Gly Pro Cys Cys Gly Pro Asp Thr Leu Ile Pro Pro Pro Pro
    140                 145                 150 gcg gat gct tct ctg tta cct gag ggg ctg agg acc tcc cag tta tta      712
Ala Asp Ala Ser Leu Leu Pro Glu Gly Leu Arg Thr Ser Gln Leu Leu
155                 160                 165                 170 cct tgc tca ccc agc aag cag tca gag gat ggt ccc aaa ccc tcc aac      760
Pro Cys Ser Pro Ser Lys Gln Ser Glu Asp Gly Pro Lys Pro Ser Asn
                175                 180                 185 caa gaa ggg aag tcc cct gct cgg ttc cag ttc acg gag gag gac ctg      808
```

```
                Gln Glu Gly Lys Ser Pro Ala Arg Phe Gln Phe Thr Glu Glu Asp Leu
                            190                 195                 200 cac ttc gtt ctg tac ggg gtc act ccc agc ctg gag cac cca gcc agc            856
His Phe Val Leu Tyr Gly Val Thr Pro Ser Leu Glu His Pro Ala Ser
            205                 210                 215 ctg cac cat gcg att tca ggc ctc ctg gtc ccc cca gac agc tct gga            904
Leu His His Ala Ile Ser Gly Leu Leu Val Pro Pro Asp Ser Ser Gly
            220                 225                 230 tct gat tct ctt cct caa act ctg gat aaa gac tcc ctt caa ctt cca            952
Ser Asp Ser Leu Pro Gln Thr Leu Asp Lys Asp Ser Leu Gln Leu Pro
235                 240                 245                 250 gaa ggt cta tgc ctc atg cag acg gtg ttt ggt gaa gtc cca cat ttt           1000
Glu Gly Leu Cys Leu Met Gln Thr Val Phe Gly Glu Val Pro His Phe
                255                 260                 265 ggt gtg ttc tgc agt agt ttt atc gcc aaa gga gtc agg ttt ggg ccc           1048
Gly Val Phe Cys Ser Ser Phe Ile Ala Lys Gly Val Arg Phe Gly Pro
                270                 275                 280 ttt caa ggt aaa gtg gtc aat gcc agt gaa gtg aag acc tac gga gac           1096
Phe Gln Gly Lys Val Val Asn Ala Ser Glu Val Lys Thr Tyr Gly Asp
            285                 290                 295 aat tct gtg atg tgg gag atc ttt gaa gat ggt cat ttg agc cac ttt           1144
Asn Ser Val Met Trp Glu Ile Phe Glu Asp Gly His Leu Ser His Phe
300                 305                 310 ata gat gga aaa gga ggt acg ggg aac tgg atg tcc tat gtc aac tgt           1192
Ile Asp Gly Lys Gly Gly Thr Gly Asn Trp Met Ser Tyr Val Asn Cys
315                 320                 325                 330 gcc cgc ttc ccc aag gag cag aac cta gtt gct gtg cag tgt caa ggg           1240
Ala Arg Phe Pro Lys Glu Gln Asn Leu Val Ala Val Gln Cys Gln Gly
                335                 340                 345 cat ata ttt tat gag agc tgc aaa gag atc cat cag aac caa gag ctc           1288
His Ile Phe Tyr Glu Ser Cys Lys Glu Ile His Gln Asn Gln Glu Leu
            350                 355                 360 ctt gtg tgg tat gga gac tgc tat gag aaa ttt ctg gat att cct gtg           1336
Leu Val Trp Tyr Gly Asp Cys Tyr Glu Lys Phe Leu Asp Ile Pro Val
            365                 370                 375 agc ctt cag gtc aca gag ccg ggg aag cag cca tct ggg ccc tct gaa           1384
Ser Leu Gln Val Thr Glu Pro Gly Lys Gln Pro Ser Gly Pro Ser Glu
380                 385                 390 gag tct gca gaa ggc tac aga tgt gaa aga tgt ggg aag gta ttt acc           1432
Glu Ser Ala Glu Gly Tyr Arg Cys Glu Arg Cys Gly Lys Val Phe Thr
395                 400                 405                 410 tac aaa tat tac aga gat aag cac ctc aag tac acc ccc tgt gtg gac           1480
Tyr Lys Tyr Tyr Arg Asp Lys His Leu Lys Tyr Thr Pro Cys Val Asp
                415                 420                 425 aag ggc gat agg aaa ttt ccc tgt tct ctc tgc aaa cga tcc ttt gag           1528
Lys Gly Asp Arg Lys Phe Pro Cys Ser Leu Cys Lys Arg Ser Phe Glu
            430                 435                 440 aag cgg gac cgg ctt cgg atc cac att ctt cat gtt cat gag aag cac           1576
Lys Arg Asp Arg Leu Arg Ile His Ile Leu His Val His Glu Lys His
            445                 450                 455 cgg cct cac aag tgt tct aca tgt ggg aaa tgt ttc tct cag tct tcc           1624
Arg Pro His Lys Cys Ser Thr Cys Gly Lys Cys Phe Ser Gln Ser Ser
            460                 465                 470 agc cta aac aaa cac atg cga gtc cac tct gga gac aga cca tac cag           1672
Ser Leu Asn Lys His Met Arg Val His Ser Gly Asp Arg Pro Tyr Gln
475                 480                 485                 490 tgt gtg tat tgt act aag agg ttc aca gcc tcc agc ata ctc cgc aca           1720
Cys Val Tyr Cys Thr Lys Arg Phe Thr Ala Ser Ser Ile Leu Arg Thr
                495                 500                 505
```

-continued

```
cac atc agg cag cac tcc ggg gag aag ccc ttc aaa tgc aag tac tgt    1768
His Ile Arg Gln His Ser Gly Glu Lys Pro Phe Lys Cys Lys Tyr Cys
            510                 515                 520 ggt aaa tct ttt gca tcc cat gct gcc cat gac agc cat gtc cgg cgt    1816
Gly Lys Ser Phe Ala Ser His Ala Ala His Asp Ser His Val Arg Arg
525                 530                 535 tca cac aag gag gat gat ggc tgc tca tgc agc atc tgt ggg aaa atc    1864
Ser His Lys Glu Asp Asp Gly Cys Ser Cys Ser Ile Cys Gly Lys Ile
        540                 545                 550 ttc tca gat caa gaa aca ttc tac tcc cac atg aag ttt cat gaa gac    1912
Phe Ser Asp Gln Glu Thr Phe Tyr Ser His Met Lys Phe His Glu Asp
555                 560                 565                 570 tac tagccctgcc aggcacaatg actcacgcct gtaatcccag cactttggga         1965
Tyr ggcagaggtg ggtggatcac tcaagtccag gagttcgaga ccagcctggg caacatggtg  2025
aaatcctgtc tctaccaaaa aaatacaaaa atcagctggg ggtggtggca catgcctgtg  2085
gttccagcca ctcaggaggt cgaggtggcg ggatggtttg agcacaggag acggaggttg  2145
ctgtgagctg agatcgcccc actgcttttc aacctgggtg acagaaccag accctgtctc  2205
aaaac                                                              2210
```

<210> SEQ ID NO 12
<211> LENGTH: 571
<212> TYPE: PRT
<213> ORGANISM: Human

<400> SEQUENCE: 12

```
Met Ala Leu Pro Arg Pro Ser Glu Ala Val Pro Gln Asp Lys Val Cys
1               5                   10                  15

Tyr Pro Pro Glu Ser Ser Pro Gln Asn Leu Ala Ala Tyr Tyr Thr Pro
            20                  25                  30

Phe Pro Ser Tyr Gly His Tyr Arg Asn Ser Leu Ala Thr Val Glu Glu
        35                  40                  45

Asp Phe Gln Pro Phe Arg Gln Leu Glu Ala Ala Ser Ala Ala Pro
    50                  55                  60

Ala Met Pro Pro Phe Pro Phe Arg Met Ala Pro Pro Leu Leu Ser Pro
65                  70                  75                  80

Gly Leu Gly Leu Gln Arg Glu Pro Leu Tyr Asp Leu Pro Trp Tyr Ser
                85                  90                  95

Lys Leu Pro Pro Trp Tyr Pro Ile Pro His Val Pro Arg Glu Val Pro
            100                 105                 110

Pro Phe Leu Ser Ser Ser His Glu Tyr Ala Gly Ala Ser Ser Glu Asp
        115                 120                 125

Leu Gly His Gln Ile Ile Gly Gly Asp Asn Glu Ser Gly Pro Cys Cys
    130                 135                 140

Gly Pro Asp Thr Leu Ile Pro Pro Ala Asp Ala Ser Leu Leu
145                 150                 155                 160

Pro Glu Gly Leu Arg Thr Ser Gln Leu Leu Pro Cys Ser Pro Ser Lys
                165                 170                 175

Gln Ser Glu Asp Gly Pro Lys Pro Ser Asn Gln Glu Gly Lys Ser Pro
            180                 185                 190

Ala Arg Phe Gln Phe Thr Glu Glu Asp Leu His Phe Val Leu Tyr Gly
        195                 200                 205

Val Thr Pro Ser Leu Glu His Pro Ala Ser Leu His Ala Ile Ser
    210                 215                 220
```

-continued

```
Gly Leu Leu Val Pro Pro Asp Ser Gly Ser Asp Ser Leu Pro Gln
225                 230                 235                 240

Thr Leu Asp Lys Asp Ser Leu Gln Leu Pro Glu Gly Leu Cys Leu Met
            245                 250                 255

Gln Thr Val Phe Gly Glu Val Pro His Phe Gly Val Phe Cys Ser Ser
        260                 265                 270

Phe Ile Ala Lys Gly Val Arg Phe Gly Pro Phe Gln Gly Lys Val Val
    275                 280                 285

Asn Ala Ser Glu Val Lys Thr Tyr Gly Asp Asn Ser Val Met Trp Glu
290                 295                 300

Ile Phe Glu Asp Gly His Leu Ser His Phe Ile Asp Gly Lys Gly Gly
305                 310                 315                 320

Thr Gly Asn Trp Met Ser Tyr Val Asn Cys Ala Arg Phe Pro Lys Glu
            325                 330                 335

Gln Asn Leu Val Ala Val Gln Cys Gln Gly His Ile Phe Tyr Glu Ser
        340                 345                 350

Cys Lys Glu Ile His Gln Asn Gln Glu Leu Leu Val Trp Tyr Gly Asp
    355                 360                 365

Cys Tyr Glu Lys Phe Leu Asp Ile Pro Val Ser Leu Gln Val Thr Glu
370                 375                 380

Pro Gly Lys Gln Pro Ser Gly Pro Ser Glu Glu Ser Ala Glu Gly Tyr
385                 390                 395                 400

Arg Cys Glu Arg Cys Gly Lys Val Phe Thr Tyr Lys Tyr Tyr Arg Asp
            405                 410                 415

Lys His Leu Lys Tyr Thr Pro Cys Val Asp Lys Gly Asp Arg Lys Phe
        420                 425                 430

Pro Cys Ser Leu Cys Lys Arg Ser Phe Glu Lys Arg Asp Arg Leu Arg
    435                 440                 445

Ile His Ile Leu His Val His Glu Lys His Arg Pro His Lys Cys Ser
450                 455                 460

Thr Cys Gly Lys Cys Phe Ser Gln Ser Ser Ser Leu Asn Lys His Met
465                 470                 475                 480

Arg Val His Ser Gly Asp Arg Pro Tyr Gln Cys Val Tyr Cys Thr Lys
            485                 490                 495

Arg Phe Thr Ala Ser Ser Ile Leu Arg Thr His Ile Arg Gln His Ser
        500                 505                 510

Gly Glu Lys Pro Phe Lys Cys Lys Tyr Cys Gly Lys Ser Phe Ala Ser
    515                 520                 525

His Ala Ala His Asp Ser His Val Arg Arg Ser His Lys Glu Asp Asp
530                 535                 540

Gly Cys Ser Cys Ser Ile Cys Gly Lys Ile Phe Ser Asp Gln Glu Thr
545                 550                 555                 560

Phe Tyr Ser His Met Lys Phe His Glu Asp Tyr
            565                 570
```

<210> SEQ ID NO 13
<211> LENGTH: 2965
<212> TYPE: DNA
<213> ORGANISM: Human
<220> FEATURE:
<221> NAME/KEY: CDS
<222> LOCATION: (112)...(2964)

<400> SEQUENCE: 13
cgctgccccg tccacgccgc ccgcgccccg cagtcccacc cgcaggaccc ccggccgcgc      60

-continued

| | |
|---|---|
| cagggtctcg cctgcgcccc ccgcgcccgc ccgcggacta caagtcccgc c atg ccc<br>                                                                                                   Met Pro<br>                                                                                                    1 | 117 |
| cgc cgc cgc ccc ccg gct tcc ggt gct gcg cag ttt ccg gag cgg atc<br>Arg Arg Arg Pro Pro Ala Ser Gly Ala Ala Gln Phe Pro Glu Arg Ile<br>          5                    10                   15 | 165 |
| gca acc cgg agt ccg gat ccg atc ccg ctc tgc aca ttc caa agg caa<br>Ala Thr Arg Ser Pro Asp Pro Ile Pro Leu Cys Thr Phe Gln Arg Gln<br>    20                    25                   30 | 213 |
| ccg cgc gcc gcc ccg gtc cag ccg cca tgc cga ctg ttc ttt gtt aca<br>Pro Arg Ala Ala Pro Val Gln Pro Pro Cys Arg Leu Phe Phe Val Thr<br>35                    40                   45                 50 | 261 |
| ttc gcc ggc tgc ggg cac cgt tgg cga tcg gag tca aaa ccc ggc tgg<br>Phe Ala Gly Cys Gly His Arg Trp Arg Ser Glu Ser Lys Pro Gly Trp<br>                55                   60                       65 | 309 |
| att tcc cgg agc cgc tcc ggg atc gcc ctg cgc gcc gcc cgc ccg ccg<br>Ile Ser Arg Ser Arg Ser Gly Ile Ala Leu Arg Ala Ala Arg Pro Pro<br>        70                       75                   80 | 357 |
| ggg tct tcg ccg ccc cgg ccc gcg gcc ccg cgg ccc ccg ccg ccg ggc<br>Gly Ser Ser Pro Pro Arg Pro Ala Ala Pro Arg Pro Pro Pro Pro Gly<br>          85                    90                   95 | 405 |
| ggc gtc gtc gcc gag gcc cca ggg gat gtc gtt atc ccc cgc cct cgg<br>Gly Val Val Ala Glu Ala Pro Gly Asp Val Val Ile Pro Arg Pro Arg<br>     100                    105                 110 | 453 |
| gta cag ccc atg cgg gtc gca cgg ggg ggt ccc tgg acc ccc aac ccc<br>Val Gln Pro Met Arg Val Ala Arg Gly Gly Pro Trp Thr Pro Asn Pro<br>115                   120                  125              130 | 501 |
| gcg ttt aga gaa gct gag tcc tgg tcc cag att ggg aac cag agg gtc<br>Ala Phe Arg Glu Ala Glu Ser Trp Ser Gln Ile Gly Asn Gln Arg Val<br>                135                  140                  145 | 549 |
| agt gag cag ctc ttg gaa aca tct cta ggg aat gag gtg tcc gac act<br>Ser Glu Gln Leu Leu Glu Thr Ser Leu Gly Asn Glu Val Ser Asp Thr<br>          150                    155                 160 | 597 |
| gag cca ctg agc cct gcg agt gca ggc ctg cga cgc aat cct gcc cta<br>Glu Pro Leu Ser Pro Ala Ser Ala Gly Leu Arg Arg Asn Pro Ala Leu<br>               165                  170                 175 | 645 |
| cct cct gga ccc ttt gca caa aac ttt tcc tgg ggg aac cag gaa aat<br>Pro Pro Gly Pro Phe Ala Gln Asn Phe Ser Trp Gly Asn Gln Glu Asn<br>     180                    185                 190 | 693 |
| ctg ccc cca gcc ctg ggg aag att gcg aac gga gga gga act ggg gca<br>Leu Pro Pro Ala Leu Gly Lys Ile Ala Asn Gly Gly Gly Thr Gly Ala<br>195                  200                  205              210 | 741 |
| ggc aag gcc gaa tgc ggc tat gaa act gag tca cac ttg cta gag ccg<br>Gly Lys Ala Glu Cys Gly Tyr Glu Thr Glu Ser His Leu Leu Glu Pro<br>               215                  220                 225 | 789 |
| cac gag ata cct ttg aac gtg aat aca cac aag ttc agt gac tgt gag<br>His Glu Ile Pro Leu Asn Val Asn Thr His Lys Phe Ser Asp Cys Glu<br>     230                    235                  240 | 837 |
| ttt cca tat gag ttt tgc acg gtc tgc ttt tca ccc ttc aag ctg ctg<br>Phe Pro Tyr Glu Phe Cys Thr Val Cys Phe Ser Pro Phe Lys Leu Leu<br>         245                   250                255 | 885 |
| ggg atg agc ggg gtg gag ggc gtg tgg aat cag cat tca aga agt gcc<br>Gly Met Ser Gly Val Glu Gly Val Trp Asn Gln His Ser Arg Ser Ala<br>     260                    265                 270 | 933 |
| agc atg cac act ttc cta aac cac tca gca acg ggc atc aga gaa gca<br>Ser Met His Thr Phe Leu Asn His Ser Ala Thr Gly Ile Arg Glu Ala<br>275                   280                  285              290 | 981 |
| ggt tgc agg aag gac atg ccc gtg tca gag atg gct gaa gat ggg agc<br>Gly Cys Arg Lys Asp Met Pro Val Ser Glu Met Ala Glu Asp Gly Ser<br>               295                  300                 305 | 1029 |

| | |
|---|---|
| gaa gag atc atg ttc atc tgg tgt gaa gac tgc agc cag tac cac gac<br>Glu Glu Ile Met Phe Ile Trp Cys Glu Asp Cys Ser Gln Tyr His Asp<br>310 315 320 | 1077 |
| tcc gaa tgt ccc gag ctg ggc cca gtg gtc atg gtc aaa gac tcc ttt<br>Ser Glu Cys Pro Glu Leu Gly Pro Val Val Met Val Lys Asp Ser Phe<br>325 330 335 | 1125 |
| gtg tta agc agg gca agg tct tgg cct gcc agc gga cac gtg cac acc<br>Val Leu Ser Arg Ala Arg Ser Trp Pro Ala Ser Gly His Val His Thr<br>340 345 350 | 1173 |
| cag gcg ggg cag ggg atg cgg ggt tat gag gac agg gac agg gct gac<br>Gln Ala Gly Gln Gly Met Arg Gly Tyr Glu Asp Arg Asp Arg Ala Asp<br>355 360 365 370 | 1221 |
| cca cag cag ctt cca gaa gca gtc cct gca ggc ctg gtg agg cgg ctc<br>Pro Gln Gln Leu Pro Glu Ala Val Pro Ala Gly Leu Val Arg Arg Leu<br>375 380 385 | 1269 |
| agt ggg cag cag ctg ccc tgc cgt tcc acc ctc acc tgg ggg agg ctg<br>Ser Gly Gln Gln Leu Pro Cys Arg Ser Thr Leu Thr Trp Gly Arg Leu<br>390 395 400 | 1317 |
| tgc cac ctg gtg gcc cag ggc agg tca tcc ctt cct ccc aac ttg gag<br>Cys His Leu Val Ala Gln Gly Arg Ser Ser Leu Pro Pro Asn Leu Glu<br>405 410 415 | 1365 |
| atc aga cga ctg gaa gat gga gcc gag ggg gtg ttc gcc atc act cag<br>Ile Arg Arg Leu Glu Asp Gly Ala Glu Gly Val Phe Ala Ile Thr Gln<br>420 425 430 | 1413 |
| ctc gtc aag cgg aca cag ttc ggt ccc ttt gag tcc agg agg gtc gcc<br>Leu Val Lys Arg Thr Gln Phe Gly Pro Phe Glu Ser Arg Arg Val Ala<br>435 440 445 450 | 1461 |
| aaa tgg gaa aag gag tct gca ttt ccc ctg aag gtg ttc cag aag gac<br>Lys Trp Glu Lys Glu Ser Ala Phe Pro Leu Lys Val Phe Gln Lys Asp<br>455 460 465 | 1509 |
| ggg cac ccc gtg tgc ttc gac acc tcc aac gag gat gac tgc aac tgg<br>Gly His Pro Val Cys Phe Asp Thr Ser Asn Glu Asp Asp Cys Asn Trp<br>470 475 480 | 1557 |
| atg atg ctg gtg cgg cca gcg gcg gag gcc gag cac cag aac ctg acg<br>Met Met Leu Val Arg Pro Ala Ala Glu Ala Glu His Gln Asn Leu Thr<br>485 490 495 | 1605 |
| gcc tac cag cac ggc agc gac gtg tac ttc acc acc tcc aga gac atc<br>Ala Tyr Gln His Gly Ser Asp Val Tyr Phe Thr Thr Ser Arg Asp Ile<br>500 505 510 | 1653 |
| ccc ccg ggt acc gag ctg cgc gtg tgg tat gcg gcc ttc tat gcc aag<br>Pro Pro Gly Thr Glu Leu Arg Val Trp Tyr Ala Ala Phe Tyr Ala Lys<br>515 520 525 530 | 1701 |
| aag atg gac aag ccc atg ctg aag cag gcc ggc tct ggc gtc cac gct<br>Lys Met Asp Lys Pro Met Leu Lys Gln Ala Gly Ser Gly Val His Ala<br>535 540 545 | 1749 |
| gca ggc acc cca gaa aac agc gcc ccc gtg gag tcg gag ccc agc cag<br>Ala Gly Thr Pro Glu Asn Ser Ala Pro Val Glu Ser Glu Pro Ser Gln<br>550 555 560 | 1797 |
| tgg gcg tgt aaa gtg tgt tct gcc acc ttc ctg gag ctg cag ctc ctc<br>Trp Ala Cys Lys Val Cys Ser Ala Thr Phe Leu Glu Leu Gln Leu Leu<br>565 570 575 | 1845 |
| aat gaa cat ctg ttg ggc cac tta gaa caa gcc aaa agc ctt cct cca<br>Asn Glu His Leu Leu Gly His Leu Glu Gln Ala Lys Ser Leu Pro Pro<br>580 585 590 | 1893 |
| ggc agc caa agc gag gca gca gct ccc gag aag gag cag gac aca ccc<br>Gly Ser Gln Ser Glu Ala Ala Ala Pro Glu Lys Glu Gln Asp Thr Pro<br>595 600 605 610 | 1941 |
| cgg ggg gaa ccc cct gca gtg ccc gag agc gag aat gtt gcc acc aaa<br>Arg Gly Glu Pro Pro Ala Val Pro Glu Ser Glu Asn Val Ala Thr Lys | 1989 |

-continued

|  |  |  | 615 |  |  |  | 620 |  |  |  | 625 |  |  |  |
|---|---|---|---|---|---|---|---|---|---|---|---|---|---|---|
| gaa | cag | aag | aaa | aag | cct | cga | agg | ggg | aga | aaa | ccc | aaa | gtg | tcc | aaa | 2037 |
| Glu | Gln | Lys | Lys | Lys | Pro | Arg | Arg | Gly | Arg | Lys | Pro | Lys | Val | Ser | Lys |
|  |  |  | 630 |  |  |  | 635 |  |  |  | 640 |  |  |

```
gct gag cag cct cta gtc atc gtg gaa gac aag gaa ccc aca gag caa      2085
Ala Glu Gln Pro Leu Val Ile Val Glu Asp Lys Glu Pro Thr Glu Gln
            645                 650                 655 gtg gca gag atc att acc gag gtc cct ccg gat gag cct gtg agt gca      2133
Val Ala Glu Ile Ile Thr Glu Val Pro Pro Asp Glu Pro Val Ser Ala
            660                 665                 670 acg cca gat gag cgg atc atg gag ctg gtt ctg ggg aag ctg gcc acc      2181
Thr Pro Asp Glu Arg Ile Met Glu Leu Val Leu Gly Lys Leu Ala Thr
675                 680                 685                 690 acc acc act gac acc agc tcg gtt cca aag ttc acc cat cat cag aat      2229
Thr Thr Thr Asp Thr Ser Ser Val Pro Lys Phe Thr His His Gln Asn
                695                 700                 705 aac acc atc acg ctc aag agg agc tta att ctc tca agc aga cac ggc      2277
Asn Thr Ile Thr Leu Lys Arg Ser Leu Ile Leu Ser Ser Arg His Gly
            710                 715                 720 atc cgg cgc aag ctc atc aaa cag ctc ggg gag cac aag cgg gtt tac      2325
Ile Arg Arg Lys Leu Ile Lys Gln Leu Gly Glu His Lys Arg Val Tyr
            725                 730                 735 cag tgc aat atc tgc agc aag atc ttc cag aac agc agc aac ctg agc      2373
Gln Cys Asn Ile Cys Ser Lys Ile Phe Gln Asn Ser Ser Asn Leu Ser
            740                 745                 750 agg cac gtg cgc tcg cat ggt gac aag ctg ttt aag tgc gaa gag tgt      2421
Arg His Val Arg Ser His Gly Asp Lys Leu Phe Lys Cys Glu Glu Cys
755                 760                 765                 770 gca aaa ttg ttc agc cgc aaa gag agc cta aag cag cac gtt tcc tac      2469
Ala Lys Leu Phe Ser Arg Lys Glu Ser Leu Lys Gln His Val Ser Tyr
                775                 780                 785 aag cac agc agg aac gag gtg gac ggc gag tac agg tac cgc tgc ggc      2517
Lys His Ser Arg Asn Glu Val Asp Gly Glu Tyr Arg Tyr Arg Cys Gly
            790                 795                 800 act tgt gag aag acc ttc cgc atc gag agc gcg ctg gag ttc cac aac      2565
Thr Cys Glu Lys Thr Phe Arg Ile Glu Ser Ala Leu Glu Phe His Asn
            805                 810                 815 tgc agg aca gat gac aag acg ttc caa tgt gag atg tgt ttc aga ttc      2613
Cys Arg Thr Asp Asp Lys Thr Phe Gln Cys Glu Met Cys Phe Arg Phe
820                 825                 830 ttc tcc acc aac agc aac ctc tcc aag cac aag aag aag cac ggc gac      2661
Phe Ser Thr Asn Ser Asn Leu Ser Lys His Lys Lys Lys His Gly Asp
835                 840                 845                 850 aag aag ttt gcc tgt gag gtc tgc agc aag atg ttc tac cgc aag gac      2709
Lys Lys Phe Ala Cys Glu Val Cys Ser Lys Met Phe Tyr Arg Lys Asp
                855                 860                 865 gtc atg ctg gac cac cag cgc cgg cac ctg gaa gga gtg cgg cga gtg      2757
Val Met Leu Asp His Gln Arg Arg His Leu Glu Gly Val Arg Arg Val
            870                 875                 880 aag cga gag gac ctg gag gcc ggt ggg gag aac ctg gtc cgt tac aag      2805
Lys Arg Glu Asp Leu Glu Ala Gly Gly Glu Asn Leu Val Arg Tyr Lys
            885                 890                 895 aag gag cct tcc ggg tgc ccg gtg tgt ggc aag gtg ttc tcc tgc cgg      2853
Lys Glu Pro Ser Gly Cys Pro Val Cys Gly Lys Val Phe Ser Cys Arg
900                 905                 910 agc aat atg aac aag cac ctg ctc acc cac ggg gac aag aag tac acc      2901
Ser Asn Met Asn Lys His Leu Leu Thr His Gly Asp Lys Lys Tyr Thr
915                 920                 925                 930 tgc gag atc tgc ggg cgc aag ttc ttc cgc gtg gat gtg ctc agg gac      2949
```

```
Cys Glu Ile Cys Gly Arg Lys Phe Phe Arg Val Asp Val Leu Arg Asp
                935                 940                 945
cac atc cat gtc cac t                                                        2965
His Ile His Val His
            950
```

<210> SEQ ID NO 14
<211> LENGTH: 951
<212> TYPE: PRT
<213> ORGANISM: Human

<400> SEQUENCE: 14

```
Met Pro Arg Arg Pro Pro Ala Ser Gly Ala Ala Gln Phe Pro Glu
1               5                   10                  15

Arg Ile Ala Thr Arg Ser Pro Asp Pro Ile Pro Leu Cys Thr Phe Gln
                20                  25                  30

Arg Gln Pro Arg Ala Ala Pro Val Gln Pro Pro Cys Arg Leu Phe Phe
            35                  40                  45

Val Thr Phe Ala Gly Cys Gly His Arg Trp Arg Ser Glu Ser Lys Pro
    50                  55                  60

Gly Trp Ile Ser Arg Ser Arg Ser Gly Ile Ala Leu Arg Ala Ala Arg
65                  70                  75                  80

Pro Pro Gly Ser Ser Pro Pro Arg Pro Ala Ala Pro Arg Pro Pro
                85                  90                  95

Pro Gly Gly Val Val Ala Glu Ala Pro Gly Asp Val Val Ile Pro Arg
            100                 105                 110

Pro Arg Val Gln Pro Met Arg Val Ala Arg Gly Gly Pro Trp Thr Pro
        115                 120                 125

Asn Pro Ala Phe Arg Glu Ala Glu Ser Trp Ser Gln Ile Gly Asn Gln
    130                 135                 140

Arg Val Ser Glu Gln Leu Leu Glu Thr Ser Leu Gly Asn Glu Val Ser
145                 150                 155                 160

Asp Thr Glu Pro Leu Ser Pro Ala Ser Ala Gly Leu Arg Arg Asn Pro
                165                 170                 175

Ala Leu Pro Pro Gly Pro Phe Ala Gln Asn Phe Ser Trp Gly Asn Gln
            180                 185                 190

Glu Asn Leu Pro Pro Ala Leu Gly Lys Ile Ala Asn Gly Gly Thr
        195                 200                 205

Gly Ala Gly Lys Ala Glu Cys Gly Tyr Glu Thr Glu Ser His Leu Leu
    210                 215                 220

Glu Pro His Glu Ile Pro Leu Asn Val Asn Thr His Lys Phe Ser Asp
225                 230                 235                 240

Cys Glu Phe Pro Tyr Glu Phe Cys Thr Val Cys Phe Ser Pro Phe Lys
                245                 250                 255

Leu Leu Gly Met Ser Gly Val Glu Gly Val Trp Asn Gln His Ser Arg
            260                 265                 270

Ser Ala Ser Met His Thr Phe Leu Asn His Ser Ala Thr Gly Ile Arg
        275                 280                 285

Glu Ala Gly Cys Arg Lys Asp Met Pro Val Ser Glu Met Ala Glu Asp
    290                 295                 300

Gly Ser Glu Glu Ile Met Phe Ile Trp Cys Glu Asp Cys Ser Gln Tyr
305                 310                 315                 320

His Asp Ser Glu Cys Pro Glu Leu Gly Pro Val Val Met Val Lys Asp
                325                 330                 335

Ser Phe Val Leu Ser Arg Ala Arg Ser Trp Pro Ala Ser Gly His Val
```

-continued

```
                340                 345                 350
        His Thr Gln Ala Gly Gln Gly Met Arg Gly Tyr Glu Asp Arg Asp Arg
                    355                 360                 365
        Ala Asp Pro Gln Gln Leu Pro Glu Ala Val Pro Ala Gly Leu Val Arg
            370                 375                 380
        Arg Leu Ser Gly Gln Gln Leu Pro Cys Arg Ser Thr Leu Thr Trp Gly
        385                 390                 395                 400
        Arg Leu Cys His Leu Val Ala Gln Gly Arg Ser Ser Leu Pro Pro Asn
                        405                 410                 415
        Leu Glu Ile Arg Arg Leu Glu Asp Gly Ala Glu Gly Val Phe Ala Ile
                    420                 425                 430
        Thr Gln Leu Val Lys Arg Thr Gln Phe Gly Pro Phe Glu Ser Arg Arg
                    435                 440                 445
        Val Ala Lys Trp Glu Lys Glu Ser Ala Phe Pro Leu Lys Val Phe Gln
                450                 455                 460
        Lys Asp Gly His Pro Val Cys Phe Asp Thr Ser Asn Glu Asp Asp Cys
        465                 470                 475                 480
        Asn Trp Met Met Leu Val Arg Pro Ala Ala Glu Ala Glu His Gln Asn
                        485                 490                 495
        Leu Thr Ala Tyr Gln His Gly Ser Asp Val Tyr Phe Thr Thr Ser Arg
                    500                 505                 510
        Asp Ile Pro Pro Gly Thr Glu Leu Arg Val Trp Tyr Ala Ala Phe Tyr
                    515                 520                 525
        Ala Lys Lys Met Asp Lys Pro Met Leu Lys Gln Ala Gly Ser Gly Val
                530                 535                 540
        His Ala Ala Gly Thr Pro Glu Asn Ser Ala Pro Val Glu Ser Glu Pro
        545                 550                 555                 560
        Ser Gln Trp Ala Cys Lys Val Cys Ser Ala Thr Phe Leu Glu Leu Gln
                        565                 570                 575
        Leu Leu Asn Glu His Leu Leu Gly His Leu Glu Gln Ala Lys Ser Leu
                    580                 585                 590
        Pro Pro Gly Ser Gln Ser Glu Ala Ala Ala Pro Glu Lys Glu Gln Asp
                    595                 600                 605
        Thr Pro Arg Gly Glu Pro Pro Ala Val Pro Glu Ser Glu Asn Val Ala
                610                 615                 620
        Thr Lys Glu Gln Lys Lys Lys Pro Arg Arg Gly Arg Lys Pro Lys Val
        625                 630                 635                 640
        Ser Lys Ala Glu Gln Pro Leu Val Ile Val Glu Asp Lys Glu Pro Thr
                        645                 650                 655
        Glu Gln Val Ala Glu Ile Ile Thr Glu Val Pro Pro Asp Glu Pro Val
                    660                 665                 670
        Ser Ala Thr Pro Asp Glu Arg Ile Met Glu Leu Val Leu Gly Lys Leu
                    675                 680                 685
        Ala Thr Thr Thr Thr Asp Thr Ser Ser Val Pro Lys Phe Thr His His
                690                 695                 700
        Gln Asn Asn Thr Ile Thr Leu Lys Arg Ser Leu Ile Leu Ser Ser Arg
        705                 710                 715                 720
        His Gly Ile Arg Arg Lys Leu Ile Lys Gln Leu Gly Glu His Lys Arg
                        725                 730                 735
        Val Tyr Gln Cys Asn Ile Cys Ser Lys Ile Phe Gln Asn Ser Ser Asn
                    740                 745                 750
        Leu Ser Arg His Val Arg Ser His Gly Asp Lys Leu Phe Lys Cys Glu
                    755                 760                 765
```

| | | |
|---|---|---|
| Glu Cys Ala Lys Leu Phe Ser Arg Lys Glu Ser Leu Lys Gln His Val | | |
| 770 775 780 | | |
| Ser Tyr Lys His Ser Arg Asn Glu Val Asp Gly Glu Tyr Arg Tyr Arg | | |
| 785 790 795 800 | | |
| Cys Gly Thr Cys Glu Lys Thr Phe Arg Ile Glu Ser Ala Leu Glu Phe | | |
| 805 810 815 | | |
| His Asn Cys Arg Thr Asp Asp Lys Thr Phe Gln Cys Glu Met Cys Phe | | |
| 820 825 830 | | |
| Arg Phe Phe Ser Thr Asn Ser Asn Leu Ser Lys His Lys Lys Lys His | | |
| 835 840 845 | | |
| Gly Asp Lys Lys Phe Ala Cys Glu Val Cys Ser Lys Met Phe Tyr Arg | | |
| 850 855 860 | | |
| Lys Asp Val Met Leu Asp His Gln Arg Arg His Leu Glu Gly Val Arg | | |
| 865 870 875 880 | | |
| Arg Val Lys Arg Glu Asp Leu Glu Ala Gly Gly Glu Asn Leu Val Arg | | |
| 885 890 895 | | |
| Tyr Lys Lys Glu Pro Ser Gly Cys Pro Val Cys Gly Lys Val Phe Ser | | |
| 900 905 910 | | |
| Cys Arg Ser Asn Met Asn Lys His Leu Leu Thr His Gly Asp Lys Lys | | |
| 915 920 925 | | |
| Tyr Thr Cys Glu Ile Cys Gly Arg Lys Phe Phe Arg Val Asp Val Leu | | |
| 930 935 940 | | |
| Arg Asp His Ile His Val His | | |
| 945 950 | | |

<210> SEQ ID NO 15
<211> LENGTH: 4376
<212> TYPE: DNA
<213> ORGANISM: Human
<220> FEATURE:
<221> NAME/KEY: CDS
<222> LOCATION: (64)...(3837)

<400> SEQUENCE: 15

| | |
|---|---|
| gaagatagtg tgtggctgct tctggactca aggaggagga gagagattcc gcgagccgac | 60 |
| acc atg cga tcc aag gcg agg gcg agg aag cta gcc aaa agt gac ggt<br>Met Arg Ser Lys Ala Arg Ala Arg Lys Leu Ala Lys Ser Asp Gly<br>1 5 10 15 | 108 |
| gac gtt gta aat aat atg tat gag ccc aac cgg gac ctg ctg gcc agc<br>Asp Val Val Asn Asn Met Tyr Glu Pro Asn Arg Asp Leu Leu Ala Ser<br>20 25 30 | 156 |
| cac agc gcg gag gac gag gcc gag gac agt gcc atg tcg ccc atc ccc<br>His Ser Ala Glu Asp Glu Ala Glu Asp Ser Ala Met Ser Pro Ile Pro<br>35 40 45 | 204 |
| gtg ggg tca ccg ccc ccc ttc ccc acc agc gag gac ttc acc ccc aag<br>Val Gly Ser Pro Pro Pro Phe Pro Thr Ser Glu Asp Phe Thr Pro Lys<br>50 55 60 | 252 |
| gag ggc tcg ccg tac gag gcc cct gtc tac att cct gaa gac att ccg<br>Glu Gly Ser Pro Tyr Glu Ala Pro Val Tyr Ile Pro Glu Asp Ile Pro<br>65 70 75 | 300 |
| atc cca gca gac ttc gag ctc cga gag tcc atc cca ggg gct ggc<br>Ile Pro Ala Asp Phe Glu Leu Arg Glu Ser Ser Ile Pro Gly Ala Gly<br>80 85 90 95 | 348 |
| ctg ggg gtc tgg gcc aag agg aag atg gaa gcc ggg gag agg ctg ggc<br>Leu Gly Val Trp Ala Lys Arg Lys Met Glu Ala Gly Glu Arg Leu Gly<br>100 105 110 | 396 |
| ccc tgc gtg gtg gtg ccc cgg gcg gcg gca aag gag aca gac ttc gga<br> | 444 |

```
                    Pro Cys Val Val Val Pro Arg Ala Ala Ala Lys Glu Thr Asp Phe Gly
                                115                 120                 125 tgg gag caa ata ctg acg gac gtg gaa gtg tcg ccc cag gaa ggc tgc                492
Trp Glu Gln Ile Leu Thr Asp Val Glu Val Ser Pro Gln Glu Gly Cys
        130                 135                 140 atc aca aag atc tcc gaa gac ctg ggc agt gag aag ttc tgc gtg gat                540
Ile Thr Lys Ile Ser Glu Asp Leu Gly Ser Glu Lys Phe Cys Val Asp
    145                 150                 155 gca aat cag gcg ggg gct ggc agc tgg ctc aag tac atc cgt gtg gcg                588
Ala Asn Gln Ala Gly Ala Gly Ser Trp Leu Lys Tyr Ile Arg Val Ala
160                 165                 170                 175 tgc tcc tgc gat gac cag aac ctc acc atg tgt cag atc agt gag cag                636
Cys Ser Cys Asp Asp Gln Asn Leu Thr Met Cys Gln Ile Ser Glu Gln
                180                 185                 190 gta att tac tat aaa gtc att aag gac att gag cca ggt gag gag ctg                684
Val Ile Tyr Tyr Lys Val Ile Lys Asp Ile Glu Pro Gly Glu Glu Leu
            195                 200                 205 ctg gtg cac gtg aag gaa ggc gtc tac ccc ctg ggc aca gtg ccg ccc                732
Leu Val His Val Lys Glu Gly Val Tyr Pro Leu Gly Thr Val Pro Pro
        210                 215                 220 ggc ctg gac gag gag ccc acg ttc cgc tgt gac gag tgt gac gaa ctc                780
Gly Leu Asp Glu Glu Pro Thr Phe Arg Cys Asp Glu Cys Asp Glu Leu
    225                 230                 235 ttc cag tcc aag ctg gac ctg cgg cgc cat aag aag tac acg tgt ggc                828
Phe Gln Ser Lys Leu Asp Leu Arg Arg His Lys Lys Tyr Thr Cys Gly
240                 245                 250                 255 tca gtg ggg gct gcg ctc tac gag ggc ctg gct gag gag ctc aag ccc                876
Ser Val Gly Ala Ala Leu Tyr Glu Gly Leu Ala Glu Glu Leu Lys Pro
                260                 265                 270 gag ggc ctt ggc ggt ggc agc ggc caa gcc cac gag tgc aag gac tgc                924
Glu Gly Leu Gly Gly Gly Ser Gly Gln Ala His Glu Cys Lys Asp Cys
            275                 280                 285 gag cgg atg ttc ccc aac aag tac agc ctg gag cag cac atg gtc atc                972
Glu Arg Met Phe Pro Asn Lys Tyr Ser Leu Glu Gln His Met Val Ile
        290                 295                 300 cac acg gag gag cgc gag tac aaa tgc gac cag tgt ccc aag gcc ttc               1020
His Thr Glu Glu Arg Glu Tyr Lys Cys Asp Gln Cys Pro Lys Ala Phe
    305                 310                 315 aac tgg aag tcc aac ttc atc cgc cac cag atg tcc cac gac agc ggc               1068
Asn Trp Lys Ser Asn Phe Ile Arg His Gln Met Ser His Asp Ser Gly
320                 325                 330                 335 aaa cgc ttc gaa tgt gaa aac tgc gtg aag gtg ttc acg gac ccc agc               1116
Lys Arg Phe Glu Cys Glu Asn Cys Val Lys Val Phe Thr Asp Pro Ser
                340                 345                 350 aac ctt cag cgg cac atc cgc tcg cag cac gtg ggc gct cgg gcc cac               1164
Asn Leu Gln Arg His Ile Arg Ser Gln His Val Gly Ala Arg Ala His
            355                 360                 365 gcc tgc ccc gac tgc ggg aag acc ttc gcc acg tcc tcc ggc ctc aag               1212
Ala Cys Pro Asp Cys Gly Lys Thr Phe Ala Thr Ser Ser Gly Leu Lys
        370                 375                 380 cag cac aag cat atc cac agc acg gtg aag cct ttc ata tgt gag gtc               1260
Gln His Lys His Ile His Ser Thr Val Lys Pro Phe Ile Cys Glu Val
    385                 390                 395 tgc cac aag tcc tac acg cag ttc tcc aac ctg tgc cgg cac aag cgg               1308
Cys His Lys Ser Tyr Thr Gln Phe Ser Asn Leu Cys Arg His Lys Arg
400                 405                 410                 415 atg cac gcc gac tgc cgc acg cag atc aag tgc aag gac tgt ggc cag               1356
Met His Ala Asp Cys Arg Thr Gln Ile Lys Cys Lys Asp Cys Gly Gln
                420                 425                 430
```

```
atg ttc agc act acc tcc tcc ctc aac aag cac cgg cgc ttc tgc gag    1404
Met Phe Ser Thr Thr Ser Ser Leu Asn Lys His Arg Arg Phe Cys Glu
        435                 440                 445 ggc aag aac cat tac acg ccg ggc ggc atc ttt gcc ccg ggc ctg ccc    1452
Gly Lys Asn His Tyr Thr Pro Gly Gly Ile Phe Ala Pro Gly Leu Pro
450                 455                 460 ttg acc ccc agc ccc atg atg gac aag gca aaa ccc tcc ccc agc ctc    1500
Leu Thr Pro Ser Pro Met Met Asp Lys Ala Lys Pro Ser Pro Ser Leu
    465                 470                 475 aat cac gcc agc ctg ggc ttc aac gag tac ttt ccc tac agg ccg cac    1548
Asn His Ala Ser Leu Gly Phe Asn Glu Tyr Phe Pro Tyr Arg Pro His
480                 485                 490                 495 ccg ggg agc ctg ccc ttc tcc acg gcg cct ccc acg ttc ccc gca ctc    1596
Pro Gly Ser Leu Pro Phe Ser Thr Ala Pro Pro Thr Phe Pro Ala Leu
                500                 505                 510 acc ccc ggc ttc ccg ggc atc ttc cct cca tcc ttg tac ccc cgg ccg    1644
Thr Pro Gly Phe Pro Gly Ile Phe Pro Pro Ser Leu Tyr Pro Arg Pro
            515                 520                 525 cct ctg cta cct ccc aca tcg ctg ctc aag agc ccc ctg aac cac acc    1692
Pro Leu Leu Pro Pro Thr Ser Leu Leu Lys Ser Pro Leu Asn His Thr
        530                 535                 540 cag gac gcc aag ctc ccc agt ccc ctg ggg aac cca gcc ctg ccc ctg    1740
Gln Asp Ala Lys Leu Pro Ser Pro Leu Gly Asn Pro Ala Leu Pro Leu
    545                 550                 555 gtc tcc gcc gtc agc aac agc agc cag ggc acg acg gca gct gcg ggg    1788
Val Ser Ala Val Ser Asn Ser Ser Gln Gly Thr Thr Ala Ala Ala Gly
560                 565                 570                 575 ccc gag gag aag ttc gag agc cgc ctg gag gac tcc tgt gtg gag aag    1836
Pro Glu Glu Lys Phe Glu Ser Arg Leu Glu Asp Ser Cys Val Glu Lys
                580                 585                 590 ctg aag acc agg agc agc gac atg tcg gac ggc agt gac ttt gag gac    1884
Leu Lys Thr Arg Ser Ser Asp Met Ser Asp Gly Ser Asp Phe Glu Asp
            595                 600                 605 gtc aac acc acc acg ggg acc gac ctg gac acg acc acg ggg acg ggc    1932
Val Asn Thr Thr Thr Gly Thr Asp Leu Asp Thr Thr Thr Gly Thr Gly
        610                 615                 620 tcg gac ctg gac agc gac gtg gac agc gac cct gac aag gac aag ggc    1980
Ser Asp Leu Asp Ser Asp Val Asp Ser Asp Pro Asp Lys Asp Lys Gly
    625                 630                 635 aag ggc aag tcc gcc gag ggc cag ccc aag ttt ggg ggc ggc ttg gcg    2028
Lys Gly Lys Ser Ala Glu Gly Gln Pro Lys Phe Gly Gly Gly Leu Ala
640                 645                 650                 655 ccc ccg ggg gcc ccg aac agc gtg gcc gag gtg cct gtc ttc tat tcc    2076
Pro Pro Gly Ala Pro Asn Ser Val Ala Glu Val Pro Val Phe Tyr Ser
                660                 665                 670 cag cac tca ttc ttc ccg cca ccc gac gag cag ctg ctg act gca acg    2124
Gln His Ser Phe Phe Pro Pro Pro Asp Glu Gln Leu Leu Thr Ala Thr
            675                 680                 685 ggc gcc gcc ggg gac tcc atc aag gcc atc gca tcc att gcc gag aag    2172
Gly Ala Ala Gly Asp Ser Ile Lys Ala Ile Ala Ser Ile Ala Glu Lys
        690                 695                 700 tac ttt ggc ccc ggc ttc atg ggg atg cag gag aag aag ctg ggc tcg    2220
Tyr Phe Gly Pro Gly Phe Met Gly Met Gln Glu Lys Lys Leu Gly Ser
    705                 710                 715 ctc ccc tac cac tcg gcg ttc ccc ttc cag ttc ctg ccc aac ttc ccc    2268
Leu Pro Tyr His Ser Ala Phe Pro Phe Gln Phe Leu Pro Asn Phe Pro
720                 725                 730                 735 cac tcc ctt tac ccc ttc acg gac cga gcc ctc gcc cac aac ttg ctg    2316
His Ser Leu Tyr Pro Phe Thr Asp Arg Ala Leu Ala His Asn Leu Leu
                740                 745                 750
```

```
gtc aag gcc gag cca aag tca ccc cgg gac gcc ctc aag gtg ggc ggc        2364
Val Lys Ala Glu Pro Lys Ser Pro Arg Asp Ala Leu Lys Val Gly Gly
            755                 760                 765 ccc agt gcc gag tgc ccc ttt gat ctc acc acc aag ccc aaa gac gtg        2412
Pro Ser Ala Glu Cys Pro Phe Asp Leu Thr Thr Lys Pro Lys Asp Val
        770                 775                 780 aag ccc atc ctg ccc atg ccc aag ggc ccc tcg gcc ccc gca tcc ggc        2460
Lys Pro Ile Leu Pro Met Pro Lys Gly Pro Ser Ala Pro Ala Ser Gly
    785                 790                 795 gag gag cag ccg ctg gac ctg agc atc ggc agc cgg gcc cgt gcc agc        2508
Glu Glu Gln Pro Leu Asp Leu Ser Ile Gly Ser Arg Ala Arg Ala Ser
800                 805                 810                 815 caa aac ggc ggc ggg cgg gag ccc cgc aag aac cac gtc tat ggg gaa        2556
Gln Asn Gly Gly Gly Arg Glu Pro Arg Lys Asn His Val Tyr Gly Glu
                820                 825                 830 cgc aag ctg ggc gcc ggc gag ggg ctg ccc cag gtg tgc ccg gcg cgg        2604
Arg Lys Leu Gly Ala Gly Glu Gly Leu Pro Gln Val Cys Pro Ala Arg
            835                 840                 845 atg ccc cag cag ccc ccg ctc cac tac gcc aag ccc tcg ccc ttc ttc        2652
Met Pro Gln Gln Pro Pro Leu His Tyr Ala Lys Pro Ser Pro Phe Phe
        850                 855                 860 atg gac ccc atc tac agg gta gaa aag cgg aag gtc aca gac ccc gtg        2700
Met Asp Pro Ile Tyr Arg Val Glu Lys Arg Lys Val Thr Asp Pro Val
    865                 870                 875 gga gcc ctg aag gag aag tac ctg cgg ccg tcc ccg ctg ctc ttc cac        2748
Gly Ala Leu Lys Glu Lys Tyr Leu Arg Pro Ser Pro Leu Leu Phe His
880                 885                 890                 895 ccc cag atg tca gcc ata gag acc atg aca gag aag ctg gag agc ttt        2796
Pro Gln Met Ser Ala Ile Glu Thr Met Thr Glu Lys Leu Glu Ser Phe
                900                 905                 910 gca gcc atg aag gcg gac tcg ggc agc tcc ctg cag ccc ctc ccc cac        2844
Ala Ala Met Lys Ala Asp Ser Gly Ser Ser Leu Gln Pro Leu Pro His
            915                 920                 925 cac ccc ttc aac ttc cgg tcc cca ccc cca acg ctc tcc gac ccc atc        2892
His Pro Phe Asn Phe Arg Ser Pro Pro Pro Thr Leu Ser Asp Pro Ile
        930                 935                 940 ctc agg aag ggc aag gag cga tac acg tgc agg tac tgt ggg aag atc        2940
Leu Arg Lys Gly Lys Glu Arg Tyr Thr Cys Arg Tyr Cys Gly Lys Ile
    945                 950                 955 ttc ccc aga tca gcc aat ctc acc aga cac ctg agg acg cac act ggg        2988
Phe Pro Arg Ser Ala Asn Leu Thr Arg His Leu Arg Thr His Thr Gly
960                 965                 970                 975 gag cag ccg tac agg tgt aag tac tgc gac cgc tcc ttc agc atc tct        3036
Glu Gln Pro Tyr Arg Cys Lys Tyr Cys Asp Arg Ser Phe Ser Ile Ser
                980                 985                 990 tcg aac ctc cag cgg cac gtc cgg aac atc cac aac aag gag aag cct        3084
Ser Asn Leu Gln Arg His Val Arg Asn Ile His Asn Lys Glu Lys Pro
            995                 1000                1005 ttc aag tgc cac ctg tgc aac cgc tgc ttc ggg cag cag acc aac ctg        3132
Phe Lys Cys His Leu Cys Asn Arg Cys Phe Gly Gln Gln Thr Asn Leu
        1010                1015                1020 gac cgg cac ctc aag aag cac gag cac gag aac gca cca gtg agc cag        3180
Asp Arg His Leu Lys Lys His Glu His Glu Asn Ala Pro Val Ser Gln
    1025                1030                1035 cac ccc ggg gtc ctc acg aac cac ctg ggg acc agc gcg tcc tct ccc        3228
His Pro Gly Val Leu Thr Asn His Leu Gly Thr Ser Ala Ser Ser Pro
1040                1045                1050                1055 acc tca gag tcg gac aac cac gca ctt tta gac gag aaa gaa gac tct        3276
Thr Ser Glu Ser Asp Asn His Ala Leu Leu Asp Glu Lys Glu Asp Ser
```

-continued

| | | | | | | | | | | | | | | | | |
|---|---|---|---|---|---|---|---|---|---|---|---|---|---|---|---|---|
| | | 1060 | | | | 1065 | | | | | 1070 | | | | | |
| tat | ttc | tcg | gaa | atc | aga | aac | ttt | att | gcc | aat | agt | gag | atg | aac | caa | 3324 |
| Tyr | Phe | Ser | Glu | Ile | Arg | Asn | Phe | Ile | Ala | Asn | Ser | Glu | Met | Asn | Gln | |
| | | | | 1075 | | | | 1080 | | | | | 1085 | | | |
| gca | tca | acg | cga | aca | gag | aaa | cgg | gcg | gac | atg | cag | atc | gtg | gac | ggc | 3372 |
| Ala | Ser | Thr | Arg | Thr | Glu | Lys | Arg | Ala | Asp | Met | Gln | Ile | Val | Asp | Gly | |
| | | | 1090 | | | | | 1095 | | | | | 1100 | | | |
| agt | gcc | cag | tgt | cca | ggc | cta | gcc | agt | gag | aag | cag | gag | gac | gtg | gag | 3420 |
| Ser | Ala | Gln | Cys | Pro | Gly | Leu | Ala | Ser | Glu | Lys | Gln | Glu | Asp | Val | Glu | |
| | | 1105 | | | | | 1110 | | | | | 1115 | | | | |
| gag | gag | gac | gac | gat | gac | ctg | gag | gag | gac | gat | gag | gac | agc | ctg | gcc | 3468 |
| Glu | Glu | Asp | Asp | Asp | Asp | Leu | Glu | Glu | Asp | Asp | Glu | Asp | Ser | Leu | Ala | |
| 1120 | | | | | 1125 | | | | | 1130 | | | | | 1135 | |
| ggg | aag | tcg | cag | gat | gac | acc | gtg | tcc | ccc | gca | ccc | gag | ccc | cag | gcc | 3516 |
| Gly | Lys | Ser | Gln | Asp | Asp | Thr | Val | Ser | Pro | Ala | Pro | Glu | Pro | Gln | Ala | |
| | | | | 1140 | | | | | 1145 | | | | | 1150 | | |
| gcc | tac | gag | gat | gag | gag | gat | gag | gag | cca | gcc | gcc | tcc | ctg | gcc | gtg | 3564 |
| Ala | Tyr | Glu | Asp | Glu | Glu | Asp | Glu | Glu | Pro | Ala | Ala | Ser | Leu | Ala | Val | |
| | | | 1155 | | | | | 1160 | | | | | 1165 | | | |
| ggc | ttt | gac | cac | acc | cga | agg | tgt | gct | gag | gac | cac | gaa | ggc | ggt | ctg | 3612 |
| Gly | Phe | Asp | His | Thr | Arg | Arg | Cys | Ala | Glu | Asp | His | Glu | Gly | Gly | Leu | |
| | | 1170 | | | | | 1175 | | | | | 1180 | | | | |
| tta | gct | ttg | gag | ccg | atg | ccg | act | ttt | ggg | aag | ggg | ctg | gac | ctc | cgc | 3660 |
| Leu | Ala | Leu | Glu | Pro | Met | Pro | Thr | Phe | Gly | Lys | Gly | Leu | Asp | Leu | Arg | |
| | 1185 | | | | | 1190 | | | | | 1195 | | | | | |
| aga | gca | gct | gag | gaa | gca | ttt | gaa | gtt | aaa | gat | gtg | ctt | aat | tcc | acc | 3708 |
| Arg | Ala | Ala | Glu | Glu | Ala | Phe | Glu | Val | Lys | Asp | Val | Leu | Asn | Ser | Thr | |
| 1200 | | | | | 1205 | | | | | 1210 | | | | | 1215 | |
| tta | gat | tct | gag | gct | tta | aaa | cat | aca | ctg | tgc | agg | cag | gct | aag | aac | 3756 |
| Leu | Asp | Ser | Glu | Ala | Leu | Lys | His | Thr | Leu | Cys | Arg | Gln | Ala | Lys | Asn | |
| | | | | 1220 | | | | | 1225 | | | | | 1230 | | |
| cag | gca | tat | gca | atg | atg | ctg | tcc | ctt | tcc | gaa | gac | act | cct | ctc | cac | 3804 |
| Gln | Ala | Tyr | Ala | Met | Met | Leu | Ser | Leu | Ser | Glu | Asp | Thr | Pro | Leu | His | |
| | | | 1235 | | | | | 1240 | | | | | 1245 | | | |
| acc | ccc | tcc | cag | ggt | tct | ctg | gac | gct | tgg | ttg | aaggtcactg | | gagccacgtc | | | 3857 |
| Thr | Pro | Ser | Gln | Gly | Ser | Leu | Asp | Ala | Trp | Leu | | | | | | |
| | | 1250 | | | | | 1255 | | | | | | | | | |

| | |
|---|---|
| ggagtctgga gcatttcacc ccatcaacca cctctgacgg gctgggcagc cggggggccgg | 3917 |
| tggccagagc gagggcacca gccacgaagg acggaggcgg gcggggcccc ggagaaccct | 3977 |
| gtccctgcgt gtggccactc tcagcatcc tccccaccca ccatggttca ttccgacttt | 4037 |
| tccaatggaa actcagatcc caaaagtccc taaagcagtc gtagagtctc accatctcca | 4097 |
| aggattggtc ttgagaacac tgttcagtga cggccatgca ggtggccgtc caaagacagc | 4157 |
| caacggagct gcctcgcaga atcagccagt gggcaggtgg acgctctgct gagacagaag | 4217 |
| ctggtggcca ctgccgggtg cccgcgtggg gtcgcggaag ggaatggata gactggtgtg | 4277 |
| ctcaaaagag agagatcact caaatgattt ttataatgaa atgacaagaa taacccttt | 4337 |
| ggtaaccgta ttgactgcag agtctatta agcatgtgg | 4376 |

<210> SEQ ID NO 16
<211> LENGTH: 1258
<212> TYPE: PRT
<213> ORGANISM: Human

<400> SEQUENCE: 16

Met Arg Ser Lys Ala Arg Ala Arg Lys Leu Ala Lys Ser Asp Gly Asp
1               5                   10                  15

-continued

```
Val Val Asn Asn Met Tyr Glu Pro Asn Arg Asp Leu Leu Ala Ser His
            20                  25                  30

Ser Ala Glu Asp Glu Ala Glu Asp Ser Ala Met Ser Pro Ile Pro Val
        35                  40                  45

Gly Ser Pro Pro Pro Phe Pro Thr Ser Glu Asp Phe Thr Pro Lys Glu
    50                  55                  60

Gly Ser Pro Tyr Glu Ala Pro Val Tyr Ile Pro Glu Asp Ile Pro Ile
65                  70                  75                  80

Pro Ala Asp Phe Glu Leu Arg Glu Ser Ser Ile Pro Gly Ala Gly Leu
                85                  90                  95

Gly Val Trp Ala Lys Arg Lys Met Glu Ala Gly Glu Arg Leu Gly Pro
            100                 105                 110

Cys Val Val Val Pro Arg Ala Ala Lys Glu Thr Asp Phe Gly Trp
            115                 120                 125

Glu Gln Ile Leu Thr Asp Val Glu Val Ser Pro Gln Glu Gly Cys Ile
    130                 135                 140

Thr Lys Ile Ser Glu Asp Leu Gly Ser Glu Lys Phe Cys Val Asp Ala
145                 150                 155                 160

Asn Gln Ala Gly Ala Gly Ser Trp Leu Lys Tyr Ile Arg Val Ala Cys
                165                 170                 175

Ser Cys Asp Asp Gln Asn Leu Thr Met Cys Gln Ile Ser Glu Gln Val
            180                 185                 190

Ile Tyr Tyr Lys Val Ile Lys Asp Ile Glu Pro Gly Glu Glu Leu Leu
    195                 200                 205

Val His Val Lys Glu Gly Val Tyr Pro Leu Gly Thr Val Pro Pro Gly
    210                 215                 220

Leu Asp Glu Glu Pro Thr Phe Arg Cys Asp Glu Cys Asp Glu Leu Phe
225                 230                 235                 240

Gln Ser Lys Leu Asp Leu Arg Arg His Lys Lys Tyr Thr Cys Gly Ser
                245                 250                 255

Val Gly Ala Ala Leu Tyr Glu Gly Leu Ala Glu Glu Leu Lys Pro Glu
            260                 265                 270

Gly Leu Gly Gly Gly Ser Gly Gln Ala His Glu Cys Lys Asp Cys Glu
            275                 280                 285

Arg Met Phe Pro Asn Lys Tyr Ser Leu Glu Gln His Met Val Ile His
            290                 295                 300

Thr Glu Glu Arg Glu Tyr Lys Cys Asp Gln Cys Pro Lys Ala Phe Asn
305                 310                 315                 320

Trp Lys Ser Asn Phe Ile Arg His Gln Met Ser His Asp Ser Gly Lys
                325                 330                 335

Arg Phe Glu Cys Glu Asn Cys Val Lys Val Phe Thr Asp Pro Ser Asn
            340                 345                 350

Leu Gln Arg His Ile Arg Ser Gln His Val Gly Ala Arg Ala His Ala
    355                 360                 365

Cys Pro Asp Cys Gly Lys Thr Phe Ala Thr Ser Ser Gly Leu Lys Gln
    370                 375                 380

His Lys His Ile His Ser Thr Val Lys Pro Phe Ile Cys Glu Val Cys
385                 390                 395                 400

His Lys Ser Tyr Thr Gln Phe Ser Asn Leu Cys Arg His Lys Arg Met
                405                 410                 415

His Ala Asp Cys Arg Thr Gln Ile Lys Cys Lys Asp Cys Gly Gln Met
            420                 425                 430

Phe Ser Thr Thr Ser Ser Leu Asn Lys His Arg Arg Phe Cys Glu Gly
```

-continued

```
            435                 440                 445
Lys Asn His Tyr Thr Pro Gly Gly Ile Phe Ala Pro Gly Leu Pro Leu
450                 455                 460

Thr Pro Ser Pro Met Met Asp Lys Ala Lys Pro Ser Pro Ser Leu Asn
465                 470                 475                 480

His Ala Ser Leu Gly Phe Asn Glu Tyr Phe Pro Tyr Arg Pro His Pro
                485                 490                 495

Gly Ser Leu Pro Phe Ser Thr Ala Pro Pro Thr Phe Pro Ala Leu Thr
                500                 505                 510

Pro Gly Phe Pro Gly Ile Phe Pro Pro Ser Leu Tyr Pro Arg Pro Pro
                515                 520                 525

Leu Leu Pro Pro Thr Ser Leu Leu Lys Ser Pro Leu Asn His Thr Gln
530                 535                 540

Asp Ala Lys Leu Pro Ser Pro Leu Gly Asn Pro Ala Leu Pro Leu Val
545                 550                 555                 560

Ser Ala Val Ser Asn Ser Ser Gln Gly Thr Thr Ala Ala Ala Gly Pro
                565                 570                 575

Glu Glu Lys Phe Glu Ser Arg Leu Glu Asp Ser Cys Val Glu Lys Leu
                580                 585                 590

Lys Thr Arg Ser Ser Asp Met Ser Asp Gly Ser Asp Phe Glu Asp Val
                595                 600                 605

Asn Thr Thr Thr Gly Thr Asp Leu Asp Thr Thr Thr Gly Thr Gly Ser
610                 615                 620

Asp Leu Asp Ser Asp Val Asp Ser Asp Pro Asp Lys Asp Lys Gly Lys
625                 630                 635                 640

Gly Lys Ser Ala Glu Gly Gln Pro Lys Phe Gly Gly Gly Leu Ala Pro
                645                 650                 655

Pro Gly Ala Pro Asn Ser Val Ala Glu Val Pro Val Phe Tyr Ser Gln
                660                 665                 670

His Ser Phe Phe Pro Pro Asp Glu Gln Leu Leu Thr Ala Thr Gly
                675                 680                 685

Ala Ala Gly Asp Ser Ile Lys Ala Ile Ala Ser Ile Ala Glu Lys Tyr
690                 695                 700

Phe Gly Pro Gly Phe Met Gly Met Gln Glu Lys Lys Leu Gly Ser Leu
705                 710                 715                 720

Pro Tyr His Ser Ala Phe Pro Phe Gln Phe Leu Pro Asn Phe Pro His
                725                 730                 735

Ser Leu Tyr Pro Phe Thr Asp Arg Ala Leu Ala His Asn Leu Leu Val
                740                 745                 750

Lys Ala Glu Pro Lys Ser Pro Arg Asp Ala Leu Lys Val Gly Gly Pro
                755                 760                 765

Ser Ala Glu Cys Pro Phe Asp Leu Thr Thr Lys Pro Lys Asp Val Lys
770                 775                 780

Pro Ile Leu Pro Met Pro Lys Gly Pro Ser Ala Pro Ala Ser Gly Glu
785                 790                 795                 800

Glu Gln Pro Leu Asp Leu Ser Ile Gly Ser Arg Ala Arg Ala Ser Gln
                805                 810                 815

Asn Gly Gly Gly Arg Glu Pro Arg Lys Asn His Val Tyr Gly Glu Arg
                820                 825                 830

Lys Leu Gly Ala Gly Glu Gly Leu Pro Gln Val Cys Pro Ala Arg Met
                835                 840                 845

Pro Gln Gln Pro Pro Leu His Tyr Ala Lys Pro Ser Pro Phe Phe Met
850                 855                 860
```

-continued

```
Asp Pro Ile Tyr Arg Val Glu Lys Arg Lys Val Thr Asp Pro Val Gly
865                 870                 875                 880

Ala Leu Lys Glu Lys Tyr Leu Arg Pro Ser Pro Leu Leu Phe His Pro
                885                 890                 895

Gln Met Ser Ala Ile Glu Thr Met Thr Glu Lys Leu Glu Ser Phe Ala
            900                 905                 910

Ala Met Lys Ala Asp Ser Gly Ser Ser Leu Gln Pro Leu Pro His His
            915                 920                 925

Pro Phe Asn Phe Arg Ser Pro Pro Thr Leu Ser Asp Pro Ile Leu
    930                 935                 940

Arg Lys Gly Lys Glu Arg Tyr Thr Cys Arg Tyr Cys Gly Lys Ile Phe
945                 950                 955                 960

Pro Arg Ser Ala Asn Leu Thr Arg His His Leu Arg Thr His Thr Gly Glu
                965                 970                 975

Gln Pro Tyr Arg Cys Lys Tyr Cys Asp Arg Ser Phe Ser Ile Ser Ser
            980                 985                 990

Asn Leu Gln Arg His Val Arg Asn Ile His Asn Lys Glu Lys Pro Phe
            995                 1000                1005

Lys Cys His Leu Cys Asn Arg Cys Phe Gly Gln Gln Thr Asn Leu Asp
    1010                1015                1020

Arg His Leu Lys Lys His Glu His Glu Asn Ala Pro Val Ser Gln His
1025                1030                1035                1040

Pro Gly Val Leu Thr Asn His Leu Gly Thr Ser Ala Ser Ser Pro Thr
                1045                1050                1055

Ser Glu Ser Asp Asn His Ala Leu Leu Asp Glu Lys Glu Asp Ser Tyr
            1060                1065                1070

Phe Ser Glu Ile Arg Asn Phe Ile Ala Asn Ser Glu Met Asn Gln Ala
            1075                1080                1085

Ser Thr Arg Thr Glu Lys Arg Ala Asp Met Gln Ile Val Asp Gly Ser
            1090                1095                1100

Ala Gln Cys Pro Gly Leu Ala Ser Glu Lys Gln Glu Asp Val Glu Glu
1105                1110                1115                1120

Glu Asp Asp Asp Leu Glu Glu Asp Asp Glu Asp Ser Leu Ala Gly
                1125                1130                1135

Lys Ser Gln Asp Asp Thr Val Ser Pro Ala Pro Glu Pro Gln Ala Ala
            1140                1145                1150

Tyr Glu Asp Glu Glu Asp Glu Glu Pro Ala Ala Ser Leu Ala Val Gly
            1155                1160                1165

Phe Asp His Thr Arg Arg Cys Ala Glu Asp His Glu Gly Gly Leu Leu
    1170                1175                1180

Ala Leu Glu Pro Met Pro Thr Phe Gly Lys Gly Leu Asp Leu Arg Arg
1185                1190                1195                1200

Ala Ala Glu Glu Ala Phe Glu Val Lys Asp Val Leu Asn Ser Thr Leu
                1205                1210                1215

Asp Ser Glu Ala Leu Lys His Thr Leu Cys Arg Gln Ala Lys Asn Gln
            1220                1225                1230

Ala Tyr Ala Met Met Leu Ser Leu Ser Glu Asp Thr Pro Leu His Thr
            1235                1240                1245

Pro Ser Gln Gly Ser Leu Asp Ala Trp Leu
    1250                1255
```

<210> SEQ ID NO 17
<211> LENGTH: 2442

```
<212> TYPE: DNA
<213> ORGANISM: Human
<220> FEATURE:
<221> NAME/KEY: CDS
<222> LOCATION: (232)...(2391)

<400> SEQUENCE: 17
```

| | | |
|---|---|---|
| agctttccca gctagtcgaa tcactggtgc acctccggaa tccgaggttc gcattgctct | 60 |
| cggacagagt tctgcctccc cagtactccc aaactcccag tcctgtgcac caatgaggtc | 120 |
| cagctctgag gcttctttcc tgagaaaaaa atttggaagt ccgtgactgt ttcctggagg | 180 |
| agctgagaag aggaagctca cttccggcgt agggaggctt ctgacccgg a atg gag | 237 |
| | Met Glu |
| | 1 |

```
gag gcg gag gag ctg ctc ttg gag ggg aag aag gcg ctg caa ctc gcc      285
Glu Ala Glu Glu Leu Leu Leu Glu Gly Lys Lys Ala Leu Gln Leu Ala
      5                  10                  15 cgc gag ccg cgc ctg ggc ctg gac tta gga tgg aac cct tcc gga gaa      333
Arg Glu Pro Arg Leu Gly Leu Asp Leu Gly Trp Asn Pro Ser Gly Glu
 20                  25                  30 ggc tgt acg cag ggc ctc aaa gac gtc cca ccc gag ccg acc cga gac      381
Gly Cys Thr Gln Gly Leu Lys Asp Val Pro Pro Glu Pro Thr Arg Asp
 35                  40                  45                  50 atc ctc gct tta aag agc ctt ccc cgg ggc ttg gcc ctt ggc ccc tca      429
Ile Leu Ala Leu Lys Ser Leu Pro Arg Gly Leu Ala Leu Gly Pro Ser
                 55                  60                  65 ctc gcc aag gaa cag cgc ttg ggg gtc tgg tgt gtc ggg gac ccc ctg      477
Leu Ala Lys Glu Gln Arg Leu Gly Val Trp Cys Val Gly Asp Pro Leu
             70                  75                  80 cag ccc ggc ctg ctg tgg ggg ccg ctg gaa gag gag tct gcc tcc aag      525
Gln Pro Gly Leu Leu Trp Gly Pro Leu Glu Glu Glu Ser Ala Ser Lys
         85                  90                  95 gag aag ggc gag gga gta aag cca cgg cag gag gag aac ctg tca tta      573
Glu Lys Gly Glu Gly Val Lys Pro Arg Gln Glu Glu Asn Leu Ser Leu
    100                 105                 110 ggc cca tgg gga gac gtg tgt gcc tgt gag cag agt tct ggc tgg act      621
Gly Pro Trp Gly Asp Val Cys Ala Cys Glu Gln Ser Ser Gly Trp Thr
115                 120                 125                 130 agc ttg gta caa cgg ggc agg ctg gag agt gag gga aat gtg gcc cca      669
Ser Leu Val Gln Arg Gly Arg Leu Glu Ser Glu Gly Asn Val Ala Pro
                135                 140                 145 gtg cgg atc agc gag agg ctt cat ctg caa gtg tac cag ctg gtg ctg      717
Val Arg Ile Ser Glu Arg Leu His Leu Gln Val Tyr Gln Leu Val Leu
            150                 155                 160 cca ggc tct gaa ctg ctg ctg tgg ccc cag cct tcc tct gag ggc cca      765
Pro Gly Ser Glu Leu Leu Leu Trp Pro Gln Pro Ser Ser Glu Gly Pro
        165                 170                 175 agt ctc acc cag cct ggg ctg gac aaa gag gca gct gta gca gtg gtg      813
Ser Leu Thr Gln Pro Gly Leu Asp Lys Glu Ala Ala Val Ala Val Val
    180                 185                 190 aca gaa gtg gag tct gct gta cag cag gaa gtg gcc tcc cct ggg gag      861
Thr Glu Val Glu Ser Ala Val Gln Gln Glu Val Ala Ser Pro Gly Glu
195                 200                 205                 210 gat gca gca gaa cct tgc ata gat cct ggt tcc cag tca ccc tct ggc      909
Asp Ala Ala Glu Pro Cys Ile Asp Pro Gly Ser Gln Ser Pro Ser Gly
                215                 220                 225 atc cag gca gag aat atg gtg agc cct gga ctt aag ttc cca acc cag      957
Ile Gln Ala Glu Asn Met Val Ser Pro Gly Leu Lys Phe Pro Thr Gln
            230                 235                 240 gac cga att tcc aag gat agc cag cca ctt ggc cca ttg ctt cag gat     1005
Asp Arg Ile Ser Lys Asp Ser Gln Pro Leu Gly Pro Leu Leu Gln Asp
```

```
                    -continued

Asp Arg Ile Ser Lys Asp Ser Gln Pro Leu Gly Pro Leu Leu Gln Asp
        245                 250                 255 ggc gac gtg gat gag gaa tgc ccg gcc cag gca cag atg cca cct gaa      1053
Gly Asp Val Asp Glu Glu Cys Pro Ala Gln Ala Gln Met Pro Pro Glu
260                 265                 270 ctt cag agc aat tcg gct acc cag cag gac cca gat ggc agt gga gcc      1101
Leu Gln Ser Asn Ser Ala Thr Gln Gln Asp Pro Asp Gly Ser Gly Ala
275                 280                 285                 290 agt ttc tca tct tct gcc agg ggc acc cag ccg cat ggc tac ctg gcc      1149
Ser Phe Ser Ser Ser Ala Arg Gly Thr Gln Pro His Gly Tyr Leu Ala
                    295                 300                 305 aag aag tta cac agc ccc agt gat cag tgc cca ccc aga gca aag acc      1197
Lys Lys Leu His Ser Pro Ser Asp Gln Cys Pro Pro Arg Ala Lys Thr
                310                 315                 320 cca gag cct gga gcc cag cag tct ggc ttc cct aca ctc tcg cgg agc      1245
Pro Glu Pro Gly Ala Gln Gln Ser Gly Phe Pro Thr Leu Ser Arg Ser
            325                 330                 335 cct cct ggc cca gca gga agc tcc cca aag cag ggg cga cgg tac cgg      1293
Pro Pro Gly Pro Ala Gly Ser Ser Pro Lys Gln Gly Arg Arg Tyr Arg
        340                 345                 350 tgt gga gag tgt ggc aag gca ttc cta cag ctg tgc cac cta aag aag      1341
Cys Gly Glu Cys Gly Lys Ala Phe Leu Gln Leu Cys His Leu Lys Lys
355                 360                 365                 370 cac gca ttt gtg cac acg ggc cac aag ccc ttt ctt tgc act gag tgt      1389
His Ala Phe Val His Thr Gly His Lys Pro Phe Leu Cys Thr Glu Cys
                    375                 380                 385 ggc aag agc tat agc tca gag gag agc ttc aaa gcc cat atg ctg ggc      1437
Gly Lys Ser Tyr Ser Ser Glu Glu Ser Phe Lys Ala His Met Leu Gly
                390                 395                 400 cac cgt ggg gtg cgg ccc ttc ccc tgt cca caa tgc gac aag gcc tat      1485
His Arg Gly Val Arg Pro Phe Pro Cys Pro Gln Cys Asp Lys Ala Tyr
            405                 410                 415 ggc acc cag cga gac ctc aaa gag cac cag gtg gta cat tca ggt gcc      1533
Gly Thr Gln Arg Asp Leu Lys Glu His Gln Val Val His Ser Gly Ala
        420                 425                 430 cgg ccc ttt gct tgt gac cag tgt ggc aag gcc ttt gcc cgc cgg ccc      1581
Arg Pro Phe Ala Cys Asp Gln Cys Gly Lys Ala Phe Ala Arg Arg Pro
435                 440                 445                 450 tcc ctg cgg ctg cat cgc aag acc cac cag gtg cca gct gcc cct gcc      1629
Ser Leu Arg Leu His Arg Lys Thr His Gln Val Pro Ala Ala Pro Ala
                    455                 460                 465 cct tgc cca tgc cct gtg tgt ggg cgg ccc ctg gcc aac cag ggc tcc      1677
Pro Cys Pro Cys Pro Val Cys Gly Arg Pro Leu Ala Asn Gln Gly Ser
                470                 475                 480 ctg cgg aac cat atg agg ctc cat aca gga gaa aag cct ttc ctg tgc      1725
Leu Arg Asn His Met Arg Leu His Thr Gly Glu Lys Pro Phe Leu Cys
            485                 490                 495 ccg cac tgt ggc cgg gcg ttt cgt cag cgg ggc aac ctg cgt ggg cat      1773
Pro His Cys Gly Arg Ala Phe Arg Gln Arg Gly Asn Leu Arg Gly His
        500                 505                 510 ttg cgg ctc cac acc ggg gag cgt cct tac cgc tgc cca cac tgt gcc      1821
Leu Arg Leu His Thr Gly Glu Arg Pro Tyr Arg Cys Pro His Cys Ala
515                 520                 525                 530 gat gcc ttc ccc cag ctg cct gaa ctg cgg cgc cat ctc atc tca cac      1869
Asp Ala Phe Pro Gln Leu Pro Glu Leu Arg Arg His Leu Ile Ser His
                    535                 540                 545 acc ggg gag gcc cac ttg tgc ccg gtg tgt ggc aag gcc ctc cga gac      1917
Thr Gly Glu Ala His Leu Cys Pro Val Cys Gly Lys Ala Leu Arg Asp
                550                 555                 560
```

-continued

```
cca cac acg ctc cga gct cac gag cgt ctg cac tcc gga gag agg ccc         1965
Pro His Thr Leu Arg Ala His Glu Arg Leu His Ser Gly Glu Arg Pro
        565                 570                 575 ttt ccc tgt ccc cag tgt ggc cgt gct tac acg ctg gcc acc aag ctg         2013
Phe Pro Cys Pro Gln Cys Gly Arg Ala Tyr Thr Leu Ala Thr Lys Leu
    580                 585                 590 cgg cgc cac ctc aaa tct cac ttg gag gac aag ccc tac cgc tgc ccc         2061
Arg Arg His Leu Lys Ser His Leu Glu Asp Lys Pro Tyr Arg Cys Pro
595                 600                 605                 610 acc tgt ggc atg ggc tac acc ctc ccg cag agc ctc agg cgg cat cag         2109
Thr Cys Gly Met Gly Tyr Thr Leu Pro Gln Ser Leu Arg Arg His Gln
                615                 620                 625 ctc agt cac cgg cct gag gca ccc tgc agc cca ccc tct gtg cct tct         2157
Leu Ser His Arg Pro Glu Ala Pro Cys Ser Pro Pro Ser Val Pro Ser
        630                 635                 640 gct gct tct gag ccc act gtg gtg ctc ctg cag gct gag cca caa ctg         2205
Ala Ala Ser Glu Pro Thr Val Val Leu Leu Gln Ala Glu Pro Gln Leu
    645                 650                 655 ctg gac aca cac aga gag gag gaa gtc tcc ccc gcc agg gat gtt gtt         2253
Leu Asp Thr His Arg Glu Glu Glu Val Ser Pro Ala Arg Asp Val Val
660                 665                 670 gag gtc acc att tca gaa agc cag gag aag tgc ttt gtg gtg cca gag         2301
Glu Val Thr Ile Ser Glu Ser Gln Glu Lys Cys Phe Val Val Pro Glu
675                 680                 685                 690 gag cca gat gcc gcc ccc agc ctg gtg cta atc cat aag gac atg ggc         2349
Glu Pro Asp Ala Ala Pro Ser Leu Val Leu Ile His Lys Asp Met Gly
                695                 700                 705 ctc ggc gcc tgg gca gag gtg gtg gag gtg gag atg ggc acc                 2391
Leu Gly Ala Trp Ala Glu Val Val Glu Val Glu Met Gly Thr
        710                 715                 720 tgacagcttt gccttttgct gacacagctc cataaagact cgtgctttct c                2442

<210> SEQ ID NO 18
<211> LENGTH: 720
<212> TYPE: PRT
<213> ORGANISM: Human

<400> SEQUENCE: 18

Met Glu Glu Ala Glu Glu Leu Leu Glu Gly Lys Lys Ala Leu Gln
1               5                   10                  15

Leu Ala Arg Glu Pro Arg Leu Gly Leu Asp Leu Gly Trp Asn Pro Ser
                20                  25                  30

Gly Glu Gly Cys Thr Gln Gly Leu Lys Asp Val Pro Glu Pro Thr
            35                  40                  45

Arg Asp Ile Leu Ala Leu Lys Ser Leu Pro Arg Gly Leu Ala Leu Gly
        50                  55                  60

Pro Ser Leu Ala Lys Glu Gln Arg Leu Gly Val Trp Cys Val Gly Asp
65                  70                  75                  80

Pro Leu Gln Pro Gly Leu Leu Trp Gly Pro Leu Glu Glu Glu Ser Ala
                85                  90                  95

Ser Lys Glu Lys Gly Glu Gly Val Lys Pro Arg Gln Glu Glu Asn Leu
            100                 105                 110

Ser Leu Gly Pro Trp Gly Asp Val Cys Ala Cys Glu Gln Ser Ser Gly
        115                 120                 125

Trp Thr Ser Leu Val Gln Arg Gly Arg Leu Glu Ser Glu Gly Asn Val
    130                 135                 140

Ala Pro Val Arg Ile Ser Glu Arg Leu His Leu Gln Val Tyr Gln Leu
145                 150                 155                 160
```

```
Val Leu Pro Gly Ser Glu Leu Leu Trp Pro Gln Pro Ser Ser Glu
                165                 170                 175

Gly Pro Ser Leu Thr Gln Pro Gly Leu Asp Lys Glu Ala Ala Val Ala
                180                 185                 190

Val Val Thr Glu Val Glu Ser Ala Val Gln Gln Glu Val Ala Ser Pro
                195                 200                 205

Gly Glu Asp Ala Ala Glu Pro Cys Ile Asp Pro Gly Ser Gln Ser Pro
        210                 215                 220

Ser Gly Ile Gln Ala Glu Asn Met Val Ser Pro Gly Leu Lys Phe Pro
225                 230                 235                 240

Thr Gln Asp Arg Ile Ser Lys Asp Ser Gln Pro Leu Gly Pro Leu Leu
                245                 250                 255

Gln Asp Gly Asp Val Asp Glu Glu Cys Pro Ala Gln Ala Gln Met Pro
                260                 265                 270

Pro Glu Leu Gln Ser Asn Ser Ala Thr Gln Asp Pro Asp Gly Ser
            275                 280                 285

Gly Ala Ser Phe Ser Ser Ala Arg Gly Thr Gln Pro His Gly Tyr
        290                 295                 300

Leu Ala Lys Lys Leu His Ser Pro Ser Asp Gln Cys Pro Pro Arg Ala
305                 310                 315                 320

Lys Thr Pro Glu Pro Gly Ala Gln Gln Ser Gly Phe Pro Thr Leu Ser
                325                 330                 335

Arg Ser Pro Pro Gly Pro Ala Gly Ser Ser Pro Lys Gln Gly Arg Arg
                340                 345                 350

Tyr Arg Cys Gly Glu Cys Gly Lys Ala Phe Leu Gln Leu Cys His Leu
                355                 360                 365

Lys Lys His Ala Phe Val His Thr Gly His Lys Pro Phe Leu Cys Thr
        370                 375                 380

Glu Cys Gly Lys Ser Tyr Ser Ser Glu Glu Ser Phe Lys Ala His Met
385                 390                 395                 400

Leu Gly His Arg Gly Val Arg Pro Phe Pro Cys Pro Gln Cys Asp Lys
                405                 410                 415

Ala Tyr Gly Thr Gln Arg Asp Leu Lys Glu His Gln Val Val His Ser
                420                 425                 430

Gly Ala Arg Pro Phe Ala Cys Asp Gln Cys Gly Lys Ala Phe Ala Arg
            435                 440                 445

Arg Pro Ser Leu Arg Leu His Arg Lys Thr His Gln Val Pro Ala Ala
    450                 455                 460

Pro Ala Pro Cys Pro Cys Pro Val Cys Gly Arg Pro Leu Ala Asn Gln
465                 470                 475                 480

Gly Ser Leu Arg Asn His Met Arg Leu His Thr Gly Glu Lys Pro Phe
                485                 490                 495

Leu Cys Pro His Cys Gly Arg Ala Phe Arg Gln Arg Gly Asn Leu Arg
            500                 505                 510

Gly His Leu Arg Leu His Thr Gly Glu Arg Pro Tyr Arg Cys Pro His
        515                 520                 525

Cys Ala Asp Ala Phe Pro Gln Leu Pro Glu Leu Arg Arg His Leu Ile
    530                 535                 540

Ser His Thr Gly Glu Ala His Leu Cys Pro Val Cys Gly Lys Ala Leu
545                 550                 555                 560

Arg Asp Pro His Thr Leu Arg Ala His Glu Arg Leu His Ser Gly Glu
                565                 570                 575
```

```
Arg Pro Phe Pro Cys Pro Gln Cys Gly Arg Ala Tyr Thr Leu Ala Thr
            580                 585                 590

Lys Leu Arg Arg His Leu Lys Ser His Leu Glu Asp Lys Pro Tyr Arg
            595                 600                 605

Cys Pro Thr Cys Gly Met Gly Tyr Thr Leu Pro Gln Ser Leu Arg Arg
            610                 615                 620

His Gln Leu Ser His Arg Pro Glu Ala Pro Cys Ser Pro Pro Ser Val
625                 630                 635                 640

Pro Ser Ala Ala Ser Glu Pro Thr Val Val Leu Leu Gln Ala Glu Pro
                645                 650                 655

Gln Leu Leu Asp Thr His Arg Glu Glu Val Ser Pro Ala Arg Asp
            660                 665                 670

Val Val Glu Val Thr Ile Ser Glu Ser Gln Lys Cys Phe Val Val
            675                 680                 685

Pro Glu Glu Pro Asp Ala Ala Pro Ser Leu Val Leu Ile His Lys Asp
690                 695                 700

Met Gly Leu Gly Ala Trp Ala Glu Val Val Glu Val Glu Met Gly Thr
705                 710                 715                 720

<210> SEQ ID NO 19
<211> LENGTH: 1431
<212> TYPE: DNA
<213> ORGANISM: Human
<220> FEATURE:
<221> NAME/KEY: CDS
<222> LOCATION: (151)...(1185)

<400> SEQUENCE: 19
ctaagaaaca aaagaatttc aagataatta ggtggagcgg gcgggctggc tgctgaggac      60
gcgccgcctg cgccttcctc cctgcgtgcc tcgccccggg cggcccgggg ctgccgcggt     120
gcgcgggtgc cgggccctgc cttgccggcc atg ggg gaa ggg ggc gcc gcg gcg     174
                                Met Gly Glu Gly Gly Ala Ala Ala
                                 1                5 gcg ctg gtg gcg gcg gca gca gca gca gcg gca gcg gca gcg gtg            222
Ala Leu Val Ala Ala Ala Ala Ala Ala Ala Ala Ala Ala Ala Val
     10                  15                  20 gtg gcc ggg cag cgg cgg cgg cgg cta ggg cgc agg gcg cgc tgc cat        270
Val Ala Gly Gln Arg Arg Arg Arg Leu Gly Arg Arg Ala Arg Cys His
 25                  30                  35                  40 ggg cct ggc cgg gct gca ggc ggg aag atg tcc aag ccc tgc gcg gtg        318
Gly Pro Gly Arg Ala Ala Gly Gly Lys Met Ser Lys Pro Cys Ala Val
                 45                  50                  55 gag gcg gcg gcg gcg gcg gtg gca gcg acg gcc ccg ggc ccg gag atg        366
Glu Ala Ala Ala Ala Ala Val Ala Ala Thr Ala Pro Gly Pro Glu Met
             60                  65                  70 gtg gag cgg agg ggc ccg ggg agg ccc cgc acc gac ggg gag aac gta        414
Val Glu Arg Arg Gly Pro Gly Arg Pro Arg Thr Asp Gly Glu Asn Val
         75                  80                  85 ttt acc ggg cag tca aag atc tat tcc tac atg agc ccg aac aaa tgc        462
Phe Thr Gly Gln Ser Lys Ile Tyr Ser Tyr Met Ser Pro Asn Lys Cys
     90                  95                 100 tct gga atg cgt ttc ccc ctt cag gaa gag aac tca gtt aca cat cac        510
Ser Gly Met Arg Phe Pro Leu Gln Glu Glu Asn Ser Val Thr His His
105                 110                 115                 120 gaa gtc aaa tgc cag ggg aaa cca tta gct gga atc tac agg aaa cga        558
Glu Val Lys Cys Gln Gly Lys Pro Leu Ala Gly Ile Tyr Arg Lys Arg
                125                 130                 135 gaa gag aaa aga aat gct ggg aac gca gta cgg agc gcc atg aag tcc        606
```

```
                    Glu Glu Lys Arg Asn Ala Gly Asn Ala Val Arg Ser Ala Met Lys Ser
                                    140                 145                 150 gag gaa cag aag atc aaa gac gcc agg aga cgt ccc ctg aag gaa aaa          654
Glu Glu Gln Lys Ile Lys Asp Ala Arg Arg Arg Pro Leu Lys Glu Lys
            155                 160                 165 cgc aac aga atc gca aac acg gat ttc tac cct gtc cga agg agc tcc          702
Arg Asn Arg Ile Ala Asn Thr Asp Phe Tyr Pro Val Arg Arg Ser Ser
        170                 175                 180 agg aag agc aaa gcc gag ctg cag tct gaa gaa agg aaa aga ata gat          750
Arg Lys Ser Lys Ala Glu Leu Gln Ser Glu Glu Arg Lys Arg Ile Asp
185                 190                 195                 200 gaa ttg att gaa agt ggg aag gaa gaa gga atg aag atc gac ctc atc          798
Glu Leu Ile Glu Ser Gly Lys Glu Glu Gly Met Lys Ile Asp Leu Ile
                205                 210                 215 gat ggc aaa ggc agg ggt gtg att gcc acc aag cag ttc tcc cgg ggt          846
Asp Gly Lys Gly Arg Gly Val Ile Ala Thr Lys Gln Phe Ser Arg Gly
            220                 225                 230 gcc ttt gtg gtg gaa tac cac ggg gac ctc atc gag atc acc gac gcc          894
Ala Phe Val Val Glu Tyr His Gly Asp Leu Ile Glu Ile Thr Asp Ala
        235                 240                 245 aag aaa cgg gag gct ctg tac gca cag gac cct tcc acg ggc tgc tac          942
Lys Lys Arg Glu Ala Leu Tyr Ala Gln Asp Pro Ser Thr Gly Cys Tyr
    250                 255                 260 atg tac tat ttt cag tat ctg agc aaa acc tac tgc gtg gat gca act          990
Met Tyr Tyr Phe Gln Tyr Leu Ser Lys Thr Tyr Cys Val Asp Ala Thr
265                 270                 275                 280 aga gag aca aat cgc cta gga aga ctg atc aat cac agc aaa cgt ggg         1038
Arg Glu Thr Asn Arg Leu Gly Arg Leu Ile Asn His Ser Lys Arg Gly
                285                 290                 295 aac tgc caa acc aaa ctg cac gac atc gac ggc gta cct cac ctc atc         1086
Asn Cys Gln Thr Lys Leu His Asp Ile Asp Gly Val Pro His Leu Ile
            300                 305                 310 ctc atc gcc tcc cga gac atc gcg gct ggg gag gag ccc ctg tat gac         1134
Leu Ile Ala Ser Arg Asp Ile Ala Ala Gly Glu Glu Pro Leu Tyr Asp
        315                 320                 325 tat ggg gac cgc agc aag gct tcc att gaa gcc cac cca tgg ctg aag         1182
Tyr Gly Asp Arg Ser Lys Ala Ser Ile Glu Ala His Pro Trp Leu Lys
    330                 335                 340 cat taaccggtgg gccccgcgcc ctccccgccc cactttccct tcttcaaagg              1235
His
345 acaaagtgcc ctcaagggaa attgaatttt tttttacaca cttaatctta gcggattact       1295 tcagatgttt ttaaaaagta tattaagatg ccttttcact gtagtattta aatatctgtt       1355 acaggtttcc aaggtggact tgaacagatg gccttatatt accaaaactt ttatattcta       1415 gttgtttttg tacttt                                                       1431

<210> SEQ ID NO 20
<211> LENGTH: 345
<212> TYPE: PRT
<213> ORGANISM: Human

<400> SEQUENCE: 20

Met Gly Glu Gly Gly Ala Ala Ala Ala Leu Val Ala Ala Ala Ala Ala
1               5                   10                  15

Ala Ala Ala Ala Ala Ala Ala Val Val Ala Gly Gln Arg Arg Arg Arg
            20                  25                  30

Leu Gly Arg Arg Ala Arg Cys His Gly Pro Gly Arg Ala Ala Gly Gly
        35                  40                  45
```

```
Lys Met Ser Lys Pro Cys Ala Val Glu Ala Ala Ala Ala Val Ala
 50                  55                  60

Ala Thr Ala Pro Gly Pro Glu Met Val Glu Arg Arg Gly Pro Gly Arg
 65                  70                  75                  80

Pro Arg Thr Asp Gly Glu Asn Val Phe Thr Gly Gln Ser Lys Ile Tyr
                 85                  90                  95

Ser Tyr Met Ser Pro Asn Lys Cys Ser Gly Met Arg Phe Pro Leu Gln
            100                 105                 110

Glu Glu Asn Ser Val Thr His His Glu Val Lys Cys Gln Gly Lys Pro
            115                 120                 125

Leu Ala Gly Ile Tyr Arg Lys Arg Glu Glu Lys Arg Asn Ala Gly Asn
130                 135                 140

Ala Val Arg Ser Ala Met Lys Ser Glu Glu Gln Lys Ile Lys Asp Ala
145                 150                 155                 160

Arg Arg Arg Pro Leu Lys Glu Lys Arg Asn Arg Ile Ala Asn Thr Asp
                165                 170                 175

Phe Tyr Pro Val Arg Arg Ser Ser Arg Lys Ser Lys Ala Glu Leu Gln
            180                 185                 190

Ser Glu Glu Arg Lys Arg Ile Asp Glu Leu Ile Glu Ser Gly Lys Glu
            195                 200                 205

Glu Gly Met Lys Ile Asp Leu Ile Asp Gly Lys Gly Arg Gly Val Ile
210                 215                 220

Ala Thr Lys Gln Phe Ser Arg Gly Ala Phe Val Val Glu Tyr His Gly
225                 230                 235                 240

Asp Leu Ile Glu Ile Thr Asp Ala Lys Lys Arg Glu Ala Leu Tyr Ala
                245                 250                 255

Gln Asp Pro Ser Thr Gly Cys Tyr Met Tyr Tyr Phe Gln Tyr Leu Ser
            260                 265                 270

Lys Thr Tyr Cys Val Asp Ala Thr Arg Glu Thr Asn Arg Leu Gly Arg
            275                 280                 285

Leu Ile Asn His Ser Lys Arg Gly Asn Cys Gln Thr Lys Leu His Asp
290                 295                 300

Ile Asp Gly Val Pro His Leu Ile Leu Ile Ala Ser Arg Asp Ile Ala
305                 310                 315                 320

Ala Gly Glu Glu Pro Leu Tyr Asp Tyr Gly Asp Arg Ser Lys Ala Ser
                325                 330                 335

Ile Glu Ala His Pro Trp Leu Lys His
            340                 345

<210> SEQ ID NO 21
<211> LENGTH: 26
<212> TYPE: DNA
<213> ORGANISM: Human
<220> FEATURE:
<223> OTHER INFORMATION: Primer

<400> SEQUENCE: 21
tgtccctgca cgcccggaag tagatg                                        26

<210> SEQ ID NO 22
<211> LENGTH: 22
<212> TYPE: DNA
<213> ORGANISM: Human
<220> FEATURE:
<223> OTHER INFORMATION: Primer

<400> SEQUENCE: 22
```

```
<210> SEQ ID NO 23
<211> LENGTH: 23
<212> TYPE: DNA
<213> ORGANISM: Human
<220> FEATURE:
<223> OTHER INFORMATION: Primer

<400> SEQUENCE: 23
gggggtagac gccttggttc acg                                              23

<210> SEQ ID NO 24
<211> LENGTH: 21
<212> TYPE: DNA
<213> ORGANISM: Human
<220> FEATURE:
<223> OTHER INFORMATION: Primer

<400> SEQUENCE: 24
catcgcagga gcacgccaca c                                                21

<210> SEQ ID NO 25
<211> LENGTH: 967
<212> TYPE: DNA
<213> ORGANISM: Human

<400> SEQUENCE: 25
gtcttgagga ccatctctcc cggcagcata ccgtgtggct tcacactgct ctgcctctct        60
gaacctcggt ttcttcatct ataaaatggg aataagagta agccacctca atggactgtg       120
ggaggcttaa gtaaattgaa gtgccatgca agtagctagc atgcagttgc agctcaatga       180
atattatgat ggccgcagat acgatggcta cagctggggc acccatttcg ggtcacaagg       240
tagggttcaa tgttgaagat ggcagagcca attgcatccc tgatgatcgt ggagtgccgg       300
gcctgcctga gatgctcacc tctcttcctt taccagagag agaaagacag aatgaccgag       360
aacatgaagg agtgccttgg ccagaccaat gcagccgtgg gggatatggt gacggtggtg       420
aatccgagcc aggagtatgg ccagccctgc tctaggagac cggactcctc ggccatggaa       480
gttgagccca gaaactgaa agggaagcgc gacctcatcg tgcccaaaag cttccagcaa       540
gtggacttct ggttttgtga gtcctgccag gagtacttcg tggatgaatg cccaaaccat       600
ggccccccgg tgtttgtgtc tgacacaccg gtgcccgtgg gcatcccaga ccgggcggcg       660
ctcaccatcc cacagggcat ggaggtggtc aaggacacta gtggagagag tgacgtgcga       720
tgtgtaaacg aggtcatccc caagggccac atcttcggcc cctatgaggg gcagatctcc       780
acccaggaca aatcagctgg cttcttctcc tggctgattg tggacaagaa caaccgctat       840
aagtccatag atggctcaga cgagaccgaa gccaactgga tgaggtacgt ggtcatctcc       900
cgggaggaga gggagcagaa cctgctggcg ttccagcaca gtgagcgcat ctacttccgg       960
gcgtgca                                                               967

<210> SEQ ID NO 26
<211> LENGTH: 622
<212> TYPE: DNA
<213> ORGANISM: Human

<400> SEQUENCE: 26
gaagatagtg tgtggctgct tctggactca aggaggagga gagagattcc gcgagccgac        60
```

-continued

| | |
|---|---|
| accatgcgat ccaaggcgag ggcgaggaag ctagccaaaa gtgacggtga cgttgtaaat | 120 |
| aatatgtatg agcccaaccg ggacctgctg gccagccaca gcgcgaggga cgaggccgag | 180 |
| gacagtgcca tgtcgcccat ccccgtgggg tcaccgcccc ccttccccac cagcgaggac | 240 |
| ttcacccca aggagggctc gccgtacgag gcccctgtct acattcctga agacattccg | 300 |
| atcccagcag acttcgagct ccgagagtcc tccatcccag gggctggcct ggggtctgg | 360 |
| gccaagagga agatggaagc cggggagagg ctgggcccct gcgtggtggt gccccgggcg | 420 |
| gcggcaaagg agacagactt cggatggag caaatactga cggacgtgga agtgtcgccc | 480 |
| caggaaggct gcatcacaaa gatctccgaa gacctgggca gtgagaagtt ctgcgtggat | 540 |
| gcaaatcagg cggggctgg cagctggctc aagtacatcc gtgtggcgtg ctcctgcgat | 600 |
| gaccagaacc tcaccatgtg tc | 622 |

<210> SEQ ID NO 27
<211> LENGTH: 114
<212> TYPE: PRT
<213> ORGANISM: Human

<400> SEQUENCE: 27

Lys Thr Arg Ile Phe Val Trp Ala Thr Lys Pro Ile Leu Lys Gly Lys
1               5                   10                  15

Lys Phe Gly Pro Glu Val Gly Asp Lys Lys Arg Ser Gln Val Lys
        20                  25                  30

Asn Asn Val Tyr Met Trp Glu Val Tyr Tyr Pro Asn Leu Gly Trp Met
            35                  40                  45

Cys Ile Asp Ala Thr Asp Pro Glu Lys Gly Asn Trp Leu Arg Tyr Val
    50                  55                  60

Asn Trp Ala Cys Ser Gly Glu Glu Gln Asn Leu Phe Pro Leu Glu Ile
65                  70                  75                  80

Asn Arg Ala Ile Tyr Tyr Lys Thr Leu Lys Pro Ile Ala Pro Gly Glu
                85                  90                  95

Glu Leu Leu Val Trp Tyr Asn Gly Glu Asp Asn Pro Glu Ile Ala Ala
            100                 105                 110

Ala Ile

<210> SEQ ID NO 28
<211> LENGTH: 117
<212> TYPE: PRT
<213> ORGANISM: Human

<400> SEQUENCE: 28

Glu Glu Val Ile Gly Val Met Ser Lys Glu Tyr Ile Pro Lys Gly Thr
1               5                   10                  15

Arg Phe Gly Pro Leu Ile Gly Glu Ile Tyr Thr Asn Asp Thr Val Pro
        20                  25                  30

Lys Asn Ala Asn Arg Lys Tyr Phe Trp Arg Ile Tyr Ser Arg Gly Glu
            35                  40                  45

Leu His His Phe Ile Asp Gly Phe Asn Glu Lys Ser Asn Trp Met
    50                  55                  60

Arg Tyr Val Asn Pro Ala His Ser Pro Arg Glu Gln Asn Leu Ala Ala
65                  70                  75                  80

Cys Gln Asn Gly Met Asn Ile Tyr Phe Tyr Thr Ile Lys Pro Ile Pro
                85                  90                  95

Ala Asn Gln Glu Leu Leu Val Trp Tyr Cys Arg Asp Phe Ala Glu Arg
            100                 105                 110

```
Leu His Tyr Pro Tyr
        115

<210> SEQ ID NO 29
<211> LENGTH: 111
<212> TYPE: PRT
<213> ORGANISM: Human

<400> SEQUENCE: 29

Gly Ala Gly Leu Gly Ile Trp Thr Lys Arg Lys Ile Glu Val Gly Glu
1               5                   10                  15

Lys Phe Gly Pro Tyr Val Gly Glu Gln Arg Ser Asn Leu Lys Asp Pro
            20                  25                  30

Ser Tyr Gly Trp Glu Ile Leu Asp Glu Phe Tyr Asn Val Lys Phe Cys
        35                  40                  45

Ile Asp Ala Ser Gln Pro Asp Val Gly Ser Trp Leu Lys Tyr Ile Arg
50                  55                  60

Phe Ala Gly Cys Tyr Asp Gln His Asn Leu Val Ala Cys Gln Ile Asn
65                  70                  75                  80

Asp Gln Ile Phe Tyr Arg Val Val Ala Asp Ile Ala Pro Gly Glu Glu
                85                  90                  95

Leu Leu Leu Phe Met Lys Ser Glu Asp Tyr Pro His Glu Thr Met
            100                 105                 110

<210> SEQ ID NO 30
<211> LENGTH: 117
<212> TYPE: PRT
<213> ORGANISM: Human

<400> SEQUENCE: 30

Ile His Gly Arg Gly Leu Phe Cys Lys Arg Asn Ile Asp Ala Gly Glu
1               5                   10                  15

Met Val Ile Glu Tyr Ala Gly Asn Val Ile Arg Ser Ile Gln Thr Asp
            20                  25                  30

Lys Arg Glu Lys Tyr Tyr Asp Ser Lys Gly Ile Gly Cys Tyr Met Phe
        35                  40                  45

Arg Ile Asp Asp Ser Glu Val Val Asp Ala Thr Met His Gly Asn Arg
50                  55                  60

Ala Arg Phe Ile Asn His Ser Cys Glu Pro Asn Cys Tyr Ser Arg Val
65                  70                  75                  80

Ile Asn Ile Asp Gly Gln Lys His Ile Val Ile Phe Ala Met Arg Lys
                85                  90                  95

Ile Tyr Arg Gly Glu Glu Leu Thr Tyr Asp Tyr Lys Phe Pro Ile Glu
            100                 105                 110

Asp Ala Ser Asn Lys
        115

<210> SEQ ID NO 31
<211> LENGTH: 119
<212> TYPE: PRT
<213> ORGANISM: Human

<400> SEQUENCE: 31

Ile His Asn Trp Gly Leu Tyr Ala Leu Asp Ser Ile Ala Ala Lys Glu
1               5                   10                  15

Met Ile Ile Glu Tyr Val Gly Glu Arg Ile Arg Gln Pro Val Ala Glu
            20                  25                  30
```

```
Met Arg Glu Lys Arg Tyr Leu Lys Asn Gly Ile Gly Ser Ser Tyr Leu
            35                  40                  45

Phe Arg Val Asp Glu Asn Thr Val Ile Asp Ala Thr Lys Lys Gly Gly
 50                  55                  60

Ile Ala Arg Phe Ile Asn His Cys Cys Asp Pro Asn Cys Thr Ala Lys
 65                  70                  75                  80

Ile Ile Lys Val Gly Gly Arg Arg Ile Val Ile Tyr Ala Leu Arg
                 85                  90                  95

Asp Ile Ala Ala Ser Glu Glu Leu Thr Tyr Asp Tyr Lys Phe Glu Arg
             100                 105                 110

Glu Lys Asp Asp Glu Glu Arg
            115
```

<210> SEQ ID NO 32
<211> LENGTH: 89
<212> TYPE: PRT
<213> ORGANISM: Human

<400> SEQUENCE: 32

```
Gly Ser Gly Trp Gly Val Arg Ala Ala Thr Ala Leu Arg Lys Gly Glu
 1               5                  10                  15

Phe Val Cys Glu Tyr Ile Glu Glu Ile Ile Thr Ser Asp Glu Ala Asn
             20                  25                  30

Glu Arg Gly Lys Ala Tyr Asp Asp Asn Gly Arg Thr Tyr Leu Phe Asp
            35                  40                  45

Leu Asp Tyr Asn Thr Ala Gln Asp Ser Glu Tyr Thr Ile Asp Ala Ala
 50                  55                  60

Asn Tyr Gly Asn Ile Ser His Phe Ile Asn His Phe Asp Tyr Ile Arg
 65                  70                  75                  80

Ala Asp Asn Glu Asp Val Pro Tyr Glu
                 85
```

<210> SEQ ID NO 33
<211> LENGTH: 118
<212> TYPE: PRT
<213> ORGANISM: Human

<400> SEQUENCE: 33

```
Asp Lys Gly Trp Gly Val Arg Thr Lys Leu Pro Ile Ala Lys Gly Thr
 1               5                  10                  15

Tyr Ile Leu Glu Tyr Val Gly Glu Val Val Thr Glu Lys Glu Phe Lys
             20                  25                  30

Gln Arg Met Ala Ser Ile Tyr Leu Asn Asp Thr His His Tyr Cys Leu
            35                  40                  45

His Leu Asp Gly Gly Leu Val Ile Asp Gly Gln Arg Met Gly Ser Asp
 50                  55                  60

Cys Arg Phe Val Asn His Ser Cys Glu Pro Asn Cys Glu Met Gln Lys
 65                  70                  75                  80

Trp Ser Val Asn Gly Leu Ser Arg Met Val Leu Phe Ala Lys Arg Ala
                 85                  90                  95

Ile Glu Glu Gly Glu Glu Leu Thr Tyr Asp Tyr Asn Phe Ser Leu Phe
            100                 105                 110

Asn Pro Ser Glu Gly Gln
            115
```

<210> SEQ ID NO 34
<211> LENGTH: 1490

-continued

```
<212> TYPE: DNA
<213> ORGANISM: Human
<220> FEATURE:
<221> NAME/KEY: CDS
<222> LOCATION: (64)...(1473)

<400> SEQUENCE: 34
cttggctcag tgttaaataa ctgccgcgct ggcctgacag tctctgagat gacaataggg      60 aga atg gag aac gtg gag gtc ttc acc gct gag ggc aaa gga agg ggt      108
    Met Glu Asn Val Glu Val Phe Thr Ala Glu Gly Lys Gly Arg Gly
    1               5                   10                  15 ctg aag gcc acc aag gag ttc tgg gct gca gat atc atc ttt gct gag      156
Leu Lys Ala Thr Lys Glu Phe Trp Ala Ala Asp Ile Ile Phe Ala Glu
                20                  25                  30 cgg gct tat tcc gca gtg gtt ttt gac agc ctt gtt aat ttt gtg tgc      204
Arg Ala Tyr Ser Ala Val Val Phe Asp Ser Leu Val Asn Phe Val Cys
            35                  40                  45 cac acc tgc ttc aag agg cag gag aag ctc cat cgc tgt ggg cag tgc      252
His Thr Cys Phe Lys Arg Gln Glu Lys Leu His Arg Cys Gly Gln Cys
        50                  55                  60 aag ttt gcc cat tac tgc gac cgc acc tgc cag aag gat gct tgg ctg      300
Lys Phe Ala His Tyr Cys Asp Arg Thr Cys Gln Lys Asp Ala Trp Leu
    65                  70                  75 aac cac aag aat gaa tgt tcg gcc atc aag aga tat ggg aag gtg ctg      348
Asn His Lys Asn Glu Cys Ser Ala Ile Lys Arg Tyr Gly Lys Val Leu
80                  85                  90                  95 gcg gcg cgc atc atg tgg cgg gtg gag aga gaa ggc acc ggg ctc acg      396
Ala Ala Arg Ile Met Trp Arg Val Glu Arg Glu Gly Thr Gly Leu Thr
                100                 105                 110 gag ggc tgc ctg gtg tcc gtg gac gac ttg cag aac cac gtg gag cac      444
Glu Gly Cys Leu Val Ser Val Asp Asp Leu Gln Asn His Val Glu His
            115                 120                 125 ttt ggg gag gag gag cag aag gac ctg cgg gtg gac gtg gac aca ttc      492
Phe Gly Glu Glu Glu Gln Lys Asp Leu Arg Val Asp Val Asp Thr Phe
        130                 135                 140 ttg cag tac tgg ccg ccg cag agc cag cag ttc agc atg cag tac atc      540
Leu Gln Tyr Trp Pro Pro Gln Ser Gln Gln Phe Ser Met Gln Tyr Ile
    145                 150                 155 tcg cac atc ttc gga gtg gta att aac tgc aac ggt ttt act ctc agt      588
Ser His Ile Phe Gly Val Val Ile Asn Cys Asn Gly Phe Thr Leu Ser
160                 165                 170                 175 gat cag aga ggc ctg cag gcc gtg ggc gta ggc atc ttc ccc aac ctg      636
Asp Gln Arg Gly Leu Gln Ala Val Gly Val Gly Ile Phe Pro Asn Leu
                180                 185                 190 ggc ctg gtg aac cat gac tgt tgg ccc aac tgt act gtc ata ttt aac      684
Gly Leu Val Asn His Asp Cys Trp Pro Asn Cys Thr Val Ile Phe Asn
            195                 200                 205 aat ggc aag aga att gag ctc cgg gcc cta ggc aag atc tca gaa gga      732
Asn Gly Lys Arg Ile Glu Leu Arg Ala Leu Gly Lys Ile Ser Glu Gly
        210                 215                 220 gag gag ctg act gtg tcc tat att gac ttc ctc aac gtt agt gaa gaa      780
Glu Glu Leu Thr Val Ser Tyr Ile Asp Phe Leu Asn Val Ser Glu Glu
    225                 230                 235 cgc aag agg cag ctg aag aag cag tac tac ttt gac tgc aca tgt gaa      828
Arg Lys Arg Gln Leu Lys Lys Gln Tyr Tyr Phe Asp Cys Thr Cys Glu
240                 245                 250                 255 cac tgc cag aaa aaa ctg aag gat gac ctc ttc ctg ggg gtg aaa gac      876
His Cys Gln Lys Lys Leu Lys Asp Asp Leu Phe Leu Gly Val Lys Asp
                260                 265                 270 aac ccc aag cag ccc tct cag gaa gtg gtg aag gag atg ata caa ttc      924
```

```
                Asn Pro Lys Gln Pro Ser Gln Glu Val Val Lys Glu Met Ile Gln Phe
                            275                 280                 285 tcc aag gat aca ttg gaa aag ata gac aag gct cgt tcc gag ggt ttg          972
Ser Lys Asp Thr Leu Glu Lys Ile Asp Lys Ala Arg Ser Glu Gly Leu
            290                 295                 300 tat cat gag gta gtt gtg aaa tta tgc cgg gag tgc ctg gag aag cag         1020
Tyr His Glu Val Val Val Lys Leu Cys Arg Glu Cys Leu Glu Lys Gln
305                 310                 315 gag cca gtg ttt gct gac acc aac atc tac atg ctg cgg atg ctg agc         1068
Glu Pro Val Phe Ala Asp Thr Asn Ile Tyr Met Leu Arg Met Leu Ser
320                 325                 330                 335 att gtt tcg gag gtc ctt tcc tac ctc cag gcc ttt gag gag gcc tcg         1116
Ile Val Ser Glu Val Leu Ser Tyr Leu Gln Ala Phe Glu Glu Ala Ser
                340                 345                 350 ttc tat gcc agg agg atg gtg gac ggc tat atg aag ctc tac cac ccc         1164
Phe Tyr Ala Arg Arg Met Val Asp Gly Tyr Met Lys Leu Tyr His Pro
            355                 360                 365 aac aat gcc caa ctg ggc atg gcc gtg atg cgg gca ggg ctg acc aac         1212
Asn Asn Ala Gln Leu Gly Met Ala Val Met Arg Ala Gly Leu Thr Asn
        370                 375                 380 tgg cat gct ggt aac att gag gtg ggg cac ggg atg atc tgc aaa gcc         1260
Trp His Ala Gly Asn Ile Glu Val Gly His Gly Met Ile Cys Lys Ala
385                 390                 395 tat gcc att ctc ctg gtg aca cac gga ccc tcc cac ccc atc act aag         1308
Tyr Ala Ile Leu Leu Val Thr His Gly Pro Ser His Pro Ile Thr Lys
400                 405                 410                 415 gac tta gag gcc atg cgg gtg cag acg gag atg gag cta cgc atg ttc         1356
Asp Leu Glu Ala Met Arg Val Gln Thr Glu Met Glu Leu Arg Met Phe
                420                 425                 430 cgc cag aac gaa ttc atg tac tac aag atg cgc gag gct gcc ctg aac         1404
Arg Gln Asn Glu Phe Met Tyr Tyr Lys Met Arg Glu Ala Ala Leu Asn
            435                 440                 445 aac cag ccc atg cag gtc atg gcc gag ccc agc aat gag cca tcc cca         1452
Asn Gln Pro Met Gln Val Met Ala Glu Pro Ser Asn Glu Pro Ser Pro
        450                 455                 460 gct ctg ttc cac aag aag caa tgaggactgc ccagtgg                          1490
Ala Leu Phe His Lys Lys Gln
    465                 470

<210> SEQ ID NO 35
<211> LENGTH: 470
<212> TYPE: PRT
<213> ORGANISM: Human

<400> SEQUENCE: 35

Met Glu Asn Val Glu Val Phe Thr Ala Glu Gly Lys Gly Arg Gly Leu
1               5                   10                  15

Lys Ala Thr Lys Glu Phe Trp Ala Ala Asp Ile Ile Phe Ala Glu Arg
            20                  25                  30

Ala Tyr Ser Ala Val Val Phe Asp Ser Leu Val Asn Phe Val Cys His
        35                  40                  45

Thr Cys Phe Lys Arg Gln Glu Lys Leu His Arg Cys Gly Gln Cys Lys
    50                  55                  60

Phe Ala His Tyr Cys Asp Arg Thr Cys Gln Lys Asp Ala Trp Leu Asn
65                  70                  75                  80

His Lys Asn Glu Cys Ser Ala Ile Lys Arg Tyr Gly Lys Val Leu Ala
                85                  90                  95

Ala Arg Ile Met Trp Arg Val Glu Arg Glu Gly Thr Gly Leu Thr Glu
            100                 105                 110
```

-continued

Gly Cys Leu Val Ser Val Asp Asp Leu Gln Asn His Val Glu His Phe
            115                 120                 125

Gly Glu Glu Glu Gln Lys Asp Leu Arg Val Asp Val Asp Thr Phe Leu
    130                 135                 140

Gln Tyr Trp Pro Pro Gln Ser Gln Gln Phe Ser Met Gln Tyr Ile Ser
145                 150                 155                 160

His Ile Phe Gly Val Val Ile Asn Cys Asn Gly Phe Thr Leu Ser Asp
                165                 170                 175

Gln Arg Gly Leu Gln Ala Val Gly Val Gly Ile Phe Pro Asn Leu Gly
            180                 185                 190

Leu Val Asn His Asp Cys Trp Pro Asn Cys Thr Val Ile Phe Asn Asn
        195                 200                 205

Gly Lys Arg Ile Glu Leu Arg Ala Leu Gly Lys Ile Ser Glu Gly Glu
    210                 215                 220

Glu Leu Thr Val Ser Tyr Ile Asp Phe Leu Asn Val Ser Glu Glu Arg
225                 230                 235                 240

Lys Arg Gln Leu Lys Lys Gln Tyr Tyr Phe Asp Cys Thr Cys Glu His
                245                 250                 255

Cys Gln Lys Lys Leu Lys Asp Asp Leu Phe Leu Gly Val Lys Asp Asn
            260                 265                 270

Pro Lys Gln Pro Ser Gln Glu Val Val Lys Glu Met Ile Gln Phe Ser
        275                 280                 285

Lys Asp Thr Leu Glu Lys Ile Asp Lys Ala Arg Ser Glu Gly Leu Tyr
    290                 295                 300

His Glu Val Val Lys Leu Cys Arg Glu Cys Leu Glu Lys Gln Glu
305                 310                 315                 320

Pro Val Phe Ala Asp Thr Asn Ile Tyr Met Leu Arg Met Leu Ser Ile
                325                 330                 335

Val Ser Glu Val Leu Ser Tyr Leu Gln Ala Phe Glu Glu Ala Ser Phe
            340                 345                 350

Tyr Ala Arg Arg Met Val Asp Gly Tyr Met Lys Leu Tyr His Pro Asn
        355                 360                 365

Asn Ala Gln Leu Gly Met Ala Val Met Arg Ala Gly Leu Thr Asn Trp
    370                 375                 380

His Ala Gly Asn Ile Glu Val Gly His Gly Met Ile Cys Lys Ala Tyr
385                 390                 395                 400

Ala Ile Leu Leu Val Thr His Gly Pro Ser His Pro Ile Thr Lys Asp
                405                 410                 415

Leu Glu Ala Met Arg Val Gln Thr Glu Met Glu Leu Arg Met Phe Arg
            420                 425                 430

Gln Asn Glu Phe Met Tyr Tyr Lys Met Arg Glu Ala Ala Leu Asn Asn
        435                 440                 445

Gln Pro Met Gln Val Met Ala Glu Pro Ser Asn Glu Pro Ser Pro Ala
    450                 455                 460

Leu Phe His Lys Lys Gln
465                 470

<210> SEQ ID NO 36
<211> LENGTH: 348
<212> TYPE: DNA
<213> ORGANISM: Human
<220> FEATURE:
<221> NAME/KEY: CDS
<222> LOCATION: (1)...(348)

<400> SEQUENCE: 36

| att tgc gac atg aat ccg tcc gtt ccg aag ttc gcc gtc gtc gtg cag | 48 |
|---|---|
| Ile Cys Asp Met Asn Pro Ser Val Pro Lys Phe Ala Val Val Val Gln | |
| 1               5                   10                  15 | |

| cca agt ccc atc gac ggg atg ggc gtg ttc gca gcg gag ccg atc ccc | 96 |
|---|---|
| Pro Ser Pro Ile Asp Gly Met Gly Val Phe Ala Ala Glu Pro Ile Pro | |
|         20                  25                  30 | |

| gcg tac aag aag atc gga gag ttg cgt ggc gag tcg atc agc gtg cgg | 144 |
|---|---|
| Ala Tyr Lys Lys Ile Gly Glu Leu Arg Gly Glu Ser Ile Ser Val Arg | |
|     35                  40                  45 | |

| gag gcg cgt cgg cga gcc aag cgg cag cag cgc atc atg atc gtc gag | 192 |
|---|---|
| Glu Ala Arg Arg Arg Ala Lys Arg Gln Gln Arg Ile Met Ile Val Glu | |
| 50                  55                  60 | |

| gtg tcc gac aag cgg gcg atc gat gcg tcg caa tcc cca gac gcc atg | 240 |
|---|---|
| Val Ser Asp Lys Arg Ala Ile Asp Ala Ser Gln Ser Pro Asp Ala Met | |
| 65                  70                  75                  80 | |

| cgc tac aac aac cac tca tgc tcg ccc aac acc gtg ctg cgc atc cgc | 288 |
|---|---|
| Arg Tyr Asn Asn His Ser Cys Ser Pro Asn Thr Val Leu Arg Ile Arg | |
|                 85                  90                  95 | |

| cag ggg cgg gtc gag ttc tac gcc ttg cgc ccg atc gct gcc gga gaa | 336 |
|---|---|
| Gln Gly Arg Val Glu Phe Tyr Ala Leu Arg Pro Ile Ala Ala Gly Glu | |
|             100                 105                 110 | |

| gaa ctg acg gcc | 348 |
|---|---|
| Glu Leu Thr Ala | |
|     115 | |

<210> SEQ ID NO 37
<211> LENGTH: 116
<212> TYPE: PRT
<213> ORGANISM: Human

<400> SEQUENCE: 37

Ile Cys Asp Met Asn Pro Ser Val Pro Lys Phe Ala Val Val Val Gln
1               5                   10                  15

Pro Ser Pro Ile Asp Gly Met Gly Val Phe Ala Ala Glu Pro Ile Pro
            20                  25                  30

Ala Tyr Lys Lys Ile Gly Glu Leu Arg Gly Glu Ser Ile Ser Val Arg
        35                  40                  45

Glu Ala Arg Arg Arg Ala Lys Arg Gln Gln Arg Ile Met Ile Val Glu
    50                  55                  60

Val Ser Asp Lys Arg Ala Ile Asp Ala Ser Gln Ser Pro Asp Ala Met
65                  70                  75                  80

Arg Tyr Asn Asn His Ser Cys Ser Pro Asn Thr Val Leu Arg Ile Arg
                85                  90                  95

Gln Gly Arg Val Glu Phe Tyr Ala Leu Arg Pro Ile Ala Ala Gly Glu
            100                 105                 110

Glu Leu Thr Ala
        115

<210> SEQ ID NO 38
<211> LENGTH: 121
<212> TYPE: PRT
<213> ORGANISM: Human
<220> FEATURE:
<221> NAME/KEY: VARIANT
<222> LOCATION: 31, 32, 33, 34, 35, 36, 37, 38, 39, 40, 41, 42, 43, 44,
      45, 46, 47, 48, 49, 50, 51, 52, 53, 54, 87, 88, 89, 90
<223> OTHER INFORMATION: synthetic peptide
<220> FEATURE:
<221> NAME/KEY: VARIANT
<222> LOCATION: 91, 92, 93

```
<223> OTHER INFORMATION: Xaa = Any Amino Acid
<223> OTHER INFORMATION: Xaa = Any Amino Acid

<400> SEQUENCE: 38

Gly Arg Gly Trp Gly Val Arg Thr Leu Glu Lys Ile Arg Lys Asn Ser
1               5                   10                  15

Phe Val Met Glu Tyr Val Gly Glu Ile Ile Thr Ser Glu Glu Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Val Tyr Thr Val Asp Ala Ala Tyr Tyr Gly
    50                  55                  60

Asn Ile Ser His Phe Val Asn His Ser Cys Asp Pro Asn Leu Gln Val
65                  70                  75                  80

Tyr Asn Val Phe Ile Asp Xaa Xaa Xaa Xaa Xaa Xaa Xaa Arg Ile Ala
                85                  90                  95

Phe Phe Ala Thr Arg Thr Ile Arg Ala Gly Glu Glu Leu Thr Phe Asp
            100                 105                 110

Tyr Asn Met Gln Val Asp Pro Val Asp
        115                 120

<210> SEQ ID NO 39
<211> LENGTH: 114
<212> TYPE: PRT
<213> ORGANISM: Human
<220> FEATURE:
<221> NAME/KEY: VARIANT
<222> LOCATION: 31, 32, 33, 34, 35, 36, 37, 38, 39, 40, 41, 42, 43, 44,
      45, 46, 47, 48, 49, 50, 51
<223> OTHER INFORMATION: synthetic peptide
<223> OTHER INFORMATION: Xaa = Any Amino Acid

<400> SEQUENCE: 39

Val Ala Gly Trp Gly Ile Phe Ile Lys Asp Pro Val Gln Lys Asn Glu
1               5                   10                  15

Phe Ile Ser Glu Tyr Cys Gly Glu Ile Ile Ser Gln Asp Glu Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Asp Phe Val Val Asp Ala Thr Arg Lys Gly Asn Lys Ile
    50                  55                  60

Arg Phe Ala Asn His Ser Val Asn Pro Asn Cys Tyr Ala Lys Val Met
65                  70                  75                  80

Met Val Asn Gly Asp His Arg Ile Gly Ile Phe Ala Lys Arg Ala Ile
                85                  90                  95

Gln Thr Gly Glu Glu Leu Phe Phe Asp Tyr Arg Tyr Ser Gln Ala Asp
            100                 105                 110

Ala Leu

<210> SEQ ID NO 40
<211> LENGTH: 114
<212> TYPE: PRT
<213> ORGANISM: Human
<220> FEATURE:
<221> NAME/KEY: VARIANT
<222> LOCATION: 31, 32, 33, 34, 35, 36, 37, 38, 39, 40, 41, 42, 43, 44,
      45, 46, 47, 48, 49, 50, 51, 52
<223> OTHER INFORMATION: synthetic peptide
<223> OTHER INFORMATION: Xaa = Any Amino Acid

<400> SEQUENCE: 40
```

-continued

```
Ile His Gly Arg Gly Leu Phe Cys Lys Arg Asn Ile Asp Ala Gly Glu
1               5                   10                  15

Met Val Ile Glu Tyr Ala Gly Asn Val Ile Arg Ser Ile Gln Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Glu Val Val Asp Ala Thr Met His Gly Asn Arg Ala
    50                  55                  60

Arg Phe Ile Asn His Ser Cys Glu Pro Asn Cys Tyr Ser Arg Val Ile
65                  70                  75                  80

Asn Ile Asp Gly Gln Lys His Ile Val Ile Phe Ala Met Arg Lys Ile
                85                  90                  95

Tyr Arg Gly Glu Glu Leu Thr Tyr Asp Tyr Lys Phe Pro Ile Glu Asp
            100                 105                 110

Ala Ser

<210> SEQ ID NO 41
<211> LENGTH: 113
<212> TYPE: PRT
<213> ORGANISM: Human
<220> FEATURE:
<221> NAME/KEY: VARIANT
<222> LOCATION: 31, 32, 33, 34, 35, 36, 37, 38, 39, 40, 41, 42, 43, 44,
      45, 46, 47, 48, 49
<223> OTHER INFORMATION: synthetic peptide
<223> OTHER INFORMATION: Xaa = Any Amino Acid

<400> SEQUENCE: 41

Glu Glu Val Ile Gly Val Met Ser Lys Glu Tyr Ile Pro Lys Gly Thr
1               5                   10                  15

Arg Phe Gly Pro Leu Ile Gly Glu Ile Tyr Thr Asn Asp Thr Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa His His Phe Ile Asp Gly Phe Asn Glu Glu Lys Ser Asn Trp Met
    50                  55                  60

Arg Tyr Val Asn Pro Ala His Ser Pro Arg Glu Gln Asn Leu Ala Ala
65                  70                  75                  80

Cys Gln Asn Gly Met Asn Ile Tyr Phe Tyr Thr Ile Lys Pro Ile Pro
                85                  90                  95

Ala Asn Gln Glu Leu Leu Val Trp Tyr Cys Arg Asp Phe Ala Glu Arg
            100                 105                 110

Leu

<210> SEQ ID NO 42
<211> LENGTH: 110
<212> TYPE: PRT
<213> ORGANISM: Human
<220> FEATURE:
<221> NAME/KEY: VARIANT
<222> LOCATION: 31, 32, 33, 34, 35, 36, 37, 38, 39, 40, 41, 42, 43, 44,
      45, 46
<223> OTHER INFORMATION: synthetic peptide
<223> OTHER INFORMATION: Xaa = Any Amino Acid

<400> SEQUENCE: 42

Lys Thr Arg Ile Gly Val Trp Ala Thr Lys Pro Ile Leu Lys Gly Lys
1               5                   10                  15

Lys Phe Gly Pro Phe Val Gly Asp Lys Lys Lys Arg Ser Gln Xaa Xaa
```

```
                 20                  25                  30
Xaa Xaa Xaa Xaa Xaa Xaa Xaa Xaa Xaa Xaa Xaa Xaa Trp Met
             35                  40                  45
Cys Ile Asp Ala Thr Asp Pro Glu Lys Gly Asn Trp Leu Arg Tyr Val
 50                  55                  60
Asn Trp Ala Cys Ser Gly Glu Glu Gln Asn Leu Phe Pro Leu Glu Ile
 65                  70                  75                  80
Asn Arg Ala Ile Tyr Tyr Lys Thr Leu Lys Pro Ile Ala Pro Gly Glu
                 85                  90                  95
Glu Leu Leu Val Trp Tyr Asn Gly Glu Asp Asn Pro Glu Ile
                100                 105                 110

<210> SEQ ID NO 43
<211> LENGTH: 236
<212> TYPE: PRT
<213> ORGANISM: Human
<220> FEATURE:
<221> NAME/KEY: VARIANT
<222> LOCATION: (32)...(167)
<223> OTHER INFORMATION: synthetic peptide
<220> FEATURE:
<221> NAME/KEY: VARIANT
<222> LOCATION: (196)...(205)
<223> OTHER INFORMATION: Xaa = Any Amino Acid
<223> OTHER INFORMATION: Xaa = Any Amino Acid

<400> SEQUENCE: 43

Pro Leu Gln Glu Glu Gly Val Ile Thr Ala Lys Thr Pro Val Lys Ala
 1               5                  10                  15
Ser Val Val Thr Glu Gly Leu Gly Leu Val Ala Leu Lys Asp Ile Xaa
                 20                  25                  30
Xaa Xaa Xaa Xaa Xaa Xaa Xaa Xaa Xaa Xaa Xaa Xaa Xaa Xaa Xaa Xaa
             35                  40                  45
Xaa Xaa Xaa Xaa Xaa Xaa Xaa Xaa Xaa Xaa Xaa Xaa Xaa Xaa Xaa Xaa
 50                  55                  60
Xaa Xaa Xaa Xaa Xaa Xaa Xaa Xaa Xaa Xaa Xaa Xaa Xaa Xaa Xaa Xaa
 65                  70                  75                  80
Xaa Xaa Xaa Xaa Xaa Xaa Xaa Xaa Xaa Xaa Xaa Xaa Xaa Xaa Xaa Xaa
                 85                  90                  95
Xaa Xaa Xaa Xaa Xaa Xaa Xaa Xaa Xaa Xaa Xaa Xaa Xaa Xaa Xaa Xaa
                100                 105                 110
Xaa Xaa Xaa Xaa Xaa Xaa Xaa Xaa Xaa Xaa Xaa Xaa Xaa Xaa Xaa Xaa
             115                 120                 125
Xaa Xaa Xaa Xaa Xaa Xaa Xaa Xaa Xaa Xaa Xaa Xaa Xaa Xaa Xaa Xaa
             130                 135                 140
Xaa Xaa Xaa Xaa Xaa Xaa Xaa Xaa Xaa Xaa Xaa Xaa Xaa Xaa Xaa Xaa
145                 150                 155                 160
Xaa Xaa Xaa Xaa Xaa Xaa Xaa Leu Arg Asn Glu Asn Leu Val Val Val
                165                 170                 175
Pro Met Ala Asp Leu Ile Asn His Ser Ala Gly Val Thr Thr Glu Asp
                180                 185                 190
His Ala Tyr Xaa Xaa Xaa Xaa Xaa Xaa Xaa Xaa Xaa Xaa Trp Asp Tyr
             195                 200                 205
Leu Phe Ser Leu Lys Ser Pro Leu Ser Val Lys Ala Gly Glu Gln Val
             210                 215                 220
Tyr Ile Gln Tyr Asp Leu Asn Lys Ser Asn Ala Glu
225                 230                 235
```

```
<210> SEQ ID NO 44
<211> LENGTH: 228
<212> TYPE: PRT
<213> ORGANISM: Human
<220> FEATURE:
<221> NAME/KEY: VARIANT
<222> LOCATION: (31)...(158)
<223> OTHER INFORMATION: synthetic peptide
<220> FEATURE:
<221> NAME/KEY: VARIANT
<222> LOCATION: (189)...(197)
<223> OTHER INFORMATION: Xaa = Any Amino Acid
<223> OTHER INFORMATION: Xaa = Any Amino Acid

<400> SEQUENCE: 44

Leu Arg Asp Gln Gly Val Val Ser Gly Lys Ser Val Ala Glu Pro Ala
1               5                   10                  15

Val Val Pro Glu Gly Leu Gly Leu Val Ala Arg Arg Asp Ile Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Leu Glu
145                 150                 155                 160

Leu Asn Arg Glu Ser Leu Thr Ser Met Phe Glu Phe Glu Gln Ile Asn
                165                 170                 175

His Asn Pro Ala Ile Lys Thr Glu Asp Tyr Ala Tyr Xaa Xaa Xaa Xaa
            180                 185                 190

Xaa Xaa Xaa Xaa Xaa Arg Asp Leu Leu Phe Ser Leu Lys Ser Pro Val
        195                 200                 205

Tyr Val Lys Ala Gly Glu Gln Val Tyr Ile Gln Tyr Asp Leu Asn Lys
    210                 215                 220

Ser Asn Ala Glu
225

<210> SEQ ID NO 45
<211> LENGTH: 321
<212> TYPE: DNA
<213> ORGANISM: Homo sapiens
<220> FEATURE:
<221> NAME/KEY: CDS
<222> LOCATION: (1)...(321)

<400> SEQUENCE: 45 aag ttc gcc gtc gtc gtg cag cca agt ccc atc gac ggg atg ggc gtg      48
Lys Phe Ala Val Val Val Gln Pro Ser Pro Ile Asp Gly Met Gly Val
1               5                   10                  15 ttc gca gcg gag ccg atc ccc gcg tac aag aag atc gga gag ttg cgt      96
Phe Ala Ala Glu Pro Ile Pro Ala Tyr Lys Lys Ile Gly Glu Leu Arg
```

```
                20                  25                  30
ggc gag tcg atc agc gtg cgg gag gcg cgt cgg cga gcc aag cgg cag     144
Gly Glu Ser Ile Ser Val Arg Glu Ala Arg Arg Arg Ala Lys Arg Gln
         35                  40                  45 cag cgc atc atg atc gtc gag gtg tcc gac aag cgg gcg atc gat gcg     192
Gln Arg Ile Met Ile Val Glu Val Ser Asp Lys Arg Ala Ile Asp Ala
     50                  55                  60 tcg caa tcc cca gac gcc atg cgc tac aac aac cac tca tgc tcg ccc     240
Ser Gln Ser Pro Asp Ala Met Arg Tyr Asn Asn His Ser Cys Ser Pro
65                  70                  75                  80 aac acc gtg ctg cgc atc cgc cag ggg cgg gtc gag ttc tac gcc ttg     288
Asn Thr Val Leu Arg Ile Arg Gln Gly Arg Val Glu Phe Tyr Ala Leu
                 85                  90                  95 cgc ccg atc gct gcc gga gaa gaa ctg acg gcc                         321
Arg Pro Ile Ala Ala Gly Glu Glu Leu Thr Ala
            100                 105

<210> SEQ ID NO 46
<211> LENGTH: 107
<212> TYPE: PRT
<213> ORGANISM: Homo sapiens

<400> SEQUENCE: 46

Lys Phe Ala Val Val Val Gln Pro Ser Pro Ile Asp Gly Met Gly Val
1               5                   10                  15

Phe Ala Ala Glu Pro Ile Pro Ala Tyr Lys Lys Ile Gly Glu Leu Arg
            20                  25                  30

Gly Glu Ser Ile Ser Val Arg Glu Ala Arg Arg Arg Ala Lys Arg Gln
         35                  40                  45

Gln Arg Ile Met Ile Val Glu Val Ser Asp Lys Arg Ala Ile Asp Ala
     50                  55                  60

Ser Gln Ser Pro Asp Ala Met Arg Tyr Asn Asn His Ser Cys Ser Pro
65                  70                  75                  80

Asn Thr Val Leu Arg Ile Arg Gln Gly Arg Val Glu Phe Tyr Ala Leu
                 85                  90                  95

Arg Pro Ile Ala Ala Gly Glu Glu Leu Thr Ala
            100                 105
```

PR/SET-DOMAIN CONTAINING NUCLEIC ACIDS, POLYPEPTIDES, ANTIBODIES AND METHODS OF USE

This application is based on, and claims the benefit of, U.S. Provisional Application No. 60/421,147, filed Jul. 18, 2001, which was converted from U.S. Ser. No. 09/910,478, which is incorporated herein by reference.

This invention was made in part with government support under grant number CA76146, awarded by the National Institutes of Health. Accordingly, the United States government has certain rights in this invention.

BACKGROUND OF THE INVENTION

1. Field of the Invention

This invention relates generally to proliferative disorders such as cancer and, more specifically, to PR/SET-domain containing genes and gene products that can be used to diagnose and treat proliferative disorders.

2. Background Information

Cancer is one of the leading causes of death in industrialized nations. Cancerous tumors result when a cell escapes from its normal growth regulatory mechanisms and proliferates in an uncontrolled fashion. Cells from the primary tumor generally metastasize to vital organs if treatment of the primary tumor is either not complete or not initiated early enough. Thus, early diagnosis and effective treatment of tumors is essential for survival.

Cancer involves the clonal replication of populations of cells that have gained competitive advantage over normal cells through the alteration of regulatory genes. Regulatory genes can be broadly classified into "oncogenes" which, when activated or overexpressed promote unregulated cell proliferation, and "tumor suppressor genes" which, when inactivated or underexpressed fail to prevent abnormal cell proliferation. Loss of function or inactivation of tumor suppressor genes is thought to play a central role in the initiation and progression of a significant number of human cancers.

A number of tumor suppressor genes have been identified that, when inactivated, are involved in the initiation or progression of human cancers. Known tumor suppressor genes include RB, p53, DCC, APC/MCC, RIZ, NF1, NF2, WT1, VHL, BRCA1, MST1 and WAF1/CIP1. Approaches for treating cancer by modulating the function of several of these tumor suppressor genes, either with pharmaceutical compounds that target their encoded proteins, or by gene therapy methods, have yielded promising results in animal models and in human clinical trials.

Approaches for diagnosing and prognosing cancer by identifying mutations in tumor suppressor genes have also been developed. For example, identifying individuals containing germline mutations in known tumor suppressor genes has permitted the identification of individuals at increased risk of developing cancer. Such individuals are then closely monitored or treated prophylactically to improve their chance of survival. Identifying the pattern of alterations of known tumor suppressor genes in biopsy samples is also being used to determine the presence or stage of a tumor. Being able to determine whether a cancer is benign or malignant, or at an early or late stage of progression, provides the patient and clinician with a more accurate prognosis and can be used to determine and monitor the course of treatment.

One important family of tumor suppressor genes that has recently been identified are PR/SET-domain containing genes. PR and SET domains are structurally related motifs present in proteins that function in modulating gene activities from yeast to mammals. A PR domain is a motif first identified as a region of homology between the Rb-binding zinc finger protein RIZ, and the transcriptional repressor protein PRDI-BF1/Blimp1, which promotes B-cell differentiation (Buyse et al., Proc. Natl. Acad. Sci. USA 92:4467–4471 (1995); Huang, Cell 78:9 (1994)). A PR domain motif is also found in the MDS1-EVI1 myeloid leukemia gene (Fears et al., Proc. Natl. Acad. Sci. USA 93:1642–1647 (1996)). A SET domain is a motif first identified as a region of homology between the Drosophila melanogaster genes Su(var)3–9, Enhancer-of-zeste and Trithorax. PR and SET domain-encoding genes have also been identified in other mammals and in lower organisms, including C. elegans, suggesting an evolutionarily conserved function for these domains.

In view of the importance of tumor suppressor genes and related molecules in the detection and treatment of cancer, there exists a need to identify additional tumor suppressor genes. In particular, in view of the established role of PR/SET-domain containing genes as tumor suppressor genes, there exists a need to identify and characterize additional PR/SET-domain family members. The present invention satisfies this need and provides related advantages as well.

SUMMARY OF THE INVENTION

The invention provides an isolated nucleic acid molecule encoding a PFM/SET polypeptide that has at least about 80% identity with an amino acid sequence of an invention PFM/SET polypeptide.

The invention also provides an isolated nucleic acid molecule having a nucleotide sequence that encodes a functional fragment of a PFM/SET polypeptide, the functional fragment containing a PR, SET, PRAZ, or PKZL domain of a PFM/SET amino acid sequence of the invention.

Further provided is an isolated oligonucleotide containing at least 17 contiguous nucleotides of an invention PFM/SET nucleotide sequence, or the complement thereof.

Also provided are methods for detecting a PFM/SET nucleic acid molecule in a sample. In one embodiment, the method involves contacting a sample with the PFM/SET nucleic acid molecule under conditions that allow specific hybridization to PFM/SET nucleic acid, and detecting said specific hybridization. In another embodiment, the method is practiced by contacting a sample with a PFM/SET primer pair under conditions that allow amplification of PFM/SET nucleic acid, and detecting amplified PFM/SET nucleic acid.

Further provided is a method for modulating cell growth. The method involves introducing a vector containing an invention PFM/SET nucleic acid molecule into a host cell, and expressing encoded PFM/SET polypeptide in an amount effective to modulate growth of said cell.

The invention also provides an isolated PFM/SET polypeptide, containing a PFM/SET amino acid sequence having at least about 80% amino acid identity with an invention PFM/SET amino acid sequence.

Further provided by the invention is a functional fragment of a PFM/SET polypeptide, the functional fragment containing a PR, SET, PRAZ, or PKZL domain of a PFM/SET amino acid sequence of the invention Also provided is an isolated immunogenic PFM/SET peptide containing at least 8 contiguous amino acids of an invention PFM/SET amino acid sequence.

The invention also provides an antibody, or antigen binding fragment thereof, which specifically binds to a PFM/SET polypeptide of the invention.

Further provided is a method for detecting PFM/SET polypeptide in a sample. The method is practiced by contacting a sample with the antibody under conditions that allow specific binding of said antibody to PFM/SET polypeptide, and detecting specifically bound antibody.

The invention also provides a method of screening for a compound that modulates PFM/SET polypeptide histone methyltransferase activity. The method involves contacting a PFM/SET polypeptide or fragment thereof, having histone methyltransferase activity, with one or more candidate compounds and determining histone methyltransferase activity of the contacted PFM/SET polypeptide or fragment thereof.

BRIEF DESCRIPTION OF THE DRAWINGS

Figure 1:
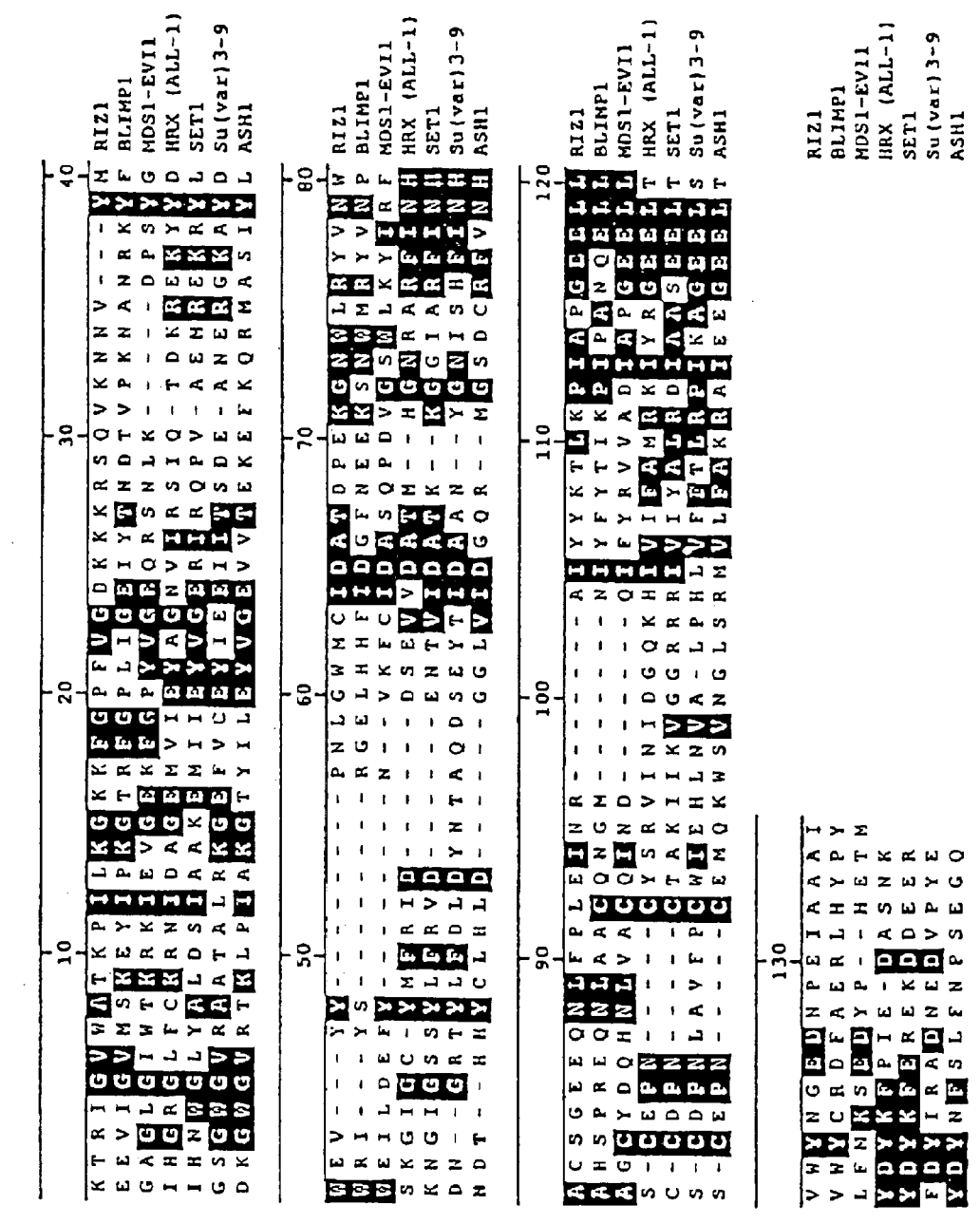

FIG. 1 shows a comparison of the amino acid sequences of the PR domains of RIZ1 (SEQ ID NO:27), BLIMP1 (SEQ ID NO:28), MDS1-EVI1 (SEQ ID NO:29), HRX (ALL-1) (SEQ ID NO:30), and the SET domains of SET1 (SEQ ID NO:31), Su(var)3–9 (SEQ ID NO:32), and ASH1 (SEQ ID NO:33).

FIG. 2 shows the amino acid sequence of PFM6 (SEQ ID NO:2). Underlined sequences are the 5' boundaries of each zinc finger motif.

FIG. 3 shows the amino acid sequence of PFM7 (SEQ ID NO:4). Underlined sequences are the 5' boundaries of each zinc finger motif.

FIG. 4 shows the amino acid sequence of PFM9 (SEQ ID NO:8). Underlined sequences are the 5' boundaries of each zinc finger motif.

FIG. 5 shows the amino acid sequence of PFM10 (SEQ ID NO:10). Underlined sequences are the 5' boundaries of each zinc finger motif.

FIG. 6 shows the amino acid sequence of PFM11 (SEQ ID NO:12). Underlined sequences are the 5' boundaries of each zinc finger motif.

FIG. 7 shows the amino acid sequence of PFM12 (SEQ ID NO:14). Underlined sequences are the 5' boundaries of each zinc finger motif.

FIG. 8 shows the amino acid sequence of PFM13 (SEQ ID NO:16). Underlined sequences are the 5' boundaries of each zinc finger motif.

FIG. 9 shows the amino acid sequence of PFM14 (SEQ ID NO:18). Underlined sequences are the 5' boundaries of each zinc finger motif.

FIG. 10 shows the amino acid sequence of BOP (SEQ ID NO:35).

FIG. 11A shows the amino acid sequence of the SET domain of SET27H (SEQ ID NO:46). FIG. 11B shows the nucleotide sequence that encodes this SET domain (SEQ ID NO:45).

FIG. 12 shows a comparison of PR/SET domain amino acid sequences of SUV39H1 (SEQ ID NO:38), EZH2 (SEQ ID NO:39), HRX/ALL1/MLL1 (SEQ ID NO:40), PRD1-BF1 (SEQ ID NO:41), RIZ1 (SEQ ID NO:42), Rubisco ISMT of P. Sativum (SEQ ID NO:43) and Rubisco ISMT of A. Thaliana (SEQ ID NO:44).

DETAILED DESCRIPTION OF THE INVENTION

Figure 13:
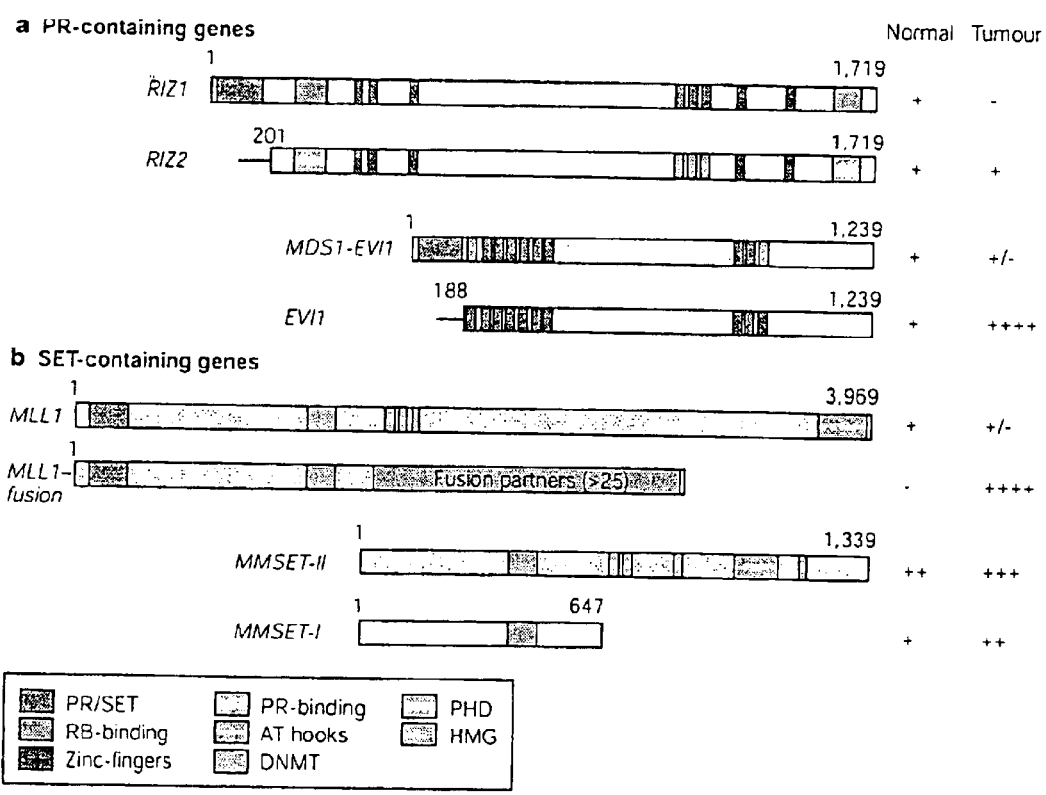
FIG. 13 shows the expression levels of two PR-domain genes and two SET-domain genes in normal and tumor tissues.

The present invention provides "PFM/SET" nucleic acid molecules, polypeptides, antibodies, modulatory compounds, and related methods. "PFM/SET" nucleic acid molecules and polypeptides contain one or more "PR" or "SET" domains, which are structurally and functionally related nucleotide and amino acid motifs. The PFM and SET nucleic acids and polypeptides of the invention can have histone methyltransferase activity and are important regulators of cell proliferation. Therefore, the molecules and methods of the invention can be used to modulate cell proliferation to prevent or treat proliferative disorders, including cancer. Additionally, the molecules and methods of the invention can be used to diagnose and prognose proliferative disorders and other disorders relating to dysregulated histone methyltransferase activity.

PFM/SET nucleic acid molecules and polypeptides are generally characterized by encoding or containing a PR domain or SET domain. Many PFM/SET nucleic acid molecules and polypeptides also encode or contain a zinc finger motif, and can contain other motifs. Exemplary PFM, or "PR family member" nucleic acid molecules include RIZ, MDS1-EVI1 and PRDI-BF1 (BLIMP1). Exemplary SET nucleic acid molecules include HRX/ALL1/MLL and MMSET.

The PR domain is about 100 to 125 amino acids in length, and contains three highly conserved sequences, designated the A, B and C boxes, each of which consists of about 6 to 12 amino acids. Each of boxes A, B and C is encoded by a separate exon. Alternative exon usage of the A, B and C boxes, and transcription from internal promoters, can result in PFM transcripts and polypeptides containing all, some or none of the A, B or C boxes.

PR and SET domains have been demonstrated to be protein binding motifs involved in the regulation of gene expression (Huang et al., *J. Biol. Chem.* 273:15933–15940 (1998); Soderholm et al., *Leukemia* 11:352–358 (1997)). In particular, the domains are considered to function in the assembly of chromatin-based multiprotein complexes involved in either euchromatin-mediated gene activation, or heterochromatin-mediated gene silencing. Lack or inactivation of the PR or SET domain can thus specifically inactivate the chromatin-associated functions of a PFM/SET polypeptide, without affecting other activities such as DNA binding and chromatin-independent transcriptional activation or repression. PFM genes encoding PR lacking isoforms of PFM polypeptides have been characterized. Differential chromatin regulation by the PR+ and PR− forms of a PFM gene may underlie the opposite roles of these products in tumorigenesis.

PR and SET domain containing genes are often expressed at lower levels in tumors than in normal tissues. Genes that have been deleted of their PR or SET domain, for example due to alternative promoter usage or translocations are often expressed at higher levels in tumors than in normal tissues. For example, in normal tissues, the MMSET gene expresses two products, MMSETII and MMSET-I, the latter of which lacks the SET domain due to alternative splicing. The t(4:14) translocation in myeloma results in a greater degree of overexpression of MMSET-I than MMSET-II relative to normal tissues, indicating that MMSET-I can function as a dominant-negative regulator of the full-length product. As shown in FIG. 12, the relative level of mRNA expression of PR and SET containing genes in normal and tumor tissues is represented by the number of "+" signs.

Several additional observations indicate that PR-domain containing gene products are negative regulators of cell growth and tumorigenesis, whereas the PR-deficient products of these genes are involved in growth promotion and oncogenesis. For example, the PR region of MDS1-EVI1 is often disrupted by leukemia-associated chromosomal insertions and translocations. These disruptions result in loss of the PR-containing MDS1-EVI1 product and selective retention of the PR-deficient EVI1 product. In contrast, the PR-EVI1 product is overexpressed in some tumor cells, and acts as an oncogene (Morishita et al., *Cell* 54:831–840 (1988); Morishita et al., *Proc. Natl. Acad. Sci.* USA 89:3937–3941 (1992))

Similarly, the RIZ gene produces two products, a PR-containing protein, RIZ1, and a PR-deficient protein, RIZ2, which is generated from an internal promoter. RIZ1 is commonly absent or underexpressed in a number of human neoplasias, including breast cancer, neuroblastoma and lung cancer. In these cases, the PR-deficient product, RIZ2, is expressed at normal levels (He et al., *Cancer Res.* 58:4238–4244 (1998)). These results suggest that the PR-containing RIZ1 product is a negative regulator of cell proliferation and tumorigenesis, whereas maintenance of RIZ2 expression may be required for oncogenesis.

As further evidence that RIZ is a tumor suppressor gene, forced expression of the RIZ1 product in breast cancer cells causes cell cycle arrest at the G2/M phase of the cell cycle, and programmed cell death (He et al., *Cancer Res.* 58:4238–4244 (1998)). Additionally, consistent with a role of RIZ1 in growth suppression, mice in which RIZ1, but not RIZ2, is inactivated, are tumor prone.

In addition, RIZ1 expression is commonly silenced in human cancers, including, for example, breast cancer, liver cancer, colon cancer, neuroblastoma, melanoma, lung cancer and osteosarcoma (He et al., supra (1998) and Jiang et al., *Int. J. Cancer* 83:541–547 (1999)). RIZ1 gene silencing occurs through methylation of CpG island motifs contained in the promotor region of the RIZ1 gene. RIZ1 deficiency in mice causes formation of B-cell lymphomas and other tumors, as well as accelerated tumor formation in p53 mutant mice. In addition, frequent frame shift mutation of RIZ1 in colorectal tumors with DNA repair defects have been observed (Chadwick et al., *Proc. Natl. Acad. Sci. USA* 97:2662–2667 (2000), Piao et al., *Cancer Res.* 60:4701–4704 (2000), and Sakurada et al., *Genes, Chromosomes Cancer* In press (2000))

Consistent with inactivation of RIZ1 in a broad spectrum of human cancers, recombinant adenovirus-mediated RIZ1 expression can induce G2/M cell-cycle arrest, apoptosis, or both in several tumor cell lines (Chadwick et al., supra, (2000); He et al., supra (1998); Jiang et al., supra, (1999)). RIZ1 can also suppress growth of xenograft colorectal cancers (Jiang and Huang, *Histol Histopathol* 15:109–117 (2000)).

Another PR domain-containing gene, PRDI-BF1/BLIMP1 is also likely to be a tumor suppressor gene. PRDI-BF1/BLIMP1 maps to the 6q21 region commonly deleted in non-Hodgkin's lymphoma (Mock et al., *Genomics* 37:24–28 (1996)) and is thus a strong candidate tumor suppressor for B-cell non-Hodgkin's lymphoma. Additionally, PRDI-BF1/BLIMP1 is a transcriptional repressor of c-Myc (Lin et al., *Science* 276:596–598 (1997)), which is an oncogene critically involved in B cell lymphoma.

The PR-domain containing gene PFM1/SC-1 is also likely to be a tumor suppressor gene. PFM1/SC-1 localizes to a tumor suppressor locus and plays a role in promoting cell growth arrest and differentiation induced by serum starvation and nerve growth factor (Chittka and Chao, *Proc. Natl. Acad. Sci. USA*, 96:10710–10750(1999); Yang and Huang, *Genomics* 61:319–325 (1999)).

SET nucleic acid molecules and polypeptides are characterized by encoding a "SET domain." The SET domain is a 150 amino acid motif discovered to be contained in several *Drosophila* development genes (Jones and Gelbart, *Mol. Cell Biol.* 13:6357–6366 (1993); Tschiersch et al., *EMBO J.* 13:3822–3831 (1994)). SET stands for the names of three *Drosophila* genes which contain the domain, Su(var)3–9, Enhancer-of-zeste and Trithorax. Other exemplary SET nucleic acid molecules include the human trithorax homolog HRX/ALL1/MLL, mutation of which has been observed in human leukemia (Djabali et al., *Nature Genetics* 2:113–118 (1992; Gu et al., *Cell* 71:701–708 (1992); Tkachuk et al., *Cell* 71:691–700 (1992)) and the MMSET gene, mutation of which has been observed in human myeloma (Chesi et al., *Blood* 92:3025–34 (1998).

Several SET domain containing genes in both *Drosophila* and mouse function in maintaining gene expression (Yu et al., *Proc. Natl. Acad. Sci. USA* 95:10632–6 (1998)). In particular, several SET domain containing genes, members of the polycomb and trithorax groups of *Drosophila* genes, function in sustaining homeobox gene expression by maintaining genes in heterochromatin or euchromatin states (Yu et al., supra, (1998)).

SET and PR domains are structurally related. These domains share amino acid identity in about 20% of amino acid residues, typically among the most conserved residues in each domain (Huang et al., *J. Biol. Chem.* 273:15933–15940 (1998)). For example, one of the two conserved leucine residues required for RIZ1 PR protein binding activity is also conserved in the SET domain (Huang et al., supra, (1998)). FIG. 1 shows an amino acid sequence comparison of the PR domains of RIZ1, BLIMP1, MDSa-EVI1, HRX (ALL-1) and the SET domains of SET1, Su(var) 3–9, and ASH1. The conserved residues among these domains are highlighted. FIG. 12 shows an amino acid sequence comparison of the SET domains of human SUV39H1, EZH2 and MLL1, the PR domains of human BLIMP1 and RIZ1 and the PR/SET homology regions of the Rubisco LSMTs (large subunit methyltransferase) from two different plant species, *Pisum sativum* and *Arabidpsis thaliana*.

Recent data suggest that PR and SET domains are functionally related, both having protein methyltransferase activity that regulates the function of histones and other proteins, particularly during mitosis (Bannister et al., *Nature* 410:120–124 (2001); Lachner et al., *Nature* 410:116–120 (2001); Rea et al., *Nature* 406:593–599 (2000)). PR/SET domain containing genes have also been shown to function in cell memory and in maintaining gene expression patterns in differentiated cells through many cell divisions (Caldas and Aparicio, *Cancer & Metastasis Reviews* 18:313–29 (1999)). In addition, a recent study in yeast suggests a close relationship between the SET protein SET1p and the checkpoint proteins Mec3p and Rad9p (Corda et al., *Nature Genetics* 21:204–8 (1999)). The study suggests an important role of the PR/SET domain chromosomal proteins in linking checkpoint to DNA damage in the context of chromatin.

The histone methyltransferase activity of PR/SET domains contributes to the tumor suppressor function of polypeptides containing this domain. Histone site-specific methylation is associated with a variety of fundamental cellular processes, including transcriptional regulation, epigenetic silencing and heterochromatin formation. Loss of histone methyltransferase function is expected to directly contribute to the de-differentiation and genomic instability that are characteristic of cancer. The observation that altered cellular methyltransferase activity is associated with tumorigenesis supports an important role for the methyltransferase activity of PR and SET domains in PFM/SET polypeptide tumor suppressor function. For example, cancer cells commonly lose the enzyme methylthioadenosine phosphorylase (MTAP) (Toohey et al., *Biochemical and Biophysical Research Communications,* 78:1273–1280 (1977)). An inhibitor of methyltransferases, methylthioadenosine (MTA), commonly accumulates in cancer cells as a result of MTAP deficiency (Nobori, et al. *Proc. Natl. Acad. Sci. USA,* 93:6203–6208 (1996)). MTA inhibits the aminopropyltransferase enzymes that synthesize polyamines from putrescine and decarboxylated S-adenosylmethionine, and also impairs S-adenosylmethionine dependent trans-methylation reactions.

MTAP is abundant in normal tissues and prevents the inhibition by cleaving MTA to adenine and 5'-methylthioribose L-phosphate, that are recycled to adenine nucleotides and methionine, respectively. MTAP is ~100 kb apart from the tumor suppressor p16INK4A (CDKN2) on chromosome 9p21, one of the most commonly deleted (homozygous) regions in human cancer. Homozygous deletions at 9p21 commonly involve both genes in many cancers (Toohey et al., supra (1977)). MTAP deletion could facilitate tumor formation and/or progression by causing accumulation of the MTase inhibitor, MTA, which in turn could inactivate RIZ1 and related PFM/SET family of tumor suppressor genes.

Further implicating histone methyltransferases in cancer, it has been shown that a deficiency in dietary methionine or folate causes cancer. Dietary methionine and folate in turn regulate the cellular levels of S-adenosylmethionine (SAM), which is used as a methyl group donor by methyltransferases. Additionally, several independent lines of investigation have revealed that alterations in the methionine metabolic pathway, which can lead to a deficiency in SAM and/or an increase in the methyltransferase inhibitor S-adenosylhomocysteine (SAH), are associated with cancer.

In addition to encoding proteins characterized by biological activities consistent with tumor suppressor functions in cells, several PR/SET domain-containing genes are localized to regions of human chromosomes associated with a variety of cancers. Consistent with this observation, genomic sequences corresponding to the isolated PFM/SET nucleic acids of the invention have been mapped to chromosomal regions that are altered in human cancers, as summarized in Table 1. The cancers indicated in Table 1 are abbreviated as follows: B-lym—B lymphocytes, T-lym—T lymphocytes, Blad—bladder, Co—colon, Eso—esophagus, Fibr (+)—fibrosarcoma, Leu—leukemia, Li—liver, Lu—lung, Ma—mammary, Oral—oral tumor, Ov—ovary, Ov(+)—amplification, Ov(-)—deletion, Pr—prostate, Mel—melanoma, St—stomach, Nc—neurocrest tumor.

TABLE 1

| GENE | CHROMOSOME | CANCER |
| --- | --- | --- |
| PRDM1 (PRDIBF1/BLIMP1) | 6q21–q22.1 | B-lym, Mel, St |
| PRDM2 (RIZ1) | 1p36.13–p36.23 | B-lym, Li, Ma, Co, St, Nc |
| PRDM3 (MDS1-EVI1) | 3q26 | Leu (+/-), Ov (+) |
| PRDM4 (PFM1/SC1) | 12q23–24.1 | Pa, Ov, St |
| PRDM5 (PFM2) | 4q25–q26 | Ov, Ma, Li, Lu, Co |

TABLE 1-continued

| GENE | CHROMOSOME | CANCER |
| --- | --- | --- |
| PRDM6 (PFM3) | 5q21–q23 | Co, Lu, Ov St, Leu |
| PRDM7 (PFM4) | 16q24 | Ma, Pr, Li |
| PRDM8 (PFM5) | 4q21.1 | Co |
| PRDM9 (PFM6) | 5p14 | Ov (+), fibr. (+) |
| PRDM10 (PFM7) | 11q25 | Ma, Co, Ov Oral |
| PRDM11 (PFM8) | 11p11.2 | Ma |
| PRDM12 (PFM9) | 9q33–q34.1 | Ov, Blad, Eso, lu |
| PRDM13 (PFM10) | 6q16–q21 | B-lym, Mel, St |
| PRDM14 (PFM11) | 8p12–21 | Ma, Pr |
| PRDM15 (PFM12) | 21q22.3 | Leu, Blad |
| PRDM16 (PFM13) | 1p36.23–p36.33 | B-lym, Li, Ma, Co, St, Nc |
| SET07 | 13q11–q13 | Ma |
| BOP | 2p11 | T-lym, Leu |

The PFM/SET nucleic acid molecules and encoded polypeptides of the invention can additionally contain a zinc finger domain, or "ZF domain." Generally, the ZF domain contains one or several C2H2 or Kruppel-like Zinc finger motifs, which can be represented by the structure: Cys-X2-Cys-X12-His-X3-His. However, a zinc finger motif of a PFM/SET polypeptide can have an amino acid other than Cys or His at one or more of the four conserved positions, and/or alternative spacings between the four conserved positions. The zinc finger motif is found in at least 300 human genes, and is known to specifically bind DNA or RNA sequences (Bellefroid et al., *DNA* 8:377–387 (1989)).

The PFM/SET nucleic acid molecules of the invention can contain one or more individual zinc finger motifs within a zinc finger domain. For example, PFM6 contains 14 individual zinc finger motifs within the zinc finger domain, while PFM7, PFM13 and PFM14 contain 10 zinc finger motifs, and PFM9, PFM10, PFM12, and BOP contain 3, 4, 8 and 4 zinc finger motifs, respectively.

The zinc finger motifs within the PFM/SET nucleic acid molecules and polypeptides of the invention can be contained in one or more zinc finger domains. For example, the 10 zinc finger motifs of PFM7 are contained in a single zinc finger domain (amino acids 271–752) while the 10 zinc finger motifs of PFM13 are contained in two separate zinc finger domains (amino acids 149–169 and 585–682). The individual zinc finger motifs of each invention PFM/SET polypeptide are depicted in FIGS. 2 through 11, which show the amino acid sequences of PFM6, PFM7, PFM9, PFM10, PFM11, PFM12, PFM13, PFM14, SET07, BOP, and the SET domain of SET27H, respectively. Zinc finger motifs are identified by underlining.

PFM/SET nucleic acid molecules and encoded polypeptides can additionally contain a variety of other motifs, including, for example, acidic motifs, PKZL domains and PRAZ domains, as described below for each PFM/SET nucleic-acid molecule of the invention.

The PFM/SET nucleic acid molecules and polypeptides of the invention are designated PFM6, PFM7, PFM8, PFM9, PFM10, PFM11, PFM12, PFM13, PFM14 and SET07, BOP and SET27H. The nucleotide sequences of these PFM/SET nucleic acid molecules are set forth as SEQ ID NO:1 (PFM6); SEQ ID NO:3 (PFM7); SEQ ID NO:5 (PFM8); SEQ ID NO:7 (PFM9); SEQ ID NO:9 (PFM10); SEQ ID NO:11 (PFM11); SEQ ID NO:13 (PFM12); SEQ ID NO:15

(PFM13), SEQ ID NO:17 (PFM14); SEQ ID NO:19 (SET07); SEQ ID NO:34 (BOP) and SEQ ID NO:45 (SET domain of SET27H). The amino acid sequences of the encoded PFM/SET polypeptides are set forth as SEQ ID NO:2 (PFM6); SEQ ID NO:4 (PFM7); SEQ ID NO:6 (PFM8); SEQ ID NO:8 (PFM9); SEQ ID NO:10 (PFM10); SEQ ID NO:12 (PFM11); SEQ ID NO:14 (PFM12); SEQ ID NO:16 (PFM13), SEQ ID NO:18 (PFM14); SEQ ID NO:10 (SET07); SEQ ID NO:35 (BOP) and SEQ ID NO:46 (SET domain of SET27H).

The amino acid boundaries of the PR and ZF domains of PFM6, PFM7, PFM8, PFM9, PFM10, PFM11, PFM12, PFM13, and PFM14 are provided in Table 2, below.

TABLE 2

| PFM molecule | PR domain amino acid residues | ZF domain amino acid residues |
| --- | --- | --- |
| PFM6 | 1–160 | 335–690 |
| PFM7 | 116–258 | 271–753 |
| PFM8 | 128–165 | not present |
| PFM9 | 84–217 | 245–333 |
| PFM10 | 1–131 | 149–169, 585–682 |
| PFM11 | 252–292 | 402–566 |
| PFM12 | 414–539 | 248–277, 565–951 |
| PFM13 | 93–218 | 219–448, 915–1030 |
| PFM14 | 45–182 | 355–624 |

PFM6 additionally contains a domain of approximately 100 amino acids having about 35–40% identity to the KRAB-domain-containing zinc finger protein 133 (ZNF133). This domain is designated PKZL, for "PR and KRAB zinc finger protein-linked." The PKZL domain of PFM6 corresponds to amino acids 211–310 of SEQ ID NO:2. The PKZL domain likely is important in mediating protein-protein interactions with cellular regulatory molecules.

PFM7, PFM8 and PFM12 additionally contain a PRAZ domain. PFM6 contains a partial PRAZ domain at the N-terminus. PRAZ stands for PR-domain Associated Zinc Finger motif. The signature sequence of the PRAZ domain is $CX_2CX_7CX_2H/L$. The PRAZ domain is typically located 5' to the PR domain in PFM polypeptide sequences, and has thus far been identified only in PFM polypeptides. The PRAZ domain participates in the methyltransferase activity function of the PR domain. The PRAZ domain of PFM6 corresponds to amino acids 1–13 of SEQ ID NO:2. The PRAZ domain of PFM7 corresponds to amino acids 87–108 of SEQ ID NO:4. The PRAZ domain of PFM8 corresponds to amino acids 103–117 of SEQ ID NO:6. The PRAZ domain of PFM12 corresponds to amino acids 313–328 of SEQ ID NO:14.

The SET07 polypeptide of the invention contains a single SET domain. The SET domain of SET07 corresponds to amino acids 215–334 of SEQ ID NO:20. The BOP polypeptide of the invention contains a single SET domain. The SET domain of BOP corresponds to the amino acid sequence referenced as SEQ ID NO:46.

The PFM and SET genes disclosed herein are localized to regions of human chromosomes predicted to harbor tumor suppressor genes, because deletion of these regions is closely associated with various human tumors. In particular, PFM6 localizes to chromosome band 5p14, a region commonly rearranged or gained in ovarian and breast cancer (Sonoda et al. Genes, Chromosomes & Cancer 20(4):320–8, (1997)).

PFM7 localizes to chromosome band 11q25, a region commonly deleted in breast, ovary, colon and oral cancer (Connolly et al., Cancer Research 59:2806–2809 (1999); Koreth et al., Oncogene 14:431–437 (1997); Launonen et al., Genecologic Oncology 71:299–304 (1998); Uzawa et al., Intl. J. Cancer 67:510–4 (1996)). It has also been demonstrated that 11q25 YAC clones can suppress tumor growth in vivo (Koreth et al., Oncogene 18:1157–64 (1999)).

PFM8 localizes to chromosome band 11p11. This region of chromosome 11 is commonly deleted in breast cancer (Nakata et al., European J. Cancer 34:417–21 (1998)).

PFM9 localizes to chromosome band chromosome 9q33-34.1, which is commonly deleted in ovarian, bladder, esophageal, and lung cancers (Devlin et al., British J. Cancer 73:420–423 (1996); Hornigold et al., Oncogene 18:2657–61 (1999); Simoneau et al., Oncogene 18:157–63 (1999)).

PFM10 localizes to chromosome band 6q16-21, a region commonly deleted in B-cell lymphoma, melanoma, and stomach cancers (Gaidano et al. Curr. Opin. Oncol. 5:778–784 (1993), Millikin et al. Cancer Res. 51:5449–5453 (1991), Trent et al. Cytogenet. Cell Genet. 62:67–87 (1990), and Queimado et al. Genes Chromosomes Cancer 14:28–34 (1995)). This region also contains another PR-family member, the candidate tumor suppressor PRDIBF1/BLIMP1 (PRDM1) (Mock et al., Genomics 37:24–28 (1996)).

PFM11 localizes to chromosome band 8p12-21, a region commonly deleted in breast and prostate cancers (Van Alewijk et al., Genes, Chromosomes & Cancer 24:119–26 (1999); Verma et al., Cancer Investigation 17:441–7 (1999); Vocke et al., Cancer Research 56:2411–6 (1996)).

PFM12 localizes to chromosome band 21q22.3. This region is found to be deleted in human leukemia.

PFM13 localizes to chromosome band 1p36.23-33, a region deleted in more than a dozen different types of human cancers. This region also contains other PR-family members, the tumor suppressors MDS1-EVI1 and RIZ1. These observations are consistent with a role for these PFMs as tumor suppressors.

SET07 localizes to chromosome band 13q11-q13, in proximity to the retinoblastoma locus on 13q14. This region is commonly deleted in many cancers including breast cancers, bladder cancers, lung cancers and osteosarcomas.

BOP localizes to chromosome band 2p11. This region is found to be deleted in T cell lymphomas and leukemias.

PFM/SET Nucleic Acid Molecules

The invention provides isolated PFM/SET nucleic acid molecules. The isolated PFM/SET nucleic acid molecules of the invention can be used in a variety of diagnostic and therapeutic applications. For example, as described in more detail below, the isolated PFM/SET nucleic acid molecules of the invention can be used as probes and primers to detect PFM and SET nucleic acid molecules in samples; as templates for the recombinant expression of PFM and SET polypeptides; in two-hybrid assays to identify cellular molecules that bind PFM and SET; and in vivo and ex vivo gene therapy applications to positively or negatively modulate cell proliferation.

In one embodiment, the invention provides an isolated PFM/SET nucleic acid molecule encoding a PFM/SET polypeptide selected from the group consisting of SEQ ID NOS:2, 4, 6, 8, 10, 12, 14, 16, 18, 20 and 34. In another embodiment, the invention provides an isolated SET domain-encoding nucleic acid molecule, SEQ ID NO:45, which encodes the SET domain of human SET 27H. Modifications of these sequences that having at least 80% identity thereto are also provided. Such modifications can have at least 90%, 95% and 98% identity with a reference PFM/SET nucleotide sequence.

Exemplary isolated PFM/SET nucleic acid molecules provided by the invention are nucleic acid molecules having the sequence of SEQ ID NOS:1, 3, 5, 7, 8, 11, 13, 15, 17, 19, 34 and 45.

The invention also provides an isolated nucleic acid molecule containing a nucleotide sequence encoding a functional fragment of a PFM/SET polypeptide, said fragment comprising a PR, SET, PRAZ, or PKZL domain of a PFM/SET amino acid sequence selected from the group consisting of SEQ ID NOS:2, 4, 6, 8, 10, 12, 14, 16, 18, 20, 35 and 46.

The term "isolated," in reference to a PFM/SET nucleic acid molecule is intended to mean that the molecule is substantially removed or separated from components with which it is naturally associated, or otherwise modified by the hand of man. Thus, the term "isolated PFM/SET nucleic acid molecule" excludes PFM/SET nucleic acid molecules as they exist in nature.

The term "nucleic acid molecule," as used herein, refers to an oligonucleotide or polynucleotide of natural or synthetic origin. A nucleic acid molecule can be single- or double-stranded genomic DNA, cDNA or RNA, and can represent the sense strand, the antisense strand, or both.

Identity of any two nucleic acid sequences can be determined by those skilled in the art based, for example, on a BLAST 2.0 computer alignment. BLAST 2.0 searching is available at the National Institutes of Health web site (.ncbi.nlm.nih.gov), and is described in Tatusova et al., *FEMS Microbiol Lett.* 174:247–250 (1999).

A "modification" of a reference nucleic acid sequence can include one or several nucleotide additions, deletions, or substitutions with respect to the recited sequence. Such modifications can correspond to variations that are made deliberately, or which occur as mutations during nucleic acid replication.

Exemplary "modifications" of the recited PFM/SET sequences include sequences that correspond to homologs of other species, such as primates, mouse, rat, rabbit, bovine, porcine, ovine, canine or feline species. The sequences of corresponding PFM/SET polypeptides of non-human species can be determined by methods known in the art, such as by PCR or by screening genomic, cDNA or expression libraries.

Furthermore, exemplary "modifications" of the recited PFM/SET nucleic acid or polypeptide can correspond to splice variant forms of recited PFM/SET sequences. Thus, for example, a modification of a PFM nucleic acid molecule of the invention can lack one or more of the exons that encode the A, B or C boxes of the PR domain. A, B, and C boxes of a PR domain can be determined by alignment of PR domain nucleotide sequences with known PR domain A, B, and C box sequences, or by comparing the sequence of a PFM/SET cDNA to the sequence of the corresponding genomic DNA. Exon usage by splice variants of PFM/SET nucleic acid molecules can be readily determined by those skilled in the art by comparing the sequence of the PFM/SET cDNA to the sequence of the corresponding PFM/SET genomic DNA.

Additionally, a "modification" of a reference sequence can include one or more non-native nucleotides, having, for example, modifications to the base, the sugar, or the phosphate portion, or having a modified phosphodiester linkage. Such modifications can be advantageous in increasing the stability of the nucleic acid molecule.

Furthermore, a "modification" of a reference sequence can include, for example, a detectable moiety, such as a radiolabel, a fluorochrome, a ferromagnetic substance, a luminescent tag or a detectable binding agent such as biotin. Such modifications can be advantageous in applications where detection of a PFM nucleic acid molecule is desired.

Nucleic acid molecules having nucleic acid sequences that encode modified polypeptides that are immunologically equivalent to the recited PFM amino acid sequences are also provided.

The term "isolated PFM/SET nucleic acid molecule" specifically excludes nucleic acid molecules consisting of certain nucleotide sequences, such as Expressed Sequence Tags (ESTs), Sequence Tagged Sites (STSs) and genomic fragments, deposited in public databases such as the nr, dbest, dbsts, gss and htgs databases, which are available for searching at .ncbi.nlm.nlh.gov/blast/blast.cgi?Jform=0, using the program BLASTN 2.0.9 [May 7, 1999] described by Altschul et al., *Nucleic Acids Res.* 25:3389–3402 (1997).

In particular, the term "PFM/SET nucleic acid molecule" specifically excludes nucleic acid molecules consisting of any of the nucleotide sequences having the GenBank (gb), EMBL (emb) or DDBJ (dbj) Accession numbers set forth in Table 3, below:

TABLE 3

| PFM/SET nucleic acid | Accession Number of Excluded Sequence | |
|---|---|---|
| PFM6 | gb\|AC010432.6 | gb\|AF274348.1 |
|  | gb\|AC025451.5 | emb\|AL137711 |
|  | gb\|AF274347.1 | emb\|Z96314 |
| PFM7 | dbj\|AB033057 | gb\|BE962422.1 |
|  | dbj\|AK000234 | gb\|BE994100.1 |
|  | gb\|AA324539.1 | gb\|BF333514.1 |
|  | gb\|AA331245.1 | gb\|BF693866.1 |
|  | gb\|AA807222.1 | gb\|BG498843.1 |
|  | gb\|AI348386.1 | gb\|G05930.1 |
|  | gb\|AI610587.1 | gb\|G20316.1 |
|  | gb\|AI699177.1 | gb\|N32595.1 |
|  | gb\|AI907429.1 | gb\|R14616.1 |
|  | gb\|AI917820.1 | gb\|R15777.1 |
|  | gb\|AW027068.1 | gb\|R16283.1 |
|  | gb\|AW131841.1 | gb\|R35195.1 |
|  | gb\|AW274834.1 | gb\|R42665.1 |
|  | gb\|AW978331.1 | gb\|R45605.1 |
|  | gb\|AW992560.1 | gb\|R50855.1 |
|  | gb\|BE304522.1 | gb\|T16683.1 |
|  | gb\|BE617458.1 |  |
| PFM8 | gb\|AA468023.1 | gb\|BE884008.1 |
|  | gb\|AA468074.1 | gb\|BE956829.1 |
|  | gb\|AC013602.4 | gb\|BE980340.1 |
|  | gb\|AW968153.1 | gb\|D59353.1 |
|  | gb\|BE648497.1 |  |
| PFM9 | gb\|AW529888.1 | gb\|BE096442.1 |
|  | gb\|AW532948.1 | gb\|BE096447.1 |
|  | gb\|BE096110.1 | gb\|BE294489.1 |
|  | gb\|BE096155.1 | gi\|13274746 |
| PFM10 | emb\|AL137784.14 | emb\|AL035087.20 |
| PFM11 | dbj\|AK022595.1 | gb\|BF770200 |
|  | dbj\|AU124563 | gb\|G51347.1 |
|  | dbj\|AU148392 | gi\|13375635 |
|  | emb\|Z65361.1 |  |
| PFM12 | djb\|AP001618.1 | gb\|AW501914.1 |
|  | djb\|AP001619.1 | gb\|AW503893.1 |
|  | djb\|AP001745.1 | gb\|AW968839.1 |
|  | gb\|AA279563.1 | gb\|BF904312.1 |
|  | gb\|AA490433.1 |  |
| PFM13 | dbj\|AB051462.1 | gb\|BG086572.1 |
|  | dbj\|AK017846.1 | gi\|13628859 |
|  | gb\|BF982577.1 |  |
| PFM14 | dbj\|AU130916 | gb\|BE793683.1 |
|  | emb\|AL535257 | gb\|BE798564.1 |
|  | emb\|AL565845 | gb\|BE870276.1 |
|  | gb\|AA635466.1 | gb\|BE883835.1 |
|  | gb\|AA639997.1 | gb\|BF061011.1 |
|  | gb\|AA759024.1 | gb\|BF182733.1 |

TABLE 3-continued

| PFM/SET nucleic acid | Accession Number of Excluded Sequence | |
|---|---|---|
| | gb\|AI092401.1 | gb\|BF346948.1 |
| | gb\|AI242496.1 | gb\|BF529537.1 |
| | gb\|AI357201.1 | gb\|BF685622.1 |
| | gb\|AI816535.1 | gb\|BF814715.1 |
| | gb\|AU128198.1 | 9b\|BG177268.1 |
| PFM14 | gb\|AU147298.1 | gb\|BG470196.1 |
| | gb\|AU152780.1 | gb\|BG481345.1 |
| | gb\|AW129728.1 | gb\|BG678255.1 |
| | gb\|AW157409.1 | gb\|BG745296.1 |
| | gb\|AW245524.1 | gb\|BG746115.1 |
| | gb\|AW245967.1 | gb\|BG753045.1 |
| | gb\|AW246726.1 | gb\|BG753749.1 |
| | gb\|AW273736.1 | gb\|BG822286.1 |
| | gb\|BE244872.1 | gb\|BG914332.1 |
| | gb\|BE246083.1 | gb\|BI116711.1 |
| | gb\|BE247252.1 | gb\|BI117664.1 |
| | gb\|BE732157.1 | gb\|H63042.1 |
| | gb\|BE744525.1 | gb\|H85444.1 |
| | gb\|BE791132.1 | |
| PFM14 | gb\|AI887341.1 | gb\|BE897305.1 |
| | gb\|AW163472.1 | gb\|H85725.1 |
| | gb\|BE048089.1 | gb\|R37802.1 |
| | gb\|BE266801.1 | |
| | gb\|BE867579.1 | |
| SET07 | dbj\|AV752467 | gb\|BE018920.1 |
| | emb\|AL120271.1 | gb\|BE074968.1 |
| | emb\|AL548156.1 | gb\|BE074969.1 |
| | emb\|AL555671 | gb\|BE074974.1 |
| | emb\|AL578116 | gb\|BE305526.1 |
| | gb\|912371.1 | gb\|BE536337.1 |
| | gb\|AA085455.1 | gb\|BE797607.1 |
| | gb\|AA509936.1 | gb\|BE896201.1 |
| | gb\|AA936703.1 | gb\|BF133687.1 |
| | gb\|AI002388.1 | gb\|BF161282.1 |
| | gb\|AI383837.1 | gb\|BF245288.1 |
| | gb\|AI879547.1 | gb\|BF309152.1 |
| | gb\|AV705547.1 | gb\|BG196219.1 |
| | gb\|AW430084.1 | gb\|BG311741.1 |
| | gb\|AW986692.1 | gb\|BG389847.1 |
| | gb\|BE014950.1 | gb\|BG922564.1 |
| | | gb\|BI021983.1 |
| | | gb\|W72745.1 |
| BOP | dbj\|BB612390.1 | gb\|AI705990.1 |
| | emb\|Z21651.1 | gb\|BE113370.1 |
| | gb\|AA716121.1 | gb\|BE232487.1 |
| | gb\|AA403165.1 | gb\|BF525120.1 |
| | gb\|AA095564.1 | gb\|BF673051.1 |
| | gb\|AA140269.1 | gb\|BM722342.1 |
| | gb\|AA270924.1 | gb\|R15498.1 |
| | gb\|AA499407.1 | gb\|U76374.2 |
| | gb\|AA624796.1 | gb\|U76373.2 |
| | gb\|AA667932.1 | gb\|U76371.1 |
| | gb\|AC092836.4 | gb\|WO4738.1 |
| | gb\|AC118140.3 | gi\|10257424 |
| | gb\|AF086123.1 | gi\|18550030 |
| | gb\|AI352242.2 | |
| SET27H | gb\|AI909958.1 | gb\|AW176331.1 |

The invention also provides isolated PFM oligonucleotides containing at least 17 contiguous nucleotides of PFM6, PFM7, PFM8, PFM9, PFM10, PFM11, PFM12, PFM13, PFM14, SET07 and BOP, and at least 17 contiguous nucleotides of the nucleic acid encoding the SET domain of SET27H. As used herein, the term "oligonucleotide" refers to a nucleic acid molecule that includes at least 17 contiguous nucleotides from the reference nucleotide sequence, can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, 350, 450, 550, 650, 750, 850, 950 or more contiguous nucleotides from the reference nucleotide sequence. Therefore, an oligonucleotide can include the entire nucleotide sequence encoding a PFM/SET polypeptide. An oligonucleotide can further contain an exogenous nucleotide sequence. Such exogenous nucleotide sequence includes, for example, a nucleotide sequence that facilitates identification or purification of the oligonucleotide, a nucleotide sequence that facilitates cloning, such as a sequence containing a restriction endonuclease recognition site, or any other nucleotide sequence not contained in a naturally occurring reference PFM/SET nucleotide sequence. Excluded from the nucleotide sequence of an invention PFM/SET oligonucleotide is non-coding sequence adjacent to a naturally occurring PFM/SET nucleotide sequence, such as nucleotide sequence contained upstream or downstream of a naturally occurring PFM/SET nucleotide sequence, or portion thereof, in genomic or cDNA.

The PFM/SET oligonucleotides of the invention contain at least 17 contiguous nucleotides from the reference PFM or SET nucleotide sequence and are able to hybridize to PFM or SET nucleotide sequences under moderately stringent hybridization conditions. Therefore, PFM/SET oligonucleotides can be advantageously used, for example, as probes to detect PFM or SET DNA or RNA in a sample, and to detect splice variants thereof that contain or lack particular domains; as sequencing or PCR primers; as antisense reagents to block transcription of PFM or SET RNA in cells; or in other applications known to those skilled in the art in which hybridization to a PFM or SET is desirable.

Oligonucleotides containing at least 17 contiguous PFM/SET nucleotides are able to specifically hybridize with a PFM or SET nucleic acid molecule. Specific hybridization refers to the ability of a nucleic acid molecule to hybridize, under moderately stringent conditions as described above, to the reference PFM or SET nucleic acid molecule, without hybridization under the same conditions with nucleic acid molecules that are not PFMs or SETs, respectively, such as actin cDNA.

Moderately stringent hybridization conditions refers to hybridization conditions that permit a nucleic acid molecule to bind a nucleic acid that has substantial identity to the recited sequence. Moderately stringent conditions are conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 50°. In contrast, "highly stringent conditions" are conditions equivalent to hybridization of filter-bound nucleic acid in 50% formamide, 5× Denhart's solution, 5×SSPE, 0.2% SDS at 42° C., followed by washing in 0.2×SSPE, 0.2% SDS, at 65°. Other suitable moderately stringent and highly stringent hybridization buffers and conditions are well known to those of skill in the art and are described, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1998).

In general, a nucleic acid molecule that hybridizes to a recited sequence under moderately stringent conditions will have greater than about 60% identity, such as greater than about 70% identity, preferably greater than about 80% identity to the reference sequence over the length of the two sequences being compared. A nucleic acid molecule that hybridizes to a recited sequence under highly stringent conditions will generally have greater than about 90% identity, including greater than about 95% and 98% identity, to the reference sequence over the length of the two sequences being compared.

In one embodiment, the invention provides a primer pair for detecting a PFM or SET nucleic acid. The primer pair contains two PFM/SET oligonucleotides. The primer pair can be used, for example, to amplify PFM/SET DNA by RT-PCR or PCR.

The isolated PFM/SET nucleic acid molecules and oligonucleotides of the invention can be produced or isolated by methods known in the art. The method chosen will depend, for example, on the type of nucleic acid molecule one intends to isolate. Those skilled in the art, based on knowledge of the nucleotide sequences disclosed herein, can readily isolate PFM/SET nucleic acid molecules as genomic DNA, or desired introns, exons or regulatory sequences therefrom; as full-length cDNA or desired fragments therefrom; or as full-length mRNA or desired fragments therefrom, by methods known in the art.

One useful method for producing an isolated PFM/SET nucleic acid molecule of the invention involves amplification of the nucleic acid molecule using the polymerase chain reaction (PCR) and PFM- or SET-specific primers and, optionally, purification of the resulting product by gel electrophoresis. Either PCR or reverse-transcription PCR (RT-PCR) can be used to produce a PFM nucleic acid molecule having any desired nucleotide boundaries. Desired modifications to the nucleic acid sequence can also be introduced by choosing an appropriate primer with one or more additions, deletions or substitutions. Such nucleic acid molecules can be amplified exponentially starting from as little as a single gene or mRNA copy, from any cell, tissue or species of interest.

A further method of producing an isolated PFM/SET nucleic acid molecule of the invention is by screening a library, such as a genomic library, cDNA library or expression library, with a detectable agent. Such libraries are commercially available or can be produced from any desired tissue, cell, or species of interest using methods known in the art. For example, a cDNA or genomic library can be screened by hybridization with a detectably labeled nucleic acid molecule having a nucleotide sequence disclosed herein. Additionally, an expression library can be screened with an antibody raised against a polypeptide corresponding to the coding sequence of a PFM/SET nucleic acid disclosed herein. The library clones containing PFM molecules of the invention can be isolated from other clones by methods known in the art and, if desired, fragments therefrom can be isolated by restriction enzyme digestion and gel electrophoresis.

Furthermore, isolated PFM/SET nucleic acid molecules and oligonucleotides of the invention can be produced by synthetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as oligonucleotide probes and primers, and nucleic acid molecules containing modified nucleotides or linkages.

The invention also provides a vector containing an isolated PFM/SET nucleic acid molecule. The vectors of the invention are useful for subcloning and amplifying an isolated PFM/SET nucleic acid molecule, and for recombinantly expressing a PFM/SET polypeptide. A vector of the invention can include a variety of elements useful for cloning and/or expression of PFM/SET nucleic acid molecules, such as enhancer sequences and promoter sequences from a viral, bacterial or mammalian gene, which provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillin resistance gene, useful for selecting transformants in prokaryotic cells; and versatile multiple cloning sites for inserting nucleic acid molecules of interest.

Cloning vectors of the invention include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art.

If it is desired to express PFM/SET RNA transcripts or polypeptides, a PFM/SET nucleic acid molecule can be inserted into an expression vector such that it is operatively linked to a promoter of RNA transcription. The term "operatively linked," as used herein, is intended to mean that the nucleic acid molecule is positioned with respect to a PFM/SET promoter, or heterologous promoter, in such a manner that the promoter will direct the transcription of RNA using the nucleic acid molecule as a template. Methods for operatively linking a nucleic acid to a desired promoter are well known in the art and include, for, example, cloning the nucleic acid into a vector containing the desired promoter, or appending the promoter to a nucleic acid sequence using PCR. Thus, an expression vector containing a PFM/SET nucleic acid molecule operatively linked to a promoter of RNA transcription can be used to express PFM/SET transcripts and polypeptides in a desired host cell, or in an in vitro system, such as an extract or lysate that supports transcription and translation. Contemplated expression vectors include vectors containing regulatory sequences known in the art to provide for expression in bacterial cells, yeast cells, insect cells, mammalian cells and other vertebrate cells.

A variety of expression vectors are commercially available, and can be further modified, if desired, to include appropriate regulatory elements to provide for the desired level of expression or replication in the host cell. For example, appropriate promoter and enhancer elements can be chosen to provide for constitutive, inducible or cell type-specific expression. Useful constitutive promoter and enhancer elements for expression of PFM/SET in mammalian cells include, for example, RSV, CMV, SV40 and IgH elements. An exemplary inducible expression element is a steroid response element, while an exemplary cell-specific expression element is a prostate specific antigen (PSA) regulatory sequence. Other constitutive, inducible and cell type-specific regulatory elements are well known in the art.

Exemplary host cells that can be used to express recombinant PFM/SET molecules include mammalian primary cells; established mammalian cell lines, such as COS, CHO, HeLa, NIH3T3, HEK 293-T and PC12 cells; amphibian cells, such as Xenopus embryos and oocytes; and other vertebrate cells. Exemplary host cells also include insect cells (for example, *Drosophila*), yeast cells (for example, *S. cerevisiae, S. pombe*, or *Pichia pastoris*) and prokaryotic cells (for example, *E. coli*).

Methods for introducing a cloning or expression vector into a host cell are well known in the art and include, for example, various methods of transfection such as calcium phosphate, DEAE-dextran and lipofection methods, viral transduction, electroporation and microinjection. Host cells expressing PFM or SET nucleic acid molecules can be used, for example, as a source to isolate recombinantly expressed PFM or SET polypeptides, to identify and isolate molecules that regulate or interact with PFM/SET nucleic acids and polypeptides, or to screen for compounds that enhance or inhibit the activity of a PFM/SET molecule of the invention, as described further below.

The methods of isolating, cloning and expressing nucleic acid molecules of the invention referred to herein are routine in the art and are described in detail, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1998), which are incorporated herein by reference.

PFM/SET Polypeptides

The invention also provides isolated PFM/SET polypeptides. As disclosed herein, PFM and SET domains are similar in both amino acid sequence and in biological function. As such, a PFM and SET domains are members of a class of domains, referred to herein as PFM/SET domains. The isolated PFM/SET nucleic acid molecules and polypeptides of the invention contain either a PFM or SET domain. The isolated PFM and SET polypeptides of the invention can be used in a variety of diagnostic and therapeutic applications. For example, as described in more detail below, the isolated PFM/SET polypeptides can be used to generate antibodies that can be used as reagents to detect PFM or SET mRNA or polypeptide expression in a sample, or in screening methods to identify compounds and cellular molecules that bind PFM or SET polypeptides and modulate histone methyltransferase activity or cell proliferation.

In one embodiment, the invention provides an isolated polypeptide, containing a PFM/SET amino acid sequence selected from the group consisting of SEQ ID NOS:2, 4, 6, 8, 10, 12, 14, 16, 18, 20 and 35. Also provided are PFM/SET polypeptides that have at least 80% identity thereto. Further provided are isolated PFM/SET polypeptides having at least about 90%, 95% and 98% identity with a reference PFM/SET polypeptide amino acid sequence.

The term "isolated," in reference to a PFM/SET polypeptide of the invention, is intended to mean that the molecule is substantially removed or separated from components with which it is naturally associated, or otherwise modified by the hand of man. Thus, the term "isolated PFM/SET polypeptide" excludes PFM and SET polypeptides as they exist in nature.

Isolated PFM/SET polypeptides that have at least about 90%, 95% and 98% identity with a reference PFM/SET polypeptide amino acid sequence can further be immunologically equivalent to a reference PFM/SET polypeptide. An immunologically equivalent PFM/SET polypeptide can be recognized by an antibody that also specifically binds to the reference PFM/SET sequence. Specific binding refers to high affinity binding of an antibody to the subject polypeptide, and binding with substantially lower affinity to an unrelated polypeptide, such as bovine serum albumin. High affinity binding includes binding with a dissociation constant (Kd) of less than about $10^{-6}$ M, preferably less than about $10^{-7}$ M, such as less than about $10^{-8}$ M. Methods of determining binding affinity are well known in the art and are described, for example, in Harlow and Lane, *Antibodies: A Laboratory Manual*, Cold Spring Harbor Laboratory, New York (1989).

Those skilled in the art understand that two polypeptides with a high percentage of identity over the entire sequence, or over a substantial portion of the sequence, are more likely to exhibit similar biological activities than two molecules with the same percentage identity over a shorter portion of the sequence. Furthermore, two polypeptides that fold into common epitope structures are also more likely to exhibit similar biological activities than two molecules that do not share a common three-dimensional structure. Accordingly, an amino acid sequence that is "immunologically equivalent" to a PFM/SET polypeptide can further be "functionally equivalent" to a PFM/SET polypeptide. An exemplary "functionally equivalent" PFM/SET polypeptide is a PFM/SET "functional fragment."

The invention further provides a modification of a PFM/SET polypeptide. As used herein, a "modification" of a PFM/SET polypeptide of a reference amino acid sequence can include one or more additions, deletions or substitutions with respect to the reference sequence. In particular, a modification can include a conservative substitution, such as substitution of an apolar amino acid with another apolar amino acid (such as replacement of leucine with isoleucine), or substitution of a charged amino acid with a similarly charged amino acid (such as replacement of a glutamic acid with an aspartic acid). A modification can also include a nonconservative change, wherein a substituted amino acid has different but sufficiently similar structural or chemical properties that permits such a substitution without adversely affecting the desired immunological or biological activity.

A "modification" of a reference amino acid sequence that is "immunologically equivalent" or "biologically equivalent" to the reference amino acid sequence can also be a chemical or enzymatic modification, including but not limited to replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

Exemplary "modifications" of the recited PFM or SET sequences include sequences that correspond to homologs of other species, such as primates, mouse, rat, rabbit, bovine, porcine, ovine, canine or feline species. Furthermore, exemplary "modifications" of the recited PFM or SET sequences can correspond to splice variant forms, or internal translation products, of a recited PFM or SET sequence. Thus, for example, a modification of a PFM polypeptide of the invention can lack one or more of the A, B or C boxes of the PR domain.

Those skilled in the art can determine appropriate amino acid modifications for a given application. For example, a modification can serve to increase the stability, bioavailability, bioactiviy or immunogenicity of the polypeptide, or to facilitate its purification. Thus, introduction of a D-amino acid or an amino acid analog for its corresponding L-amino acid, or deletion of a lysine residue, can stabilize a polypeptide and reduce degradation. Addition of tag sequences, such as epitope tags, histidine tags, glutathione-S-transferase (GST) and the like, or addition of sorting sequences, can facilitate purification of a recombinant polypeptide. Addition of carrier sequences, such as keyhole limpet hemocyanin, can enhance recognition of the polypeptide by the immune system. Depending on the modification and the source of the polypeptide, the modification can be introduced into the polypeptide, or into the encoding nucleic acid sequence.

Computer programs known in the art can provide guidance in determining which amino acid residues can be modified as indicated above without abolishing the immunological activity or a desired biological activity of a PFM/SET polypeptide (see, for example, Eroshkin et al., *Comput. Appl. Biosci.* 9:491–497 (1993)). Additionally, guidance in modifying amino acid sequences while retaining functional activity is provided by aligning homologous PFM/SET polypeptides from various species. Such alignments also can be used to distinguish between PR and SET domains, and are shown in FIGS. 1 and 12. Those skilled in the art understand that evolutionarily conserved amino acid residues and domains are more likely to be important for maintaining biological activity than less well-conserved residues and domains.

In yet another embodiment, the invention provides an isolated PFM/SET peptide, having at least 8 contiguous amino acids of SEQ ID NOS:2, 4, 6, 8, 10, 12, 14, 16, 18, 20, 35 or 46. As used herein, the term "PFM/SET peptide" refers to a peptide having at least 8 contiguous amino acids of PFM/SET amino acid sequence. The amino acid length of functional fragments, peptides or polypeptide analogs of the present invention can range from about 8 amino acids up to the full-length protein sequence of an invention PFM/SET polypeptide.

In certain embodiments, the amino acid lengths include, for example, at least about 10 amino acids, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 125, at least about 150, at least about 175, at least about 200, at least about 250 or more amino acids in length up to the full-length PFM/SET polypeptide sequence. A peptide of at least about 8 amino acids can be used, for example, as an immunogen to raise antibodies specific for an invention PFM/SET polypeptide.

A peptide of such size contains at least one epitope specific to PFM/SET, and can thus be used as an immunogen to produce PFM/SET-specific antibodies, or as an antigen to purify PFM/SET antibodies. PFM/SET peptides that are likely to be antigenic or immunogenic can be predicted using methods and algorithms known in the art and described, for example, by Irnaten et al., *Protein Eng.* 11:949–955 (1998), and Savoie et al., *Pac. Symp. Biocomput.* 1999:182–189 (1999). Immunogenicity of the PFM or SET peptides of the invention can be determined by methods known in the art, such as assay of a delayed-type hypersensitivity response in an animal sensitized to a PFM/SET polypeptide, or by elicitation of PFM/SET specific antibodies. Likewise, antigenicity of the PFM/SET peptides of the invention can be determined by methods known in the art, such as by ELISA analysis, as described, for example, in Harlow and Lane, supra (1988).

As disclosed herein, the PFM/SET polypeptides of the invention share several biological activities. The biological activities of PFM/SET polypeptides include, for example, growth modulating activity, regulation of chromatin-mediated gene expression, specific binding to cellular proteins, specific binding to DNA, methyltransferase activity and other biological activities described herein. The biological activities of a PFM/SET polypeptide can be mediated by a domain within a full length PFM/SET polypeptide.

Therefore, the invention provides a PFM/SET polypeptide that is a functional fragment of a PFM/SET polypeptide, said fragment comprising a PR, SET, PRAZ, or PKZL domain of a PFM/SET amino acid sequence selected from the group consisting of SEQ ID NOS:2, 4, 6, 8, 10, 12, 14, 16, 18, 20, 35 and 46.

As used herein, the term "functional fragment" is intended to mean a portion of a PFM/SET polypeptide that has one or more of the biological activities characteristic of the reference polypeptide. As used herein, the term "fragment" refers to any truncated form, either carboxy-terminal, amino-terminal, or both, of the reference PFM/SET polypeptide. A functional fragment has an amino acid length required to maintain a portion of the biological activities characteristic of the reference PFM/SET polypeptide, from a few amino acids to a one amino acid deletion of the full length PFM/SET amino acid sequence. A functional fragment of an invention polypeptide can include, for example, of one or more of the following domains: a PR domain, a SET domain, a zinc finger domain, a PKZL domain, a PRAZ domain or an acidic region.

A functional fragment of an invention PFM/SET polypeptide, such as a region contained in SEQ ID NO:2, 4, 6, 8, 10, 12, 14, 16, 18, 35 or 46, can have one or more PFM/SET polypeptide biological functions, but lack one or more other PFM/SET polypeptide biological functions. For example, a PFM/SET polypeptide can lack methyltransferase activity but retain interaction with a binding partner. Such a functional fragment that binds to a binding partner but lack histone methyltransferase activity can be useful, for example, as a dominant-negative inhibitor. A dominant negative inhibitor that reduces or inhibits the methyltransferase activity of endogenous PFM/SET polypeptides by binding to substrate can be used to treat disorders characterized by excessive or unwanted cell proliferation.

In certain embodiments, the amino acid lengths of a functional fragment include, for example, at least about 10 amino acids, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 125, at least about 150, at least about 175, at least about 200, at least about 250 or more amino acids in length up to a one amino acid deletion of a full-length PFM/SET polypeptide sequence. The functional fragments can be contiguous amino acid sequences of an invention polypeptide, including contiguous amino acid sequences of SEQ ID NOS:2, 4, 6, 8, 10, 12, 14, 16, 18, 20, 36 and 46.

A functional fragment of a PFM/SET polypeptide can contain exogenous amino acid sequence that is not contained in a naturally occurring PFM/SET polypeptide. Exemplary exogenous amino acid sequences are tags that facilitate identification or purification of a PFM/SET polypeptide, such as histidine tags, glutathione-S transferase tags, FLAG tags and myc tags.

Another biological activity of a PFM/SET polypeptide is the ability to act as an immunogen for the production of antibodies, or other antigen binding molecules, that bind specifically to an invention PFM/SET polypeptide.

The PFM/SET peptides of the invention can also be used in screening methods to identify PFM/SET-binding cellular molecules and modulatory compounds, as described further below.

The isolated PFM/SET polypeptides and peptides of the invention can be prepared by methods known in the art, including biochemical, recombinant and synthetic methods. For example, PFM and SET polypeptides can be purified by routine biochemical methods from a cell or tissue source that expresses abundant amounts of the corresponding transcript or polypeptide. The diagnostic methods disclosed herein can be adapted for determining which cells and tissues, and which subcellular fractions therefrom, are appropriate starting materials. Biochemical purification can include, for example, steps such as solubilization of the appropriate tissue or cells, isolation of desired subcellular fractions, size or affinity chromatography, electrophoresis, and immunoaffinity procedures. The methods and conditions for biochemical purification of a polypeptide of the invention can be chosen by those skilled in the art, and purification monitored, for example, by an ELISA assay or a functional assay, such as a DNA-binding or protein-binding assay.

A PFM/SET polypeptide, functional fragment or peptide having any desired boundaries, and a polypeptide having a modification to the native PFM or SET amino acid sequences, can also be produced by recombinant methods. Recombinant methods involve expressing a nucleic acid molecule encoding the desired polypeptide or fragment in a host cell or cell extract, and isolating the recombinant polypeptide or fragment, such as by routine biochemical purification methods described above. To facilitate identification and purification of the recombinant polypeptide, it is often desirable to insert or add, in-frame with the coding sequence, nucleic acid sequences that encode epitope tags, polyhistidine tags, glutathione-S-transferase (GST) domains, and similar affinity binding sequences, or sequences that direct expression of the polypeptide in the periplasm or direct secretion. Methods for producing and expressing recombinant polypeptides in vitro and in prokaryotic and eukaryotic host cells are well known in the art.

Thus, the invention provides a method of isolating a PFM/SET polypeptide, by growing a host cell containing an expression vector encoding a PFM or SET polypeptide, under conditions appropriate for expression of the encoded PFM/SET polypeptide, and isolating the PFM/SET polypeptide.

The PFM/SET polypeptide fragments and peptides of the invention can also be produced, for example, by enzymatic or chemical cleavage of the full-length polypeptide. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990), which is incorporated herein by reference).

Furthermore, PFM/SET polypeptides and peptides can be produced by chemical synthesis. If desired, such as to optimize their functional activity, stability or bioavailability, such molecules can be modified to include D-stereoisomers, non-naturally occurring amino acids, and amino acid analogs and mimetics. Examples of modified amino acids and their uses are presented in Sawyer, *Peptide Based Drug Design*, ACS, Washington (1995) and Gross and Meienhofer, *The Peptides: Analysis, Synthesis, Biology*, Academic Press, Inc., New York (1983), both of which are incorporated herein by reference.

PFM/SET Antibodies

The invention also provides an antibody or antigen binding fragment thereof that specifically binds a PFM/SET polypeptide. Such antibodies can be used, for example, to affinity purify a PFM/SET polypeptide from a cell or tissue source, or in therapeutic and diagnostic applications described below.

An "antigen binding fragment" of an antibody of the invention includes, for example, individual heavy or light chains and fragments thereof, such as VL, VH and Fd; monovalent fragments, such as Fv, Fab, and Fab'; bivalent fragments such as F(ab')$_2$; single chain Fv (scFv); and Fc fragments. Antigen binding fragments include, for example, fragments produced by protease digestion or reduction of an antibody, as well as fragments produced by recombinant DNA methods known to those skilled in the art.

The antibodies of the invention can be produced by any method known in the art. For example, a PFM or SET polypeptide or immunogenic peptide of the invention, or a nucleic acid expressing such a polypeptide, can be administered to an animal, using standard methods, and polyclonal antibodies isolated therefrom. Such polypeptides of peptides, if desired, can be conjugated to a carrier, such as KLH, serum albumin, tetanus toxoid and the like, using standard linking techniques, to increase their immunogenicity. Additionally, such peptides can be formulated together with an adjuvant known in the art, such as Freund's complete or incomplete adjuvant. The antibodies so generated can be used in the form of serum isolated from an immunized animal, or the antibody can be affinity purified from the serum using PFM/SET peptides or polypeptides.

Additionally, the PFM/SET antibodies of the invention can be monoclonal antibodies produced by a hybridoma cell line, by chemical synthesis, or by recombinant methods. Modified antibodies, such as chimeric antibodies, humanized antibodies and CDR-grafted or bifunctional antibodies, can also be produced by methods well known to those skilled in the art.

Methods of preparing and using antibodies and antigen-binding fragments, including detectably labeled antibodies, are described, for example, in Harlow and Lane, *Antibodies: A Laboratory Manual*, Cold Spring Harbor Laboratory, New York (1989); in Day, E. D., *Advanced Immunochemistry*, Second Ed., Wiley-Liss, Inc., New York, N.Y. (1990); and in Borrebaeck (Ed.), *Antibody Engineering*, Second Ed., Oxford University Press, New York (1995), which are incorporated herein by reference.

PFM/SET Modulatory Compounds

The invention also provides methods of identifying cellular and non-cellular molecules that modulate PFM/SET expression and activity. As used herein, the term "PFM/SET modulatory compound" refers to a molecule that alters PFM/SET expression or activity. A PFM/SET modulatory compound can increase or decrease PFM/SET expression or activity. Such compounds can be used in ex vivo and in vivo therapeutic applications, as described further below, to promote or inhibit cell proliferation.

As disclosed herein, the PR and SET domains of the PFM/SET polypeptides of the invention have methyltransferase enzymatic activity and function as specific protein binding domains. Through the methyltransferase activity and specific binding to particular cellular proteins, the intact PR/SET domain contributes to the function of PFM/SET polypeptide as a suppressor of cell growth. Therefore, a PFM/SET modulatory compound can alter the activity of a PFM/SET polypeptide by modulating the methyltransferase activity or the molecular interactions of a PFM/SET with another molecule. Because of the role of PFM/SET polypeptides in modulating cell proliferation, compounds that modulate PFM/SET polypeptide activity, such as histone methyltransferase activity, or molecular interactions are expected to be useful in applications in which it desirable to positively or negatively modulate cell growth, including treatment of hyperproliferative disorders (for example, neoplasia, hyperplasia, inflammatory conditions and the like); treatment of hypoproliferative disorders (for example, various disorders of hematopoiesis, wound healing and the like); and regulate the proliferation and differentiation of particular cell types, including multipotent cells, such as stem cells. In regard to multipotent cells, a compound that increases activity or expression of a PFM/SET polypeptide can function to induce differentiation of a multipotent cell, such as a stem cell, whereas a compound that reduces activity or expression of a PFM/SET polypeptide can function to increase the multipotent potential of a differentiated cell.

The methods of the invention for identifying a PFM/SET modulatory compound can involve determining an activity of PFM/SET. Exemplary activities include, for example, methyltransferase activity and transcriptional activity (see, for example, Huang et al., *J. Biol. Chem.* 273:15933–15939 (1998). An exemplary type of PFM/SET modulatory compound is a compound that modulates histone methyltransferase activity. As described herein, the histone methyltransferase activity of PFM/SET polypeptides has an important role in cancer development in humans. As such, a compound that modulates histone methyltransferase activity can be useful for treating proliferative diseases and disorders, such as cancer, in humans.

Therefore, the invention provides a method of screening for a compound that modulates PFM/SET histone methyltransferase activity. The method is practiced by contacting a PFM/SET polypeptide or fragment thereof, having histone methyltransferase activity with one or more candidate compounds, and assaying histone methyltransferase activity of the contacted PFM/SET polypeptide fragment. A compound that modulates histone methyltransferase activity of the PFM/SET polypeptide or fragment thereof is thereby identified.

As used herein, the term "histone methyltransferase activity" or "HMT activity," with respect to a PFM/SET polypeptide or PFM/SET polypeptide fragment, refers to the ability of the PFM/SET polypeptide or PFM/SET polypeptide fragment to catalyze the methylation of histones or histone peptides under suitable assay conditions. In contrast, under the same conditions, a control polypeptide, such as glutathione-S-transferase (GST), will not be able to catalyze the methylation of histones or histone peptides. Histone methyltransferase activity can be exhibited either in an in vitro assay with purified or partially purified PFM/SET polypeptide or PFM/SET polypeptide fragment, or in a cell-based assay. Histone methyltransferase activity includes histone methyltransferase activity exhibited toward any histone, such as histone H1, H2A, H2B, H3 or H4.

Histones suitable for use as substrates in histone methyltransferase activity assays can be obtained commercially (for example, from Roche Molecular Biochemicals), prepared recombinantly based on known nucleic acid sequences, or extracted from cells using methods known in the art. Histone peptides suitable for use as substrates in histone methyltransferase assays, including peptides with native sequences and peptides modified by acetylation on lysine residues, can be obtained commercially (for example, from Upstate Biotech) or produced synthetically. Suitable histone peptides include, for example, H3 N-terminal peptides that include lys-9 (K9) (for example, H3 amino acids 1–20) and H1 N-terminal peptides that include lys-25 (K25) (for example, H1 amino acids 15–37 or 12–31). The methylation site on H4 is expected to be lys-20 (K20). Accordingly, a suitable histone H4 peptide can be an N-terminal peptide that includes lys-20.

For histone methyltransferase assays, a PFM/SET polypeptide or PFM/SET polypeptide fragment of any desired sequence can conveniently be produced recombinantly, such as by expression of the encoding nucleic acid molecule in bacteria, yeast, insect or mammalian cells. The expressed polypeptide can then be isolated with anti-RIZ antibodies, or purified or partially purified by standard biochemical fractionation methods. Alternatively, to facilitate isolation, the PFM/SET polypeptide or PFM/SET polypeptide fragment can be expressed as a fusion with a tag sequence, such as glutathione-S-transferase (GST), a 6×His tag or an epitope tag. Methods of producing and isolating tagged and untagged recombinant proteins are well known in the art (see, for example, Sambrook et al., *Molecular Cloning: A Laboratory Manual*, 3rd ed., Cold Spring Harbor Press, Plainview, N.Y. (2001); Ausubel et al. (*Current Protocols in Molecular Biology* (Supplement 47), John Wiley & Sons, New York (1999)).

As an alternative to preparing a recombinant PFM/SET polypeptide or PFM/SET polypeptide fragment, an endogenous PFM/SET polypeptide can be purified or partially purified from a convenient cell or tissue source. A PFM/SET fragment can thus be prepared by enzymatic or chemical cleavage of the endogenous PFM/SET polypeptide. Alternatively, a PFM/SET polypeptide fragment can be prepared by synthetic methods.

Histone methyltransferase activity of a PFM/SET polypeptide or fragment can be determined by methods known in the art. For example, the PFM/SET polypeptide or fragment can be incubated together with a histone or histone peptide labeled methyl donor, such as S-adenosyl-[methyl-$^{14}$C]-L-methionine, or S-adenosyl-[methyl-$^{3}$H]-L-methionine, under suitable assay conditions. Transfer of the radiolabel to the histone or histone peptide can be detected, for example, by SDS-PAGE electrophoresis and fluorography. Alternatively, following the reaction the histone or histone peptides can be separated from the methyl donor by filtration, and the amount of radiolabel retained on the filter quantitated by scintillation counting. Other suitable labels that can be attached to methyl donors, such as chromogenic and fluorescent labels, and methods of detecting transfer of these labels to histones and histone peptides, are known in the art.

Alternatively, histone methyltransferase activity of a PFM/SET polypeptide can be determined using an unlabeled methyl donor (for example, S-adenosyl-L-methionine) and reagents that selectively recognize methylated histones or histone peptides. For example, after incubation of the PFM/SET polypeptide or fragment thereof, methyl donor and histones or histone peptides, under suitable assay conditions, methylated histones or histone peptides can be detected by immunoblotting or by an ELISA assay with antibodies specific for methylated histone epitopes. Suitable antibodies are described, for example, in Nakayama et al., *Science* 292:110–113 (2001), Noma et al., *Science* 293:1150–1155 (2001) and published U.S. patent application No. 20020039776, or can be prepared by methods known in the art (see Harlow and Lane, *Antibodies: A Laboratory Manual*, Cold Spring Harbor Laboratory Press. (1988)).

Instead of using antibodies, methylated histones can be detected using reagents that selectively bind methylated histones with high affinity. Such reagents are known in the art or can be determined by screening assays known in the art. An exemplary binding reagent is heterochromatin protein HP1, which binds histone H3 when methylated at lysine 9 (H3-K9). HP1, or a binding fragment thereof, can be labeled, and the HP1 or fragment bound to methylated H3-K9 detected. Alternatively, the HP1 or fragment need not be labeled, and can instead be detected using an anti-HP1 antibody in an ELISA assay.

Various low-throughput and high-throughput enzyme assay formats are known in the art and can be readily adapted for PFM/SET polypeptide histone methyltransferase assays. For high-throughput assays, the histone or histone peptide substrate can conveniently be immobilized on a solid support, such as a multiwell plate, slide or chip. Following the reaction, the methylated product can be detected on the solid support by the methods described above. Alternatively, the histone methyltransferase reaction can take place in solution, after which the histone or histone peptide can be immobilized on a solid support, and the methylated product detected. To facilitate such assays, the solid support can be coated with streptavidin and the histone labeled with biotin, or the solid support can be coated with anti-histone antibodies. The skilled person can determine suitable assay formats depending on the desired throughput capacity of the screen.

Generally, the candidate compound will be included in a histone methyltransferase reaction together with the PFM/SET polypeptide or fragment, histone or histone peptide substrate, and methyl donor. optionally, the candidate compound and the RIZ can first be incubated together, and then the other reactants added. If desired, other components, such as different PFM/SET polypeptides or PFM/SET polypeptide fragments, can be included in the reactions, and the effect of the candidate compound on modulating histone methyltransferase activity under such conditions determined. The skilled person can determine suitable combinations of reactants and components.

For cell-based screening assays, a cell expressing a PFM/SET polypeptide or PFM/SET polypeptide fragment can be contacted with a candidate compound. Either the in vivo methylation of isolated histones can be determined following contacting, or the RIZ polypeptide can be isolated and its activity in methylating isolated histones or histone fragments assayed as described above. If desired, the ability of a candidate compound to modulate PFM/SET polypeptide activity under physiologically relevant conditions can be determined in cell-based screening assays.

Determining whether a candidate compound modulates PFM/SET polypeptide histone methyltransferase activity, either positively or negatively, generally requires comparison to a control. A control can be an identical reaction to the test reaction, except the control is not exposed to the candidate compound. The histone methyltransferase activity of the control reaction can be assessed either before, after, or at the same time as the test reaction. A compound that "modulates" histone methyltransferase activity is a compound that increases or decreases histone methyltransferase activity, in comparison to a control, by at least 2-fold, such as at least 5-fold, 10-fold or more.

Suitable assays for identifying compounds that modulate PFM/SET transcriptional activation, repression and coactivation function can be determined by the skilled person. Such assays are generally based on co-expression of PFM/SET and an appropriate promoter-linked reporter gene in a cell, under conditions where a certain amount of transcription occurs, contacting the cell with the candidate compound, and determining whether there is a change (i.e. either an increase or decrease) in transcriptional activity. Transcription based assays are well known in the art, and readily amenable to high-throughput screening assays.

A PFM/SET modulatory compound can also alter the amount of a PFM/SET polypeptide expressed in a cell, for example, by increasing or decreasing the cellular expression level or stability of a PFM/SET polypeptide. A PFM/SET modulatory compound can be identified by contacting a PFM/SET-expressing cell with a candidate compound under conditions that allow PFM/SET expression or activity. Expression of a PFM/SET refers to the generation of a PFM/SET mRNA or polypeptide. Therefore, an amount of PFM/SET expression can be represented by an amount of messenger RNA (mRNA) or an amount of polypeptide corresponding to a PFM/SET mRNA. An amount of PFM/SET mRNA expressed in a particular cell is generally determined by the transcriptional activity of the gene encoding the mRNA as well as the stability of the mRNA. The amount of polypeptide expressed in a particular cell is generally determined by the stability of the polypeptide and susceptibility to proteolysis of the polypeptide. An increase in PFM/SET can result, for example, from an increase in the amount of PFM/SET mRNA resulting from increased transcription of a PFM/SET gene, increased stability of PFM/SET mRNA and reduced degradation of PFM/SET mRNA. An alteration in the amount of PFM/SET polypeptide can result, for example, from increased or decreased stability and increased or decreased proteolysis of a PFM/SET polypeptide. An increase in PFM/SET activity can result, for example, from an increase in the amount of PFM/SET polypeptide or alteration in PFM/SET structure or conformation that leads to increased activity, including a modification of a PFM/SET polypeptide.

A PFM/SET modulatory compound can act to modulate PFM/SET activity by increasing or decreasing the amount of PFM/SET polypeptide in a cell, for example, by stimulating increased PFM/SET mRNA expression. PFM/SET mRNA expression can be modulated, for example, by inducing or derepression the transcription of a PFM/SET gene and by regulating the expression of a cellular protein that acts as a transcription factor to regulate gene expression. A compound can act to modulate the amount of PFM/SET activity by increasing or decreasing the stability of a PFM/SET mRNA or polypeptide, for example, by increasing or decreasing a cellular degradation activity, such as a protease activity. Molecules that mediate the regulation of PFM/SET expression, such as receptors and corresponding signal transduction molecules, can also be targets of compounds that increase the expression of PFM/SET in a cell. For example, a signal transduction pathway that stimulates the expression of PFM/SET can be modulated to increase or decrease the level of PFM/SET expression, for example, by increasing or decreasing the rate of PFM/SET synthesis or the length of time that PFM/SET gene expression remains active.

A compound can directly increase or decrease PFM/SET activity, for example, by binding to the enzyme and modulating catalytic activity, such as by inducing a conformational change in the PFM/SET polypeptide. A compound that directly increases or decreases the activity of a PFM/SET polypeptide can be identified, for example, by contacting a candidate compound with a PFM/SET polypeptide or functional fragment thereof, contained in a cell, cell fraction, or lysate thereof, and can be an isolated PFM/SET polypeptide. A compound that modulates the interaction of a PFM/SET polypeptide with a binding partner can also be identified by contacting a candidate compound with a PFM/SET polypeptide or functional fragment thereof in the presence of a binding partner. Methods for identifying PFM/SET binding partners are well known to those skilled in the art and are described below.

A compound that binds to a PFM/SET polypeptide can be identified using a variety of binding assay formats. A binding assay can use a detectably labeled candidate compound and an unlabeled PFM/SET (and optionally an unlabeled binding partner). Alternatively, a binding assay can use an unlabeled candidate compound or binding partner and a labeled PFM/

SET. Other appropriate combinations of labeled and unlabeled molecules can be determined by the skilled person depending on the assay format.

A variety of low- and high-throughput assays known in the art are suitable for detecting specific binding interactions between a PFM/SET nucleic acid molecule or polypeptide and a candidate PFM/SET modulatory compound. These assays include both solution-based methods and solid phase methods (for example, molecules bound to plates, chips, affinity columns and the like). Binding assays are amenable to either manual or high-throughput automated screening of compounds.

Both direct and competitive binding assays can be performed, including, for example, scintillation proximity assay (SPA) (Alouani, *Methods Mol. Biol.* 138:135–41 (2000)), UV or chemical cross-linking (Fancy, *Curr. Opin. Chem. Biol.* 4:28–33 (2000)), competition binding assays (Yamamura et al., *Methods in Neurotransmitter Receptor Analysis*, Raven Press, New York, 1990), biomolecular interaction analysis (BIA) (Weinberger et al., *Pharmacogenomics* 1:395–416 (2000)), mass spectrometry (MS) (McLafferty et al., *Science* 284:1289–1290 (1999) and Degterev, et al., *Nature Cell Biology* 3:173–182 (2001)), nuclear magnetic resonance (NMR) (Shuker et al., *Science* 274:1531–1534 (1996), Hajduk et al., *J. Med. Chem.* 42:2315–2317 (1999), and Chen and Shapiro, *Anal. Chem.* 71:669A–675A (1999)), and fluorescence polarization assays (FPA) (Degterev et al., supra, 2001) which are incorporated herein by reference. Other assays for detecting specific binding interactions include, for example ELISA assays, FACs analysis, and affinity separation methods, which as described, for example, in Harlow and Lane, Eds. *Antibodies: A Laboratory Manual*, Cold Spring Harbor Laboratory (1988).

Assays to identify compounds that modulate PFM/SET gene expression can involve first transducing cells with a PFM or SET promoter-reporter nucleic acid construct such that a change in expression of a protein such as β-lactamase, luciferase, green fluorescent protein or β-galactosidase will be detected in response to contacting the cell with a PFM/SET modulatory compound that upregulates or downregulates expression of PFM or SET. Assays and reporter systems useful for monitoring gene expression are well known in the art. Other assays to identify compounds that modulate PFM/SET gene expression include assays that measure levels of PFM or SET transcripts, such as Northern blots, RNase protection assays, and RT-PCR.

Assays to identify compounds that modulate PFM/SET polypeptide expression can involve detecting a change in PFM or SET polypeptide abundance in response to contacting the cell with a PFM or SET modulatory compound. Assays for detecting changes in polypeptide expression include, for example, immunoassays with specific PFM or SET antibodies, such as immunofluorescence, immunohistochemistry and immunoprecipitation assays.

The methods of identifying a PFM/SET modulatory compound can involve measuring changes in gene expression by determining the amount of mRNA or polypeptide present in a sample. Methods for measuring both mRNA and polypeptide quantity are well known in the art. Methods for measuring mRNA typically involve detecting nucleic acid molecules by specific hybridization with a complementary probe in solution or solid phase formats. Such methods include northern blots, polymerase chain reaction after reverse transcription of RNA (RT-PCR), and nuclease protection. Measurement of a response of a pathway component can be performed using large scale gene expression methods. For methods of the invention that involve identifying a candidate atherosclerosis drug target molecule, described below, large scale gene expression methods can be advantageously used to measure a large population of expressed genes in an organ, tissue or cell. Examples of methods well known in the art applicable to measuring a change in expression of a population of genes include cDNA sequencing, clone hybridization, differential display, subtractive hybridization, cDNA fragment fingerprinting, serial analysis of gene expression (SAGE), and DNA microarrays.

A variety of methods well known in the art can be used to determine protein levels either directly or indirectly. Such methods include immunochemical methods, such as western blotting, ELISA, immunoprecipitation, and RIA, gel electrophoresis methods including one and two-dimensional gels, methods based on protein or peptide chromatographic separation, methods that use protein-fusion reporter constructs and calorimetric readouts, methods based on characterization of actively translated polysomal mRNA, and mass spectrometric detection.

The invention screening method involves contacting a PFM/SET polypeptide or PFM/SET polypeptide fragment, such as a PFM/SET polypeptide or fragment having histone methyltransferase activity, with one or more candidate compounds. A candidate compound useful in the methods of the invention can be a naturally occurring macromolecule, such as a peptide, nucleic acid, carbohydrate, lipid, or any combination thereof. A candidate compound alternatively can be a partially or completely synthetic derivative, analog or mimetic of such a macromolecule, or a small, synthetic molecule, such as an organic molecule prepared by combinatorial chemistry methods. A candidate compound can be detectably labeled or attached to a solid support, if desired, as appropriate in a particular assay.

Methods for producing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.* 2:363–371 (1998); Sofia, *Mol. Divers.* 3:75–94 (1998); Eichler et al., *Med. Res. Rev.* 15:481–496 (1995). Libraries containing large numbers of natural and synthetic compounds also can be obtained from commercial sources.

The number of different candidate compounds to screen in a particular assay can be determined by those skilled in the art, and can be 2 or more, such as 5, 10, 15, 20, 50 or 100 or more different compounds. For certain applications, such as when a library of random compounds is to be screened, and for automated procedures, it may be desirable to screen $10^3$ or more compounds, such as $10^5$ or more compounds, including $10^7$ or more compounds. If desired, a plurality of candidate compounds can be assayed in a pool, and the pool repeatedly subdivided until a single compound with the desired activity is identified. Candidate compounds can be assayed simultaneously, in parallel, or sequentially.

The amount of candidate compound to use in a reaction can be determined by the skilled person based on the nature of the compound, the nature of the assay, and the concentration of the reactants. If desired, a range of doses of candidate compound can be tested.

PR, SET, PRAZ and PKZL domains of a PFM/SET polypeptide can bind to cellular proteins and thereby regulate a PFM/SET biological activity. Therefore, an isolated PFM/SET polypeptide, including a functional fragment of a PFM/SET polypeptide that contains a PR, SET, PRAZ or PKZL domain, can be used in assays to identify compounds that modulate the interaction of a PFM/SET polypeptide with another cellular molecule.

Various binding assays to identify cellular proteins that interact with protein binding domains are known in the art and include, for example, yeast two-hybrid screening assays (see, for example, Luban et al., *Curr. Opin. Biotechnol.* 6:59–64 (1995)) and affinity column chromatography methods using cellular extracts. By synthesizing or expressing polypeptide fragments containing various PFM or SET sequences or deletions, the PFM or SET binding interface can be readily identified.

As further disclosed herein, the zinc finger (ZF) domain of the PFM polypeptides of the invention functions as a specific DNA binding domain. By specifically binding particular DNA sequences, the ZF domain contributes to the function of PFM/SET polypeptides as a suppressor of cell growth. Thus, an isolated PFM/SET polypeptide of the invention containing a ZF domain, or one or more ZF motifs therefrom, can be used, for example, in binding assays to identify cellular DNA sequences that normally bind PFM. Such cellular DNA sequences are likely to be regulatory sequences for genes which themselves have positive or negative growth modulating activity, and which are appropriate targets for therapeutic intervention to prevent or treat proliferative disorders. Furthermore, oligonucleotides or analogs corresponding the PFM binding DNA sequences, can be administered as therapeutic compounds to specifically interfere with PFM function. Additionally, the ZF domain, or one or more ZF motifs therefrom, can be administered as therapeutic compounds to specifically interfere with PFM function.

Various assays to identify DNA sequences that bind DNA binding domains are known in the art and include, for example, Cyclic Amplification and Selection of Targets (CASTing), as described by Wright et al., *Mol. Cell. Biol.* 11:4104–4110 (1991), and the Multiplex Selection Technique (MuST), as described by Nallur et al., *Proc. Natl. Acad. Sci. USA* 93:1184–1189 (1996).

Appropriate assays to determine whether a PFM/SET modulatory compound, such as a compound that modulates PFM/SET histone methyltransferase activity, affects PFM or SET activity so as to inhibit or promote cell proliferation, can be determined by those skilled in the art. The skilled artisan appreciates that molecular pathways involved in cell proliferation are generally well conserved among eukaryotic organisms. Therefore, a proliferation assay can be performed in any eukaryotic cell type in which altered proliferation can be detected including, for example, primary mammalian cells, normal and transformed mammalian cell lines, yeast, insect cells and amphibian cells.

A PFM/SET modulatory compound that modulates cell proliferation can, for example, cause cell cycle arrest at a particular stage of mitosis or meiosis, induce or prevent apoptosis, or promote progression through the cell cycle when normal cells would arrest. Such qualitative changes in the cell cycle can be determined by methods known in the art, and which depend on the cell type used in the assay. A molecule that modulates cell proliferation can also, for example, cause faster or slower progression through the cell cycle, resulting in an increased or decreased number of cells in the population after a given period of time. Those skilled in the art can choose an appropriate assay to determine whether, and by what mechanism, a molecule of the invention affects cell proliferation.

To determine whether a PFM/SET modulatory compound, such as a compound that modulates PFM/SET histone methyltransferase activity, restores more normal proliferative characteristics on a neoplastic cell, an assay can be performed in a mammalian cell that exhibits neoplastic proliferative characteristics, such as soft agar colony formation, overgrowth of a cell monolayer, proliferation in low serum, abnormally rapid proliferation, or tumor formation in an animal. Such cells are known in the art and include both tumor cell lines and primary tumor cells. A molecule of the invention can be introduced or expressed in such a cell, and a determination can be made whether the molecule restores more normal proliferative characteristics to the cell, such as slower growth in culture, fewer foci, fewer soft agar colonies, or a reduction in tumor size, as compared to the parental cell.

As understood by those of skill in the art, assay methods for identifying compounds that increase PFM/SET activity generally require comparison to a control. One type of a "control" is a cell or isolated PFM/SET polypeptide preparation that is treated substantially the same as the test cell exposed to a candidate compound, except that a control is not exposed to a compound. A control cell or isolated PFM/SET polypeptide can be treated with a carrier solution or solvent in which a candidate compound is dissolved or contained, such as an aqueous or organic solution, if desired.

Given the teachings and guidance provided herein, the choice of measuring mRNA or polypeptide amount or polypeptide activity will be that of the user. Considerations such as the sample type, availability and amount will also influence selection of a particular assay format. For example, if a small amount of sample is available, formats which are more sensitive are suitable. Alternatively, if the user is analyzing numerous different samples simultaneously, a multisample format is suitable. Those skilled in the art will know, or can determine, which format is useful for a particular application and which methods or modifications of methods known in the art are compatible with a particular assay format.

A PFM/SET modulatory compound can be a naturally occurring macromolecule, such as a peptide, nucleic acid, carbohydrate, lipid, or any combination thereof. A PFM/SET modulatory compound also can be a partially or completely synthetic derivative, analog or mimetic of such a macromolecule, or a small organic or inorganic molecule prepared partly or completely by combinatorial chemistry methods.

Methods for producing pluralities of compounds to use in screening for PFM/SET modulatory compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.* 2:363–371 (1998); Sofia, *Mol. Divers.* 3:75–94 (1998); Eichler et al., *Med. Res. Rev.* 15:481–496 (1995); and the like. Libraries containing large numbers of natural and synthetic compounds also can be obtained from commercial sources.

Therapeutic Applications

As disclosed herein, PFM/SET nucleic acid molecules encoding PFM or SET polypeptides with intact PR/SET domains inhibit cell growth. In contrast, PFM/SET nucleic acid molecules encoding PFM or SET polypeptides with partial PR/SET domains, or lacking PR/SET domains, promote cell growth. Thus, by selectively manipulating the expression or activity of either the PR/SET domain+ or PR/SET domain– forms of the PFM/SET molecules of the invention, or both, it is readily apparent that cell growth can be modulated in either a positive or negative manner, as desired.

Accordingly, the invention provides PFM/SET molecules and therapeutic methods that can be used to inhibit the growth of cells in culture, or in a subject. Advantageously, the molecules and therapeutic methods can be used to treat proliferative disorders in a subject. As used herein, the term "proliferative disorder" refers to a condition in which unwanted cell proliferation of one or more subset of cells in a mammal, such as a human, occurs, resulting in harm (for example, discomfort or decreased life expectancy) to the mammal. Cell proliferative disorders include diseases such as cancer, in which the cells are neoplastically transformed, but also include diseases resulting from overgrowth of normal cells. For example, cell proliferative disorders include diseases associated with the overgrowth of connective tissues, such as various fibrotic diseases, including scleroderma, arthritis, alcoholic liver cirrhosis, keloid, and hypertropic scarring; vascular proliferative disorders, such as atherosclerosis; and benign tumors.

The invention also provides PFM/SET molecules and therapeutic methods that can be used to enhance proliferation of normal cells. For some therapeutic applications, it may be useful to increase the proliferation of normal cells, without rendering the cells cancerous. In particular, in diseases of cell degeneration, such as Duchenne's muscular dystrophy, insulin-dependent diabetes mellitus, Parkinson's disease, Huntington's disease, Alzheimer's disease, paralysis, cerebellar atrophy, and the like, it may be useful to remove some of the remaining normal cells from the affected tissue of the individual, and culture the cells in large numbers ex vivo for reimplantation into the patient. Additionally, in applications such as wound healing and skin grafts, it is often desirable to increase the proliferation of normal cells.

In one embodiment, the invention provides a method for modulating cell growth, by introducing a vector containing an isolated PFM6, PFM7, PFM8, PFM9, PFM10, PFM11, PFM12, PFM13, PFM14, SET07, BOP or SET27H nucleic acid molecule of the invention, operatively linked to a promoter of RNA expression, into a host cell, and expressing the encoded PFM/SET polypeptide in an amount effective to modulate growth of the cell. For applications in which inhibition of cell growth is desirable, expression vectors containing isolated full-length PFM/SET nucleic acid molecules, or modifications of full-length PFM/SET nucleic acid molecules that retain the growth inhibitory activity of PFM/SET, can be introduced into cells under conditions in which the PFM/SET polypeptide is expressed in an effective amount to inhibit cell proliferation. For applications in which promotion of cell growth is desirable, expression vectors which contain portions of the PFM/SET nucleic acid molecules that compete with PFM/SET for substrates or effectors, such as the PR domain or zinc finger domain, or both, can be introduced into cells under conditions in which the PFM/SET polypeptide is expressed in an effective amount to promote cell proliferation.

Various gene therapy strategies are well known to those skilled in the art, and are reviewed, for example in Roth et al., *Oncology* 13 (10 Suppl 5):148–54, (1999). Useful mammalian expression vectors for such therapeutic applications, and methods of introducing such vectors into mammalian cells either ex vivo or in vivo, for expression of the encoded polypeptide, are well known in the art. Viruses are specialized infectious agents that can elude host defense mechanisms and can infect and propagate in specific cell types. Viral based systems provide the advantage of being able to introduce relatively high levels of the heterologous nucleic acid into a variety of cells. Suitable viral vectors for introducing an invention PFM/SET nucleic acid into mammalian cells (for example, vascular tissue segments) are well known in the art. These viral vectors include, for example, Herpes simplex virus vectors (Latchman, *Histology and Histopathology*, 15:1253–1259 (2000)), Vaccinia virus vectors, Cytomegalovirus vectors, Moloney murine leukemia virus vectors, adenovirus vectors, adeno-associated virus vectors, retrovirus vectors, lentiviral vectors and the like.

In particular, the specificity of viral vectors for particular cell types can be utilized to target predetermined cell types. Thus, the selection of a viral vector will depend, in part, on the cell type to be targeted. For example, if a proliferative disease is to be treated by increasing the level of a PFM/SET polypeptide in a particular tissue affected by the disease, then a viral vector that targets the particular tissue can be used. For example, if a disease or pathological condition of the hematopoietic system is to be treated, then a viral vector that is specific for a particular blood cell or its precursor cell can be used. A vector based on a human immunodeficiency virus is an example of such a viral vector. In addition, a viral vector or other vector can be constructed to express a PFM/SET nucleic acid in a tissue specific manner by incorporating a tissue-specific promoter or enhancer into the vector.

Non-viral synthetic vectors and hybrid vectors are also useful for introducing a PFM/SET nucleic acid molecule of the invention into a cell. Cell-based delivery methods involving ex vivo genetic manipulation of cells are also useful for delivering a PFM/SET nucleic acid molecule into a cell of an individual.

For gene therapy, a vector containing a PFM/SET nucleic acid or an antisense nucleotide sequence can be administered to a subject by various methods. For example, if viral vectors are used, administration can take advantage of the target specificity of the vectors. In such cases, there in no need to administer the vector locally at the diseased site. However, local administration can be a particularly effective method of administering a PFM/SET nucleic acid. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a PFM/SET nucleic acid molecule into cells in a tissue-specific manner using a tissue-specific ligand or an antibody that is non-covalently complexed with the nucleic acid molecule via a bridging molecule. Direct injection of a naked or a nucleic acid molecule encapsulated, for example, in cationic liposomes also can be used for stable gene transfer into non-dividing or dividing cells in vivo. In addition, a PFM/SET nucleic acid molecule can be transferred into a variety of tissues using the particle bombardment method. Such nucleic acid molecules can be linked to the appropriate nucleotide sequences required for transcription and translation.

A particularly useful mode of administration of a PFM/SET nucleic acid is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promoter, an enhancer or other expression element specific for the desired subset of cells can be linked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

In another embodiment, the invention provides a method for modulating cell growth by introducing into a cell an effective amount of an antisense oligonucleotide or a ribozyme that inhibits expression of PFM/SET, thereby modulating growth of the cell. Methods for modulating gene expression using antisense oligonucleotides and ribozymes are also well known in the art. Thus, an antisense molecule or ribozyme that selectively inhibits expression of the PR/SET domain–, growth promoting form of PFM/SET, can be used to inhibit cell proliferation. In contrast, an antisense molecule or ribozyme that selectively inhibits expression of the PR+, growth suppressing form of PFM/SET, can be used to promote cell proliferation.

Antisense oligonucleotides that inhibit PFM/SET gene expression generally are at least about 17 nucleotides in length, and often include sequences found within the first 30 nucleotides of the transcript being targeted. The preparation and use of antisense oligonucleotides are well known in the art and described in detail, for example, in Cohen (ed), *Oligonucleotides: Antisense Inhibitors of Gene Expression*, CRC Press Inc., Boca Raton (1989). Likewise, methods of preparing and using hairpin and hammerhead ribozymes for the selective inhibition of gene expression are known in the art and are described, for example, in Poeschla et al., *Curr. Opin. Oncol.* 6:601–606 (1994).

In a further embodiment, the invention provides a method for modulating cell growth by contacting the cell with an effective amount of a PFM/SET modulatory compound. Methods of identifying PFM/SET modulatory compounds have been described above.

In yet another embodiment, the invention provides a method for modulating cell growth by administering antibodies that specifically bind a PFM or SET polypeptide. For example, antibodies that selectively detect a growth promoting structural variant of PFM or SET, such as the PR– form of PFM polypeptide, can be administered to selectively target cells that express this variant. If desired, such antibodies can be administered in conjunction with a cytotoxic or cytostatic moiety, such as a radioisotope or toxin, in order to neutralize or kill cells expressing the desired structural variant.

The PFM/SET therapeutic molecules of the invention described herein, including expression vectors, antisense oligonucleotides and ribozymes, PFM/SET modulatory compounds, and antibodies, can optionally be formulated together with a pharmaceutically acceptable carrier for delivery to a cultured cell or to a subject. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable compound that acts, for example, to stabilize or increase the solubility of a pharmaceutical composition. Such a physiologically acceptable compound can be, for example, a carbohydrate, such as glucose, sucrose or dextrans; an antioxidant, such as ascorbic acid or glutathione; a chelating agent; a low molecular weight protein; or another stabilizer or excipient. Pharmaceutically acceptable carriers, including solvents, stabilizers, solubilizers and preservatives, are well known to those skilled in the art.

Those skilled in the art can formulate the therapeutic molecules to ensure proper distribution in vivo. For example, the blood-brain barrier (BBB) excludes many highly hydrophilic compounds. To ensure that the therapeutic molecules of the invention cross the BBB, if desired, they can be formulated, for example, in liposomes, or chemically derivatized. Methods of ensuring appropriate distribution in vivo can also be provided by rechargeable or biodegradable devices, particularly where gradients of concentrations of drug in a tissue are desired. Various slow release polymeric devices are known in the art for the controlled delivery of drugs, and include both biodegradable and non-degradable polymers and hydrogels. Those skilled in the art understand that the choice of the pharmaceutical formulation and the appropriate preparation of the composition will depend on the intended use and mode of administration.

The therapeutic molecules of the invention, including expression vectors, antisense oligonucleotides and ribozymes, PFM/SET modulatory compounds and antibodies, can be administered to a subject by any effective route. Suitable routes for delivering the therapeutic molecules of the invention include topically, intraocularly, intradermally, parenterally, orally, intranasally, intravenously, intramuscularly, intraspinally, intracerebrally and subcutaneously. In a preferred embodiment, the therapeutic PFM or SET molecules are directly injected into a solid tumor, tumor-containing organ or tumor containing body cavity, in a effective amount to inhibit proliferation of the tumor cells. Alternatively, the therapeutic PFM or SET molecules of the invention can be administered systemically into the blood or lymphatic circulation to reach cells in the circulatory system or in any organ or tissue.

An effective dose of a therapeutic molecule of the invention can be determined, for example, by extrapolation from the concentration required for binding an isolated PFM/SET nucleic acid or polypeptide in binding and functional assays described herein; from the dose required to modulate PFM or SET nucleic acid or polypeptide expression in the expression assays described herein; or from the dose required to modulate cell proliferation in the proliferation assays described herein.

An effective dose of a molecule of the invention for the treatment of proliferative disorders can also be determined from appropriate animal models, such as xenografts of human tumors in rats or mice. Human cancer cells can be introduced into an animal by a number of routes, including subcutaneously, intravenously and intraperitoneally. Following establishment of a tumor, the animals can be treated with different doses of a molecule of the invention, and tumor mass or volume can be determined. An effective dose for treating cancer is a dose that results in either partial or complete regression of the tumor, reduction in metastasis, reduced discomfort, or prolonged life span.

The appropriate dose for treatment of a human subject with a therapeutic molecule of the invention can be determined by those skilled in the art, and is dependent on the nature and bioactivity of the particular compound, the desired route of administration, the gender, age and health of the individual, the number of doses and duration of treatment, and the particular condition being treated.

Diagnostic Applications

The PFM/SET nucleic acids and polypeptides disclosed herein exist in different forms, depending on the splice variant expressed. PFM nucleic acids and polypeptides that express or contain an intact PR domain (PR+) are associated with regulated, or normal, cell proliferation. A decrease in the total amount, or relative amount, of the PR+ form of a PFM, or an increase in the total amount, or relative amount, of the PR− form of a PFM, is associated with unregulated, or pathological, cell proliferation. Therefore, determining the total or relative abundance of the PR+ and PR− forms of PFM, or identifying alterations in the expression or structure of PFM nucleic acid molecules or polypeptides, can be used to distinguish between normal and pathologically proliferative cells in a sample. Similarly, detection of the presence or absence of a SET domain in a PFM/SET nucleic acid or polypeptide can be used to distinguish between normal and pathologically proliferative cells in a sample.

The invention thus provides methods of detecting PFM/SET nucleic acids and polypeptides in a sample. As used herein, the term "sample" is intended to mean any biological fluid, cell, tissue, organ or portion thereof, that includes or potentially includes PFM or SET nucleic acids or polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or protein preparation. A sample can be prepared by methods known in the art suitable for the particular format of the detection method employed.

The detection methods of the invention can advantageously be used, for example, to identify pathologically proliferative cells, such as neoplastic cells, in a sample. As used herein, the term "neoplastic cell" is intended to mean a cell that exhibits histological or proliferative features of a malignant or premalignant cell. For example, by histological methods, a neoplastic cell can be observed to invade into surrounding normal tissue, have an increased mitotic index, an increased nuclear to cytoplasmic ratio, altered deposition of extracellular matrix, or a less differentiated phenotype. A neoplastic cell can also exhibit unregulated proliferation, such as anchorage independent cell growth, proliferation in reduced-serum medium, loss of contact inhibition, or rapid proliferation compared to normal cells. The diagnostic methods described herein are applicable to the identification of any type of neoplastic cell, such as neoplastic cells present in solid tumors (carcinomas and sarcomas) such as breast, colorectal, gynecological, lung, prostate, bladder, renal, liver, urethral, endocrinal, melanoma, basal cell, central nervous system, lymphoma, stomach, esophageal, squamous cell cancers, as well as all forms of leukemias, and metastases therefrom.

The diagnostic methods described herein can also be adapted for use as prognostic assays. Such an application takes advantage of the observation that alterations in expression or structure of different tumor suppressor molecules take place at characteristic stages in the progression of a proliferative disease or of a tumor. Knowledge of the stage of the tumor allows the clinician to select the most appropriate treatment for the tumor and to predict the likelihood of success of that treatment.

The diagnostic methods described herein can also be used to identify individuals at increased risk of developing a proliferative disease, such as cancer, due to hereditary mutations in a PFM or SET.

The invention thus provides methods for detecting PFM/SET nucleic acid in a sample. In one embodiment, the method consists of contacting the sample with an isolated PFM6, PFM7, PFM8, PFM9, PFM10, PFM11, PFM12, PFM13, PFM14, SET07, BOP or SET27H nucleic acid molecule, under conditions that allow specific hybridization to PFM/SET nucleic acid, and detecting specific hybridization.

In another embodiment, the method consists of contacting the sample with a PFM/SET primer pair, under conditions that allow amplification of PFM/SET nucleic acid, and detecting amplified PFM/SET nucleic acid.

The methods of detecting PFM/SET nucleic acid in a sample can be either qualitative or quantitative, as desired. For example, the presence, abundance, integrity or structure of a PFM/SET, or of particular splice variants thereof, can be determined, as desired, depending on the assay format and the probe or primer pair chosen.

Useful assays for detecting PFM/SET nucleic acid based on specific hybridization with an isolated PFM/SET nucleic acid molecule are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A PFM/SET hybridization probe can be labeled with any suitable detectable moiety, such as a radioisotope, fluorochrome, chemiluminescent marker, biotin, or other detectable moiety known in the art that is detectable by analytical methods.

Useful assays for detecting PFM/SET nucleic acid in a sample based on amplifying PFM/SET nucleic acid with a PFM/SET primer pair are also well known in the art, and include, for example, qualitative or quantitative polymerase chain reaction (PCR); reverse-transcription PCR (RT-PCR); SSCP analysis, which can readily identify a single point mutation in DNA, such as in a PCR or RT-PCR product; and coupled PCR, transcription and translation assays, such as the Protein Truncation Test, in which a mutation in DNA is determined by an altered protein product on an electrophoresis gel. Additionally, the amplified PFM/SET nucleic acid can be sequenced to detect mutations and mutational hotspots, and specific assays for large-scale screening of samples to identify such mutations can be developed.

Such assays are also applicable to the qualitative or quantitative detection of SET nucleic acid in a sample. Therefore, the invention thus provides methods for detecting PFM/SET nucleic acid in a sample.

The invention also provides methods for detecting PFM/SET polypeptide in a sample, by contacting the sample with an agent specific for PFM/SET, under conditions that allow specific binding of the agent to PFM/SET polypeptide, and detecting the specifically bound agent. As used herein the term "agent specific for PFM/SET" refers to a molecule that specifically binds PFM/SET polypeptides. An example of a molecule that specifically binds PFM or SET is a PFM or SET antibody, respectively, or antigen binding fragment thereof. Additionally, the PFM/SET binding and modulatory compounds identified in the affinity screening methods described above are also suitable agents that can be used in methods of detecting PFM or SET polypeptides.

Assays for detecting PFM/SET polypeptides include, for example, immunohistochemistry, immunofluorescence, ELISA assays, radioimmunoassay (RIA), FACS analysis, immunoprecipitation, and immunoblot analysis, using antibodies or antigen binding fragments specific for PFM or SET. Various immunoassays are well known in the art, and can be readily modified by those skilled in the art in cases in which the agent is a PFM or SET binding molecule other than an antibody. If desired, the agent or antibody can be rendered detectable by incorporation of, or by conjugation to, a detectable moiety, or binding to a secondary molecule that is itself detectably labeled.

In the detection methods of the invention, the nucleic acid probes or primers, and polypeptide binding agents, can advantageously be directed against the PR domain of PFM, or the A, B or C boxes thereof. Therefore, these assays can be used to distinguish between PR+ growth-inhibiting, and PR−, growth-promoting, forms of PFM in a sample.

The following examples are intended to illustrate but not limit the present invention.

The involvement of PFM/SET in cell differentiation and cancer, and the chromosomal locations of PFM/SET genes, as shown in the Examples below, are consistent with a role for PFM/SET in human diseases including cancer.

EXAMPLE I

Identification and Characterization of PFM6

This example shows identification of the gene encoding the PR-domain containing polypeptide designated PFM6, and characterization of its structure and chromosomal location.

Human genome sequence databases were screened using the PR domain of RIZ1, BLIMP1 and MDS1-EVI1 as probes or queries. This led to the identification of an unfinished human chromosome 5 genomic sequence (AC010432) encoding a PR domain. Sequence analysis revealed an open reading frame encoding 683 amino acids. The predicted amino acid sequence contains a PR domain, a PKZL domain, and 14 zinc finger domains. This gene was designated PFM6 for PR family member 6.

The PKZL domain stands for "PR and KRAB zinc-finger protein linked" domain since the 100 residue domain exhibits 34% identity to the N-terminal region of the KRAB-domain containing zinc finger protein 133, ZNF133.

The structural features of PFM6 protein suggest a role for the protein as a DNA binding transcription factor. The PR domain of PFM6 is more related to PFM4 (GenBank accession number XM_006873) than to other PR genes.

Using PFM6 human cDNA as a query sequence, an STS (sequence tagged site) sequence, STS294 was identified. This STS marker maps to 5p14. Rearrangements or gains of chromosome 5p are commonly found in ovarian and breast cancers (Sonoda et al., (1997), supra).

EXAMPLE II

Identification and Characterization of PFM7

This example shows identification of the gene encoding the PR-domain containing polypeptide designated PFM7, and characterization of its structure and chromosomal location.

cDNA libraries and human genomic sequence libraries were screened using the PR domain of RIZ1, BLIMP1 and MDS1-EVI1 as probes or queries. This led to the identification of a partial cDNA sequence encoding a protein identified as KIAA1231 (GenBank Accession number AB33057) and a genomic clone on 11q25 (AP000686) that encode a PR domain. Sequence analysis revealed an open reading frame encoding 1061 amino acids. The predicted amino acid sequence contains a PRAZ motif, a PR domain, an acidic motif, and 10 zinc finger motifs. The gene is widely expressed in adult human tissues. This gene was designated PFM7.

Using PFM7 human cDNA as a query sequence, a genomic clone (AP000686), which maps to 11q25, was identified. The chromosomal locus 11q25 is frequently deleted in breast, ovary, colon and oral cancer (Connolly et al., supra; Koreth et al., *Oncogene* 14:431–7 (1997); Launonen et al., supra; Uzawa et al., *Intl. J. Cancer* 67:510–4 (1996)). It has also been demonstrated that 11q25 YAC clones can suppress tumor growth in vivo (Koreth et al., *Oncogene* 18:1157–64 (1999)).

EXAMPLE III

Identification and Characterization of PFM8

This example shows identification of the gene encoding the PR-domain containing polypeptide designated PFM8, and characterization of its structure and chromosomal location.

Human genome sequence databases were screened using the PR domain of RIZ1, BLIMP1 and MDS1-EVI1 as probes or queries. This led to the identification of an unfinished human chromosome genomic sequence (AC013602) encoding a PR domain. The full length cDNA was obtained by rapid amplification of cDNA ends (RACE) using a Marathon Race Kit (CLONETECH Laboratories, Inc., Palo Alto, Calif.) with a human brain cDNA library. The primers used for cloning the PFM cDNA sequence of about 0.9 kb were 5'-tgtccctgcacgcccggaagtagatg-3' (SEQ ID NO:21) and 5'-tgtgctggaacgccagcaggtt-3' (SEQ ID NO:22). The amplified nucleotide sequence is referenced as SEQ ID NO:25. The obtained cDNA encoded a 504 amino acid sequence predicted to contain a PR domain and a PRAZ domain. This gene was designated PFM8.

STS markers within the genomic clone were identified STS markers having Accession numbers G36915, G37367, G13751, and G52735. The STS markers that map 11p11, a region commonly deleted in breast cancer (Nakata et al., supra).

EXAMPLE IV

Characterization of PFM9

This example shows identification of the gene encoding the PR-domain containing polypeptide designated PFM9, and characterization of its structure and chromosomal location.

cDNA libraries and human genomic sequence libraries were screened using the PR domain of RIZ1, BLIMP1 and MDS1-EVI1 as probes or queries. This led to the identification of a an unfinished genomic clone (AC015497) encoding a PR domain. Sequence analysis revealed an open reading frame encoding 364 amino acids. The predicted amino acid sequence contains a PR domain and 3 zinc finger motifs. This gene was designated PFM9.

To map the chromosomal location of PFM9, the Stanford radiation hybrid panel was screened with a pair of PCR primers that amplify PFM9 gene. This mapped PFM9 to chromosome 9q33-34.1. This region is commonly deleted in ovarian, bladder, esophageal, and lung cancers (Devlin et al., supra; Hornigold et al., supra; and Simoneau et al., *Oncogene* 18:157–63 (1999)).

EXAMPLE V

Characterization of PFM10

This example shows identification of the gene encoding the PR-domain containing polypeptide designated PFM10, and characterization of its structure and chromosomal location.

cDNA libraries and human genomic sequence libraries were screened using the PR domain of RIZ1, BLIMP1 and MDS1-EVI1 as probes or queries. This led to the identification of a an unfinished genomic clone on chromosome 6q16.1-21 (AL035087) encoding a PR domain. Sequence analysis revealed an open reading frame encoding 717 amino acids. The predicted amino acid sequence contains a PR motif and 4 zinc finger motifs.

To map the chromosomal location of PFM10, the Stanford radiation hybrid panel was screened with a pair of PCR primers that amplify PFM10 gene. This mapped PFM10 to chromosome 6q16-21. The 6q16-21 region is commonly deleted in B-cell lymphoma, melanoma, and stomach cancers. This region also contains another PR-family member, the candidate tumor suppressor PRDIBF1/BLIMP1 (PRDM1) (Mock et al., supra).

EXAMPLE VI

Characterization of PFM11

This example shows identification of the gene encoding the PR-domain containing polypeptide designated PFM11, and characterization of its structure and chromosomal location.

cDNA libraries and human genomic sequence libraries were screened using the PR domain of RIZ1, BLIMP1 and MDS1-EVI1 as probes or queries. This led to the identification of a genomic clone (AC018740) that encodes a PR domain. Sequence analysis revealed an open reading frame encoding 518 amino acids. The predicted amino acid sequence contains a PR domain.

To map the chromosomal location of PFM11, the Stanford radiation hybrid panel was screened with a pair of PCR primers that amplify PFM11 gene. This mapped PFM11 to chromosome 8p12-21, a region commonly deleted in breast and prostate cancers (Van Alewijk et al., *Genes, Chromosomes & Cancer* 24:119–26 (1999); Verma et al., supra; and Vocke et al., supra).

EXAMPLE VII

Characterization of PFM12

This example shows identification of the gene encoding the PR-domain containing polypeptide designated PFM12, and characterization of its structure and chromosomal location.

cDNA libraries and human genomic sequence libraries were screened using the PR domain of RIZ1, BLIMP1 and MDS1-EVI1 as probes or queries. This led to the identification of a sequence on chromosome 21 that encodes a PR domain. Sequence analysis revealed an open reading frame encoding 951 amino acids. The predicted amino acid sequence contains a PR domain, PRAZ motif and 8 C2H2 zinc finger domains.

To map the chromosomal location of PFM12, the Stanford radiation hybrid panel was screened with a pair of PCR primers that amplify PFM12. This mapped PFM12 to chromosome 21q22.3, a region deleted in human leukemia (Hoffman et al. *Annals of Oncology,* 6(8):781–8 (1995), Pederson-Bjergaard et al. *Leukemia,* 7(12):1975–86 (1993) and Rubin et al. Blood, 76(12):2594–8 (1990)) and bladder cancer (Babu et al. *Cancer Genetics and Cytogenetics* 38(1):127–9 (1989)).

EXAMPLE VIII

Characterization of PFM13

This example shows identification of the gene encoding the PR-domain containing polypeptide designated PFM13, and characterization of its structure and chromosomal location.

cDNA libraries and human genomic sequence libraries were screened using the PR domain of RIZI, BLIMP1 and MDS1-EVI1 as probes or queries. An EST clone (AI278689) was initially identified having a partial PR domain. Sequence of the cDNA was obtained by RACE, as described above in relation to PFM8, and by analysis of sequences in the public databases. The primers used for amplifying the PFM13 cDNA were 5'-gggggtagacgccttggttcacg-3' (SEQ ID NO:23), and 5'-catcgcaggagcacgccacac-3' (SEQ ID NO:24). The amplified nucleotide sequence is referenced as SEQ ID NO:26. The full length cDNA of 4367 bp is predicted to encode 1257 amino acids. The predicted amino acid sequence contains a PR domain and 10 zinc finger domains. The sequence shares 51% peptide sequence identity with the MDS1-EVI1 cancer gene over the entire length of the protein, and is therefore a paralog of MDS1-EVI1.

By STS content mapping, the PFM13 gene was mapped to chromosome band 1p36.23-33, a region deleted in more than a dozen different types of human cancers. The proven role of MDS1-EVI1 and RIZ1 (also on 1p36) in human cancers (Huang, 1999), suggests a role for PFM13 as one of several tumor suppressors thought to reside on 1p36.

EXAMPLE IX

Characterization of PFM14

This example shows identification of the gene encoding the PR-domain containing polypeptide designated PFM14, and characterization of its structure and chromosomal location.

cDNA libraries and human genomic sequence libraries were screened using the PR domain of RIZ1, BLIMP1 and MDS1-EVI1 as probes or queries. An EST clone (BE732157.1) was initially identified having a partial PR domain. The EST clone was used to identify a genomic sequence (AC12054) on chromosome 11, which was then used to predict an open reading frame of 720 amino acids. The predicted amino acid sequence of PFM14 contains one PR domain and 10 zinc finger motifs.

EXAMPLE X

Characterization of SET07

This example shows identification of the gene encoding the SET-domain containing polypeptide designated SET07, and characterization of its structure and chromosomal location.

cDNA libraries and human genomic sequence libraries were screened using the SET domain of human HRX as a query. An EST clone (AA085455) was found to contain a SET domain. A full length cDNA containing the SET domain was assembled using sequences in the public databases. A genomic sequence (AC005283) was identified to contain the SET domain gene, termed SET07. An STS identified to correspond to the genomic sequence was used to map SET07 to chromosome 13q11–q13, in proximity to the retinoblastoma locus on 13q14. This region is commonly deleted in many cancers including breast cancers, bladder cancers, lung cancers and osteosarcomas.

EXAMPLE XI

Characterization of BOP

This example shows identification of the gene encoding the SET domain-containing polypeptide designated BOP, and characterization of its structure and chromosomal location.

The mouse BOP sequence was used as a query sequence for searching the NCBI human genome database to identify a human BOP ortholog. From identified human genome sequence located on chromosome 2p11, a full length cDNA encoding human BOP was assembled. Chromosome 2p11 is a region commonly deleted in cancers, including leukemias and cancer of T-lymphocytes. In addition, the mouse BOP has been observed to be important for heart differentiation in mice (Gottlieb, et al. Nat. Genet. Published online: 1 Apr. 2002, DOI:10.1038/ng866 (2002)).

EXAMPLE XII

Characterization of the SET Domain of SET27H

This example shows identification of the nucleotide sequence of the SET domain of a polypeptide designated SET 27H.

The nucleotide sequence of the SET domain of SET07 was used as a query sequence to search the NCBI EST database for homologous sequences. One EST clone (AW176331) was found to contain a novel SET domain.

EXAMPLE XIII

PFM/SET Modulation of Cell Proliferation

This Example describes a method for demonstrating the ability of a PFM/SET nucleic acid to modulate cell proliferation.

A human PFM/SET cDNA is inserted into a mammalian expression vector, such as pCMV-Tag4, to generate an expression construct encoding PFM/SET. The encoded PFM/SET polypeptide can be tagged with a detectable epitope, for example, with a myc, GST or FLAG epitope tag, at the C-terminus. Alternatively, the desired epitope can be placed at the N-terminus, or at an internal site, so long as the epitope does not interfere with PFM/SET activity. The PFM/SET expression construct is transfected, either transiently or stably, into cells (for example, 293 or NIH-3T3 cells) using a commercially available reagent, such as Effectene or Superfect transfection reagents (Qiagen, Valencia, Calif.). Expression of the PFM/SET protein from the construct is then confirmed by detecting the epitope or the PFM/SET polypeptide, for example, by immunostaining of cells or immunoblot analysis.

Cell proliferation in cells having or lacking PFM/SET expression is then determined. One well known method for measuring cell proliferation is by measuring BrdU incorporation. BrdU incorporation into DNA is a measure of DNA synthesis, which is required for cell proliferation. The effect of PFM/SET expression on cell proliferation is measured by growing cells for 2 h in BrdU-containing media following transfection, staining the cells with anti-BrdU monoclonal antibody and DAPI (nuclear staining reagent), and counting the number of BrdU positive and negative cells in several different microscopic views.

In this manner, the effect of PFM/SET expression on cell proliferation can be determined. A variety of other cell proliferation assays are well known to those skilled in the art, and can also be used for determining cell proliferation in cells lacking or expressing a PFM/SET polypeptide.

All journal article, reference and patent citations provided above, including referenced sequence accession numbers of nucleotide and amino acid sequences contained in various databases, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. An isolated PR family member 7 (PFM7) nucleic acid molecule, comprising a nucleotide sequence encoding a PMF7 polypeptide comprising the amino acid sequence referenced as SEQ ID NO:4.

2. The isolated nucleic acid molecule of claim 1, encoding a PFM7 polypeptide consisting of the amino acid sequence referenced as SEQ ID NO:4.

3. The isolated nucleic acid molecule of claim 1, wherein said PFM7 polypeptide is encoded by a nucleotide sequence comprising the nucleotide sequence referenced as SEQ ID NO:3.

4. The isolated nucleic acid molecule of claim 3, wherein said PFM7 polypeptide is encoded by a nucleotide sequence consisting of the nucleotide sequence referenced as SEQ ID NO:3.

5. An isolated nucleic acid molecule encoding a polypeptide, wherein said polypeptide consists of a functional fragment of the of SEQ ID NO:4, wherein said fragment comprises at least amino acids 116–258 of SEQ ID NO:4 or amino acids 87–108 of SEQ ID NO:4.

6. A vector, comprising the isolated nucleic acid molecule of claim 1.

7. The vector of claim 6, wherein said isolated nucleic acid molecule is operatively linked to a transcription promoter of RNA transcription.

8. A host cell, comprising the vector of claim 7.

9. A method for isolating a PFM/SET polypeptide, comprising growing the host cell of claim 8 under conditions appropriate for expression of the encoded PFM/SET polypeptide, and isolating said PFM/SET polypeptide.

* * * * *